US009364567B2

(12) United States Patent
Vitalis et al.

(10) Patent No.: US 9,364,567 B2
(45) Date of Patent: Jun. 14, 2016

(54) FRAGMENTS OF P97 AND USES THEREOF

(71) Applicant: biOasis Technologies, Inc., Richmond (CA)

(72) Inventors: Timothy Z. Vitalis, Vancouver (CA); Reinhard Gabathuler, Montreal (CA)

(73) Assignee: biOasis Technologies, Inc., Richmond (CA)

( * ) Notice: Subject to any disclaimer, the term of this patent is extended or adjusted under 35 U.S.C. 154(b) by 0 days.

(21) Appl. No.: 14/210,029

(22) Filed: Mar. 13, 2014

(65) Prior Publication Data

US 2014/0322132 A1   Oct. 30, 2014

Related U.S. Application Data

(60) Provisional application No. 61/780,170, filed on Mar. 13, 2013, provisional application No. 61/885,387, filed on Oct. 1, 2013.

(51) Int. Cl.
| | |
|---|---|
| *C07K 14/47* | (2006.01) |
| *A61K 49/00* | (2006.01) |
| *C07K 7/06* | (2006.01) |
| *C07K 7/08* | (2006.01) |
| *C07K 16/00* | (2006.01) |
| *C07K 14/79* | (2006.01) |

(52) U.S. Cl.
CPC .............. *A61K 49/0002* (2013.01); *C07K 7/06* (2013.01); *C07K 7/08* (2013.01); *C07K 14/79* (2013.01); *C07K 16/00* (2013.01)

(58) Field of Classification Search
None
See application file for complete search history.

(56) References Cited

U.S. PATENT DOCUMENTS

| | | | |
|---|---|---|---|
| 4,391,904 A | 7/1983 | Litman et al. |
| 4,394,448 A | 7/1983 | Szoka, Jr. et al. |
| 4,399,216 A | 8/1983 | Axel et al. |
| 4,683,195 A | 7/1987 | Mullis et al. |
| 4,683,202 A | 7/1987 | Mullis |
| 4,704,362 A | 11/1987 | Itakura et al. |
| 4,766,075 A | 8/1988 | Goeddel et al. |
| 4,784,950 A | 11/1988 | Hagen et al. |
| 4,800,159 A | 1/1989 | Mullis et al. |
| 4,801,542 A | 1/1989 | Murray et al. |
| 4,866,042 A | 9/1989 | Neuwelt |
| 4,935,349 A | 6/1990 | McKnight et al. |
| 4,946,778 A | 8/1990 | Ladner et al. |
| 5,091,513 A | 2/1992 | Huston et al. |
| 5,132,405 A | 7/1992 | Huston et al. |
| 5,186,941 A | 2/1993 | Callahan et al. |
| 5,672,683 A | 9/1997 | Friden et al. |
| 5,677,171 A | 10/1997 | Hudziak et al. |
| 5,720,937 A | 2/1998 | Hudziak et al. |
| 5,720,954 A | 2/1998 | Hudziak et al. |
| 5,725,856 A | 3/1998 | Hudziak et al. |
| 5,770,195 A | 6/1998 | Hudziak et al. |
| 5,772,997 A | 6/1998 | Hudziak et al. |
| 5,798,239 A | 8/1998 | Wilson et al. |
| 5,844,093 A | 12/1998 | Kettleborough et al. |
| 5,932,211 A | 8/1999 | Wilson et al. |
| 5,962,012 A | 10/1999 | Lin et al. |
| 5,981,194 A | 11/1999 | Jefferies et al. |
| 6,015,557 A | 1/2000 | Tobinick et al. |
| 6,165,464 A | 12/2000 | Hudziak et al. |
| 6,177,077 B1 | 1/2001 | Tobinick |
| 6,261,595 B1 | 7/2001 | Stanley et al. |
| 6,387,371 B1 | 5/2002 | Hudziak et al. |
| 6,399,063 B1 | 6/2002 | Hudziak et al. |
| 6,419,934 B1 | 7/2002 | Tobinick |
| 6,419,944 B2 | 7/2002 | Tobinick |
| 6,455,494 B1 | 9/2002 | Jefferies et al. |
| 6,537,549 B2 | 3/2003 | Tobinick |
| 6,596,541 B2 | 7/2003 | Murphy et al. |
| 6,765,087 B1 | 7/2004 | Casterman et al. |
| 6,838,254 B1 | 1/2005 | Hamers et al. |
| 6,982,089 B2 | 1/2006 | Tobinick |
| 7,132,511 B2 | 11/2006 | Carr et al. |
| 7,138,371 B2 | 11/2006 | DeFrees et al. |
| 7,179,617 B2 | 2/2007 | DeFrees et al. |
| 7,214,658 B2 | 5/2007 | Tobinick |
| 7,244,592 B2 | 7/2007 | Hoogenboom et al. |
| 7,247,301 B2 | 7/2007 | van de Winkel et al. |
| 7,462,697 B2 | 12/2008 | Couto et al. |
| 7,595,378 B2 | 9/2009 | van de Winkel et al. |
| 7,700,554 B2 | 4/2010 | Beliveau et al. |
| 7,723,484 B2 | 5/2010 | Beidler et al. |
| 7,939,072 B2 | 5/2011 | Yarden et al. |
| 7,960,516 B2 | 6/2011 | Matheus et al. |

(Continued)

FOREIGN PATENT DOCUMENTS

| | | |
|---|---|---|
| GB | 2188637 | 10/1987 |
| WO | WO 89/04663 | 6/1989 |

(Continued)

OTHER PUBLICATIONS

Supplementary European Search Report for European Application No. 03717870.4, mailed Oct. 2, 2007, 4 pages.
Office Action in U.S. Appl. No. 10/501,028 mailed Dec. 23, 2009, 8 pages.
Office Action in U.S. Appl. No. 10/501,028 mailed Aug. 17, 2009, 8 pages.
Office Action in U.S. Appl. No. 10/501,028 mailed Oct. 29, 2008, 11 pages.
Office Action in U.S. Appl. No. 10/501,028 mailed Jul. 31, 2008, 9 pages.
Office Action in U.S. Appl. No. 10/501,028 mailed Jan. 29, 2008, 8 pages.
International Search Report for International Application No. PCT/US2003/000894, mailed Sep. 10, 2003, 3 pages.
International Preliminary Examination Report for International Application No. PCT/US2003/000894, dated Feb. 14, 2005, 5 pages.
Supplementary European Search Report for European Application No. 11178022.7, mailed Nov. 25, 2011, 6 pages.
Office Action for U.S. Appl. No. 12/729,792, mailed Jun. 12, 2013, 9 pages.
Office Action for U.S. Appl. No. 12/729,792, mailed Aug. 20, 2012, 9 pages.

(Continued)

*Primary Examiner* — John Ulm
(74) *Attorney, Agent, or Firm* — Cooley LLP

(57) ABSTRACT

Provided are fragments of human p97 (melanotransferrin) polypeptides having blood-brain barrier (BBB) transport activity, including variants and combinations thereof, conjugates comprising the p97 fragments, and related methods of use thereof, for instance, to facilitate delivery of therapeutic or diagnostic agents across the BBB.

25 Claims, 26 Drawing Sheets

(56) References Cited

U.S. PATENT DOCUMENTS

| | | | |
|---|---|---|---|
| 8,546,319 | B2 | 10/2013 | Starr et al. |
| 8,722,019 | B2 | 5/2014 | Jefferies et al. |
| 2002/0059032 | A1* | 5/2002 | Ferrer et al. ............... 702/20 |
| 2002/0119095 | A1 | 8/2002 | Gabathuler et al. |
| 2003/0072761 | A1 | 4/2003 | LeBowitz |
| 2003/0129186 | A1 | 7/2003 | Beliveau et al. |
| 2004/0055022 | A1 | 3/2004 | Cheng et al. |
| 2004/0137557 | A1 | 7/2004 | DeFrees et al. |
| 2005/0026823 | A1 | 2/2005 | Zankel et al. |
| 2005/0158296 | A1 | 7/2005 | Starr et al. |
| 2007/0167365 | A1 | 7/2007 | Beliveau et al. |
| 2008/0014188 | A1 | 1/2008 | Zankel et al. |
| 2009/0226421 | A1 | 9/2009 | Parren et al. |
| 2010/0183581 | A1 | 7/2010 | Beliveau et al. |
| 2010/0297120 | A1 | 11/2010 | Beliveau et al. |
| 2011/0093962 | A1 | 4/2011 | Heidbrink et al. |
| 2011/0142763 | A1 | 6/2011 | Zankel et al. |
| 2012/0107302 | A1 | 5/2012 | Berry et al. |
| 2013/0108548 | A1 | 5/2013 | Vlieghe et al. |
| 2013/0183368 | A1 | 7/2013 | Hutchison et al. |
| 2014/0105880 | A1 | 4/2014 | Starr et al. |
| 2014/0178350 | A1 | 6/2014 | Vitalis et al. |
| 2015/0056218 | A1 | 2/2015 | Jeffries et al. |
| 2015/0093399 | A1 | 4/2015 | Jefferies |

FOREIGN PATENT DOCUMENTS

| | | |
|---|---|---|
| WO | WO 93/11161 | 6/1993 |
| WO | WO 94/01463 | 1/1994 |
| WO | WO 94/13804 | 6/1994 |
| WO | WO 98/23646 | 6/1998 |
| WO | WO 00/50636 | 8/2000 |
| WO | WO 01/59459 | 8/2001 |
| WO | WO 01/83722 | 8/2001 |
| WO | WO 02/13843 | 2/2002 |
| WO | WO 02/13873 | 2/2002 |
| WO | WO 03/009815 | 2/2003 |
| WO | WO 03/057179 | 7/2003 |
| WO | WO 2004/078215 | 9/2004 |
| WO | WO 2006/079372 | 8/2006 |
| WO | WO 2008/022349 | 2/2008 |
| WO | WO 2009/019314 | 2/2009 |
| WO | WO 2011/044542 | 4/2011 |
| WO | WO 2011/163649 | 12/2011 |
| WO | WO 2013/006706 | 1/2013 |
| WO | WO 2013/022738 | 2/2013 |
| WO | WO 2014/022515 | 2/2014 |
| WO | WO 2014/160438 | 10/2014 |
| WO | WO 2015/031673 | 3/2015 |

OTHER PUBLICATIONS

Office Action for U.S. Appl. No. 12/729,792, mailed Jan. 11, 2013, 11 pages.
Office Action for U.S. Appl. No. 13/969,280, mailed Sep. 22, 2014, 5 pages.
Office Action for U.S. Appl. No. 13/969,280, mailed Mar. 4, 2015, 10 pages.
International Search Report and Written Opinion for International Application No. PCT/US2014/026620, mailed Sep. 17, 2014, 15 pages.
Examination Report for Australian Application No. 2012278944, dated Aug. 26, 2014, 3 pages.
Office Action for U.S. Appl. No. 13/542,435, mailed Dec. 3, 2014, 27 pages.
International Preliminary Report on Patentability for International Application No. PCT/US2012/045568, dated Jan. 7, 2014, 5 pages.
International Search Report and Written Opinion for International Application No. PCT/US2012/045568, mailed on Sep. 27, 2012, 9 pages.
Examination Report for Australian Application No. 2012294673, dated Sep. 16, 2014, 4 pages.
Notice of Allowance in U.S. Appl. No. 13/566,260, mailed Dec. 26, 2013, 8 pages.
Office Action in U.S. Appl. No. 13/566,260, mailed Sep. 5, 2013, 6 pages.
International Preliminary Report on Patentability for International Application No. PCT/US2012/049475, dated Feb. 11, 2014, 7 pages.
International Search Report and Written Opinion for International Application No. PCT/US2012/049475, mailed on Oct. 25, 2012, 9 pages.
International Search Report and Written Opinion for International Application No. PCT/US2013/052939, mailed Oct. 31, 2013, 14 pages.
International Preliminary Report on Patentability for International Application No. PCT/US2013/052939, dated Feb. 3, 2015, 9 pages.
Invitation to Pay Additional Fees and Partial International Search for International Application No. PCT/US2014/053257, mailed Jan. 12, 2015, 10 pages.
Aktas, Y. et al., "Development and brain delivery of chitosan-PEG nanoparticles functionalized with the monoclonal antibody OX26," Bioconjugate Chem,16(6):1503-1511 (2005).
Asano, N. et al., "In vitro inhibition and intracellular enhancement of lysosomal α-galactosidase A activity in Fabry lymphoblasts by 1-deoxygalactonojirimycin and its derivatives," Eur. J. Biochem., 267(13):4179-4186 (2000).
Begley, D. J. et al., "Lysosomal storage diseases and the blood-brain barrier," Current Pharmaceutical Design, 14(16):1566-1580 (2008).
Bickel, U. et al., "Pharmacologic effects in vivo in brain by vector-mediated peptide drug delivery," Proc. Natl. Acad. Sci. USA, 90(7):2618-2622 (1993).
Bickel, U. et al., "In vivo demonstration of subcellular localization of anti-transferrin receptor monoclonal antibody-colloidal gold conjugate in brain capillary endothelium," Journal of Histochemistry and Cytochemistry, 42(11):1493-1497 (1994).
Bickel, U. et al., "In vivo cleavability of a disulfide-based chimeric opioid peptide in rat brain," Bioconjugate Chem, 6(2):211-218 (1995).
Bickel, U. et al., "Delivery of peptides and proteins through the blood-brain barrier," Advanced Drug Delivery Review, 46(1-3):247-279 (2001).
Bielicki, J. et al., "Recombinant human iduronate-2-sulphatase: correction of mucopolysaccharidosis-type II fibroblasts and characterization of the purified enzyme," Biochemical Journal, 289(Pt. 1):241-246 (1993).
Blattler, W. A. et al., "New heterobifunctional protein cross-linking reagent that forms an acid-labile link," Biochem., 24:1517-1524 (1985).
Boado, R. J. et al., "Cloning and expression in Pichia pastoris of a genetically engineered single chain antibody against the rat transferrin receptor," Journal of Drug Targeting, 8(6):403-412 (2000).
Broadwell, R. D. et al., "Transcytosis of protein through the mammalian cerebral epithelium and endothelium. III. Receptor-mediated transcytosis through the blood-brain barrier of blood-borne transferrin and antibody against the transferrin receptor," Experimental Neurology, 142(1):47-65 (1996).
Carter, P. et al., "Humanization of an anti-p185$^{HER2}$ antibody for human cancer therapy," Proc. Natl. Acad. Sci. USA, 89:4285-4289 (1992).
Cerletti, A. et al., "Endocytosis and transcytosis of an immunoliposome-based brain drug delivery system," Journal of Drug Targeting, 8(6):435-446 (2000).
Chakraborty, C. et al., "Future prospects of nanoparticles on brain targeted drug delivery," Journal of Neuro-Oncology, 93(2):285-286 (2008).
Chen, Q. et al., "Efficient Synthesis of Doxorubicin Melanotransferrin p97 Conjugates Through SMCC Linker," Synthetic Communications, 34(13):2407-2414 (2004).
Chen, C.-H. B. et al., "Aptamer-based endocytosis of a lysosomal enzyme," Proceedings of the National Academy of Sciences, 105(41):15908-15913 (2008).
Co, M. S. et al., "Humanized antibodies for antiviral therapy," Proc. Natl. Acad. Sci. USA, 88(7):2869-2873 (1991).
Co, M. S. et al. "Chimeric and humanized antibodies with specificity for the CD33 antigen," J. Immunol., 148(4):1149-1154 (1992).

(56) References Cited

OTHER PUBLICATIONS

Daniele, A. et al., "Uptake of recombinant iduronate-2-sulfatase into neuronal and glial cells in vitro," Biochimica et Biophysica Acta., 1588(3):203-209 (2002).
Deguchi, Y. et al., "Retention of biologic activity of human epidermal growth factor following conjugation to a blood-brain barrier drug delivery vector via an extended poly (ethylene glycol) linker," Bioconjugate Chem., 10(1):32-37 (1999).
Delabarre, B. et al., "Central Pore Residues Mediate the p97/VCP activity required for ERAD," Molecular Cell, 22(4):451-462 (2006).
Demeule, M. et al., "High transcytosis of melanotransferrin (P97) across the blood-brain barrier," Journal of Neurochemistry, 83:924-933 (2002).
Demeule, M. et al., "Regulation of plasminogen activation: A role for melantransferrin (p97) in cell migration," Blood, 102(5):1723-1731 (2003).
Dorr, R. T. et al., "In vitro rat myocyte cardiotoxicity model for antitumor antibiotics using adenosine triphosphate/protein ratios," Cancer Research, 48:5222-5227 (1988).
Endo, N. et al., "In-Vitro Cytotoxicity of a Human Serum Albumin-mediated Conjugate of Methotrexate with Anti-MM46 Monoclonal Antibody," Cancer Research, 47(4):1076-1080 (1987).
Enzyme: L-iduronidase. EC 3.2.1.76. http://www.chem.qmul.ac.uk/iubmb/enzyme/EC3/2/1/76.html, 2 pages (Printed Feb. 17, 2009).
Enzyme: N-acetylglucosaminidase. EC 3.2.1.96. http://www.chem.qmul.ac.uk/iubmb/enzyme/EC3/2/1/96.html, 2 pages (Printed Feb. 17, 2009).
Enzyme: β-N-acetylhexosaminidase. EC 3.2.1.52. http://www.chem.qmul.ac.uk/iubmb/enzyme/EC3/2/1/52.html, 2 pages (Printed Dec. 17, 2009).
Friden, P. M., "Anti-transferrin receptor antibody and antibody-drug conjugates cross the blood-brain barrier," Proc. Natl. Acad. Sci. USA, 88(11):4771-4775 (1991).
Gabathuler, R. et al., "Incorporation of transcend (melanotransferrin or MTf) in a therapeutic antibody allows its transport across the blood-brain barrier for the treatment of brain disorders," Society for Neuroscience Abstract Viewer and Itinerary Planner, vol. 42 (2012), XP8173954, & 42nd Annual Meeting of the Society for Neuroscience, New Orleans, LA, USA, Oct. 13-17, 2012.
Geuze, H. J. et al., "Possible Pathways for Lysosomal Enzyme Delivery," Journal of Cell Biology, 101:2253-2262 (1985).
Gosk, S. et al., "Targeting anti-transferrin receptor antibody (OX26) and OX26-conjugated liposomes to brain capillary endothelial cells using in situ perfusion," Journal of Cerebral Blood Flow & Metabolism, 24(11):1193-1204 (2004).
Grubb, J. H. et al., "Chemically modified β-glucuronidase crosses blood-brain barrier and clears neuronal storage in murine mucopolysaccharidosis VII," Proceedings of the National Academy of Sciences, 105(7):2616-2621 (2008).
Holliger, P. et al., "'Diabodies': Small bivalent and bispecific antibody fragments," Proc. Natl. Acad. Sci., 90:6444-6448 (1993).
Hu, S. et al., "Minibody: A Novel Engineered Anti-Carcinoembryonic Antigen Antibody Fragment (Single-Chain Fv-CH3) Which Exhibits Rapid, High-Level Targeting of Xenografts," Cancer Res., 56:3055-3061 (1996).
Huston, J. S. et al., "Protein engineering of antibody binding sites: recovery of specific activity in an anti-digoxin single-chain Fv analogue produced in *Escherichia coli*," Proc. Natl. Acad. Sci. USA, 85(16):5879-5883 (1988).
Huwyler, J. et al., "Receptor mediated delivery of daunomycin using immunoliposomes: pharmacokinetics and tissue distribution in the rat," Journal of Phamacology & Experimental Therapeutics, 282(3):1541-1546 (1997).
Inoue, T. et al., "Predictive in vitro cardiotoxicity and hepatotoxicity screening system using neonatal rat heart cells and rat hepatocytes," AATEX 14, Special Issue, Proc. 6th World Congress on Alternatives & Animal Use in the Life Sciences, pp. 457-462 (Aug. 21-25, 2007).
Jefferies, W. A. et al., "Transferrin receptor on endothelium of brain capillaries," Nature, 312:162-163 (1984).
Jefferies, W. A. et al., "Analysis of lymphopoletic stem cells with a monoclonal antibody to the rat transferrin receptor," Immunology, 54(2):333-341 (1985).
Jolly, R. D. et al., "Lysosomal storage diseases of animals: an essay in comparative pathology," Veterinary Pathology Online, 34:527-548 (1997).
Kakkis, E. et al., "Successful induction of immune tolerance to enzyme replacement therapy in canine mucopolysaccharidosis I," Proceedings of the National Academy of Sciences, 101(3):829-834 (2004).
Kang, Y. S. et al., "Pharmacokinetics and organ clearance of a 3'-biotinylated, internaly [32P]-labeled phosphodiester oligodeoxynucleotide coupled to a neutral avidin/monoclonal antibody conjugate," Drug Metabolism and Disposition, 23(1):55-59 (1995).
Kang, Y. S. et al., "Stability of the disulfide bond in an avidin-biotin linked chimeric peptide during in vivo transcytosis through brain endothelial cells," Journal of Drug Targeting, 8(6):425-434 (2000).
Kang, Y. S. et al., "Use of neutral avidin improves pharmacokinetics and brain delivery of biotin bound to an avidin-monoclonal antibody conjugate," Journal of Pharmacology & Experimental Therapeutics, 269(1):344-350 (1994).
Karkan, D. et al., "A unique carrier for delivery of therapeutic compounds beyond the blood-brain barrier," PLOS One, 3(6):E2469.1-E2469.14 (2008).
King, T. P. et al., "Preparation of protein conjugates via intermolecular hydrazone linkage," Biochem, 25(19):5774-5779 (1986).
Kurihara, A. et al., "Aβ1-40 Peptide radiopharmaceuticals for brain amyloid imaing: III-Inchelation, conjugation to poly(ethylene glycol)-biotin linkers, and autoradiography with Alzheimer's disease brain sections," Bioconjugate Chem, 11:380-386 (2000).
Mahapatro, A. et al., "Biodegradable nanoparticles are excellent vehicle for site directed in-vivo delivery of drugs and vaccines," Journal of Nanobiotechnology, 9(1):55 (2011).
Moos, T. et al., "Restricted transport of anti-transferrin receptor antibody (OX26) through the blood-brain barrier in the rat," Journal of Neurochemistry, 79(1):119-129 (2001).
Moroo, I. et al., "Identification of a novel route of iron transcytosis across the mammalian blood-brain barrier," Microcirculation, 10(6):457-462 (2003).
Muraszoko, K. et al., "Pharmacokinetics and toxicology of immunotoxins administered into the subarachnoid space in nonhuman primates and rodents," Cancer Research, 53(16):3752-3757 (1993).
Muruganandam, A. et al., "Selection of phage-displayed llama single-domain antibodies that transmigrate across human blood-brain barrier endothelium," FASEB Journal, 16(2):240-242 (2001).
Pardridge, W. M., "Drug transport across the blood-brain barrier," Journal of Cerebral Blood Flow & Metabolism, 32(11):1959-1972 (2012).
Pardridge, W. M. et al., "Transport of human recombinant brain-derived neurotrophic factor (BDNF) through the rat blood-brain barrier in vivo using vector-mediated peptide drug delivery," Pharmaceutical Research, 11(50:738-746 (1994).
Pardridge, W. M. et al., "Vector-mediated delivery of a polyamide ("peptide") nucleic acid analogue through the blood-brain barrier in vivo," Proc. Natl. Acad. Sci. USA, 92(12):5592-5596 (1995).
Parenti, G., "Treating lysosomal storage diseases with pharmacological chaperones: from concept to clinics," EMBO Mol. Med., 1:268-279 (2009).
Qian, Z. M. et al., "Targeted drug delivery via the transferrin receptor-mediated endocytosis pathway," Pharmacol. Rev., 54(4):561-587 (2002).
Queen, C. et al., "A humanized antibody that binds to the interleukin 2 receptor," Proc. Natl. Acad. Sci. USA, 86:10029-10033 (1988).
Richardson, D. R. et al., "The uptake of iron and transferrin by the human malignant melanoma cell," Biochimica et Biophysica Acta, 1053:1-12 (1990).
Robinson, L. J. et al., "NSF is required for transport from early to late endosomes," Journal of Cell Science, 110:2079-2087 (1997).
Rose, T. M. et al., "Primary structure of the human melanoma-associated antigen p97 (melanotransferrin) deduced from the mRNA sequence," Proc. Natl. Acad. Sci. USA, 83(5):1261-1265 (1986).

(56) References Cited

OTHER PUBLICATIONS

Saito, Y. et al., "Vector-mediated delivery of $^{125}$I-labeled beta-amyloid peptide Aβ1-40 through the blood-brain barrier and binding to Alzheimer's disease amytoid of the Aβ1-40/vector complex," Proc. Natl. Acad. Sci. USA, 92(22):10227-10231 (1995).

Sala, R. et al., "The Human Melanoma Associated Protein Melanotransferrin Promotes Endothelial Cell Migration and Angiogenesis in vivo," European Journal of Cell Biology, 81(11):599-607 (2002).

Sands, M. S., "Biodistribution, kinetics, and efficacy of highly phosphorylated and non-phosphorylated beta-glucuronidase in the murine model of mucopolysaccharidosis VII," Journal of Biological Chemistry, 276(46):43160-43165 (2001).

Sato, K. et al., "Reshaping a human antibody to inhibit the interleukin 6-dependent tumor cell growth," Cancer Res., 53:851-856 (1993).

Shi, N. et al., "Noninvasive gene targeting to the brain," Proc. Natl. Acad. Sci. USA, 97(13):7567-7572 (2000).

Skarlatos, S. et al., "Transport of [125]transferrin through the rat blood-brain barrier," Brain Research, 683(2):164-171 (1995).

Song, B. W. et al., "Enhanced neuroprotective effects of basic fibroblast growth factor in regional brain ischemia after conjugation to a blood-brain barrier delivery vector," Journal of Pharmacology and Experimental Therapeutics, 301(2):605-610 (2002).

Srinivasachar, K. et al., "New protein cross-linking reagents that are cleaved by mild acid," Biochem. 28:2501-2509 (1989).

Stefano, J. E. et al., "In vitro and in vivo evaluation of a non-carbohydrate targeting platform for lysosomal proteins," Journal of Controlled Release, 135:113-118 (2009).

Tang, Y. et al., "Directing adenovirus across the blood-brain barrier via melanotransferrin (P97) transcytosis pathway in an vitro model," Gene Therapy, 14(6):523-532 (2007).

Thomas, F. C. et al., "Uptake of ANG1005, a novel paclitaxel derivative, through the blood-brain barrier into brain and experimental brain metastases of breast cancer," Pharmaceutical Research, 26(11):2486-2494 (2009).

WikiPedia Foundation, Inc., Sandhoff disease, http://en.wikipedia.org/wiki/Sandhof_disease, Modified 2007 (Printed Jan. 16, 2008).

Woodbury, R. G. et al., "Identification of a cell surface protein, p. 97, in human melanomas and certain other neoplasms," Proc. Natl. Acad. Sci. USA, 77(4):2183-2187 (1980).

Wu, D. et al., "Pharmacokinetics and brain uptake of biotinylated basic fibroblast growth factor conjugated to a blood-brain barrier drug delivery system," Journal of Drug Targeting, 10(3):239-245 (2002).

Wu, D. et al., "Central nervous system pharmacologic effect in conscious rate after intravenous injection of a biotinylated vasoactive intestinal peptide analog coupled to a blood-brain barrier drug delivery system," Journal of Pharmacology and Experimental Therapeutics, 279(1):77-83 (1996).

Wu, D. et al., "Pharmacokinetics and blood-brain transport of [3H]-biotinylated phosphorothioate oligodeoxynucleotide conjugated to a vector-mediated drug delivery system," Journal of Pharmacology and Experimental Therapeutics, 276(1):206-211 (1996).

Yang, J. et al., "Deletion of the GPI pre-anchor sequence in human p97-a general approach for generating the soluble form of GPI-linked proteins," Protein Expression and Purification, 34(1):28-48 (2004).

Yoshikawa, T. et al., "Biotin delivery to brain with a covalent conjugate of avidin and a monoclonal antibody to the transferrin receptor," Journal of Pharmacology and Experimental Therapeutics, 263(2):897-903 (1992).

Zhang, Y. et al., "Conjugation of brain-derived neurotrophic factor to a blood-brain barrier drug targeting system enables neuroprotection in regional brain ischemia following intravenous injection of the neurotrophin," Brain Research, 889(1-2):49-56 (2001).

\* cited by examiner

| Confi dence | Sequence | Modifications | Charge | MH+ [Da] | ΔM [ppm] | RT [min] | # Missed Cleava ges |
|---|---|---|---|---|---|---|---|
| High | LFSHEGSSFQMFSSEAYGQK | | 2 | 2267. 00762 | 0.08 | 43. 95 | 0 |
| High | HTTVFDNTNGHNSEPWAAELR | | 2 | 2396. 10185 | 0.15 | 36. 39 | 0 |
| High | TLPSWGQALLSQDFELLcR | C18(Carbamidom ethyl) | 2 | 2234. 13017 | 1.19 | 72. 07 | 0 |
| High | AVSDYFGGScVPGAGETSYSESLcR | C10(Carbamidom ethyl); C24(Carbamidom ethyl) | 2 | 2656. 12822 | -.033 | 44. 59 | 0 |
| High | NYPSSLcALcVGDEQGR | C7(Carbamidomet hyl); C10(Carbamidom ethyl) | 2 | 1925. 84819 | 0.05 | 39. 87 | 0 |
| High | ADTDGGLIFR | | 2 | 1064. 53679 | -0.35 | 75. 63 | 0 |
| High | mFDSSNYHGQDLLFK | M1(Oxidation) | 2 | 1817. 8167 | 0.18 | 40. 07 | 0 |
| High | cGDMAVAFR | C1(Carbamidomet hyl) | 2 | 1026. 45098 | 1.32 | 35. 91 | 0 |
| High | AQDLFGDDHNKnGFK | N12(Deamidated) | 2 | 1706. 77641 | -0.32 | 27. 41 | 1 |
| High | LFSHEGSSFQmFSSEAYGQK | N11(Oxidation) | 2 | 2283. 00176 | -0.26 | 38. 56 | 0 |
| High | LLNEGQRLFSHEGSSFFQMFSSEAYGQK | | 3 | 3077. 44004 | -0.73 | 47. 85 | 1 |

*FIG. 2A*

| | | | | | | |
|---|---|---|---|---|---|---|
| High | LFSHEGSSFQMFSSEAYGQKDLLFK | | 3 | 2883.36435 | -0.54 | 52.06 | 1 |
| High | MFDSSNYHGQDLLFK | | 2 | 1801.82317 | 0.95 | 45.29 | 0 |
| High | SEDYELLcPNGAR | C8(Carbamidomethyl) | 2 | 1523.67937 | -0.12 | 35.44 | 0 |
| High | cGDmAVAFR | C1(Carbamidomethyl); M4(Oxidation) | 2 | 1042.4439 | -0.61 | 22.74 | 0 |
| High | LcRGDSSGEGVcDK | C2(Carbamidomethyl); C12(Carbamidomethyl) | 2 | 1539.65276 | 0.04 | 13.54 | 1 |
| High | EAGIQPSLLcVR | C10(Carbamidomethyl) | 2 | 1342.71453 | -0.22 | 40.47 | 0 |
| High | LKPEIQcVSAK | C7(Carbamidomethyl) | 3 | 1272.69797 | -0.1 | 21.58 | 0 |
| High | HSTVLENTDGK | | 2 | 1200.5855 | -0.05 | 15.92 | 0 |
| High | GTSADHcVQLIAAQEADAITLDGGAIYEAGK | C7(Carbamidomethyl) | 3 | 3145.51023 | -0.18 | 55.77 | 0 |
| High | GDSSGEGVcDK | C9(Carbamidomethyl) | 2 | 1110.43633 | -0.48 | 10.07 | 0 |
| High | cLAEGAGDVAFVK | C1(Carbamidomethyl) | 2 | 1336.65605 | -0.44 | 37.26 | 0 |
| High | SSHVTIDTLKGVK | | 3 | 1384.77948 | -0.02 | 24.42 | 1 |
| High | TVGWNVPVGYLVESGR | | 2 | 1732.90166 | -0.06 | 54.48 | 0 |
| High | RDSSHAFTLDELR | | 3 | 1546.76072 | -0.13 | 32.63 | 1 |
| High | IQAEQVDAVTLSGEDIYTAGK | | 3 | 2208.10361 | -0.22 | 44.72 | 1 |
| High | YYDYSGAFR | | 2 | 1141.49394 | -0.85 | 68 | 0 |
| High | AQDLFGDDHNK | | 3 | 1259.56464 | -0.41 | 20.56 | 0 |
| High | DSSHAFTLDELR | | 2 | 1390.65898 | -0.58 | 76.84 | 0 |
| High | GDSSGEGVcDKSPLER | C9(Carbamidomethyl) | 3 | 1692.74961 | 0.1 | 21.09 | 1 |
| High | WcATSDPEQHK | C2(Carbamidomethyl) | 2 | 1358.57903 | -0.29 | 19.94 | 0 |
| High | LLnEGqRLFSHEGSSFqMFSSEAYGQK | N3(Deamidated); Q6(Deamidated); Q17(Deamidated) | 3 | 3080.3928 | -0.5 | 57.33 | 1 |

*FIG. 2B*

| | | | | | | | |
|---|---|---|---|---|---|---|---|
| High | cLVENAGDVAFVR | C1(Carbamidomethyl) | 2 | 1449.71599 | 0.3 | 39.92 | 0 |

FIG. 2B (Continued)

| | | | | | | | |
|---|---|---|---|---|---|---|---|
| High | RSSHVTIDTLK | | 3 | 1256.69574 | -0.02 | 19.02 | 1 |
| High | GLLcDPNRLPPYLR | C4(Carbamidomethyl) | 4 | 1683.89943 | -0.33 | 43.29 | 1 |
| High | MFDSSnYHGQDLLFK | N6(Deamidated) | 3 | 1802.8024 | -1.71 | 45.84 | 0 |
| High | AQDLFGDDHNKNGFK | | 4 | 1705.79641 | 2.03 | 25.95 | 1 |
| High | HTTVFDNTnGHHSEPWAAELR | N9(Deamidated) | 4 | 2397.08584 | 0.13 | 38.77 | 0 |
| High | SEDYELLcPnGAR | C8(Carbamidomethyl) N10(Deamidated) | 2 | 1524.65764 | -3.88 | 36.12 | 0 |
| High | TLPSWGqALLSqDFELLcR | Q7(Deamidated); Q12(Deamidated); C18(Carbamidomethyl) | 2 | 2236.106 | 4.68 | 71.93 | 0 |
| High | LSVmGcDVLK | M4(Oxidation); C6(Carbamidomethyl) | 2 | 1137.56389 | -0.37 | 32.07 | 0 |
| High | SSHVTIDTLK | | 2 | 1100.59477 | 0.11 | 22.53 | 0 |
| High | EHGLKPVVGEVYDQEVGTSYYAVAVVRR | | 4 | 3120.61098 | -0.13 | 44.41 | 1 |
| High | LSVMGcDVLK | C6(Carbamidomethyl) | 2 | 1121.56914 | -0.23 | 41.14 | 0 |
| High | cGNMSEAFR | C1(Carbamidomethyl) | 2 | 1071.43474 | 0.05 | 24.39 | 0 |
| High | SPQHcmER | C5(Carbamidomethyl) | 2 | 1044.43474 | -0.25 | 9.67 | 0 |
| Medium | ADVTEWR | | 2 | 876.42131 | 0.3 | 26.04 | 0 |

FIG. 2C

| | | | | | | | |
|---|---|---|---|---|---|---|---|
| Medium | SPQHcmER | C5(Carbamidomethyl); M6(Oxidation) | 2 | 1060.42974 | -0.17 | 0.92 | 0 |
| Medium | GLLcDPNR | C4(Carbamidomethyl) | 2 | 944.4616 | -0.3 | 23.83 | 0 |
| Medium | TVGWNVPVGYLVESGRLSVMGcDVLK | C22(Carbamidomethyl) | 3 | 2835.45389 | 0.2 | 64.55 | 1 |
| Medium | GLLcDPnRLPPYLR | C4(Carbamidomethyl); M7(Deamidated) | 3 | 1684.88028 | -2.21 | 45.01 | 1 |
| Low | DLLFKDSTSELVPIATQTYEAWLGHEYLHAMK | | 4 | 3706.85024 | 1.06 | 70.87 | 1 |
| Low | LLNEGQR | | 2 | 829.45293 | 0.3 | 15.59 | 0 |
| Low | DSTSELVPIATQTYEAWLGHEYLHAMK | | 3 | 3090.48777 | -0.02 | 64.02 | 0 |

FIG. 2C (Continued)

| | | | | | | | |
|---|---|---|---|---|---|---|---|
| Low | DSTSELVPIATQTYEAWLGHEYLHAMK GLLcDPNR | C31(Carbamidomethyl) | 3 | 4015.92771 | -1.03 | 70.52 | 1 |
| Low | VPAHAVVVR | | 2 | 947.57927 | 0.75 | 18.33 | 0 |
| Low | DSTSELVPIATqTYEAWLGHEYLHAMK GLLcDPNR | Q12(Deamidated); C31(Carbamidomethyl) | 3 | 4016.93406 | 4.53 | 70.55 | 1 |

FIG. 2D

MRGPSGALWL LLALRTVLGG MEVRWCATSD PEQHKCGNMS EAFREAGIQP SLLCVRGTSA DHCVQLIAAQ EADAITLDGG AIYEAGKEHG LKPVVGEVYD
QEVGTSYYAV AVVRRSSHVT IDTLKGVKSC HTGINRTVGW NVPVGYLVES GRLSVMGCDV LKAVSDYFGG SCVPGAGETS YSESLCRLCR GDSSGEGVCD
KSPLERYYDY SGAFRCLAEG AGDVAFVKHS TVLENTDGKT LPSWGQALLS QDFELLCRDG SRADVTEWRQ CHLARVPAHA VVVRADTDGG LIFRLLNEGQ
RLFSHEGSSF QMFSSEAYGQ KDLLFKDSTS ELVPIATQTY EAWLGHEYLH AMKGLLCDPN RLPPYLRWCV LSTPEIQKCG DMAVAFRRQR LKPEIQCVSA
KSPQHCMERI QAEQVDAVTL SGEDIYTAGK KYGLVPAAGE HYAPEDSSNS YVVAVVRRD SSHAFTLDEL RGKRSCHAGF GSPAGWDVPV GALIQRGFIR
PKDCDVLTAV SEFFNASCVP VNNPKNYPSS LCALCVGDEQ GRNKCVGNSQ ERYYGYRGAF RCLVENAGDV AFVRHTTVFD NTNGHNSEPW AAELRSEDYE
LLCPNGARAE VSQFAACNLA QIPPHAVMVR PDTNIFTVYG LLDKAQDLFG DDHNKNGFKM FDSSNYHGQD LLFKDATVRA VPVGEKTTYR GWLGLDYVAA
LEGMSSQQCS GAAAPAPGAP LLPLLLPALA ARLLPPAL  SEQ ID NO:1

*FIG. 2E*

Band 1

MRGPSGALWL LLALRTVLGG MEVRWCATSD PEQHKCGNMS EAFREAGIQP SLLCVRGTSA DHCVQLIAAQ EADAITLDGG AIYEAGKEHG LKPVVGEVYD

QEVGTSYYAV AVVRRSSHVT IDTLKGVKSC HTGINRTVGW NVPVGYLVES GRLSWMGCDV LKAVSDYFGG SCVPGAGETS YSESLCRLCR GDSSGEGVCD

KSPLERYYDY SGAFRCLAEG AGDVAFVKHS TVLENTDGKT LPSWGQALLS QDFELLCRDG SRADVTEWRQ CHLARVPAHA VVVRADTDGG LIFRLLNEGQ

RLFSHEGSSF QMFSSEAYGQ KDLLFKDSTS ELVPIATQTY EAWLGHEYLH AMKGLLCDPN RLPPYLRWCV LSTPEIQKCG DMAVAFRRQR LKPEIQCVSA

KSPQHCMERI QAEQVDAVIL SGEDIYTAGK KYGLVPAAGE HYAPEDSSNS YVVAVVRRD SSHAFTLDEL RGKRSCHAGF GSPAGWDVPV GALIQRGFIR

PKDCDVLTAV SEFFNASCVP VNNPKNYPSS LCALCVGDEQ GRNKCVGNSQ ERYYGYRGAF RCLVENAGDV AFVRHTTVFD NTNGHNSEPW AAELRSEDYE

LLCPNGARAE VSQFAACNLA QIPPHAVMVR PDTNIFTVYG LLDKAQDLFG DDHNKNGFKM FDSSNYHGQD LLFKDATVRA VPVGEKTTYR GWLGLDYVAA

LEGMSSQQCS GAAAPAPGAP LLPLILPALA ARLLPPAL     SEQ ID NO:1

FIG. 3A

Band 2

```
                                    C
MRGPSGALWL LLALRTVLGG MEVR WCATSD  PEQHK CGNMS EAFREAGIQP SLLCVRGTSA DHCVQLIAAQ EADAITLDGG AIYEAGKEHG LKPVVGEVYD
                                                              D                    D          D             D
 D                                                                            P         P
QEVGTSYYAV AVVRRSSHVT IDTLKGVKSC HTGINRTVGW NVPVGYLVES GRLSVMGCDV LKAVSDYFGG SCVPGAGETS YSESLCRLCR GDSSGEGVCD
      D                                                   D                       C
     C                           D    D   C
KSPLERYYDY SGAFRCLAEG AGDVAFVKHS TVLENTDGKT LPSWCQALLS QDFELLCRDG SRADVTEWRQ CHLARVPAHA VVVRADTDGG LIFRLLNEGQ
 D                                                                                                       DC
 C                                                                                          DC
RLFSHEGSSF QMFSSEAYGQ KDLLLFKDSTS ELVPIATQTY EAWLGHEYLH AMKGLLCDPN RLPPYLRWCV LSTPEIQKCG DMAVAFRRQR LKPEIQCVSA

C                        D D  D
KSPQHCMERI QAEQVDAVIL SGEDIYTACK KYGLVPAAGE HYAPEDSSNS LCALCVGDEQ GRNKCVGNSQ ERYYGYRGAF RCLVENAGDV AFVRHTTVFD NTNGHNSEPW AAELRSEDYE
                                                      C C                   D       D
PKDCDVLTAV SEFFNASCVP VNNPKNYPSS LCALCVGDEQ QIPPHAVMVR PDTNIFTVYG LLDKAQDLFG DDHNKNGFKM FDSSNYHGQD LLFKDATVRA VPVGEKTTYR GWLGLDYVAA
 C
LLCPNGARAE VSQFAACNLA QIPPHAVMVR PDTNIFTVYG LLDKAQDLFG DDHNKNGFKM FDSSNYHGQD LLFKDATVRA VPVGEKTTYR GWLGLDYVAA

LEGMSSQQCS GAAAPAPGAP LLPLLLPALA ARLLPPAL      SEQ ID NO:1
```

FIG. 3B

Band 3

```
        1       101       201       301       401       501       601       701  738
```

MRGPSGALWL LLALRTVLGG MEVRWCATSD PEQHKCGNMS EAFREAGIQP SLLCVRGTSA DHCVQLIAAQ EADAITLDGG AIYEAGKEHG LKPVVGEVYD

C  
D  
QEVGTSYYAV AVVRRSSHVT IDTLKGVKSC HTGINRTVGW NVPVGYLVES GRLSVMGCDV LKAVSDYFGG SCVPGAGETS YSESLCRLCR GDSSGEGVCD

D         D                                     P           P  
KSPLERYYDY SGAFRCLAEG AGDVAFVKHS TVLENTDGKT LPSWGQALLS QDFELLCRDG SRADVTEWRQ CHLARVPAHA VVVRADTDGG LIFRLLNEGQ

O  C  D                                                      P  
                                                                                                                 P  
                                                                                                                                              DC  
RLFSHEGSSF QMFSSEAYGQ KDILLFKDSTS ELVPIATQTY EAWLGHEYLH AMKGLLCDPN R[LPPYLR]WCV LSTPEIQKCG DMAVAFRRQR LKPEIQCVSA

D  D  D  
KSPQHCMERI QAEQVDAVTL SGEDIYTAGK KYGLVPAAGE HYAPEDSSNS YYVAVVRRD SSHAFTLDEL RGKRSCHAGF GSPAGWDVPV GALIQRGFIR

C                                                 DD  D  
PKDCDVLTAV SEFFNASCVP VNNPKNYPSS LCALCVGDEQ GRNKCVGNSQ ERYYGYRGAF RCLVENAGDV AFVRHTTVFD NTNGHNSEPW AAELRSEDYE

D        D   D                  D  
C  
LLCPNGARAE VSQFAACNLA QIPPHAVMVR PDTNIFTVYG LLDKAQDLFG DDHNKNGFKM FDSSNYHGQD LLFKDATVRA VPVGEKTTYR GWLGLDYVAA

LEGMSSQQCS GAAAPAPGAP LLPLLLPALA ARLLPPAL    SEQ ID NO:1

*FIG. 3C*

Band 1 (~28-38 kDa)

```
  1 MRGPSGALWL LLALRTVLGG MEVRWCATSD PEQHKCGNMS EAFREAGIQP
 51 SLLCVRGTSA DHCVQLIAAQ EADAITLDGG AIYEAGKEHG LKPVVGEVYD
101 QEVGTSYYAV AVVRRSSHVT IDTLKGVKSC HTGINRTVGW NVPVGYLVES
151 GRLSVMGCDV LKAVSDYFGG SCVPGAGETS YSESLCRLCR GDSSGEGVCD
201 KSPLERYYDY SGAFRCLAEG AGDVAFVKHS TVLENTDGKT LPSWGQALLS
251 QDFELLCRDG SRADVTEWRQ CHLARVPAHA VVVRADTDGG LIFRLLNEGQ
301 RLFSHEGSSF QMFSSEAYGQ KDLLFKDSTS ELVPIATQTY EAWLGHEYLH
351 AMKGLLCDPN RLPPYLRWCV LSTPEIQKCG DMAVAFRRQR LKPEIQCVSA
401 KSPQHCMERI QAEQVDAVTL SGEDIYTAGK KYGLVPAAGE HYAPEDSSNS
451 YVVAVVRRD SSHAFTLDEL RGKRSCHAGF GSPAGWDVPV GALIQRGFIR
501 PKDCDVLTAV SEFFNASCVP VNNPKNYPSS LCALCVGDEQ GRNKCVGNSQ
551 ERYYGYRGAF RCLVENAGDV AFVRHTTVFD NTNGHNSEPW AAELRSEDYE
601 LLCPNGARAE VSQFAACNLA QIPPHAVMVR PDTNIFTVYG LLDKAQDLFG
651 DDHNKNGFKM FDSSNYHGQD LLFKDATVRA VPVGEKTTYR GWLGLDYVAA
701 LEGMSSQQCS GAAAPAPGAP ARLLPPAL   [SEQ ID NO:1]
```

Figure 4A

| Confidence | Sequence | Modifications | IonScore | Exp Value | Charge | MH+ [Da] | ΔM [ppm] | RT [min] |
|---|---|---|---|---|---|---|---|---|
| Low | GDSSGEGVcDKSPLER | C9(Carbamidomethyl) | 24 | 0.585637876 | 3 | 1692.74906 | -0.23 | 11.73 |
| Low | LKPEIQcVSAK | C7(Carbamidomethyl) | 27 | 0.722587143 | 3 | 1272.69925 | 0.91 | 11.84 |
| Low | SSHVTIDTLK |  | 32 | 0.183325902 | 2 | 1100.59270 | -1.77 | 12.05 |
| Low | AQDLFGDDHNK |  | 49 | 0.001586224 | 2 | 1259.56499 | -0.14 | 12.30 |
| High | SSHVTIDTLKGVK |  | 34 | 0.10947824 | 2 | 1384.77971 | 0.14 | 12.63 |
| Low | AqDLFGDDHNK | Q2(Deamidated) | 24 | 0.316471818 | 3 | 1260.55002 | 0.67 | 13.00 |
| Low | GLLcDPNR | C4(Carbamidomethyl) | 20 | 1.450983432 | 2 | 944.46153 | -0.36 | 13.13 |
| Low | ADVTEWR |  | 40 | 0.02157799 | 2 | 876.42064 | -0.47 | 13.55 |
| High | RDSSHAFTLDELR |  | 36 | 0.102069849 | 3 | 1546.76017 | -0.48 | 14.62 |
| High | LSVmGcDVLK | M4(Oxidation); C6(Carbamidomethyl) | 57 | 0.000594205 | 2 | 1137.56389 | -.037 | 15.19 |
| Low | YYDYSGAFR |  | 22 | 0.582859505 | 2 | 1141.49455 | -0.31 | 16.14 |
| High | SEDYELLcPNGAR | C8(Carbamidomethyl) | 63 | 7.9564E-05 | 2 | 1523.67949 | -0.04 | 16.22 |
| High | cLAEGAGDVAFVK | C1(Carbamidomethyl) | 47 | 0.007423868 | 2 | 1336.65703 | 0.29 | 16.22 |
| High | DSSHAFTLDELR |  | 39 | 0.031508659 | 3 | 1390.65891 | -0.63 | 16.48 |
| High | SEDYELLcPnGAR | C8(Carbamidomethyl); N10(Deamidated) | 65 | 4.30461E-05 | 2 | 1524.66850 | 3.24 | 16.59 |
| High | HTTVFDNTNGHNSEPWAAELR |  | 65 | 0.000115457 | 2 | 2396.10161 | 0.05 | 16.63 |
| High | HTTVFDNTnGHNSEPWAAELR | N9(Deamidated) | 29 | 0.352597977 | 4 | 2397.08681 | 0.54 | 16.95 |
| Low | SEDYELLcPNGAR | C8(Propionamide); C8(Carbamidomethyl) | 21 | 1.495576912 | 2 | 1537.69609 | -37081.82 | 16.98 |
| High | ADTDGGLIFR |  | 85 | 1.02686E-06 | 2 | 1064.53740 | 0.23 | 17.05 |
| High | cLVENAGDVAFVR | C1(Carbamidomethyl) | 82 | 2.76997E-06 | 2 | 1449.71514 | -0.29 | 17.22 |
| Low | mFDSSNYHGQDLLFK | M1(Oxidation) | 25 | 0.599293128 | 3 | 1817.81559 | -0.43 | 17.30 |
| High | HTTVFDNTnGHnSEPWAAELR | N9(Deamidated); N12(Deamidated) | 17 | 5.447408025 | 4 | 2398.08730 | 7.41 | 17.41 |
| High | NYPSSLcALcVGDEQGR | C7(Carbamidomethyl); C10(Carbamidomethyl) | 113 | 8.74972E-10 | 2 | 1925.84770 | -0.21 | 17.42 |
| Low | SEDYELLcPnGAR | C8(Propionamide); C8(Carbamidomethyl) | 14 | 5.97825186 | 2 | 1538.67668 | -37060.41 | 17.45 |

*FIG. 4B*

| Confidence | Sequence | Modifications | IonScore | Exp Value | Charge | MH+ [Da] | ΔM [ppm] | RT [min] |
|---|---|---|---|---|---|---|---|---|
| High | NYPSSLcALcVGDEqGR | C7(Carbamidomethyl); C10(Carbamidomethyl) | 106 | 4.05712E-09 | 2 | 1926.83391 | 0.93 | 17.71 |
| High | cLVEnAGDVVAFVR | C1(Carbamidomethyl); N5(Deamidated) | 77 | 7.23432E-06 | 2 | 1450.69866 | -0.63 | 17.95 |
| High | EAGIQPSLLcVR | C10(Carbamidomethyl) | 76 | 7.27757E-06 | 2 | 1342.71514 | 0.24 | 17.97 |
| Low | NYPSSLcALcVGDEQGR | C7(Carbamidomethyl); C10(Propionamide) | 44 | 0.00733681 | 2 | 1939.86528 | -29393.76 | 18.07 |
| High | cLVENAGDVAFVR | C1(Propionamide); C1(Carbamidomethyl) | 61 | 0.000356625 | 2 | 1463.73357 | -38954.56 | 18.40 |
| Low | NYPSSLcALcVGDEqGR | C7(Carbamidomethyl); C10(Propionamide) | 47 | 0.003457106 | 2 | 1940.84905 | -29378.99 | 18.43 |
| High | AVSDYFGGScVPGAGETSYSESLcR | C10(Carbamidomethyl); C24(Carbamidomethyl) | 93 | 5.3769E-08 | 2 | 2656.13042 | 0.49 | 18.51 |
| High | EAGIqPSLLcVR | Q5(Deamidated); C10(Carbamidomethyl) | 55 | 0.001031465 | 2 | 1343.69878 | -0.04 | 18.52 |
| Low | ScHAGFGSPAGWDVPVGALIqR | C2(Propionamide); C2(Carbamidomethyl) | 14 | 19.48150831 | 3 | 2297.11759 | -24821.17 | 18.74 |
| High | EHGLKPVWGEVYDQEVGTSYYAVAVVR | | 39 | 0.080559493 | 4 | 2964.51186 | 0.54 | 18.75 |
| High | ScHAGFGSPAGWDVPVGALIQR | C2(Carbamidomethyl) | 50 | 0.005390434 | 3 | 2282.11502 | 0.62 | 20.48 |
| High | ScHAGFGSPAGWDVPVGALIqR | C2(Carbamidomethyl); Q21(Deamidated) | 22 | 3.584246826 | 3 | 2283.09995 | 1.02 | 20.97 |
| Medium | KYGLVPAAGEHYAPEDSSNSYYVVAVVR | | 11 | 55.84334183 | 3 | 3041.47208 | -9.32 | 21.45 |
| High | TVGWNVPGYLVESGR | | 75 | 1.83654E-05 | 2 | 1732.90264 | 0.50 | 21.62 |
| High | GTSADHcVQLIAAQEADAITLDGGAIYEAGK | C7(Carbamidomethyl) | 28 | 1.02247977 | 3 | 3145.51316 | 0.75 | 22.45 |
| High | IQAEQVDAVTLSGEDIYTAGK | | 121 | 4.90258E-10 | 2 | 2208.10674 | 1.63 | 23.33 |

*FIG. 4B (Continued)*

Band 2 (~14-17 kDa)

```
  1 MRGPSGALWL LLALRTVLGG MEVRWCATSD PEQHKCGNMS EAFREAGIQP
 51 SLLCVRGTSA DHCVQLIAAQ EADAITLDGG AIYEAGKEHG VGEVYD
101 QEVGTSYYAV AVVRRSSHVT IDTLKGVKSC HTGINRTVGW NVPVGYIVES
151 GRLSVMGCDV LKAVSDYFGG SCVPGAGETS YSESLCRLCR GDSSGEGVCD
201 KSPLERYYDY SGAFRCLAEG AGDVAFVKHS TVLENTDGKT LPSWGQALLS
251 QDFELLCRDG SRADVTEWRQ CHLARVPAHA VVVRADTDGG LIFRLLNEGQ
301 RLFSHEGSSF QMFSSEAYGQ KDLLFKDSTS ELVPIATQTY EAWLGHEYLH
351 AMKGLLCDPN RLPPYLRWCV LSTPEIQKCG DMAVAFRRQR LKPEIQCVSA
401 KSPQHCMERI QAEQVDAVTL SGEDIYTAGK KYGLVPAAGE HYAPEDSSNS
451 YVVAVVRRD SSHAFTIDEL RGKRSCHAGF GSPAGWDVPV GALIQRGFIR
501 PKDCDVLTAV SEFFNASCVP VNNPKNYPSS LCALCVGDEQ GRNKCVGNSQ
551 ERYGYRGAF RCLVENAGDV AFVRHTTVFD NTNGHNSEPW AAELRSEDYE
601 LLCPNGARAE VSQFAACNLA QIPPHAVMVR PDTNIFTVYG LLDKAQDLFG
651 DDHNKNGFKM FDSSNYHGQD LLFKDATVRA VPVGEKTTYR GWLGLDYVAA
701 LEGMSSQQCS GAAAPAPGAP ARLLPPAL [SEQ ID NO:1]
```

Figure 5A

| Confidence | Sequence | Modifications | IonScore | Exp Value | Charge | MH+ [Da] | ΔM [ppm] | RT [min] |
|---|---|---|---|---|---|---|---|---|
| High | AVSDYFGGScVPGAGETSYSESLcR | C10(Carbamidomethyl); C24(Carbamidomethyl) | 105 | 3.32619E-09 | 2 | 2656.13091 | 0.68 | 18.42 |
| High | ADTDGGLIFR | | 88 | 5.66332E-07 | 2 | 1064.53667 | -0.46 | 16.92 |
| High | IQAEQVDAVTLSGEDIYTAGK | | 83 | 2.68245E-06 | 2 | 2208.10503 | 0.86 | 18.53 |
| High | cLVENAGDVAFVR | C1(Carbamidomethyl) | 73 | 2.18803E-05 | 2 | 1449.71599 | 0.30 | 17.53 |
| High | EAGIQPSLLcVR | C10(Carbamidomethyl) | 72 | 1.893E-05 | 2 | 1342.71526 | 0.33 | 17.87 |
| High | EAGIqPSLLcVR | Q5(Deamidated); C10(Carbamidomethyl) | 72 | 2.09047E-05 | 2 | 1343.69927 | 0.32 | 18.46 |
| High | TVGWNVPVGYLVESGR | | 64 | 0.000214885 | 2 | 1732.90276 | 0.57 | 21.54 |
| High | TVGWnVPVGYLVESGR | N5(Deamidated) | 61 | 0.00037243 | 2 | 1733.88884 | 1.76 | 22.34 |
| High | cLAEGAGDVAFVKHSTVLENTDGK | C1(Carbamidomethyl) | 59 | 0.000716311 | 3 | 2518.22568 | 0.53 | 15.87 |
| High | GTSADHcVQLIAAQEADAITLDGGAIYEAGK | C7(Carbamidomethyl) | 50 | 0.006393688 | 3 | 3145.50913 | -0.53 | 22.11 |
| High | HSTVLENTDGK | | 49 | 0.002664503 | 2 | 1200.58537 | -0.15 | 8.94 |
| High | SSHVTIDTLKGVK | | 47 | 0.005004121 | 2 | 1384.77959 | 0.06 | 12.56 |
| High | SEDYELLcPNGAR | C8(Carbamidomethyl) | 44 | 0.007060764 | 2 | 1523.67925 | -0.20 | 16.38 |
| High | cLAEGAGDVAFVK | C1(Carbamidomethyl) | 43 | 0.015618173 | 2 | 1336.65764 | 0.74 | 17.35 |
| High | NYPSSLcALcVGDEQGR | C7(Carbamidomethyl); C10(Carbamidomethyl) | 42 | 0.011117546 | 2 | 1925.85039 | 1.19 | 17.48 |
| High | DSSHAFTLDELR | | 40 | 0.02400093 | 2 | 1390.65923 | -0.41 | 17.41 |
| High | LFSHEGSSFQmFSSEAYGQK | M11(Oxidation) | 34 | 0.067830844 | 3 | 2283.00125 | -0.48 | 16.73 |
| High | EHGLKPWGEVYDQEVGTSYYAVAVVR | | 18 | 9.497357658 | 3 | 2964.48630 | -8.09 | 20.83 |
| Medium | VPAHAVVVR | | 37 | 0.016034535 | 2 | 947.57823 | -0.35 | 9.83 |
| Medium | YYDYSGAFR | | 32 | 0.058131104 | 2 | 1141.49529 | 0.33 | 16.02 |
| Low | ADVTEWR | | 42 | 0.014791458 | 2 | 876.42088 | -0.19 | 13.46 |
| Low | SSHVTIDTLK | | 45 | 0.008209964 | 2 | 1100.59307 | -1.44 | 12.00 |
| Low | GTSADHcVQLIAqEADAITLDGGAIYEAGK | C7(Carbamidomethyl); Q14(Deamidated) | 13 | 30.54462867 | 3 | 3146.51181 | 5.41 | 21.09 |

FIG. 5B

| Confidence | Sequence | Modifications | IonScore | Exp Value | Charge | MH+ [Da] | ΔM [ppm] | RT [min] |
|---|---|---|---|---|---|---|---|---|
| Low | RSSHVTIDTLK | | 21 | 2.359482024 | 3 | 1256.69629 | 0.41 | 10.68 |
| Low | cLAEGAGDVAFVK | C1(Propionamide); C1(Carbamidomethyl) | 49 | 0.004630097 | 2 | 1350.67266 | -42216.82 | 17.34 |
| Low | RDSSHAFTLDELR | | 18 | 7.055056021 | 3 | 1546.75998 | -0.60 | 15.58 |
| Low | GDSSGEGVcDKSPLER | C9(Carbamidomethyl) | 26 | 0.349899255 | 2 | 1692.75029 | 0.50 | 11.53 |
| Low | GLLcDPNR | C4(Carbamidomethyl) | 17 | 2.628224465 | 2 | 944.46153 | -0.36 | 13.06 |
| Low | SEDYELLcPnGAR | C8(Carbamidomethyl); N10(Deamidated) | 12 | 7.790573694 | 2 | 1524.66240 | -0.76 | 16.62 |
| Low | AVSDYFGScVPGAGETSYSESLcR | C10(Carbamidomethyl); C24(Propionamide) | 32 | 0.094002039 | 2 | 2670.14946 | -21353.40 | 19.02 |
| Low | GTSADHcVQLIAAQEADAITLDGGAIYEAGK | C7(Propionamide); C7(Carbamidomethyl) | 11 | 56.65840641 | 3 | 3159.52512 | -18047.90 | 26.07 |
| Low | GDSSGEGVcDKSPLER | C9(Propionamide); C9(Carbamidomethyl) | 35 | 0.066541439 | 3 | 1706.76413 | -33409.67 | 12.28 |
| Low | LKPEIQcVSAK | C7(Carbamidomethyl) | 12 | 25.47451421 | 2 | 1272.69792 | -0.13 | 11.81 |

*FIG. 5B (Continued)*

Band 3 (~3-5 kDa)

```
  1  MRGPSGALWL LLALRTVLGG MEVRWCATSD PEQHKCGNMS EAFREAGIQP
 51  SLLCVRGTSA DHCVQLIAAQ EADAITLDGG AIYEAGKEHG LKPVVGEVYD
101  QEVGTSYYAV AVVRRSSHVT IDTLKGVKSC HTGINRTVGW NVPVGYLVES
151  GRLSVMGCDV LKAVSDYFGG SCVPGAGETS YSESLCRLCR GDSSGEGVCD
201  KSPLERYYDY SGAFRCLAEG AGDVAFVKHS TVLENTDGKT LPSWGQALLS
251  QDFELLCRDG SRADVTEWRQ CHLARVPAHA VVVRADTDGG LIFRLLNEGQ
301  RLFSHEGSSF QMFSSEAYGQ KDLLFKDSTS ELVPIATQTY EAWLGHEYLH
351  AMKGLLCDPN RLPPYLRWCV LSTPEIQKCG DMAVAFRRQR LKPEIQCVSA
401  KSPQHCMERI QAEQVDAVTL SGEDIYTAGK KYGLVPAAGE HYAPEDSSNS
451  YVVAVVRRD SSHAFTLDEL RGKRSCHAGF GSPAGWDVPV GALIQRGFIR
501  PKDCDVLTAV SEFFNASCVP VNNPKNYPSS LCALCVGDEQ GRNKCVGNSQ
551  ERYGYRGAF RCLVENAGDV AFVRHTTVFD NTNGHNSEPW AAELRSEDYE
601  LLCPNGARAE VSQFAACNLA QIPPHAVMVR PDTNIFTVYG LIDKAQDLFG
651  DDHNKNGFKM FDSSNYHGQD LLFKDATVRA VPVGEKTTYR GWLGLDYVAA
701  LEGMSSQQCS GAAAPAPGAP ARLLPPAL   [SEQ ID NO:1]
```

Figure 6A

| Confidence | Sequence | Modifications | IonScore | Exp Value | Charge | MH+ [Da] | ΔM [ppm] | RT [min] |
|---|---|---|---|---|---|---|---|---|
| High | EHGLKPWGEVYDQEVGTSYYAVAVVRR | | 92 | 3.98408E-07 | 3 | 2964.51340 | 1.06 | 18.72 |
| High | ADTDGGLIFR | | 80 | 3.43802E-06 | 2 | 1064.53630 | -0.81 | 17.05 |
| High | IQAEQVDAVTLSGEDIYTAGK | | 77 | 1.11566E-05 | 2 | 2208.10503 | 0.86 | 18.53 |
| High | cLAEGAGDVAFVK | C1(Carbamidomethyl) | 69 | 4.64898E-05 | 2 | 1336.65679 | 0.11 | 16.37 |
| High | AQDLFGDDHNK | | 54 | 0.000515661 | 2 | 1259.56474 | -0.33 | 12.27 |
| High | LKPEIQcVSAK | C7(Carbamidomethyl) | 46 | 0.011480148 | 2 | 1272.69829 | 0.15 | 11.78 |
| High | DSSHAFTLDELR | | 45 | 0.00851981 | 3 | 1390.65900 | -0.57 | 17.45 |
| High | YYDYSGAFR | | 42 | 0.005301934 | 2 | 1141.49443 | -0.42 | 16.22 |
| High | WcVLSTPEIQK | C2(Carbamidomethyl) | 41 | 0.035667619 | 2 | 1360.69390 | 0.65 | 18.09 |
| High | LKPEIqcVSAK | Q6(Deamidated); C7(Carbamidomethyl) | 40 | 0.045361318 | 2 | 1273.68242 | 0.24 | 12.30 |
| High | GTSADHcVQLIAAQEADAITLDGGAIYEAGK | C7(Carbamidomethyl) | 16 | 15.050040921 | 3 | 3145.51242 | 0.52 | 22.45 |
| Medium | mFDSSNYHGQDLLFK | M1(Oxidation) | 13 | 10.33638211 | 3 | 1817.81614 | -0.13 | 17.30 |
| Low | SEDYELLcPNGAR | C8(Carbamidomethyl) | 43 | 0.008580171 | 2 | 1523.68059 | 0.69 | 16.37 |
| Low | AqDLFGDDHNK | Q2(Deamidated) | 20 | 0.820984659 | 3 | 1260.54947 | 0.23 | 12.97 |
| Low | LFSHEGSSFQmFSSEAYGQK | M11(Oxidation) | 16 | 5.227925584 | 3 | 2283.00437 | 0.88 | 16.79 |
| Low | RDSSHAFTLDELR | | 20 | 3.778030027 | 3 | 1546.76053 | -0.25 | 15.62 |
| Low | GLLcDPNR | C4(Carbamidomethyl) | 28 | 0.21544481 | 2 | 944.46129 | -0.62 | 13.00 |
| Low | GLLcDPNRLPPYLR | C4(Carbamidomethyl) | 19 | 4.54838221 | 3 | 1683.89920 | -0.47 | 18.45 |
| Low | LKPEIQcVSAK | C7(Propionamide); C7(Carbamidomethyl) | 14 | 13.9717555 | 2 | 1286.71367 | -44315.64 | 12.39 |

FIG. 6B

AA: GMEVRWCATSDPEQHKCGNMSEAFREAGIQPSLLCVRGTSADHCVQLIAAQEADAITLDG
Pred: -EEEEEEE-HHHHHHHHHHHHHH---EEEEE---HHHHHHHHH----EEEE-H AA: GAIYEAGKEHGLKPVVGEVYDQEVGTSYYAVAVVRRSSHVTIDTLKGVKSCHTGINRTVG
Pred: HHHHHH------EEEEEEE----EEEEEEEEEE-----HHH-------

AA: WNVPVGYLVESGRLSVMGCDVLKAVSDYFGGSCVPGAGETSYSESLCRLCRGDSSGEGVC
Pred: EEEEHHHHHHHH------HHHHHHHHHH------HHHHHH---------

AA: <u>DKSPLERYYDYSGAFRCLAEGAGDVAFVKHSTVLENTDGKTLPSWGQALLSQDFELLCRD</u>
Pred: --------HHHHHHHH----EEEEE-------------HHHHHHH-----

AA: GSRADVTEWRQCHLARVPAHAVVVRADTDGGLIFRLLNEGQRLFSHEGSSFQMFSSEAYG
Pred: -------EEEEE---HHHHHHHHHHHHHHH----------HHH- AA: QKDLLFKDSTSELVPIATQTYEAWLGHEYLHAMKGLLCDPNRLPPYLRWCVLSTPEIQ<u>KC</u>
Pred: ---EEEE--------HHHHHHHHHHHHH-------EEEEEEE---HHHHHH AA: <u>GDMAVAFRRQRLKPEIQCVSAK</u>SPQHCMERIQAEQVDAVTLSGEDIYTAGKTYGLVPAAG
Pred: HHHHHHHHHH-----EEEEEE--HHHHHHHHH---EEEEEE-HHHHHHHHHH---EEEEE AA: EHYAPEDSSNSYYVVAVVRRD<u>SSHAFTLDELRGKRSCHAGFGSPAGWDVPVGALIQRGFI</u>
Pred: EE----EEEEEEEE--------HHH-----EEE----EEEE-HHHHH----

AA: <u>RPKDCDVLTAVSEFFNASCVPVNNPKNYPSSLCALCVGDEQGRNKCVGNSQERYYGYRGA</u>
Pred: ---EEEE-----------------------------H AA: FRCLVENAGDVAFVRHTTVFDNTNGHNSEPWAAELRSEDYELLCPN<u>GARAEVSQFAACNL</u>
Pred: HHHHH---EEEEE--HHHH------HHHHHHH----HHHHHH-----EE------EE AA: <u>AQIPPHAVMVRPDTNIFTVYGLLDKAQDLFGDDHNKNGFK</u>MFDSSNYHGQDLLFKDATVR
Pred: EEE---EEEE---HHHHHHHHHHHHHH----------HHHHHHHH-------EEEE---EE AA: AVPVGEKTTYRGWLGLDYVAALEGMSSQQC
Pred: EEEE------HHHH--HHHHHHHHHH------

Figure 9A

Bold: N-LOBE
Normal: C-LOBE
<u>Underlined: Tryptic peptides</u>
AA: Target sequence
Pred: (H)=Helix, (E)=Strand, (-)=Coil AA: GMEVRWCATSDPEQHKCGNMSEAFREAGIQPSLLCVRGTSADHCVQLIAAQEADAITLDG
Pred: -EEEEEEE-HHHHHHHHHHHHHH----EEEEE---HHHHHHHHH----EEEE-H AA: GAIYEAGKEHGLKPVVGEVYDQEVGTSYYAVAVVRRSSHVTIDTLKGVKSCHTGINRTVG
Pred: HHHHHH------EEEEEEE-----EEEEEEEEEE-----HHH--------------

AA: WNVPVGYLVESGRLSVMGCDVLKAVSDYFGGSCVPGAGETSYSESLCRLCRGDSSGEGVC
Pred: EEEEHHHHHHH--------HHHHHHHHHHH-------HHHHHH-------

AA: DKSPLERYYDYSGAFRCLAEGAGDVAFVKHSTVLENTDGKTLPSWGQALLSQDFELLCRD
Pred: ------HHHHHHH---EEEEE--------------------HHHHHH---

AA: GSRADVTEWRQCHLARVPAHAVVVRADTDGGLIFRLLNEGQRLFSHEGSSFQMFSSEAYG
Pred: ----------EEEEE---HHHHHHHHHHHHHHH--------------HHH- AA: Q<u>KDLLFKDSTSELVPIATQTYEAWLGHEYLHAMKGLLCDPNRLPPYLRWCVLSTPEIQKC</u>
Pred: ---EEEE----------HHHHHHHHHHHHHHH---------EEEEEEE--HHHHHH AA: <u>GDMAVAFRRQRLKPEIQCVSAKSPQHCMERIQAEQVDAVTLSGEDIYTAGKTYGLVPAAG</u>
Pred: HHHHHHHHH----EEEEEE----HHHHHHHH----EEEEEE-HHHHHHHHHH---EEEEE AA: <u>EHYAPEDSSNSYYVVAVVRRDSSHAFTLDELRGKRSCHAGFGSPAGWDVPVGALIQRGFI</u>
Pred: EE-------EEEEEEEEE--------HHH-------EEE-------EEEE-HHHHH----

AA: <u>RPKDCDVLTAVSEFFNASCVPVNNPKNYPSSLCALCVGDEQGRNKCVGNSQERYYGYRGA</u>
Pred: --------EEEE------------------HHHHHH---------H AA: <u>FRCLVENAGDVAFVRHTTVFDNTNGHNSEPWAAELRSEDYELLCPNGARAEVSQFAACNL</u>
Pred: HHHHHH-----EEEEE---HHHH--------HHHHHHH-------EEEE---------EE AA: <u>AQIPPHAVM</u> VRPDTNIFTVYGLLDKAQDLFGDDHNKNGFKMFDSSNYHGQDLLFKDATVR
Pred: EEE---EEEE ---HHHHHHHHHHHHHHHHH---------------EEEE---EE AA: AVPVGEKTTYRGWLGLDYVAALEGMSSQQC
Pred: EEEE------HHHH--HHHHHHHHHHHH---

Figure 9B

Bold: N-LOBE
Normal: C-LOBE
<u>Underlined: CNBr large fragments</u>
AA: Target sequence
Pred: (H)=Helix, (E)=Strand, (-)=Coil

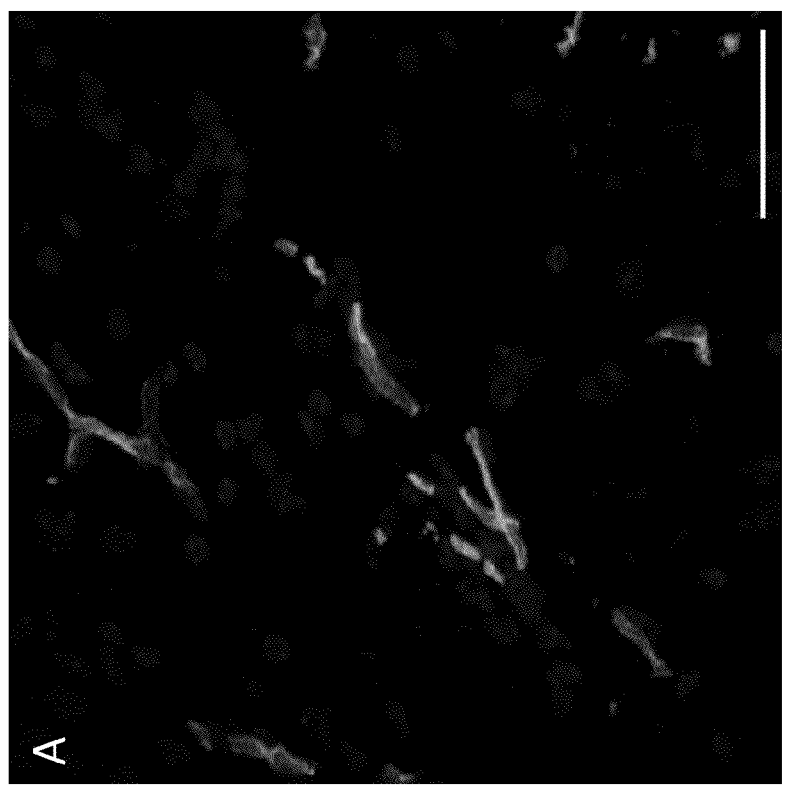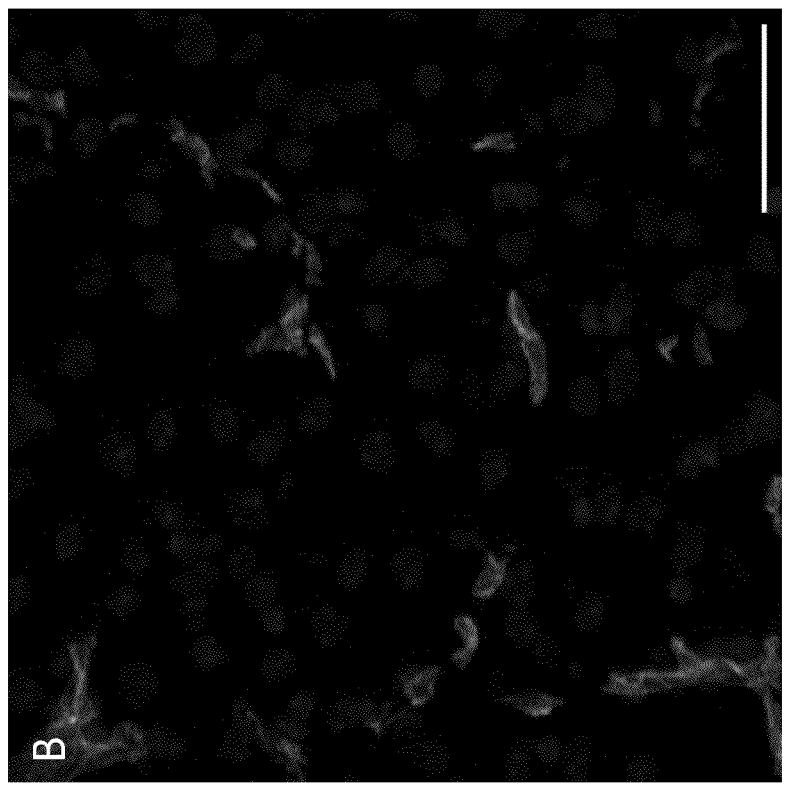
Figure 13

FRAGMENTS OF P97 AND USES THEREOF

CROSS-REFERENCE TO RELATED APPLICATION

This application claims the benefit under 35 U.S.C §119(e) of U.S. Provisional Patent Application No. 61/780,170 filed Mar. 13, 2013 and U.S. Provisional Patent Application 61/885,387 filed Oct. 1, 2013, each of which is incorporated herein by reference in its entirety.

STATEMENT REGARDING THE SEQUENCE LISTING

The Sequence Listing associated with this application is provided in text format in lieu of a paper copy, and is hereby incorporated by reference into the specification. The name of the text file containing the Sequence Listing is BIOA_002_02US_SubSeqList_ST25.txt. The text file is about 41 KB, was created on Oct. 1, 2015, and is being submitted electronically via EFS-Web.

BACKGROUND

1. Technical Field

The present invention relates generally to fragments of human p97 (melanotransferrin) polypeptides having transport activity, including variants and combinations thereof, conjugates comprising said p97 fragments, and related methods of use thereof, for instance, to facilitate delivery of therapeutic and/or diagnostic agents across the blood-brain barrier (BBB) and into the central nervous system.

2. Description of the Related Art

Overcoming the difficulties of delivering therapeutic or diagnostic agents to specific regions of the brain represents a major challenge to treatment or diagnosis of many central nervous system (CNS) disorders, including those of the brain. In its neuroprotective role, the blood-brain barrier (BBB) functions to hinder the delivery of many potentially important diagnostic and therapeutic agents to the brain.

Therapeutic molecules and genes that might otherwise be effective in diagnosis and therapy do not cross the BBB in adequate amounts. It is reported that over 95% of all therapeutic molecules do not cross the blood-brain barrier.

Accordingly, there is a need for compositions and methods that facilitate the delivery of therapeutic agents and other molecules across the blood-brain-barrier, for instance, to effectively treat certain diseases of the central nervous system (CNS) such as cancers, particularly those that have metastasized to the CNS. The present invention addresses these needs and offers other related advantages.

BRIEF SUMMARY OF THE INVENTION

Embodiments of the present invention include isolated p97 (melanotransferrin) polypeptides of up to about 300, 400, 500, 600, or 700 amino acids in length, where the polypeptide comprises an amino acid sequence at least 70% identical to any one or more of SEQ ID NO:2-18, or an active fragment or variant thereof. In certain embodiments, the p97 polypeptide comprises one of SEQ ID NO:2-18, optionally including adjacent C-terminal and/or N-terminal sequences as defined by SEQ ID NO:1. In certain embodiments, the polypeptide comprises 2, 3, 4, or 5 of SEQ ID NOS:2-18, optionally including any intervening sequences as defined by SEQ ID NO:1.

In certain embodiments, the p97 polypeptide comprises one or both of SEQ ID NO:13 and/or 14, optionally including intervening sequences as defined by SEQ ID NO:1. In certain embodiments, the p97 polypeptide is about or up to about 250, 240, 230, 220, 210, 200, 190, 180, 170, 160, 150, 140, 130, 120, 110, 100, 90, 80, 70, 60, 50, 40, 30, 25, 20, 15, or 10 amino acids in length.

In certain embodiments, the p97 polypeptide is fused to a heterologous protein.

Also included are conjugates, comprising the p97 polypeptide described herein, where the p97 polypeptide is covalently or operatively linked to an agent, to form a p97-agent conjugate. In certain embodiments, the agent is a small molecule, a polypeptide, a peptide mimetic, a peptoid, an aptamer, or a detectable entity.

In certain embodiments, the small molecule is a cytotoxic or chemotherapeutic or anti-angiogenic agent selected from one or more of alkylating agents, anti-metabolites, anthracyclines, anti-tumor antibiotics, platinums, type I topoisomerase inhibitors, type II topoisomerase inhibitors, vinca alkaloids, and taxanes. In certain embodiments, the small molecule is selected from one or more of chlorambucil, cyclophosphamide, cilengitide, lomustine (CCNU), melphalan, procarbazine, thiotepa, carmustine (BCNU), enzastaurin, busulfan, daunorubicin, doxorubicin, gefitinib, erlotinib idarubicin, temozolomide, epirubicin, mitoxantrone, bleomycin, cisplatin, carboplatin, oxaliplatin, camptothecins, irinotecan, topotecan, amsacrine, etoposide, etoposide phosphate, teniposide, temsirolimus, everolimus, vincristine, vinblastine, vinorelbine, vindesine, CT52923, paclitaxel, imatinib, dasatinib, sorafenib, pazopanib, sunitnib, vatalanib, geftinib, erlotinib, AEE-788, dichoroacetate, tamoxifen, fasudil, SB-681323, semaxanib, donepizil, galantamine, memantine, rivastigmine, tacrine, rasigiline, naltrexone, lubiprostone, safinamide, istradefylline, pimavanserin, pitolisant, isradipine, pridopidine (ACR16), tetrabenazine, bexarotene, glatirimer acetate, fingolimod, and mitoxantrone, including pharmaceutically acceptable salts and acids thereof.

In certain embodiments, the polypeptide is an antibody or antigen-binding fragment thereof, or an immunoglobulin-like molecule.

In certain embodiments, the antibody or antigen-binding fragment thereof specifically binds to a cancer-associated antigen. In certain embodiments, the cancer-associated antigen is one or more of human Her2/neu, Her1/EGF receptor (EGFR), Her3, A33 antigen, B7H3, CD5, CD19, CD20, CD22, CD23 (IgE Receptor), C242 antigen, 5T4, IL-6, IL-13, vascular endothelial growth factor VEGF (e.g., VEGF-A) VEGFR-1, VEGFR-2, CD30, CD33, CD37, CD40, CD44, CD51, CD52, CD56, CD74, CD80, CD152, CD200, CD221, CCR4, HLA-DR, CTLA-4, NPC-1C, tenascin, vimentin, insulin-like growth factor 1 receptor (IGF-1R), alpha-fetoprotein, insulin-like growth factor 1 (IGF-1), carbonic anhydrase 9 (CA-IX), carcinoembryonic antigen (CEA), integrin $\alpha_v\beta_3$, integrin $\alpha_5\beta_1$, folate receptor 1, transmembrane glycoprotein NMB, fibroblast activation protein alpha (FAP), glycoprotein 75, TAG-72, MUC1, MUC16 (or CA-125), phosphatidylserine, prostate-specific membrane antigen (PMSA), NR-LU-13 antigen, TRAIL-R1, tumor necrosis factor receptor superfamily member 10b (TNFRSF10B or TRAIL-R2), SLAM family member 7 (SLAMF7), EGP40 pancarcinoma antigen, B-cell activating factor (BAFF), platelet-derived growth factor receptor, glycoprotein EpCAM (17-1A), Programmed Death-1, protein disulfide isomerase (PDI), Phosphatase of Regenerating Liver 3 (PRL-3), prostatic acid phosphatase, Lewis-Y antigen, GD2 (a disialoganglioside expressed on tumors of neuroectodermal origin), glypican-3 (GPC3), or mesothelin.

In certain embodiments, antibody or antigen-binding fragment thereof specifically binds to a pain-associated antigen. In certain embodiments, the pain associated-antigen is one or more of nerve growth factor (NGF) or tropomyosin-related kinase A (TrkA).

In certain embodiments, the antibody or antigen-binding fragment thereof or immunoglobulin-like molecule specifically binds to a pro-inflammatory molecule, optionally a pro-inflammatory cytokine or chemokine.

In certain embodiments, the pro-inflammatory molecule is one or more of TNF-α, TNF-β, FasL, CD27L, CD30L, CD40L, Ox40L, 4-1BBL, TRAIL, TWEAK, and Apo3L, IL-1α, IL-1β, IL-2, interferon-γ (IFN-γ), IFN-α, IFN-β, IL-6, IL-8, IL-12, IL-15, IL-17, IL-18, IL-21, LIF, CCL5, GROα, MCP-1, MIP-1α, MIP-1β, macrophage colony stimulating factor (MCSF), or granulocyte macrophage colony stimulating factor (GM-CSF). In certain embodiments, the pro-inflammatory molecule is TNF-α, and the antibody or immunoglobulin-like molecule is adalimumab, certolizumab pegol, etanercept, golimumab, infliximab, D2E7, CDP 571, or CDP 870, or an antigen-binding fragment or variant thereof.

In certain embodiments, the antibody or antigen-binding fragment thereof specifically binds to one or more of human Her2/neu, Her1/EGFR, TNF-α, B7H3 antigen, CD20, VEGF, CD52, CD33, CTLA-4, tenascin, alpha-4 (α4) integrin, IL-23, amyloid-β, Huntingtin, CD25, nerve growth factor (NGF), TrkA, or α-synuclein.

In certain embodiments, the antibody is selected from one or more of trastuzumab, cetuximab, daclizumab, tanezumab, 3F8, 8H9, abagovomab, adecatumumab, afutuzumab, alemtuzumab, alacizumab (pegol), amatuximab, apolizumab, bavituximab, bectumomab, belimumab, bevacizumab, bivatuzumab (mertansine), brentuximab vedotin, cantuzumab (mertansine), cantuzumab (ravtansine), capromab (pendetide), catumaxomab, citatuzumab (bogatox), cixutumumab, clivatuzumab (tetraxetan), conatumumab, dacetuzumab, dalotuzumab, detumomab, drozitumab, ecromeximab, edrecolomab, elotuzumab, enavatuzumab, ensituximab, epratuzumab, ertumaxomab, etaracizumab, farletuzumab, FBTA05, figitumumab, flanvotumab, galiximab, gemtuzumab, ganitumab, gemtuzumab (ozogamicin), girentuximab, glembatumumab (vedotin), ibritumomab tiuxetan, icrucumab, igovomab, indatuximab ravtansine, intetumumab, inotuzumab ozogamicin, ipilimumab (MDX-101), iratumumab, labetuzumab, lexatumumab, lintuzumab, lorvotuzumab (mertansine), lucatumumab, lumiliximab, mapatumumab, matuzumab, milatuzumab, mitumomab, mogamulizumab, moxetumomab (pasudotox), nacolomab (tafenatox), naptumomab (estafenatox), narnatumab, necitumumab, nimotuzumab, nivolumab, Neuradiab® (with or without radioactive iodine), NR-LU-10, ofatumumab, olaratumab, onartuzumab, oportuzumab (monatox), oregovomab, panitumumab, patritumab, pemtumomab, pertuzumab, pritumumab, racotumomab, radretumab, ramucirumab, rilotumumab, rituximab, robatumumab, samalizumab, sibrotuzumab, siltuximab, tabalumab, taplitumomab (paptox), tenatumomab, teprotumumab, TGN1412, ticilimumab, tremelimumab, tigatuzumab, TNX-650, tositumomab, TRBS07, tucotuzumab (celmoleukin), ublituximab, urelumab, veltuzumab, volociximab, votumumab, and zalutumumab, including antigen-binding fragments thereof.

In certain embodiments, the polypeptide is an interferon-β polypeptide, or an active fragment or variant thereof.

In certain embodiments, the polypeptide associates with a lysosomal storage disease. In certain embodiments, the polypeptide is selected from one or more of aspartylglucosaminidase, acid lipase, cysteine transporter, Lamp-2, α-galactosidase A, acid ceramidase, α-L-fucosidase, β-hexosaminidase A, GM2-ganglioside activator (GM2A), α-D-mannosidase, β-D-mannosidase, arylsulfatase A, saposin B, neuraminidase, α-N-acetylglucosaminidase phosphotransferase, phosphotransferase γ-subunit, L-iduronidase, iduronate-2-sulfatase, heparan-N-sulfatase, α-N-acetylglucosaminidase, acetylCoA:N-acetyltransferase, N-acetylglucosamine 6-sulfatase, galactose 6-sulfatase, β-galactosidase, N-acetylgalactosamine 4-sulfatase, hyaluronoglucosaminidase, sulfatases, palmitoyl protein thioesterase, tripeptidyl peptidase I, acid sphingomyelinase, cathepsin A, cathepsin K, α-galactosidase B, NPC1, NPC2, sialin, and sialic acid transporter, including active fragments and variants thereof.

In certain embodiments, the detectable entity is selected from one or more of diatrizoic acid, a radioisotope, a fluorophore/fluorescent dye, and a nanoparticle.

In certain embodiments, the agent is a cardiotoxic agent in its unconjugated form. In certain embodiments, the cardiotoxic agent is an anthracycline/anthraquinolone, cyclophosphamide, antimetabolite, antimicrotubule agent, tyrosine kinase inhibitor, bevacizumab, or trastuzumab. In certain embodiments, the cardiotoxic agent is cyclopentenyl cytosine, 5-fluorouracil, capecitabine, paclitaxel, docataxel, adriamycin, doxorubucin, epirubicin, emetine, isotamide, mitomycin C, erlotinib, gefitinib, imatinib, sorafenib, sunitinib, cisplatin, thalidomide, busulfan, vinblastine, bleomycin, vincristine, arsenic trioxide, methotrexate, rosiglitazone, or mitoxantrone.

Some embodiments include compositions (e.g., pharmaceutical compositions, therapeutic compositions, diagnostic compositions), comprising a p97 protein or conjugate described herein, and a pharmaceutically acceptable or pharmaceutical grade carrier.

Also included are methods of treating a subject in need thereof, comprising administering to the subject a p97 conjugate or composition described herein.

Certain embodiments include methods for treating a cancer of the central nervous system (CNS), optionally the brain. Certain embodiments include methods for treating primary cancer of the CNS, optionally the brain. Certain embodiments include methods for treating a metastatic cancer of the CNS, optionally the brain. Certain embodiments include methods for treating a glioma, meningioma, pituitary adenoma, vestibular schwannoma, primary CNS lymphoma, neuroblastoma, or primitive neuroectodermal tumor (medulloblastoma). In some embodiments, the glioma is an astrocytoma, oligodendroglioma, ependymoma, or a choroid plexus papilloma. Certain embodiments include methods for treating glioblastoma multiforme. In some embodiments, the glioblastoma multiforme is a giant cell gliobastoma or a gliosarcoma.

Certain embodiments include methods for treating a lysosomal storage disease. In some embodiments, the lysosomal storage disease is selected from one or more of aspartylglucosaminuria, cholesterol ester storage disease, Wolman disease, cystinosis, Danon disease, Fabry disease, Farber lipogranulomatosis, Farber disease, fucosidosis, galactosialidosis types I/II, Gaucher disease types I/II/III, Gaucher disease, globoid cell leucodystrophy, Krabbe disease, glycogen storage disease II, Pompe disease, GM1-gangliosidosis types I/II/III, GM2-gangliosidosis type I, Tay Sachs disease, GM2-gangliosidosis type II, Sandhoff disease, GM2-gangliosidosis, α-mannosidosis types I/II, β-mannosidosis, metachromatic leucodystrophy, mucolipidosis type I, sialidosis types I/II mucolipidosis types II/III I-cell disease, mucolipidosis type IIIC pseudo-Hurler polydystrophy, mucopolysaccharidosis type I, mucopolysaccharidosis type II (Hunter syndrome), mucopolysaccharidosis type IIIA, Sanfilippo syndrome, mucopolysaccharidosis type IIIB, mucopolysaccharidosis type IIIC, mucopolysaccharidosis type IIID, mucopolysaccharidosis type IVA, Morquio syndrome, mucopolysaccharidosis type IVB, mucopolysaccharidosis type VI, mucopolysaccharidosis type VII, Sly syndrome, mucopolysaccharidosis type IX, multiple sulfatase deficiency, neuronal ceroid lipofuscinosis, CLN1 Batten disease, Niemann-Pick disease types NB, Niemann-Pick disease, Niemann-Pick disease type C1, Niemann-Pick disease type C2, pycnodysostosis, Schindler disease types I/II, Schindler disease, and sialic acid storage disease.

Certain embodiments include methods for treating a degenerative or autoimmune disorder of the central nervous system (CNS). In particular embodiments, the degenerative or autoimmune disorder of the CNS is Alzheimer's disease, Huntington's disease, Parkinson's disease, or multiple sclerosis (MS).

In some embodiments, the subject is undergoing therapy with an otherwise cardiotoxic agent. In certain embodiments, the cardiotoxic agent is an anthracycline/anthraquinolone, cyclophosphamide, antimetabolite, antimicrotubule agent, tyrosine kinase inhibitor, bevacizumab, or trastuzumab. In particular embodiments, the cardiotoxic agent is cyclopentenyl cytosine, 5-fluorouracil, capecitabine, paclitaxel, docataxel, adriamycin, doxorubucin, epirubicin, emetine, isotamide, mitomycin C, erlotinib, gefitinib, imatinib, sorafenib, sunitinib, cisplatin, thalidomide, busulfan, vinblastine, bleomycin, vincristine, arsenic trioxide, methotrexate, rosiglitazone, or mitoxantrone.

In certain embodiments, the subject has cancer. In certain embodiments, the cancer is one or more of breast cancer, prostate cancer, gastrointestinal cancer, lung cancer, ovarian cancer, testicular cancer, head and neck cancer, stomach cancer, bladder cancer, pancreatic cancer, liver cancer, kidney cancer, squamous cell carcinoma, CNS or brain cancer, melanoma, non-melanoma cancer, thyroid cancer, endometrial cancer, an epithelial tumor, bone cancer, or a hematopoietic cancer.

In certain embodiments, administration of the conjugate reduces cardiotoxicity of the agent, relative to an unconjugated form of the agent.

Certain embodiments include methods for treating pain. In some embodiments, the pain is acute pain, chronic pain, neuropathic pain, and/or central pain.

Certain embodiments include methods for treating an inflammatory condition. In some embodiments, the inflammatory condition has a central nervous system component. In certain embodiments, the inflammatory condition is one or more of meningitis, myelitis, encephaloymyelitis, arachnoiditis, sarcoidosis, granuloma, drug-induced inflammation, Alzheimer's disease, stroke, HIV-dementia, encephalitis, parasitic infection, an inflammatory demyeleniating disorder, a CD8+ T Cell-mediated autoimmune disease of the CNS, Parkinson's disease, myasthenia gravis, motor neuropathy, Guillain-Barre syndrome, autoimmune neuropathy, Lambert-Eaton myasthenic syndrome, paraneoplastic neurological disease, paraneoplastic cerebellar atrophy, non-paraneoplastic stiff man syndrome, progressive cerebellar atrophy, Rasmussen's encephalitis, amyotrophic lateral sclerosis, Sydeham chorea, Gilles de la Tourette syndrome, autoimmune polyendocrinopathy, dysimmune neuropathy, acquired neuromyotonia, arthrogryposis multiplex, optic neuritis, stroke, traumatic brain injury (TBI), spinal stenosis, acute spinal cord injury, and spinal cord compression.

In certain embodiments, the inflammatory condition is associated with an infection of the central nervous system. In certain embodiments, the infection is a bacterial infection caused by one or more of group B streptococci (e.g., subtypes III), *Streptococcus pneumoniae* (e.g., serotypes 6, 9, 14, 18 and 23), *Escherichia coli* (e.g., carrying K1 antigen), *Listeria monocytogenes* (e.g., serotype IVb), neisserial infection such as *Neisseria meningitidis* (meningococcus), staphylococcal infection, heamophilus infection such as *Haemophilus influenzae* type B, *Klebsiella, Mycobacterium tuberculosis, Treponema pallidum*, or *Borrelia burgdorferi*. In certain embodiments, the infection is a viral infection caused by one or more of an enterovirus, herpes simplex virus type 1 or 2, human T-lymphotrophic virus, varicella zoster virus, mumps virus, human immunodeficiency virus (HIV), or lymphocytic choriomeningitis virus (LCMV).

In certain embodiments, the inflammatory condition is associated with a cancer of the CNS, optionally a malignant meningitis.

Also included are methods for imaging an organ or tissue component in a subject, comprising (a) administering to the subject a human p97 polypeptide described herein, where the polypeptide is conjugated to a detectable entity, and (b) visualizing the detectable entity in the subject. In certain embodiments, the organ or tissue compartment comprises the central nervous system. In certain embodiments, the organ or tissue compartment comprises the brain. In certain embodiments, visualizing the detectable entity comprises one or more of fluoroscopy, projectional radiography, X-ray CT-scanning, positron emission tomography (PET), single photon emission computed tomography (SPECT), or magnetic resonance imaging (MRI).

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

FIGS. 2A-2D show a list of p97 fragments identified by MS/MS analysis of an in-solution trypsin digest of human p97 (FIG. 2A top to bottom SEQ ID NOs: 55, 56, 59, 57, 58, 10, 61, 11, 15, 55, 137; FIG. 2B top to bottom SEQ ID NOs: 62, 61, 14, 11, 5, 66, 12, 77, 90, 5, 60, 4, 78, 63, 76, 7, 64, 13, 6, 2, 137, 74; FIG. 2C top to bottom SEQ ID NOs: 3, 71, 61, 15, 56, 14, 59, 65, 67, 72, 65, 82, 138, 8, 138, 69, 139, 71, 84, 79, 75; FIG. 2D top to bottom SEQ ID NOs: 140, 9, 140), and FIG. 2E shows the sequence coverage map of that analysis.

FIG. 3 shows the sequence coverage maps of the p97 fragments identified by MS/MS analysis of a CNBr digest of human p97. The 3 bands identified in the SDS-PAGE of FIG. 1 were subject to trypsin digestion and LC-MS/MS analysis; FIG. 3A shows the results for band 1, FIG. 3B shows the results for band 2, and FIG. 3C shows the results for band 3.

FIG. 4A shows the matching of the peptides detected in band 1 to the amino acid sequence of human p97; the sequence coverage of the matched peptides is indicated in bold. FIG. 4B lists the individual peptides along with certain physical characteristics (top to bottom SEQ ID NOs: 6, 12, 67, 64, 4, 64, 69, 8, 63, 65, 7, 14, 60, 13, 14, 56, 56, 14, 10, 74, 61, 56, 58, 14, 58, 74, 66, 58, 74, 58, 57, 66, 141, 72, 141, 141, 142, 78, 90, 76).

FIG. 5A shows the matching of the peptides detected in band 2 to the amino acid sequence of human p97; the sequence coverage of the matched peptides is indicated in bold. FIG. 5B lists the individual peptides along with certain physical characteristics (top to bottom SEQ ID NOs: 57, 10, 76, 74, 66, 66, 78, 78, 143, 90, 77, 4, 14, 60, 58, 13, 55, 72, 9, 7, 8, 67, 90, 3, 60, 63, 6, 69, 14, 57, 90, 6, 12).

FIG. 6A shows the matching of the peptides detected in band 3 to the amino acid sequence of human p97; the sequence coverage of the matched peptides is indicated in bold. FIG. 6B lists the individual peptides along with certain physical characteristics (top to bottom SEQ ID NOs: 72, 10, 76, 60, 64, 12, 13, 7, 68, 12, 90, 61, 14, 64, 55, 63, 69, 71, 12).

FIG. 9 shows a YASPIN secondary structure prediction (see Yin et al., *Bioinformatics*. 21:152-159, 2005) of human soluble p97 (SEQ ID NO:91; residues 20-709 of SEQ ID NO:1) along with some of the p97 peptide fragments identified as having significant transport activity in the in vitro model of the BBB. FIG. 9A shows certain of the tryptic digest peptide fragments that cross the BBB (underlined), and FIG. 9B shows three of the CNBr digest peptide fragments that cross the BBB (underlined).

FIG. 13A shows the results for PBS, FIG. 13B shows the results for AF680-labeled HRP, and FIG. 13C shows the results for AF680-labeled MTf$_{PEP}$-HRP conjugate. The arrows in FIG. 13C highlight the AF680 fluorescence of the AF680-labeled MTf$_{PEP}$-HRP conjugate in brain tissues.

DETAILED DESCRIPTION OF THE INVENTION

Figure 1:
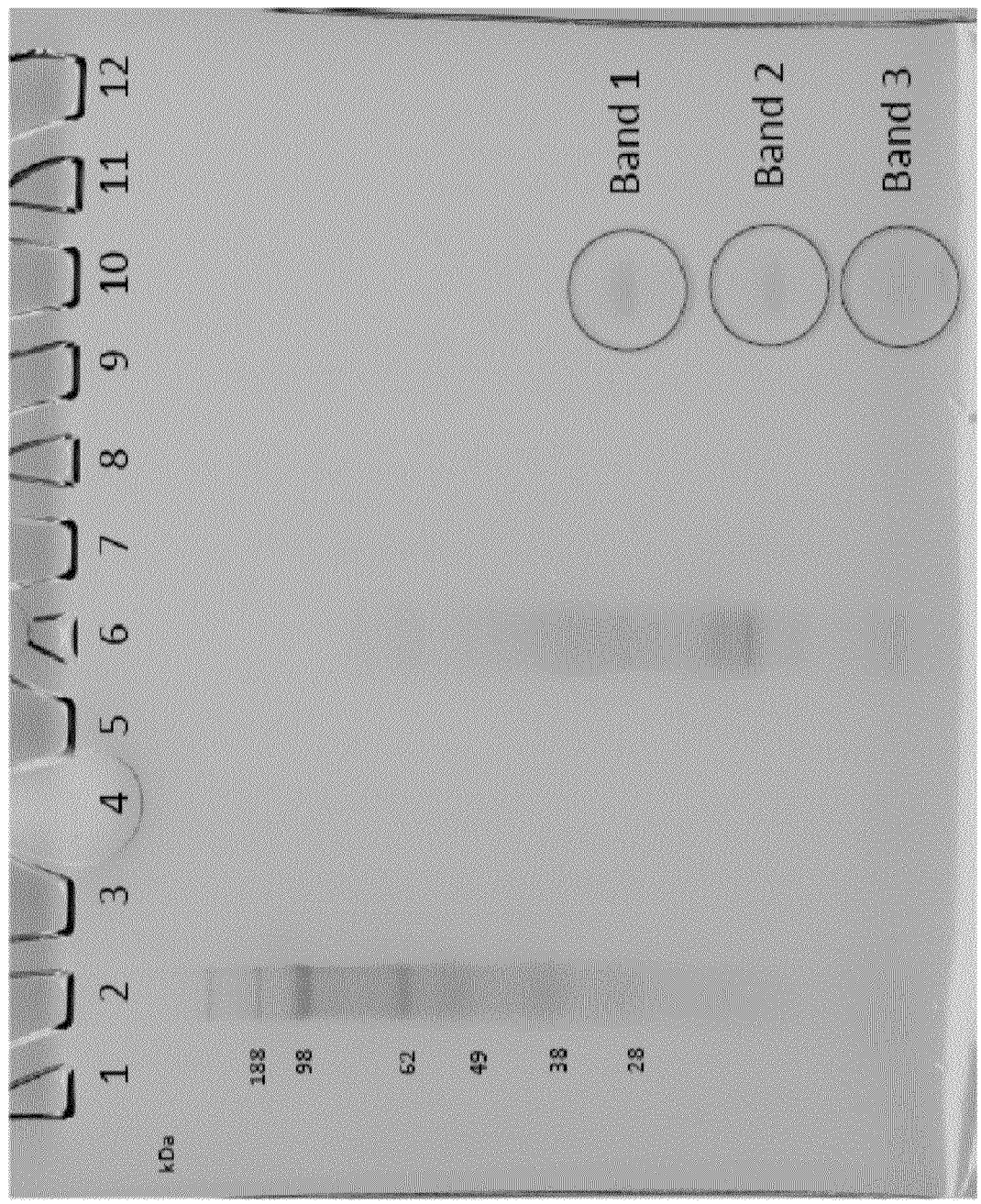
FIG. 1 shows an SDS-PAGE analysis of CNBr-digested human melanotransferrin (p97).

Embodiments of the present invention are based partly on the discovery of minimal fragments of human p97 (melanotransferrin) having the ability to transport across the blood-brain barrier (BBB).

Hence, embodiments of the present invention relate to particular polypeptide fragments of human p97 and variants thereof, compositions that comprise the polypeptide fragments, conjugates or mixtures of p97 fragments having an attached or operatively linked agent of interest, and related methods of use, including methods of treatment, diagnosis, and testing, such as medical imaging.

The human p97 polypeptide fragments described herein can find a variety of uses in the therapeutic and diagnostic arts, for instance, to improve transfer of agents across the BBB. Also, by identifying the minimal fragments required for BBB transport activity, certain aspects of the present invention allow the use of smaller p97 polypeptides, thereby reducing some of the difficulties associated with the synthesis/production, purification, and pharmaceutical formulation of larger polypeptides.

Other advantages and benefits will be apparent to persons skilled in the art.

DEFINITIONS

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e., to at least one) of the grammatical object of the article. By way of example, "an element" means one element or more than one element.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length.

As used herein, the term "amino acid" is intended to mean both naturally occurring and non-naturally occurring amino acids as well as amino acid analogs and mimetics. Naturally occurring amino acids include the 20 (L)-amino acids utilized during protein biosynthesis as well as others such as 4-hydroxyproline, hydroxylysine, desmosine, isodesmosine, homocysteine, citrulline and ornithine, for example. Non-naturally occurring amino acids include, for example, (D)-amino acids, norleucine, norvaline, p-fluorophenylalanine, ethionine and the like, which are known to a person skilled in the art. Amino acid analogs include modified forms of naturally and non-naturally occurring amino acids. Such modifications can include, for example, substitution or replacement of chemical groups and moieties on the amino acid or by derivatization of the amino acid. Amino acid mimetics include, for example, organic structures which exhibit functionally similar properties such as charge and charge spacing characteristic of the reference amino acid. For example, an organic structure which mimics Arginine (Arg or R) would have a positive charge moiety located in similar molecular space and having the same degree of mobility as the e-amino group of the side chain of the naturally occurring Arg amino acid. Mimetics also include constrained structures so as to maintain optimal spacing and charge interactions of the amino acid or of the amino acid functional groups. Those skilled in the art know or can determine what structures constitute functionally equivalent amino acid analogs and amino acid mimetics.

Throughout this specification, unless the context requires otherwise, the words "comprise," "comprises," and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The term "conjugate" is intended to refer to the entity formed as a result of covalent or non-covalent attachment or linkage of an agent or other molecule, e.g., a biologically active molecule, to a p97 polypeptide. One example of a conjugate polypeptide is a "fusion protein" or "fusion polypeptide," that is, a polypeptide that is created through the joining of two or more coding sequences, which originally coded for separate polypeptides; translation of the joined coding sequences results in a single, fusion polypeptide, typically with functional properties derived from each of the separate polypeptides.

As used herein, the terms "function" and "functional" and the like refer to a biological, enzymatic, or therapeutic function.

"Homology" refers to the percentage number of amino acids that are identical or constitute conservative substitutions. Homology may be determined using sequence comparison programs such as GAP (Deveraux et al., *Nucleic Acids Research*. 12, 387-395, 1984), which is incorporated herein by reference. In this way sequences of a similar or substantially different length to those cited herein could be compared by insertion of gaps into the alignment, such gaps being determined, for example, by the comparison algorithm used by GAP.

By "isolated" is meant material that is substantially or essentially free from components that normally accompany it in its native state. For example, an "isolated peptide" or an "isolated polypeptide" and the like, as used herein, includes the in vitro isolation and/or purification of a peptide or polypeptide molecule from its natural cellular environment, and from association with other components of the cell; i.e., it is not significantly associated with in vivo substances.

The term "linkage," "linker," "linker moiety," or "1" is used herein to refer to a linker that can be used to separate a p97 polypeptide fragment from an agent of interest, or to separate a first agent from another agent, for instance where two or more agents are linked to form a p97 conjugate. The linker may be physiologically stable or may include a releasable linker such as an enzymatically degradable linker (e.g., proteolytically cleavable linkers). In certain aspects, the linker may be a peptide linker, for instance, as part of a p97 fusion protein. In some aspects, the linker may be a non-peptide linker or non-proteinaceous linker. In some aspects, the linker may be particle, such as a nanoparticle.

The terms "modulating" and "altering" include "increasing," "enhancing" or "stimulating," as well as "decreasing" or "reducing," typically in a statistically significant or a physiologically significant amount or degree relative to a control. An "increased," "stimulated" or "enhanced" amount is typically a "statistically significant" amount, and may include an increase that is 1.1, 1.2, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the amount produced by no composition (e.g., the absence of polypeptide of conjugate of the invention) or a control composition, sample or test subject. A "decreased" or "reduced" amount is typically a "statistically significant" amount, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease in the amount produced by no composition or a control composition, including all integers in between. As one non-limiting example, a control could compare the activity, such as the amount or rate of transport/delivery across the blood brain barrier, the rate and/or levels of distribution to central nervous system tissue, and/or the $C_{max}$ for plasma, central nervous system tissues, or any other systemic or peripheral non-central nervous system tissues, of a p97-agent conjugate relative to the agent alone. Other examples of comparisons and "statistically significant" amounts are described herein.

In certain embodiments, the "purity" of any given agent (e.g., a p97 conjugate such as a fusion protein) in a composition may be specifically defined. For instance, certain compositions may comprise an agent that is at least 80%, 85%, 90%, 91%, 92%, 93%, 94%, 95%, 96%, 97%, 98%, 99%, or 100% pure, including all decimals in between, as measured, for example and by no means limiting, by high pressure liquid chromatography (HPLC), a well-known form of column chromatography used frequently in biochemistry and analytical chemistry to separate, identify, and quantify compounds.

The terms "polypeptide" and "protein" are used interchangeably herein to refer to a polymer of amino acid residues and to variants and synthetic analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers. The polypeptides described herein are not limited to a specific length of the product; thus, peptides, oligopeptides, and proteins are included within the definition of polypeptide, and such terms may be used interchangeably herein unless specifically indicated otherwise. The polypeptides described herein may also comprise post-expression modifications, such as glycosylations, acetylations, phosphorylations and the like, as well as other modifications known in the art, both naturally occurring and non-naturally occurring. A polypeptide may be an entire protein, or a subsequence, fragment, variant, or derivative thereof.

A "physiologically cleavable" or "hydrolyzable" or "degradable" bond is a bond that reacts with water (i.e., is hydrolyzed) under physiological conditions. The tendency of a bond to hydrolyze in water will depend not only on the general type of linkage connecting two central atoms but also on the substituents attached to these central atoms. Appropriate hydrolytically unstable or weak linkages include, but are not limited to: carboxylate ester, phosphate ester, anhydride, acetal, ketal, acyloxyalkyl ether, imine, orthoester, thio ester, thiol ester, carbonate, and hydrazone, peptides and oligonucleotides.

A "releasable linker" includes, but is not limited to, a physiologically cleavable linker and an enzymatically degradable linker. Thus, a "releasable linker" is a linker that may undergo either spontaneous hydrolysis, or cleavage by some other mechanism (e.g., enzyme-catalyzed, acid-catalyzed, base-catalyzed, and so forth) under physiological conditions. For example, a "releasable linker" can involve an elimination reaction that has a base abstraction of a proton, (e.g., an ionizable hydrogen atom, Ha), as the driving force. For purposes herein, a "releasable linker" is synonymous with a "degradable linker." An "enzymatically degradable linkage" includes a linkage, e.g., amino acid sequence that is subject to degradation by one or more enzymes, e.g., peptidases or proteases. In particular embodiments, a releasable linker has a half life at pH 7.4, 25° C., e.g., a physiological pH, human body temperature (e.g., in vivo), of about 30 minutes, about 1 hour, about 2 hour, about 3 hours, about 4 hours, about 5 hours, about 6 hours, about 12 hours, about 18 hours, about 24 hours, about 36 hours, about 48 hours, about 72 hours, or about 96 hours or less.

The term "reference sequence" refers generally to a nucleic acid coding sequence, or amino acid sequence, to which another sequence is being compared. All polypeptide and polynucleotide sequences described herein are included as references sequences, including those described by name and those described in the Tables and the Sequence Listing.

The terms "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Included are nucleotides and polypeptides having at least about 50%, 55%, 60%, 65%, 70%, 75%, 80%, 85%, 90%, 95%, 97%, 98%, 99% or 100% sequence identity to any of the reference sequences described herein (see, e.g., Sequence Listing), typically where the polypeptide variant maintains at least one biological activity of the reference polypeptide.

Terms used to describe sequence relationships between two or more polynucleotides or polypeptides include "reference sequence," "comparison window," "sequence identity," "percentage of sequence identity," and "substantial identity." A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., *Nucl. Acids Res.* 25:3389, 1997. A detailed discussion of sequence analysis can be found in Unit 19.3 of Ausubel et al., "Current Protocols in Molecular Biology," John Wiley & Sons Inc, 1994-1998, Chapter 15.

By "statistically significant," it is meant that the result was unlikely to have occurred by chance. Statistical significance can be determined by any method known in the art. Commonly used measures of significance include the p-value, which is the frequency or probability with which the observed event would occur, if the null hypothesis were true. If the obtained p-value is smaller than the significance level, then the null hypothesis is rejected. In simple cases, the significance level is defined at a p-value of 0.05 or less.

The term "solubility" refers to the property of a p97 polypeptide fragment or conjugate to dissolve in a liquid solvent and form a homogeneous solution. Solubility is typically expressed as a concentration, either by mass of solute per unit volume of solvent (g of solute per kg of solvent, g per dL (100 mL), mg/ml, etc.), molarity, molality, mole fraction or other similar descriptions of concentration. The maximum equilibrium amount of solute that can dissolve per amount of solvent is the solubility of that solute in that solvent under the specified conditions, including temperature, pressure, pH, and the nature of the solvent. In certain embodiments, solubility is measured at physiological pH, or other pH, for example, at pH 5.0, pH 6.0, pH 7.0, or pH 7.4. In certain embodiments, solubility is measured in water or a physiological buffer such as PBS or NaCl (with or without NaP). In specific embodiments, solubility is measured at relatively lower pH (e.g., pH 6.0) and relatively higher salt (e.g., 500 mM NaCl and 10 mM NaP). In certain embodiments, solubility is measured in a biological fluid (solvent) such as blood or serum. In certain embodiments, the temperature can be about room temperature (e.g., about 20, 21, 22, 23, 24, 25° C.) or about body temperature (~37° C.). In certain embodiments, a p97 polypeptide or conjugate has a solubility of at least about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, or 30 mg/ml at room temperature or at about 37° C.

A "subject," as used herein, includes any animal that exhibits a symptom, or is at risk for exhibiting a symptom, which can be treated or diagnosed with a p97 conjugate of the invention. Suitable subjects (patients) include laboratory animals (such as mouse, rat, rabbit, or guinea pig), farm animals, and domestic animals or pets (such as a cat or dog). Non-human primates and, preferably, human patients, are included.

"Substantially" or "essentially" means nearly totally or completely, for instance, 95%, 96%, 97%, 98%, 99% or greater of some given quantity.

"Substantially free" refers to the nearly complete or complete absence of a given quantity for instance, less than about 10%, 5%, 4%, 3%, 2%, 1%, 0.5% or less of some given quantity. For example, certain compositions may be "substantially free" of cell proteins, membranes, nucleic acids, endotoxins, or other contaminants.

"Treatment" or "treating," as used herein, includes any desirable effect on the symptoms or pathology of a disease or condition, and may include even minimal changes or improvements in one or more measurable markers of the disease or condition being treated. "Treatment" or "treating" does not necessarily indicate complete eradication or cure of the disease or condition, or associated symptoms thereof. The subject receiving this treatment is any subject in need thereof. Exemplary markers of clinical improvement will be apparent to persons skilled in the art.

The term "wild-type" refers to a gene or gene product that has the characteristics of that gene or gene product when isolated from a naturally-occurring source. A wild type gene or gene product (e.g., a polypeptide) is that which is most frequently observed in a population and is thus arbitrarily designed the "normal" or "wild-type" form of the gene.

p97 Polypeptide Sequences and Conjugates Thereof

Embodiments of the present invention relate generally to polypeptide fragments of human p97 (melanotransferrin; MTf), compositions that comprise such fragments, and conjugates thereof. In certain instances, the p97 polypeptide fragments described herein have transport activity, that is, they are ability to transport across the blood-brain barrier (BBB). In particular embodiments, the p97 fragments are covalently, non-covalently, or operatively coupled to an agent of interest, such as a therapeutic, diagnostic, or detectable agent, to form a p97-agent conjugate. Specific examples of agents include small molecules and polypeptides, such as antibodies, among other agents described herein and known in the art. Exemplary p97 polypeptide sequences and agents are described below. Also described are exemplary methods and components, such as linker groups, for coupling a p97 polypeptide to an agent of interest.

p97 Sequences.

In some embodiments, a p97 polypeptide comprises, consists essentially of, or consists of at least one of the human p97 fragments identified in Tables 1-7, or FIG. 2-6 or 9. In specific embodiments, a p97 polypeptide comprises, consists essentially of, or consists of at least one of the human p97 sequence set forth in SEQ ID NOS:2-18.

In other specific embodiments, described in greater detail below, a p97 polypeptide sequence comprises a sequence having at least 70%, 75%, 80%, 85%, 90%, 95%, 96%, 97%, 98%, or 99% identity or homology, along its length, to at least one of the human p97 fragments identified in Tables 1-7, or FIG. 2-6 or 9. In some embodiments, a variant of a p97 polypeptide sequence comprises a sequence having at least 70%, 75%, 80%, 85%, 90%, 95%, 96%, 97%, 98%, or 99% identity or homology, along its length, to at least one of the human p97 sequence set forth in SEQ ID NOS:2-18.

In some embodiments, the p97 polypeptide comprises, consists essentially of, or consists of 2, 3, 4, or 5 of the p97 fragments identified in Tables 1-7, or FIG. 2-6 or 9, optionally including any intervening p97 sequences (i.e., p97 sequences from SEQ ID NO:1 that lie between the fragments, if present). In particular embodiments, the p97 polypeptide comprises, consists essentially of, or consists of 2, 3, 4, or 5 of the p97 sequences set forth in SEQ ID NOS:2-18, optionally including any intervening p97 sequences (i.e., p97 sequences from SEQ ID NO:1 that lie between SEQ ID NOS:2-18, if present) (see also FIGS. 9A and 9B for the relationships between SEQ ID NOS:2-18 in the primary structure of human p97). As one example, a p97 polypeptide could comprise SEQ ID NO:13 and 14, optionally including any intervening p97 sequences from SEQ ID NO:1, or variants thereof.

In certain embodiments, a p97 polypeptide fragment is about, at least about, or up to about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 100, 105, 110, 115, 120, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700. 700, 710, 720, 730 or more amino acids in length, including all integers and ranges in between, and which may comprise all or a portion of the sequence of a reference p97 sequence (see, e.g., Sequence Listing, Tables 1-7, Table B, FIGS. 2-6 and 9), including any adjacent N-terminal and/or C-terminal sequences of a reference p97 fragment, as defined by SEQ ID NO:1.

In certain embodiments, a p97 polypeptide fragment is about 5-700, 5-600, 5-500, 5-400, 5-300, 5-200, 5-100, 5-50, 5-40, 5-30, 5-25, 5-20, 5-15, 5-10, 10-700, 10-600, 10-500, 10-400, 10-300, 10-200, 10-100, 10-50, 10-40, 10-30, 10-25, 10-20, 10-15, 20-700, 20-600, 20-500, 20-400, 20-300, 20-200, 20-100, 20-50, 20-40, 20-30, 20-25, 30-700, 30-600, 30-500, 30-400, 30-300, 30-200, 30-100, 30-50, 30-40, 40-700, 40-600, 40-500, 40-400, 40-300, 40-200, 40-100, 40-50, 50-700, 50-600, 50-500, 50-400, 50-300, 50-200, 50-100, 60-700, 60-600, 60-500, 60-400, 60-300, 60-200, 60-100, 60-70, 70-700, 70-600, 70-500, 70-400, 70-300, 70-200, 70-100, 70-80, 80-700, 80-600, 80-500, 80-400, 80-300, 80-200, 80-100, 80-90, 90-700, 90-600, 90-500, 90-400, 90-300, 90-200, 90-100, 100-700, 100-600, 100-500, 100-400, 100-300, 100-250, 100-200, 100-150, 200-700, 200-600, 200-500, 200-400, 200-300, or 200-250 amino acids in length, and comprises all or a portion of a reference p97 sequence (see, e.g., Sequence Listing, Tables 1-7, Table B, FIGS. 2-6 and 9), including any adjacent N-terminal and/or C-terminal sequences of a reference p97 fragment, as defined by SEQ ID NO:1.

Certain embodiments comprise one or more p97 fragments, for example, 2, 3, 4, or 5 fragments, as illustrated by the formula $[X]_n$, where X is a p97 fragment described herein and n is an integer from 1-5. In specific embodiments, X is DSSHAFTLDELR (SEQ ID NO:13).

In particular embodiments, the p97 fragment or variant thereof has the ability to cross the BBB, and optionally transport an agent of interest across the BBB and into the central nervous system. In certain embodiments, the p97 fragment or variant thereof is capable of specifically binding to a p97 receptor, an LRP1 receptor, and/or an LRP1B receptor.

In some embodiments, the p97 fragment has one or more terminal (e.g., N-terminal, C-terminal) cysteines and/or tyrosines, which can be added for conjugation and iodination, respectively.

Variants and fragments of reference p97 polypeptides and other reference polypeptides are described in greater detail below.

p97 Conjugates.

As noted above, certain embodiments comprise a p97 polypeptide that is linked to an agent of interest, for instance, a small molecule, a polypeptide (e.g., peptide, antibody), a peptide mimetic, a peptoid, an aptamer, a detectable entity, or any combination thereof. Also included are conjugates that comprise more than one agent of interest, for instance, a p97 fragment conjugated to an antibody and a small molecule.

Covalent linkages are preferred, however, non-covalent linkages can also be employed, including those that utilize relatively strong non-covalent protein-ligand interactions, such as the interaction between biotin and avidin. Operative linkages are also included, which do not necessarily require a directly covalent or non-covalent interaction between the p97 fragment and the agent of interest; examples of such linkages include liposome mixtures that comprise a p97 polypeptide and an agent of interest. Exemplary methods of generating protein conjugates are described herein, and other methods are well-known in the art.

Small Molecules.

In particular embodiments, the p97 fragment is conjugated to a small molecule. A "small molecule" refers to an organic compound that is of synthetic or biological origin (biomolecule), but is typically not a polymer. Organic compounds refer to a large class of chemical compounds whose molecules contain carbon, typically excluding those that contain only carbonates, simple oxides of carbon, or cyanides. A "biomolecule" refers generally to an organic molecule that is produced by a living organism, including large polymeric molecules (biopolymers) such as peptides, polysaccharides, and nucleic acids as well, and small molecules such as primary secondary metabolites, lipids, phospholipids, glycolipids, sterols, glycerolipids, vitamins, and hormones. A "polymer" refers generally to a large molecule or macromolecule composed of repeating structural units, which are typically connected by covalent chemical bond.

In certain embodiments, a small molecule has a molecular weight of less than about 1000-2000 Daltons, typically between about 300 and 700 Daltons, and including about 50, 100, 150, 200, 250, 300, 350, 400, 450, 500, 550, 500, 650, 600, 750, 700, 850, 800, 950, 1000 or 2000 Daltons.

Certain small molecules can have the "specific binding" characteristics described for antibodies (infra). For instance, a small molecule can specifically bind to a target described herein with a binding affinity ($K_d$) of at least about 0.01, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, or 50 nM. In certain embodiments a small specifically binds to a cell surface receptor or other cell surface protein. In some embodiments, the small molecule specifically binds to at least one cancer-associated antigen described herein. In particular embodiments, the small molecule specifically binds to at least one nervous system-associated, pain-associated, and/or autoimmune-associated antigen described herein.

Exemplary small molecules include cytotoxic, chemotherapeutic, and anti-angiogenic agents, for instance, those that have been considered useful in the treatment of various cancers, including cancers of the central nervous system and cancers that have metastasized to the central nervous system. Particular classes of small molecules include, without limitation, alkylating agents, anti-metabolites, anthracyclines, anti-tumor antibiotics, platinums, type I topoisomerase inhibitors, type II topoisomerase inhibitors, vinca alkaloids, and taxanes.

Specific examples of small molecules include chlorambucil, cyclophosphamide, cilengitide, lomustine (CCNU), melphalan, procarbazine, thiotepa, carmustine (BCNU), enzastaurin, busulfan, daunorubicin, doxorubicin, gefitinib, erlotinib idarubicin, temozolomide, epirubicin, mitoxantrone, bleomycin, cisplatin, carboplatin, oxaliplatin, camptothecins, irinotecan, topotecan, amsacrine, etoposide, etoposide phosphate, teniposide, temsirolimus, everolimus, vincristine, vinblastine, vinorelbine, vindesine, CT52923, and paclitaxel, and pharmaceutically acceptable salts, acids or derivatives of any of the above.

Additional examples of small molecules include those that target protein kinases for the treatment of nervous system (e.g., CNS) disorders, including imatinib, dasatinib, sorafenib, pazopanib, sunitnib, vatalanib, geftinib, erlotinib, AEE-788, dichoroacetate, tamoxifen, fasudil, SB-681323, and semaxanib (5U5416) (see Chico et al., *Nat Rev Drug Discov.* 8:829-909, 2009). Examples of small molecules also include donepizil, galantamine, memantine, rivastigmine, tacrine, rasigiline, naltrexone, lubiprostone, safinamide, istradefylline, pimavanserin, pitolisant, isradipine, pridopidine (ACR16), tetrabenazine, and bexarotene (e.g., for treating Alzheimer's Disease, Parkinson's Disease, Huntington's Disease); and glatirimer acetate, fingolimod, mitoxantrone (e.g., for treating MS). Also included are pharmaceutically acceptable salts, acids or derivatives of any of the above.

Further examples of small molecules include alkylating agents such as thiotepa, cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and doxetaxel (TAXOTERE®, Rhne-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylomithine (DMFO); retinoic acid derivatives such as Targretin™ (bexarotene), Panretin™ (alitretinoin); ONTAK™ (denileukin diftitox); esperamicins; capecitabine; and pharmaceutically acceptable salts, acids or derivatives of any of the above.

Also included are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

As noted above, in certain aspects the small molecule is an otherwise cardiotoxic agent. Particular examples of cardiotoxic small molecules include, without limitation, anthracyclines/anthraquinolones, cyclophosphamides, antimetabolites, antimicrotubule agents, and tyrosine kinase inhibitors. Specific examples of cardiotoxic agents include cyclopentenyl cytosine, 5-fluorouracil, capecitabine, paclitaxel, docataxel, adriamycin, doxorubucin, epirubicin, emetine, isotamide, mitomycin C, erlotinib, gefitinib, imatinib, sorafenib, sunitinib, cisplatin, thalidomide, busulfan, vinblastine, bleomycin, vincristine, arsenic trioxide, methotrexate, rosiglitazone, and mitoxantrone, among other small molecules described herein and known in the art.

Polypeptide Agents.

In particular embodiments, the agent of interest is a peptide or polypeptide. The terms "peptide" and "polypeptide" are used interchangeably herein, however, in certain instances, the term "peptide" can refer to shorter polypeptides, for example, polypeptides that consist of about 2, 3, 4, 5, 6, 7, 8, 9, 10, 11, 12, 13, 14, 15, 16, 17, 18, 19, 20, 25, 30, 35, 40, 45, or 50 amino acids, including all integers and ranges (e.g., 5-10, 8-12, 10-15) in between. Polypeptides and peptides can be composed of naturally-occurring amino acids and/or non-naturally occurring amino acids, as described herein. Antibodies are also included as polypeptides.

Exemplary polypeptide agents include polypeptides associated with lysosomal storage disorders. Examples of such polypeptides include aspartylglucosaminidase, acid lipase, cysteine transporter, Lamp-2, α-galactosidase A, acid ceramidase, α-L-fucosidase, β-hexosaminidase A, GM2-ganglioside activator (GM2A), α-D-mannosidase, β-D-mannosidase, arylsulfatase A, saposin B, neuraminidase, α-N-acetylglucosaminidase phosphotransferase, phosphotransferase γ-subunit, L-iduronidase, iduronate-2-sulfatase, heparan-N-sulfatase, α-N-acetylglucosaminidase, acetylCoA:N-acetyltransferase, N-acetylglucosamine 6-sulfatase, galactose 6-sulfatase, β-galactosidase, N-acetylgalactosamine 4-sulfatase, hyaluronoglucosaminidase, sulfatases, palmitoyl protein thioesterase, tripeptidyl peptidase I, acid sphingomyelinase, cathepsin A, cathepsin K, α-galactosidase B, NPC1, NPC2, sialin, and sialic acid transporter, including fragments, variants, and derivatives thereof.

Certain embodiments include polypeptides such as interferon-β polypeptides, such as interferon-β1a (e.g., AVONEX, REBIF) and interferon-β1b (e.g., Betaseron), which are often used for the treatment of multiple sclerosis (MS).

In some embodiments, as noted above, the polypeptide agent is an antibody or an antigen-binding fragment thereof. The antibody or antigen-binding fragment used in the conjugates or compositions of the present invention can be of essentially any type. Particular examples include therapeutic and diagnostic antibodies. As is well known in the art, an antibody is an immunoglobulin molecule capable of specific binding to a target, such as a carbohydrate, polynucleotide, lipid, polypeptide, etc., through at least one epitope recognition site, located in the variable region of the immunoglobulin molecule.

As used herein, the term "antibody" encompasses not only intact polyclonal or monoclonal antibodies, but also fragments thereof (such as dAb, Fab, Fab', F(ab')$_2$, Fv), single chain (ScFv), synthetic variants thereof, naturally occurring variants, fusion proteins comprising an antibody portion with an antigen-binding fragment of the required specificity, humanized antibodies, chimeric antibodies, and any other modified configuration of the immunoglobulin molecule that comprises an antigen-binding site or fragment (epitope recognition site) of the required specificity.

The term "antigen-binding fragment" as used herein refers to a polypeptide fragment that contains at least one CDR of an immunoglobulin heavy and/or light chains that binds to the antigen of interest. In this regard, an antigen-binding fragment of the herein described antibodies may comprise 1, 2, 3, 4, 5, or all 6 CDRs of a VH and VL sequence from antibodies that bind to a therapeutic or diagnostic target.

The term "antigen" refers to a molecule or a portion of a molecule capable of being bound by a selective binding agent, such as an antibody, and additionally capable of being used in an animal to produce antibodies capable of binding to an epitope of that antigen. An antigen may have one or more epitopes.

The term "epitope" includes any determinant, preferably a polypeptide determinant, capable of specific binding to an immunoglobulin or T-cell receptor. An epitope is a region of an antigen that is bound by an antibody. In certain embodiments, epitope determinants include chemically active surface groupings of molecules such as amino acids, sugar side chains, phosphoryl or sulfonyl, and may in certain embodiments have specific three-dimensional structural characteristics, and/or specific charge characteristics. Epitopes can be contiguous or non-contiguous in relation to the primary structure of the antigen.

A molecule such as an antibody is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to a specific epitope is an antibody that binds that specific epitope with greater affinity, avidity, more readily, and/or with greater duration than it binds to other epitopes. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

Immunological binding generally refers to the non-covalent interactions of the type which occur between an immunoglobulin molecule and an antigen for which the immunoglobulin is specific, for example by way of illustration and not limitation, as a result of electrostatic, ionic, hydrophilic and/or hydrophobic attractions or repulsion, steric forces, hydrogen bonding, van der Waals forces, and other interactions. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and on geometric parameters that equally influence the rate in both directions. Thus, both the "on rate constant" ($K_{on}$) and the "off rate constant" ($K_{off}$) can be determined by calculation of the concentrations and the actual rates of association and dissociation. The ratio of $K_{off}/K_{on}$ enables cancellation of all parameters not related to affinity, and is thus equal to the dissociation constant $K_d$.

Immunological binding properties of selected antibodies and polypeptides can be quantified using methods well known in the art (see Davies et al., *Annual Rev. Biochem.* 59:439-473, 1990). In some embodiments, an antibody or other polypeptide is said to specifically bind an antigen or epitope thereof when the equilibrium dissociation constant is about $\leq 10^{-7}$ or $10^{-8}$ M. In some embodiments, the equilibrium dissociation constant of an antibody may be about $\leq 10^{-9}$ M or $\leq 10^{-10}$ M. In certain illustrative embodiments, an antibody or other polypeptide has an affinity ($K_d$) for an antigen or target described herein (to which it specifically binds) of at least about 0.01, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, or 50 nM.

In some embodiments, the antibody or antigen-binding fragment or other polypeptide specifically binds to a cell surface receptor or other cell surface protein. In some embodiments, the antibody or antigen-binding fragment or other polypeptide specifically binds to a ligand of a cell surface receptor or other cell surface protein. In some embodiments, the antibody or antigen-binding fragment or other polypeptide specifically binds to an intracellular protein.

In certain embodiments, the antibody or antigen-binding fragment thereof or other polypeptide specifically binds to a cancer-associated antigen, or cancer antigen. Exemplary cancer antigens include cell surface proteins such as cell surface receptors. Also included as cancer-associated antigens are ligands that bind to such cell surface proteins or receptors. In specific embodiments, the antibody or antigen-binding fragment specifically binds to a intracellular cancer antigen. In some embodiments, the cancer that associates with the cancer antigen is one or more of breast cancer, metastatic brain cancer, prostate cancer, gastrointestinal cancer, lung cancer, ovarian cancer, testicular cancer, head and neck cancer, stomach cancer, bladder cancer, pancreatic cancer, liver cancer, kidney cancer, squamous cell carcinoma, CNS or brain cancer, melanoma, non-melanoma cancer, thyroid cancer, endometrial cancer, epithelial tumor, bone cancer, or a hematopoietic cancer.

In particular embodiments, the antibody or antigen-binding fragment or other polypeptide specifically binds to at least one cancer-associated antigen, or cancer antigen, such as human Her2/neu, Her1/EGF receptor (EGFR), Her3, A33 antigen, B7H3, CD5, CD19, CD20, CD22, CD23 (IgE Receptor), C242 antigen, 5T4, IL-6, IL-13, vascular endothelial growth factor VEGF (e.g., VEGF-A) VEGFR-1, VEGFR-2, CD30, CD33, CD37, CD40, CD44, CD51, CD52, CD56, CD74, CD80, CD152, CD200, CD221, CCR4, HLA-DR, CTLA-4, NPC-1C, tenascin, vimentin, insulin-like growth factor 1 receptor (IGF-1R), alpha-fetoprotein, insulin-like growth factor 1 (IGF-1), carbonic anhydrase 9 (CA-IX), carcinoembryonic antigen (CEA), integrin $\alpha_v\beta_3$, integrin $\alpha_5\beta_1$, folate receptor 1, transmembrane glycoprotein NMB, fibroblast activation protein alpha (FAP), glycoprotein 75, TAG-72, MUC1, MUC16 (or CA-125), phosphatidylserine, prostate-specific membrane antigen (PMSA), NR-LU-13 antigen, TRAIL-R1, tumor necrosis factor receptor superfamily member 10b (TNFRSF10B or TRAIL-R2), SLAM family member 7 (SLAMF7), EGP40 pancarcinoma antigen, B-cell activating factor (BAFF), platelet-derived growth factor receptor, glycoprotein EpCAM (17-1A), Programmed Death-1, protein disulfide isomerase (PDI), Phosphatase of Regenerating Liver 3 (PRL-3), prostatic acid phosphatase, Lewis-Y antigen, GD2 (a disialoganglioside expressed on tumors of neuroectodermal origin), glypican-3 (GPC3), and/or mesothelin.

In specific embodiments, the antibody or antigen-binding fragment thereof or other polypeptide specifically binds to the human Her2/neu protein. Essentially any anti-Her2/neu antibody, antigen-binding fragment or other Her2/neu-specific binding agent may be used in producing the p97-antibody conjugates of the present invention. Illustrative anti-Her2/neu antibodies are described, for example, in U.S. Pat. Nos. 5,677,171; 5,720,937; 5,720,954; 5,725,856; 5,770,195; 5,772,997; 6,165,464; 6,387,371; and 6,399,063, the contents of which are incorporated herein by reference in their entireties.

In some embodiments, the antibody or antigen-binding fragment thereof or other polypeptide specifically binds to the human Her1/EGFR (epidermal growth factor receptor). Essentially any anti-Her1/EGFR antibody, antigen-binding fragment or other Her1-EGFR-specific binding agent may be used in producing the p97-antibody conjugates of the present invention. Illustrative anti-Her1/EGFR antibodies are described, for example, in U.S. Pat. Nos. 5,844,093; 7,132,511; 7,247,301; 7,595,378; 7,723,484; 7,939,072; and 7,960,516, the contents of which are incorporated by reference in their entireties.

In certain embodiments, the antibody is a therapeutic antibody, such as an anti-cancer therapeutic antibody, including antibodies such as 3F8, 8H9, abagovomab, adecatumumab, afutuzumab, alemtuzumab, alacizumab (pegol), amatuximab, apolizumab, bavituximab, bectumomab, belimumab, bevacizumab, bivatuzumab (mertansine), brentuximab vedotin, cantuzumab (mertansine), cantuzumab (ravtansine), capromab (pendetide), catumaxomab, cetuximab, citatuzumab (bogatox), cixutumumab, clivatuzumab (tetraxetan), conatumumab, dacetuzumab, dalotuzumab, detumomab, drozitumab, ecromeximab, edrecolomab, elotuzumab, enavatuzumab, ensituximab, epratuzumab, ertumaxomab, etaracizumab, farletuzumab, FBTA05, figitumumab, flanvotumab, galiximab, gemtuzumab, ganitumab, gemtuzumab (ozogamicin), girentuximab, glembatumumab (vedotin), ibritumomab tiuxetan, icrucumab, igovomab, indatuximab ravtansine, intetumumab, inotuzumab ozogamicin, ipilimumab (MDX-101), iratumumab, labetuzumab, lexatumumab, lintuzumab, lorvotuzumab (mertansine), lucatumumab, lumiliximab, mapatumumab, matuzumab, milatuzumab, mitumomab, mogamulizumab, moxetumomab (pasudotox), nacolomab (tafenatox), naptumomab (estafenatox), narnatumab, necitumumab, nimotuzumab, nivolumab, Neuradiab® (with or without radioactive iodine), NR-LU-10, ofatumumab, olaratumab, onartuzumab, oportuzumab (monatox), oregovomab, panitumumab, patritumab, pemtumomab, pertuzumab, pritumumab, racotumomab, radretumab, ramucirumab, rilotumumab, rituximab, robatumumab, samalizumab, sibrotuzumab, siltuximab, tabalumab, taplitumomab (paptox), tenatumomab, teprotumumab, TGN1412, ticilimumab, tremelimumab, tigatuzumab, TNX-650, tositumomab, TRBS07, trastuzumab, tucotuzumab (celmoleukin), ublituximab, urelumab, veltuzumab, volociximab, votumumab, and zalutumumab. Also included are fragments, variants, and derivatives of these antibodies.

In particular embodiments, the antibody is a cardiotoxic antibody, that is, an antibody that displays cardiotoxicity when administered in an unconjugated form. Specific examples of antibodies that display cardiotoxicity include trastuzumab and bevacizumab.

In specific embodiments, the anti-Her2/neu antibody used in a p97 conjugate is trastuzumab (Herceptin®), or a fragment, variant or derivative thereof. Herceptin® is a Her2/neu-specific monoclonal antibody approved for the treatment of human breast cancer. In certain embodiments, a Her2/neu-binding antigen-binding fragment comprises one or more of the CDRs of a Her2/neu antibody. In this regard, it has been shown in some cases that the transfer of only the VHCDR3 of an antibody can be performed while still retaining desired specific binding (Barbas et al., *PNAS.* 92: 2529-2533, 1995). See also, McLane et al., *PNAS USA.* 92:5214-5218, 1995; and Barbas et al., *J. Am. Chem. Soc.* 116:2161-2162, 1994.

In other specific embodiments, the anti-Her1/EGFR antibody used in a conjugate of the invention is cetuximab (Erbitux®), or a fragment or derivative thereof. In certain embodiments, an anti-Her1/EGFR binding fragment comprises one or more of the CDRs of a Her1/EGFR antibody such as cetuximab. Cetuximab is approved for the treatment of head and neck cancer, and colorectal cancer. Cetuximab is composed of the Fv (variable; antigen-binding) regions of the 225 murine EGFR monoclonal antibody specific for the N-terminal portion of human EGFR with human IgG1 heavy and kappa light chain constant (framework) regions.

In some embodiments, the antibody or antigen-binding fragment or other polypeptide specifically binds to an antigen associated with (e.g., treatment of) at least one nervous system disorder, including disorders of the peripheral and/or central nervous system (CNS) disorder. In certain embodiments, the antibody or antigen-binding fragment or other polypeptide specifically binds to an antigen associated with (e.g., treatment of) pain, including acute pain, chronic pain, and neuropathic pain. In some embodiments, the antibody or antigen-binding fragment or other polypeptide specifically binds an antigen associated with (e.g., treatment of) an autoimmune disorder, including autoimmune disorders of the nervous system or CNS.

Examples of nervous system-, pain-, and/or autoimmune-associated antigens include, without limitation, alpha-4 (α4) integrin, CD20, CD52, IL-12, IL-23, the p40 subunit of IL-12 and IL-23, and the axonal regrowth and remyelination inhibitors Nogo-A and LINGO, IL-23, amyloid-β (e.g., $A\beta_{(1-42)}$), Huntingtin, CD25 (i.e., the alpha chain of the IL-2 receptor), nerve growth factor (NGF), neurotrophic tyrosine kinase receptor type 1 (TrkA; the high affinity catalytic receptor for NGF), and α-synuclein. These and other targets have been considered useful in the treatment of a variety of nervous system, pain, and/or autoimmune disorders, such as multiple sclerosis (α4 integrin, IL-23, CD25, CD20, CD52, IL-12, IL-23, the p40 subunit of IL-12 and IL-23, and the axonal regrowth and remyelination inhibitors Nogo-A and LINGO), Alzheimer's Disease (Aβ), Huntington's Disease (Huntingtin), Parkinson's Disease (α-synuclein), and pain (NGF and TrkA).

In specific embodiments, the anti-CD25 antibody used in a p97 conjugate is daclizumab (i.e., Zenapax™), or a fragment, variant or derivative thereof. Daclizumab a humanized monoclonal antibody that specifically binds to CD25, the alpha subunit of the IL-2 receptor. In other embodiments, the antibody is rituximab, ocrelizumab, ofatumumab, or a variant or fragment thereof that specifically binds to CD20. In particular embodiments, the antibody is alemtuzumab, or a variant or fragment thereof that specifically binds to CD52. In certain embodiments, the antibody is ustekinumab (CNTO 1275), or a variant or fragment thereof that specifically binds to the p40 subunit of IL-12 and IL-23.

In specific embodiments, the anti-NGF antibody used in a conjugate is tanezumab, or a fragment, variant or derivative thereof. Tanezumab specifically binds to NGF and prevents NGF from binding to its high affinity, membrane-bound, catalytic receptor tropomyosin-related kinase A (TrkA), which is present on sympathetic and sensory neurons; reduced stimulation of TrkA by NGF is believed to inhibit the pain-transmission activities of such neurons.

In some embodiments, the antibody or antigen-binding fragment thereof or other polypeptide (e.g., immunoglobulin-like molecule, soluble receptor, ligand) specifically binds to a pro-inflammatory molecule, for example, a pro-inflammatory cytokine or chemokine. In these and related embodiments, the p97 conjugate can be used to treat a variety of inflammatory conditions, as described herein. Examples of pro-inflammatory molecules include tumor necrosis factors (TNF) such as TNF-α and TNF-β, TNF superfamily molecules such as FasL, CD27L, CD30L, CD40L, Ox40L, 4-1BBL, TRAIL, TWEAK, and Apo3L, interleukin-1 (IL-1) including IL-1α and IL-1β, IL-2, interferon-γ (IFN-γ), IFN-α/β, IL-6, IL-8, IL-12, IL-15, IL-17, IL-18, IL-21, LIF, CCL5, GROα, MCP-1, MIP-1α, MIP-1β, macrophage colony stimulating factor (MCSF), granulocyte macrophage colony stimulating factor (GM-CSF), CXCL2, CCL2, among others. In some embodiments, the antibody or antigen-binding fragment thereof specifically binds to a receptor of one or more of the foregoing pro-inflammatory molecules, such as TNF receptor (TNFR), an IL-1 receptor (IL-1R), or an IL-6 receptor (IL-6R), among others.

In specific embodiments, as note above, the antibody or antigen-binding fragment or other polypeptide specifically binds to TNF-α or TNF-β. In particular embodiments, the anti-TNF antibody or other TNF-binding polypeptide is adalimumab (Humira®), certolizumab pegol (Cimzia®), etanercept (Enbrel®), golimumab (Cimzia®), or infliximab (Remicade®), D2E7, CDP 571, or CDP 870, or an antigen-binding fragment or variant thereof. In some embodiments, the TNF-binding polypeptide is a soluble receptor or ligand, such as TNRFSF10B, TRAIL (i.e., CD253), TNFSF10, TRADD (tumor necrosis factor receptor type 1-associated DEATH domain protein), TRAFs (TNF receptor associated factors, including TRAFS 1-7), or RIP (ribosome-inactivating proteins). Conjugates comprising an anti-TNF antibody or TNF-binding polypeptide can be used, for instance, in the treatment of various inflammatory conditions, as described herein. Such p97 conjugates can also be used in the treatment of various neurological conditions or disorders such as Alzheimer's disease, stroke, traumatic brain injury (TBI), spinal stenosis, acute spinal cord injury, and spinal cord compression (see U.S. Pat. Nos. 6,015,557; 6,177,077; 6,419,934; 6,419,944; 6,537,549; 6,982,089; and 7,214,658).

In specific embodiments, as note above, the antibody or antigen-binding fragment specifically binds to IL-1α or IL-1β. In particular embodiments, the anti-IL-1 antibody is canakinumab or gevokizumab, or a variant or fragment thereof that specifically binds to IL-1β. Among other inflammatory conditions described herein, p97 conjugates comprising an anti-IL-1 antibody can be used to treat cryopyrin-associated periodic syndromes (CAPS), including familial cold autoinflammatory syndrome, Muckle-Wells syndrome, and neonatal-onset multisystem inflammatory disease.

Antibodies may be prepared by any of a variety of techniques known to those of ordinary skill in the art. See, e.g., Harlow and Lane, *Antibodies: A Laboratory Manual*, Cold Spring Harbor Laboratory, 1988. Monoclonal antibodies specific for a polypeptide of interest may be prepared, for example, using the technique of Kohler and Milstein, *Eur. J. Immunol.* 6:511-519, 1976, and improvements thereto. Also included are methods that utilize transgenic animals such as mice to express human antibodies. See, e.g., Neuberger et al., *Nature Biotechnology* 14:826, 1996; Lonberg et al., *Handbook of Experimental Pharmacology* 113:49-101, 1994; and Lonberg et al., *Internal Review of Immunology* 13:65-93, 1995. Particular examples include the VELOCIMMUNE® platform by REGENEREX® (see, e.g., U.S. Pat. No. 6,596, 541).

Antibodies can also be generated or identified by the use of phage display or yeast display libraries (see, e.g., U.S. Pat. No. 7,244,592; Chao et al., *Nature Protocols*. 1:755-768, 2006). Non-limiting examples of available libraries include cloned or synthetic libraries, such as the Human Combinatorial Antibody Library (HuCAL), in which the structural diversity of the human antibody repertoire is represented by seven heavy chain and seven light chain variable region genes. The combination of these genes gives rise to 49 frameworks in the master library. By superimposing highly variable genetic cassettes (CDRs=complementarity determining regions) on these frameworks, the vast human antibody repertoire can be reproduced. Also included are human libraries designed with human-donor-sourced fragments encoding a light-chain variable region, a heavy-chain CDR-3, synthetic DNA encoding diversity in heavy-chain CDR-1, and synthetic DNA encoding diversity in heavy-chain CDR-2. Other libraries suitable for use will be apparent to persons skilled in the art. The p97 polypeptides described herein and known in the art may be used in the purification process in, for example, an affinity chromatography step.

In certain embodiments, antibodies and antigen-binding fragments thereof as described herein include a heavy chain and a light chain CDR set, respectively interposed between a heavy chain and a light chain framework region (FR) set which provide support to the CDRs and define the spatial relationship of the CDRs relative to each other. As used herein, the term "CDR set" refers to the three hypervariable regions of a heavy or light chain V region. Proceeding from the N-terminus of a heavy or light chain, these regions are denoted as "CDR1," "CDR2," and "CDR3" respectively. An antigen-binding site, therefore, includes six CDRs, comprising the CDR set from each of a heavy and a light chain V region. A polypeptide comprising a single CDR, (e.g., a CDR1, CDR2 or CDR3) is referred to herein as a "molecular recognition unit." Crystallographic analysis of a number of antigen-antibody complexes has demonstrated that the amino acid residues of CDRs form extensive contact with bound antigen, wherein the most extensive antigen contact is with the heavy chain CDR3. Thus, the molecular recognition units are primarily responsible for the specificity of an antigen-binding site.

As used herein, the term "FR set" refers to the four flanking amino acid sequences which frame the CDRs of a CDR set of a heavy or light chain V region. Some FR residues may contact bound antigen; however, FRs are primarily responsible for folding the V region into the antigen-binding site, particularly the FR residues directly adjacent to the CDRs. Within FRs, certain amino residues and certain structural features are very highly conserved. In this regard, all V region sequences contain an internal disulfide loop of around 90 amino acid residues. When the V regions fold into a binding-site, the CDRs are displayed as projecting loop motifs which form an antigen-binding surface. It is generally recognized that there are conserved structural regions of FRs which influence the folded shape of the CDR loops into certain "canonical" structures—regardless of the precise CDR amino acid sequence. Further, certain FR residues are known to participate in non-covalent interdomain contacts which stabilize the interaction of the antibody heavy and light chains.

The structures and locations of immunoglobulin variable domains may be determined by reference to Kabat, E. A. et al., Sequences of Proteins of Immunological Interest. 4th Edition. US Department of Health and Human Services. 1987, and updates thereof.

A "monoclonal antibody" refers to a homogeneous antibody population wherein the monoclonal antibody is comprised of amino acids (naturally occurring and non-naturally occurring) that are involved in the selective binding of an epitope. Monoclonal antibodies are highly specific, being directed against a single epitope. The term "monoclonal antibody" encompasses not only intact monoclonal antibodies and full-length monoclonal antibodies, but also fragments thereof (such as Fab, Fab', F(ab')$_2$, Fv), single chain (ScFv), variants thereof, fusion proteins comprising an antigen-binding portion, humanized monoclonal antibodies, chimeric monoclonal antibodies, and any other modified configuration of the immunoglobulin molecule that comprises an antigen-binding fragment (epitope recognition site) of the required specificity and the ability to bind to an epitope. It is not intended to be limited as regards the source of the antibody or the manner in which it is made (e.g., by hybridoma, phage selection, recombinant expression, transgenic animals). The term includes whole immunoglobulins as well as the fragments etc. described above under the definition of "antibody."

The proteolytic enzyme papain preferentially cleaves IgG molecules to yield several fragments, two of which (the F(ab) fragments) each comprise a covalent heterodimer that includes an intact antigen-binding site. The enzyme pepsin is able to cleave IgG molecules to provide several fragments, including the F(ab')$_2$ fragment which comprises both antigen-binding sites. An Fv fragment for use according to certain embodiments of the present invention can be produced by preferential proteolytic cleavage of an IgM, and on rare occasions of an IgG or IgA immunoglobulin molecule. Fv fragments are, however, more commonly derived using recombinant techniques known in the art. The Fv fragment includes a non-covalent $V_H$::$V_L$ heterodimer including an antigen-binding site which retains much of the antigen recognition and binding capabilities of the native antibody molecule. See Inbar et al., *PNAS USA*. 69:2659-2662, 1972; Hochman et al., *Biochem*. 15:2706-2710, 1976; and Ehrlich et al., *Biochem*. 19:4091-4096, 1980.

In certain embodiments, single chain Fv or scFV antibodies are contemplated. For example, Kappa bodies (III et al., *Prot. Eng*. 10:949-57, 1997); minibodies (Martin et al., *EMBO J* 13:5305-9, 1994); diabodies (Holliger et al., *PNAS* 90: 6444-8, 1993); or Janusins (Traunecker et al., *EMBO J* 10: 3655-59, 1991; and Traunecker et al., *Int. J. Cancer Suppl*. 7:51-52, 1992), may be prepared using standard molecular biology techniques following the teachings of the present application with regard to selecting antibodies having the desired specificity.

A single chain Fv (sFv) polypeptide is a covalently linked $V_H$::$V_L$ heterodimer which is expressed from a gene fusion including $V_H$- and $V_L$-encoding genes linked by a peptide-encoding linker. Huston et al. (*PNAS USA*. 85(16):5879-5883, 1988). A number of methods have been described to discern chemical structures for converting the naturally aggregated—but chemically separated—light and heavy polypeptide chains from an antibody V region into an sFv molecule which will fold into a three dimensional structure substantially similar to the structure of an antigen-binding site. See, e.g., U.S. Pat. Nos. 5,091,513 and 5,132,405, to Huston et al.; and U.S. Pat. No. 4,946,778, to Ladner et al.

In certain embodiments, an antibody as described herein is in the form of a "dia body." Diabodies are multimers of polypeptides, each polypeptide comprising a first domain comprising a binding region of an immunoglobulin light chain and a second domain comprising a binding region of an immunoglobulin heavy chain, the two domains being linked (e.g. by a peptide linker) but unable to associate with each other to form an antigen binding site: antigen binding sites are formed by the association of the first domain of one polypeptide within the multimer with the second domain of another polypeptide within the multimer (WO94/13804). A dAb fragment of an antibody consists of a VH domain (Ward et al., *Nature* 341:544-546, 1989). Dia bodies and other multivalent or multispecific fragments can be constructed, for example, by gene fusion (see WO94/13804; and Holliger et al., *PNAS USA*. 90:6444-6448, 1993)).

Minibodies comprising a scFv joined to a CH3 domain are also included (see Hu et al., *Cancer Res.* 56:3055-3061, 1996). See also Ward et al., *Nature.* 341:544-546, 1989; Bird et al., *Science.* 242:423-426, 1988; Huston et al., *PNAS USA.* 85:5879-5883, 1988); PCT/US92/09965; WO94/13804; and Reiter et al., *Nature Biotech.* 14:1239-1245, 1996.

Where bispecific antibodies are to be used, these may be conventional bispecific antibodies, which can be manufactured in a variety of ways (Holliger and Winter, *Current Opinion Biotechnol*. 4:446-449, 1993), e.g. prepared chemically or from hybrid hybridomas, or may be any of the bispecific antibody fragments mentioned above. Dia bodies and scFv can be constructed without an Fc region, using only variable domains, potentially reducing the effects of anti-idiotypic reaction.

Bispecific diabodies, as opposed to bispecific whole antibodies, may also be particularly useful because they can be readily constructed and expressed in *E. coli*. Diabodies (and many other polypeptides such as antibody fragments) of appropriate binding specificities can be readily selected using phage display (WO94/13804) from libraries. If one arm of the diabody is to be kept constant, for instance, with a specificity directed against antigen X, then a library can be made where the other arm is varied and an antibody of appropriate specificity selected. Bispecific whole antibodies may be made by knobs-into-holes engineering (Ridgeway et al., *Protein Eng.*, 9:616-621, 1996).

In certain embodiments, the antibodies described herein may be provided in the form of a UniBody®. A UniBody® is an IgG4 antibody with the hinge region removed (see GenMab Utrecht, The Netherlands; see also, e.g., US20090226421). This antibody technology creates a stable, smaller antibody format with an anticipated longer therapeutic window than current small antibody formats. IgG4 antibodies are considered inert and thus do not interact with the immune system. Fully human IgG4 antibodies may be modified by eliminating the hinge region of the antibody to obtain half-molecule fragments having distinct stability properties relative to the corresponding intact IgG4 (GenMab, Utrecht). Halving the IgG4 molecule leaves only one area on the UniBody® that can bind to cognate antigens (e.g., disease targets) and the UniBody® therefore binds univalently to only one site on target cells. For certain cancer cell surface antigens, this univalent binding may not stimulate the cancer cells to grow as may be seen using bivalent antibodies having the same antigen specificity, and hence UniBody® technology may afford treatment options for some types of cancer that may be refractory to treatment with conventional antibodies. The small size of the UniBody® can be a great benefit when treating some forms of cancer, allowing for better distribution of the molecule over larger solid tumors and potentially increasing efficacy.

In certain embodiments, the antibodies provided herein may take the form of a nanobody. Minibodies are encoded by single genes and are efficiently produced in almost all prokaryotic and eukaryotic hosts, for example, *E. coli* (see U.S. Pat. No. 6,765,087), moulds (for example *Aspergillus* or *Trichoderma*) and yeast (for example *Saccharomyces, Kluyvermyces, Hansenula* or *Pichia* (see U.S. Pat. No. 6,838, 254). The production process is scalable and multi-kilogram quantities of nanobodies have been produced. Nanobodies may be formulated as a ready-to-use solution having a long shelf life. The Nanoclone method (see WO 06/079372) is a proprietary method for generating Nanobodies against a desired target, based on automated high-throughput selection of B-cells.

In certain embodiments, the antibodies or antigen-binding fragments thereof are humanized. These embodiments refer to a chimeric molecule, generally prepared using recombinant techniques, having an antigen-binding site derived from an immunoglobulin from a non-human species and the remaining immunoglobulin structure of the molecule based upon the structure and/or sequence of a human immunoglobulin. The antigen-binding site may comprise either complete variable domains fused onto constant domains or only the CDRs grafted onto appropriate framework regions in the variable domains. Epitope binding sites may be wild type or modified by one or more amino acid substitutions. This eliminates the constant region as an immunogen in human individuals, but the possibility of an immune response to the foreign variable region remains (LoBuglio et al., *PNAS USA* 86:4220-4224, 1989; Queen et al., *PNAS USA*. 86:10029-10033, 1988; Riechmann et al., *Nature*. 332:323-327, 1988). Illustrative methods for humanization of antibodies include the methods described in U.S. Pat. No. 7,462,697.

Another approach focuses not only on providing human-derived constant regions, but modifying the variable regions as well so as to reshape them as closely as possible to human form. It is known that the variable regions of both heavy and light chains contain three complementarity-determining regions (CDRs) which vary in response to the epitopes in question and determine binding capability, flanked by four framework regions (FRs) which are relatively conserved in a given species and which putatively provide a scaffolding for the CDRs. When nonhuman antibodies are prepared with respect to a particular epitope, the variable regions can be "reshaped" or "humanized" by grafting CDRs derived from nonhuman antibody on the FRs present in the human antibody to be modified. Application of this approach to various antibodies has been reported by Sato et al., *Cancer Res.* 53:851-856, 1993; Riechmann et al., *Nature* 332:323-327, 1988; Verhoeyen et al., *Science* 239:1534-1536, 1988; Kettleborough et al., *Protein Engineering.* 4:773-3783, 1991; Maeda et al., *Human Antibodies Hybridoma* 2:124-134, 1991; Gorman et al., *PNAS USA*. 88:4181-4185, 1991; Tempest et al., *Bio/Technology* 9:266-271, 1991; Co et al., *PNAS USA*. 88:2869-2873, 1991; Carter et al., *PNAS USA*. 89:4285-4289, 1992; and Co et al., *J Immunol.* 148:1149-1154, 1992. In some embodiments, humanized antibodies preserve all CDR sequences (for example, a humanized mouse antibody which contains all six CDRs from the mouse antibodies). In other embodiments, humanized antibodies have one or more CDRs (one, two, three, four, five, six) which are altered with respect to the original antibody, which are also termed one or more CDRs "derived from" one or more CDRs from the original antibody.

In certain embodiments, the antibodies of the present invention may be chimeric antibodies. In this regard, a chimeric antibody is comprised of an antigen-binding fragment of an antibody operably linked or otherwise fused to a heterologous Fc portion of a different antibody. In certain embodiments, the heterologous Fc domain is of human origin. In other embodiments, the heterologous Fc domain may be from a different Ig class from the parent antibody, including IgA (including subclasses IgA1 and IgA2), IgD, IgE, IgG (including subclasses IgG1, IgG2, IgG3, and IgG4), and IgM. In further embodiments, the heterologous Fc domain may be comprised of CH2 and CH3 domains from one or more of the different Ig classes. As noted above with regard to humanized antibodies, the antigen-binding fragment of a chimeric antibody may comprise only one or more of the CDRs of the antibodies described herein (e.g., 1, 2, 3, 4, 5, or 6 CDRs of the antibodies described herein), or may comprise an entire variable domain (VL, VH or both).

Peptide Mimetics.

Certain embodiments employ "peptide mimetics." Peptide analogs are commonly used in the pharmaceutical industry as non-peptide drugs with properties analogous to those of the template peptide. These types of non-peptide compound are termed "peptide mimetics" or "peptidomimetics" (Luthman et al., *A Textbook of Drug Design and Development*, 14:386-406, 2nd Ed., Harwood Academic Publishers, 1996; Joachim Grante, *Angew. Chem. Int. Ed. Engl.*, 33:1699-1720, 1994; Fauchere, *Adv. Drug Res.*, 15:29, 1986; Veber and Freidinger TINS, p. 392 (1985); and Evans et al., *J. Med. Chem.* 30:229, 1987). A peptidomimetic is a molecule that mimics the biological activity of a peptide but is no longer peptidic in chemical nature. Peptidomimetic compounds are known in the art and are described, for example, in U.S. Pat. No. 6,245,886.

A peptide mimetic can have the "specific binding" characteristics described for antibodies (supra). For example, a peptide mimetic can specifically bind to a target described herein with a binding affinity ($K_d$) of at least about 0.01, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, or 50 nM. In some embodiments a peptide mimetic specifically binds to a cell surface receptor or other cell surface protein. In some embodiments, the peptide mimetic specifically binds to at least one cancer-associated antigen described herein. In particular embodiments, the peptide mimetic specifically binds to at least one nervous system-associated, pain-associated, and/or autoimmune-associated antigen described herein.

Peptoids.

The conjugates of the present invention also includes "peptoids." Peptoid derivatives of peptides represent another form of modified peptides that retain the important structural determinants for biological activity, yet eliminate the peptide bonds, thereby conferring resistance to proteolysis (Simon, et al., *PNAS USA*. 89:9367-9371, 1992). Peptoids are oligomers of N-substituted glycines. A number of N-alkyl groups have been described, each corresponding to the side chain of a natural amino acid. The peptidomimetics of the present invention include compounds in which at least one amino acid, a few amino acids or all amino acid residues are replaced by the corresponding N-substituted glycines. Peptoid libraries are described, for example, in U.S. Pat. No. 5,811,387.

A peptoid can have the "specific binding" characteristics described for antibodies (supra). For instance, a peptoid can specifically bind to a target described herein with a binding affinity ($K_d$) of at least about 0.01, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, or 50 nM. In certain embodiments a peptoid specifically binds to a cell surface receptor or other cell surface protein. In some embodiments, the peptoid specifically binds to at least one cancer-associated antigen described herein. In particular embodiments, the peptoid specifically binds to at least one nervous system-associated, pain-associated, and/or autoimmune-associated antigen described herein.

Aptamers.

The p97 conjugates of the present invention also include aptamers (see, e.g., Ellington et al., *Nature*. 346, 818-22, 1990; and Tuerk et al., *Science*. 249, 505-10, 1990). Examples of aptamers include nucleic acid aptamers (e.g., DNA aptamers, RNA aptamers) and peptide aptamers. Nucleic acid aptamers refer generally to nucleic acid species that have been engineered through repeated rounds of in vitro selection or equivalent method, such as SELEX (systematic evolution of ligands by exponential enrichment), to bind to various molecular targets such as small molecules, proteins, nucleic acids, and even cells, tissues and organisms. See, e.g., U.S. Pat. Nos. 6,376,190; and 6,387,620.

Peptide aptamers typically include a variable peptide loop attached at both ends to a protein scaffold, a double structural constraint that typically increases the binding affinity of the peptide aptamer to levels comparable to that of an antibody's (e.g., in the nanomolar range). In certain embodiments, the variable loop length may be composed of about 10-20 amino acids (including all integers in between), and the scaffold may include any protein that has good solubility and compacity properties. Certain exemplary embodiments may utilize the bacterial protein Thioredoxin-A as a scaffold protein, the variable loop being inserted within the reducing active site (-Cys-Gly-Pro-Cys- loop in the wild protein), with the two cysteines lateral chains being able to form a disulfide bridge. Methods for identifying peptide aptamers are described, for example, in U.S. Application No. 2003/0108532.

An aptamer can have the "specific binding" characteristics described for antibodies (supra). For instance, an aptamer can specifically bind to a target described herein with a binding affinity ($K_d$) of at least about 0.01, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, or 50 nM. In particular embodiments, an aptamer specifically binds to a cell surface receptor or other cell surface protein. In some embodiments, the aptamer specifically binds to at least one cancer-associated antigen described herein. In particular embodiments, the aptamer specifically binds to at least one nervous system-associated, pain-associated, and/or autoimmune-associated antigen described herein.

Detectable Entities.

In some embodiments, the p97 fragment is conjugated to a "detectable entity." Exemplary detectable entities include, without limitation, iodine-based labels, radioisotopes, fluorophores/fluorescent dyes, and nanoparticles.

Exemplary iodine-based labels include diatrizoic acid (Hypaque®, GE Healthcare) and its anionic form, diatrizoate. Diatrizoic acid is a radio-contrast agent used in advanced X-ray techniques such as CT scanning. Also included are iodine radioisotopes, described below.

Exemplary radioisotopes that can be used as detectable entities include $^{32}P$, $^{33}P$, $^{35}S$, $^{3}H$, $^{18}F$, $^{11}C$, $^{13}N$, $^{15}O$, $^{111}In$, $^{169}Yb$, $^{99m}TC$, $^{55}Fe$, and isotopes of iodine such as $^{123}I$, $^{124}I$, $^{125}I$, and $^{131}I$. These radioisotopes have different half-lives, types of decay, and levels of energy which can be tailored to match the needs of a particular protocol. Certain of these radioisotopes can be selectively targeted or better targeted to CNS tissues by conjugation to p97 polypeptides, for instance, to improve the medical imaging of such tissues.

Examples of fluorophores or fluorochromes that can be used as directly detectable entities include fluorescein, tetramethylrhodamine, Texas Red, Oregon Green®, and a number of others (e.g., Haugland, *Handbook of Fluorescent Probes*-9th Ed., 2002, Molec. Probes, Inc., Eugene Oreg.;

Haugland, *The Handbook: A Guide to Fluorescent Probes and Labeling Technologies*-10th Ed., 2005, Invitrogen, Carlsbad, Calif.). Also included are light-emitting or otherwise detectable dyes. The light emitted by the dyes can be visible light or invisible light, such as ultraviolet or infrared light. In exemplary embodiments, the dye may be a fluorescence resonance energy transfer (FRET) dye; a xanthene dye, such as fluorescein and rhodamine; a dye that has an amino group in the alpha or beta position (such as a naphthylamine dye, 1-dimethylaminonaphthyl-5-sulfonate, 1-anilino-8-naphthalende sulfonate and 2-p-touidinyl-6-naphthalene sulfonate); a dye that has 3-phenyl-7-isocyanatocoumarin; an acridine, such as 9-isothiocyanatoacridine and acridine orange; a pyrene, a bensoxadiazole and a stilbene; a dye that has 3-($\epsilon$-carboxypentyl)-3'-ethyl-5,5'-dimethyloxacarbocyanine (CYA); 6-carboxy fluorescein (FAM); 5&6-carboxyrhodamine-110 (R110); 6-carboxyrhodamine-6G (R6G); N,N,N',N'-tetramethyl-6-carboxyrhodamine (TAMRA); 6-carboxy-X-rhodamine (ROX); 6-carboxy-4',5'-dichloro-2',7'-dimethoxyfluorescein (JOE); ALEXA FLUOR™; Cy™; Texas Red and Rhodamine Red; 6-carboxy-2',4,7,7'-tetrachlorofluorescein (TET); 6-carboxy-2',4,4',5',7,7'-hexachlorofluorescein (HEX); 5-carboxy-2',4',5',7'-tetrachlorofluorescein (ZOE); NAN; NED; Cy3; Cy3.5; Cy5; Cy5.5; Cy7; and Cy7.5; IR800CW, ICG, Alexa Fluor 350; Alexa Fluor 488; Alexa Fluor 532; Alexa Fluor 546; Alexa Fluor 568; Alexa Fluor 594; Alexa Fluor 647; Alexa Fluor 680, or Alexa Fluor 750. Certain embodiments include conjugation to chemotherapeutic agents (e.g., paclitaxel, adriamycin) that are labeled with a detectable entity, such as a fluorophore (e.g., Oregon Green®, Alexa Fluor 488).

Nanoparticles usually range from about 1-1000 nm in size and include diverse chemical structures such as gold and silver particles and quantum dots. When irradiated with angled incident white light, silver or gold nanoparticles ranging from about 40-120 nm will scatter monochromatic light with high intensity. The wavelength of the scattered light is dependent on the size of the particle. Four to five different particles in close proximity will each scatter monochromatic light, which when superimposed will give a specific, unique color. Derivatized nanoparticles such as silver or gold particles can be attached to a broad array of molecules including, proteins, antibodies, small molecules, receptor ligands, and nucleic acids. Specific examples of nanoparticles include metallic nanoparticles and metallic nanoshells such as gold particles, silver particles, copper particles, platinum particles, cadmium particles, composite particles, gold hollow spheres, gold-coated silica nanoshells, and silica-coated gold shells. Also included are silica, latex, polystyrene, polycarbonate, polyacrylate, PVDF nanoparticles, and colored particles of any of these materials.

Quantum dots are fluorescing crystals about 1-5 nm in diameter that are excitable by light over a large range of wavelengths. Upon excitation by light having an appropriate wavelength, these crystals emit light, such as monochromatic light, with a wavelength dependent on their chemical composition and size. Quantum dots such as CdSe, ZnSe, InP, or InAs possess unique optical properties; these and similar quantum dots are available from a number of commercial sources (e.g., NN-Labs, Fayetteville, Ark.; Ocean Nanotech, Fayetteville, Ark.; Nanoco Technologies, Manchester, UK; Sigma-Aldrich, St. Louis, Mo.).

Polypeptide Variants and Fragments.

Certain embodiments include variants and/or fragments of the reference polypeptides described herein, whether described by name or by reference to a sequence identifier, including p97 polypeptides and polypeptide-based agents such as antibodies. The wild-type or most prevalent sequences of these polypeptides are known in the art, and can be used as a comparison for the variants and fragments described herein.

A polypeptide "variant," as the term is used herein, is a polypeptide that typically differs from a polypeptide specifically disclosed herein by one or more substitutions, deletions, additions and/or insertions. Variant polypeptides are biologically active, that is, they continue to possess the enzymatic or binding activity of a reference polypeptide. Such variants may result from, for example, genetic polymorphism and/or from human manipulation.

In many instances, a biologically active variant will contain one or more conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. As described above, modifications may be made in the structure of the polynucleotides and polypeptides of the present invention and still obtain a functional molecule that encodes a variant or derivative polypeptide with desirable characteristics. When it is desired to alter the amino acid sequence of a polypeptide to create an equivalent, or even an improved, variant or portion of a polypeptide of the invention, one skilled in the art will typically change one or more of the codons of the encoding DNA sequence according to Table A below.

TABLE A

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated that various changes may be made in the peptide sequences of the disclosed compositions, or corresponding DNA sequences which encode said peptides without appreciable loss of their utility.

In making such changes, the hydropathic index of amino acids may be considered. The importance of the hydropathic amino acid index in conferring interactive biologic function on a protein is generally understood in the art (Kyte & Doolittle, 1982, incorporated herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte & Doolittle, 1982). These values are: isoleucine (+4.5); valine (+4.2); leucine (+3.8); phenylalanine (+2.8); cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those within ±1 are particularly preferred, and those within ±0.5 are even more particularly preferred.

It is also understood in the art that the substitution of like amino acids can be made effectively on the basis of hydrophilicity. U.S. Pat. No. 4,554,101 (specifically incorporated herein by reference in its entirety), states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

Amino acid substitutions may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

A variant may also, or alternatively, contain non-conservative changes. In a preferred embodiment, variant polypeptides differ from a native sequence by substitution, deletion or addition of fewer than about 10, 9, 8, 7, 6, 5, 4, 3, 2 amino acids, or even 1 amino acid. Variants may also (or alternatively) be modified by, for example, the deletion or addition of amino acids that have minimal influence on the immunogenicity, secondary structure, enzymatic activity, and/or hydropathic nature of the polypeptide.

In certain embodiments, variants of the DSSHAFTLDELR (SEQ ID NO:13) can be based on the sequence of p97 sequences from other organisms, as shown in Table B below. Variant amino acids relative to the human sequence are underlined.

TABLE B

| Common Name | Species | Protein Name | % Identity | Sequence | SEQ ID NO: |
|---|---|---|---|---|---|
| Human | Homo Sapien | Melanotransferrin | 100% | DSSHAFTLDELR | 13 |
| Black-capped squirrel monkey | Saimiri boliviensis boliviensis | Melanotransferrin | 100% | DSSHAFTLDELR | 13 |
| Bonobo | Pan paniscus | Melanotransferrin | 100% | DSSHAFTLDELR | 13 |
| Chimpanzee | Pan troglodytes | Melanotransferrin | 100% | DSSHAFTLDELR | 13 |
| Crab-eating macaque | Macaca fascicularis | hypothetical protein | 100% | DSSHAFTLDELR | 13 |

TABLE B-continued

| Common Name | Species | Protein Name | % Identity | Sequence | SEQ ID NO: |
|---|---|---|---|---|---|
| Northern white-cheeked gibbon | Nomascus leucogenys | Melanotransferrin | 100% | DSSHAFTLDELR | 13 |
| Olive baboon | Papio anubis | Melanotransferrin | 100% | DSSHAFTLDELR | 13 |
| Rhesus macaque | Macaca mulatta | hypothetical protein | 100% | DSSHAFTLDELR | 13 |
| Rhesus macaque | Macaca mulatta | hypothetical protein | 100% | DSSHAFTLDELR | 13 |
| Western lowland gorilla | Gorilla gorilla gorilla | Melanotransferrin | 100% | DSSHAFTLDELR | 13 |
| White-tufted-ear marmoset | Callithrix jacchus | Melanotransferrin | 100% | DSSHAFTLDELR | 13 |
| Lesser Egyptian jerboa | Jaculus jaculus | Melanotransferrin | 92% | DSSDAFTLDELR | 93 |
| Northern greater galago | Otolemur garnettii | Melanotransferrin | 92% | DSSHSFTLDELR | 94 |
| Sumatran orangutan | Pongo abelii | Melanotransferrin | 92% | DSSDAFTLDELR | 95 |
| Thirteen-lined ground squirrel | Ictidomys tridecemlineatus | Melanotransferrin | 92% | DSSYAFTLDELR | 96 |
| white rhinoceros | Ceratotherium simum simum | Melanotransferrin | 92% | NSSHAFTLDELR | 97 |
| alpaca | Vicugna pacos | Melanotransferrin | 83% | NSSYAFTLDELR | 98 |
| American pika | Ochotona princeps | Melanotransferrin | 83% | DSSYAFPLDELR | 99 |
| black flying fox | Pteropus alecto | Melanotransferrin | 83% | NSSYAFTLDELR | 100 |
| bottlenosed dolphin | Tursiops truncatus | Melanotransferrin | 83% | NSSYAFTLDELR | 101 |
| Chinese tree shrew | Tupaia chinensis | Melanotransferrin | 83% | DSTHAFTVDELR | 102 |
| Chiru | Pantholops hodgsonii | Melanotransferrin | 83% | NSSYAFTLDELR | 103 |
| Domestic cat | Felis catus | Melanotransferrin | 83% | NSSYAFTLDELR | 104 |
| Domestic cattle | Bos taurus | Melanotransferrin | 83% | NSSYAFTLDELR | 105 |
| Domestic ferret | Mustela putorius furo | Melanotransferrin | 83% | NSSYAFTLDELR | 106 |
| Giant panda | Ailuropoda Melanoleuca | Melanotransferrin | 83% | NSSYAFTLDELR | 107 |
| Goat | Capra hircus | Melanotransferrin | 83% | NSSYAFTLDELR | 108 |
| House mouse | Mus musculus | Melanotransferrin | 83% | DSSYSFTLDELR | 109 |

TABLE B-continued

| Common Name | Species | Protein Name | % Identity | Sequence | SEQ ID NO: |
|---|---|---|---|---|---|
| Killer whale | Orcinus orca | Melanotransferrin | 83% | NSSNAFTLDELR | 110 |
| Long-tailed chinchilla | Chinchilla lanigera | Melanotransferrin | 83% | DSSSAFTLNELR | 111 |
| Nine-banded armadillo | Dasypus novemcinctus | Melanotransferrin | 83% | DSSYAFTLDELW | 112 |
| Norway rat | Rattus norvegicus | Melanotransferrin | 83% | DSSYSFTLDELR | 113 |
| Pacific walrus | Odobenus rosmarus divergens | Melanotransferrin | 83% | NSSSAFTLDELR | 114 |
| Prairie vole | Microtus ochrogaster | Melanotransferrin | 83% | DSSYSFTLDELR | 115 |
| Sheep | Ovis aries | Melanotransferrin | 83% | NSSYAFTLDELR | 116 |
| Weddell seal | Leptonychotes weddellii | Melanotransferrin | 83% | NSSYAFTLDELR | 117 |
| Wild Bactrian camel | Camelus ferus | Melanotransferrin | 83% | NSSYAFTLDELR | 118 |
| Wild boar | Sus scrofa | Melanotransferrin | 83% | NSSYAFTLDELR | 119 |
| Yak | Bos mutus | Melanotransferrin | 83% | NSSYAFTLDELR | 120 |
| (Fungus) | Cyphellophora europaea | hypothetical protein | 75% | ATSHAITLDELR | 121 |
| African savanna elephant | Loxodonta africana | Melanotransferrin | 75% | NSSYAFTMDELR | 122 |
| Chinese hamster | Cricetulus griseus | Melanotransferrin | 75% | DRSYSFTLDELR | 123 |
| Common rabbit | Oryctolagus cuniculus | Melanotransferrin | 75% | DSAYAFTVDELR | 124 |
| Degu | Octodon degus | Melanotransferrin | 75% | DSSSAFNLNELR | 125 |
| Domestic Dog | Canis lupus familiaris | Melanotransferrin | 75% | NSSDAFSLDELR | 126 |
| Domestic guinea pig | Cavia porcellus | Melanotransferrin | 75% | DSSSAFSLNELR | 127 |
| European shrew | Sorex araneus | Melanotransferrin | 75% | NSSDAFSLDELR | 128 |
| Florida manatee | Trichechus manatus latirostris | Melanotransferrin | 75% | NSSYAFTMDELR | 129 |
| Golden hamster | Mesocricetus auratus | Melanotransferrin | 75% | DRSYSFTLDELR | 130 |
| Gray short-tailed opossum | Monodelphis domestics | Melanotransferrin | 75% | NSSYSFTLDELR | 131 |
| Horse | Equus caballus | Melanotransferrin | 75% | NSSYAFTVDELR | 132 |
| Small Madagascar hedgehog | Echinops telfairi | Melanotransferrin | 75% | NSSYAFTVDELR | 133 |
| Star-nosed mole | Condylura cristata | Melanotransferrin | 75% | NSSYAFSLDELR | 134 |

TABLE B-continued

| Common Name | Species | Protein Name | % Identity | Sequence | SEQ ID NO: |
|---|---|---|---|---|---|
| Human | *Homo sapien* | Transferrin | 33% | SASD_LTWDNLK | 135 |
| Human | *Homo sapien* | Lactoferrin | 17% | _SDTSLTWNSVK | 136 |

Hence, in certain embodiments, the p97 peptide comprises, consists, or consists essentially of a sequence in Table B. In specific aspects, the p97 peptide retains the short alpha-helix (LDEL) at the C-terminus of the DSSHAFTLDELR (SEQ ID NO:13) peptide.

In certain embodiments, a polypeptide sequence is about, at least about, or up to about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700. 700, 710, 720, 730, 740, 750, 760, 770, 780, 790, 800. 800, 810, 820, 830, 840, 850, 860, 870, 880, 890, 900, 900, 910, 920, 930, 940, 950, 960, 970, 980, 990, 1000 or more contiguous amino acids in length, including all integers in between, and which may comprise all or a portion of a reference sequence (see, e.g., Sequence Listing, Tables 1-7, Table B, FIGS. 2-6 and 9).

In other specific embodiments, a polypeptide sequence consists of about or no more than about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800. 800, 810, 820, 830, 840, 850, 860, 870, 880, 890, 900, 900, 910, 920, 930, 940, 950, 960, 970, 980, 990, 1000 or more contiguous amino acids, including all integers in between, and which may comprise all or a portion of a reference sequence (see, e.g., Sequence Listing, Tables 1-7, Table B, FIGS. 2-6 and 9).

In still other specific embodiments, a polypeptide sequence is about 10-1000, 10-900, 10-800, 10-700, 10-600, 10-500, 10-400, 10-300, 10-200, 10-100, 10-50, 10-40, 10-30, 10-20, 20-1000, 20-900, 20-800, 20-700, 20-600, 20-500, 20-400, 20-300, 20-200, 20-100, 20-50, 20-40, 20-30, 50-1000, 50-900, 50-800, 50-700, 50-600, 50-500, 50-400, 50-300, 50-200, 50-100, 100-1000, 100-900, 100-800, 100-700, 100-600, 100-500, 100-400, 100-300, 100-200, 200-1000, 200-900, 200-800, 200-700, 200-600, 200-500, 200-400, or 200-300 contiguous amino acids, including all ranges in between, and comprises all or a portion of a reference sequence. In certain embodiments, the C-terminal or N-terminal region of any reference polypeptide may be truncated by about 1, 2, 3, 4, 5, 6, 7, 8, 9, 10, 15, 20, 25, 30, 35, 40, 45, 50, 60, 70, 80, 90, 100, 110, 120, 130, 140, 150, 160, 170, 180, 190, 200, 250, 300, 350, 400, 450, 500, 550, 600, 650, 700, 750, or 800 or more amino acids, or by about 10-50, 20-50, 50-100, 100-150, 150-200, 200-250, 250-300, 300-350, 350-400, 400-450, 450-500, 500-550, 550-600, 600-650, 650-700, 700-750, 750-800 or more amino acids, including all integers and ranges in between (e.g., 101, 102, 103, 104, 105), so long as the truncated polypeptide retains the binding properties and/or activity of the reference polypeptide. Typically, the biologically-active fragment has no less than about 1%, about 5%, about 10%, about 25%, or about 50% of an activity of the biologically-active reference polypeptide from which it is derived.

In general, variants will display at least about 30%, 40%, 50%, 55%, 60%, 65%, 70%, 75%, 80%, 85%, 90%, 91%, 92%, 93%, 94%, 95%, 96%, 97%, 98%, 99% similarity or sequence identity or sequence homology to a reference polypeptide sequence. Moreover, sequences differing from the native or parent sequences by the addition (e.g., C-terminal addition, N-terminal addition, both), deletion, truncation, insertion, or substitution of about 1, 2, 3, 4, 5, 6, 7, 8, 9, 10, 11, 12, 13, 14, 15, 16, 17, 18, 19, 20, 30, 40, 50, 60, 70, 80, 90, 100 or more amino acids but which retain the properties or activities of a parent or reference polypeptide sequence are contemplated.

In some embodiments, variant polypeptides differ from reference sequence by at least one but by less than 50, 40, 30, 20, 15, 10, 8, 6, 5, 4, 3 or 2 amino acid residue(s). In other embodiments, variant polypeptides differ from a reference sequence by at least 1% but less than 20%, 15%, 10% or 5% of the residues. (If this comparison requires alignment, the sequences should be aligned for maximum similarity. "Looped" out sequences from deletions or insertions, or mismatches, are considered differences.)

Calculations of sequence similarity or sequence identity between sequences (the terms are used interchangeably herein) are performed as follows. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In certain embodiments, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position.

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch, (*J. Mol. Biol.* 48: 444-453, 1970) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller (*Cabios*. 4:11-17, 1989) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al., (1990, *J. Mol. Biol*, 215: 403-10). BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (*Nucleic Acids Res*. 25: 3389-3402, 1997). When utilizing BLAST and Gapped BLAST programs, the default parameters of the respective programs (e.g., XBLAST and NBLAST) can be used.

In one embodiment, as noted above, polynucleotides and/or polypeptides can be evaluated using a BLAST alignment tool. A local alignment consists simply of a pair of sequence segments, one from each of the sequences being compared. A modification of Smith-Waterman or Sellers algorithms will find all segment pairs whose scores cannot be improved by extension or trimming, called high-scoring segment pairs (HSPs). The results of the BLAST alignments include statistical measures to indicate the likelihood that the BLAST score can be expected from chance alone.

The raw score, S, is calculated from the number of gaps and substitutions associated with each aligned sequence wherein higher similarity scores indicate a more significant alignment. Substitution scores are given by a look-up table (see PAM, BLOSUM).

Gap scores are typically calculated as the sum of G, the gap opening penalty and L, the gap extension penalty. For a gap of length n, the gap cost would be G+Ln. The choice of gap costs, G and L is empirical, but it is customary to choose a high value for G (10-15), e.g., 11, and a low value for L (1-2) e.g., 1.

The bit score, S', is derived from the raw alignment score S in which the statistical properties of the scoring system used have been taken into account. Bit scores are normalized with respect to the scoring system, therefore they can be used to compare alignment scores from different searches. The terms "bit score" and "similarity score" are used interchangeably. The bit score gives an indication of how good the alignment is; the higher the score, the better the alignment.

The E-Value, or expected value, describes the likelihood that a sequence with a similar score will occur in the database by chance. It is a prediction of the number of different alignments with scores equivalent to or better than S that are expected to occur in a database search by chance. The smaller the E-Value, the more significant the alignment. For example, an alignment having an E value of $e^{-117}$ means that a sequence with a similar score is very unlikely to occur simply by chance. Additionally, the expected score for aligning a random pair of amino acids is required to be negative, otherwise long alignments would tend to have high score independently of whether the segments aligned were related. Additionally, the BLAST algorithm uses an appropriate substitution matrix, nucleotide or amino acid and for gapped alignments uses gap creation and extension penalties. For example, BLAST alignment and comparison of polypeptide sequences are typically done using the BLOSUM62 matrix, a gap existence penalty of 11 and a gap extension penalty of 1.

In one embodiment, sequence similarity scores are reported from BLAST analyses done using the BLOSUM62 matrix, a gap existence penalty of 11 and a gap extension penalty of 1.

In a particular embodiment, sequence identity/similarity scores provided herein refer to the value obtained using GAP Version 10 (GCG, Accelrys, San Diego, Calif.) using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix (Henikoff and Henikoff, *PNAS USA*. 89:10915-10919, 1992). GAP uses the algorithm of Needleman and Wunsch (*J Mol Biol*. 48:443-453, 1970) to find the alignment of two complete sequences that maximizes the number of matches and minimizes the number of gaps.

In one particular embodiment, the variant polypeptide comprises an amino acid sequence that can be optimally aligned with a reference polypeptide sequence (see, e.g., Sequence Listing) to generate a BLAST bit scores or sequence similarity scores of at least about 50, 60, 70, 80, 90, 100, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, or more, including all integers and ranges in between, wherein the BLAST alignment used the BLOSUM62 matrix, a gap existence penalty of 11, and a gap extension penalty of 1.

As noted above, a reference polypeptide may be altered in various ways including amino acid substitutions, deletions, truncations, additions, and insertions. Methods for such manipulations are generally known in the art. For example, amino acid sequence variants of a reference polypeptide can be prepared by mutations in the DNA. Methods for mutagenesis and nucleotide sequence alterations are well known in the art. See, for example, Kunkel (*PNAS USA*. 82: 488-492, 1985); Kunkel et al., (*Methods in Enzymol*. 154: 367-382, 1987), U.S. Pat. No. 4,873,192, Watson, J. D. et al., ("Molecular Biology of the Gene," Fourth Edition, Benjamin/Cummings, Menlo Park, Calif., 1987) and the references cited therein. Guidance as to appropriate amino acid substitutions that do not affect biological activity of the protein of interest may be found in the model of Dayhoff et al., (1978) Atlas of Protein Sequence and Structure (Natl. Biomed. Res. Found., Washington, D.C.).

Methods for screening gene products of combinatorial libraries made by such modifications, and for screening cDNA libraries for gene products having a selected property are known in the art. Such methods are adaptable for rapid screening of the gene libraries generated by combinatorial mutagenesis of reference polypeptides. As one example, recursive ensemble mutagenesis (REM), a technique which enhances the frequency of functional mutants in the libraries, can be used in combination with the screening assays to identify polypeptide variants (Arkin and Yourvan, *PNAS USA* 89: 7811-7815, 1992; Delgrave et al., *Protein Engineering.* 6: 327-331, 1993).

Exemplary Methods for Conjugation.

Conjugation or coupling of a p97 polypeptide sequence to an agent of interest can be carried out using standard chemical, biochemical and/or molecular techniques. Indeed, it will be apparent how to make a p97 conjugate in light of the present disclosure using available art-recognized methodologies. Of course, it will generally be preferred when coupling the primary components of a p97 conjugate of the present invention that the techniques employed and the resulting linking chemistries do not substantially disturb the desired functionality or activity of the individual components of the conjugate.

The particular coupling chemistry employed will depend upon the structure of the biologically active agent (e.g., small molecule, polypeptide), the potential presence of multiple functional groups within the biologically active agent, the need for protection/deprotection steps, chemical stability of the agent, and the like, and will be readily determined by one skilled in the art. Illustrative coupling chemistry useful for preparing the p97 conjugates of the invention can be found, for example, in Wong (1991), "Chemistry of Protein Conjugation and Crosslinking", CRC Press, Boca Raton, Fla.; and Brinkley "A Brief Survey of Methods for Preparing Protein Conjugates with Dyes, Haptens, and Crosslinking Reagents," in *Bioconjug. Chem.*, 3:2013, 1992. Preferably, the binding ability and/or activity of the conjugate is not substantially reduced as a result of the conjugation technique employed, for example, relative to the unconjugated agent or the unconjugated p97 polypeptide.

In certain embodiments, a p97 polypeptide sequence may be coupled to an agent of interest either directly or indirectly. A direct reaction between a p97 polypeptide sequence and an agent of interest is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to indirectly couple a p97 polypeptide sequence and an agent of interest via a linker group, including non-peptide linkers and peptide linkers. A linker group can also function as a spacer to distance an agent of interest from the p97 polypeptide sequence in order to avoid interference with binding capabilities, targeting capabilities or other functionalities. A linker group can also serve to increase the chemical reactivity of a substituent on an agent, and thus increase the coupling efficiency. An increase in chemical reactivity may also facilitate the use of agents, or functional groups on agents, which otherwise would not be possible. The selection of releasable or stable linkers can also be employed to alter the pharmacokinetics of a p97 conjugate and attached agent of interest. Illustrative linking groups include, for example, disulfide groups, thioether groups, acid labile groups, photolabile groups, peptidase labile groups and esterase labile groups. In other illustrative embodiments, the conjugates include linking groups such as those disclosed in U.S. Pat. No. 5,208,020 or EP Patent 0 425 235 B1, and Chari et al., *Cancer Research.* 52: 127-131, 1992. Additional exemplary linkers are described below.

In some embodiments, it may be desirable to couple more than one p97 polypeptide sequence to an agent, or vice versa. For example, in certain embodiments, multiple p97 polypeptide sequences are coupled to one agent, or alternatively, one or more p97 polypeptides are conjugated to multiple agents. The p97 polypeptide sequences can be the same or different. Regardless of the particular embodiment, conjugates containing multiple p97 polypeptide sequences may be prepared in a variety of ways. For example, more than one polypeptide may be coupled directly to an agent, or linkers that provide multiple sites for attachment can be used. Any of a variety of known heterobifunctional crosslinking strategies can be employed for making conjugates of the invention. It will be understood that many of these embodiments can be achieved by controlling the stoichiometries of the materials used during the conjugation/crosslinking procedure.

In certain exemplary embodiments, a reaction between an agent comprising a succinimidyl ester functional group and a p97 polypeptide comprising an amino group forms an amide linkage; a reaction between an agent comprising a oxycarbonylimidizaole functional group and a P97 polypeptide comprising an amino group forms an carbamate linkage; a reaction between an agent comprising a p-nitrophenyl carbonate functional group and a P97 polypeptide comprising an amino group forms an carbamate linkage; a reaction between an agent comprising a trichlorophenyl carbonate functional group and a P97 polypeptide comprising an amino group forms an carbamate linkage; a reaction between an agent comprising a thio ester functional group and a P97 polypeptide comprising an n-terminal amino group forms an amide linkage; a reaction between an agent comprising a proprionaldehyde functional group and a P97 polypeptide comprising an amino group forms a secondary amine linkage.

In some exemplary embodiments, a reaction between an agent comprising a butyraldehyde functional group and a P97 polypeptide comprising an amino group forms a secondary amine linkage; a reaction between an agent comprising an acetal functional group and a P97 polypeptide comprising an amino group forms a secondary amine linkage; a reaction between an agent comprising a piperidone functional group and a P97 polypeptide comprising an amino group forms a secondary amine linkage; a reaction between an agent comprising a methylketone functional group and a P97 polypeptide comprising an amino group forms a secondary amine linkage; a reaction between an agent comprising a tresylate functional group and a P97 polypeptide comprising an amino group forms a secondary amine linkage; a reaction between an agent comprising a maleimide functional group and a P97 polypeptide comprising an amino group forms a secondary amine linkage; a reaction between an agent comprising a aldehyde functional group and a P97 polypeptide comprising an amino group forms a secondary amine linkage; and a reaction between an agent comprising a hydrazine functional group and a P97 polypeptide comprising an carboxylic acid group forms a secondary amine linkage.

In particular exemplary embodiments, a reaction between an agent comprising a maleimide functional group and a P97 polypeptide comprising a thiol group forms a thio ether linkage; a reaction between an agent comprising a vinyl sulfone functional group and a P97 polypeptide comprising a thiol group forms a thio ether linkage; a reaction between an agent comprising a thiol functional group and a P97 polypeptide comprising a thiol group forms a di-sulfide linkage; a reaction between an agent comprising a orthopyridyl disulfide functional group and a P97 polypeptide comprising a thiol group forms a di-sulfide linkage; and a reaction between an agent comprising an iodoacetamide functional group and a P97 polypeptide comprising a thiol group forms a thio ether linkage.

In a specific embodiment, an amine-to-sulfhydryl crosslinker is used for preparing a conjugate. In one preferred embodiment, for example, the crosslinker is succinimidyl-4-(N-maleimidomethyl)cyclohexane-1-carboxylate (SMCC) (Thermo Scientific), which is a sulfhydryl crosslinker containing NHS-ester and maleimide reactive groups at opposite ends of a medium-length cyclohexane-stabilized spacer arm (8.3 angstroms). SMCC is a non-cleavable and membrane permeable crosslinker that can be used to create sulfhydryl-reactive, maleimide-activated agents (e.g., polypeptides, antibodies) for subsequent reaction with p97 polypeptide sequences. NHS esters react with primary amines at pH 7-9 to form stable amide bonds. Maleimides react with sulfhydryl groups at pH 6.5-7.5 to form stable thioether bonds. Thus, the amine reactive NHS ester of SMCC crosslinks rapidly with primary amines of an agent and the resulting sulfhydryl-reactive maleimide group is then available to react with cysteine residues of p97 to yield specific conjugates of interest.

In certain specific embodiments, the p97 polypeptide sequence is modified to contain exposed sulfhydryl groups to facilitate crosslinking, e.g., to facilitate crosslinking to a maleimide-activated agent. In a more specific embodiment, the p97 polypeptide sequence is modified with a reagent which modifies primary amines to add protected thiol sulfhydryl groups. In an even more specific embodiment, the reagent N-succinimidyl-S-acetylthioacetate (SATA) (Thermo Scientific) is used to produce thiolated p97 polypeptides.

In other specific embodiments, a maleimide-activated agent is reacted under suitable conditions with thiolated p97 polypeptides to produce a conjugate of the present invention. It will be understood that by manipulating the ratios of SMCC, SATA, agent, and p97 polypeptide in these reactions it is possible to produce conjugates having differing stoichiometries, molecular weights and properties.

In still other illustrative embodiments, conjugates are made using bifunctional protein coupling agents such as N-succinimidyl-3-(2-pyridyldithio)propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particular coupling agents include N-succinimidyl-3-(2-pyridyldithio) propionate (SPDP) (Carlsson et al., *Biochem. J.* 173:723-737 [1978]) and N-succinimidyl-4-(2-pyridylthio)pentanoate (SPP) to provide for a disulfide linkage.

The specific crosslinking strategies discussed herein are but a few of many examples of suitable conjugation strategies that may be employed in producing conjugates of the invention. It will be evident to those skilled in the art that a variety of other bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Particular embodiments may employ one or more aldehyde tags to facilitate conjugation between a p97 polypeptide and an agent (see U.S. Pat. Nos. 8,097,701 and 7,985,783, incorporated by reference). Here, enzymatic modification at a sulfatase motif of the aldehyde tag through action of a formylglycine generating enzyme (FGE) generates a formylglycine (FGly) residue. The aldehyde moiety of the FGly residue can then be exploited as a chemical handle for site-specific attachment of a moiety of interest to the polypeptide. In some aspects, the moiety of interest is a small molecule, peptoid, aptamer, or peptide mimetic. In some aspects, the moiety of interest is another polypeptide, such as an antibody.

Particular embodiments thus include a p97 polypeptide or polypeptide agent that comprises 1, 2, 3, 4, 5, 6, 7, 8, 9, 10 or more heterologous sulfatase motifs, where the motif comprises the following structure:

$$X_1Z_1X_2Z_2X_3 \quad \text{(SEQ ID NO: 19)}$$

where $Z_1$ is cysteine or serine; $Z_2$ is a proline or alanine residue; $X_1$ is present or absent and, when present, is any amino acid, where $X_1$ is preferably present when the heterologous sulfatase motif is at an N-terminus of the aldehyde tagged polypeptide; and $X_2$ and $X_3$ are each independently any amino acid.

Polypeptides with the above-described motif can be modified by an FGE enzyme to generate a motif having a FGly residue, which, as noted above, can then be used for site-specific attachment of an agent, such as a second polypeptide, for instance, via a linker moiety. Such modifications can be performed, for example, by expressing the sulfatase motif-containing polypeptide (e.g., p97, antibody) in a mammalian, yeast, or bacterial cell that expresses an FGE enzyme or by in vitro modification of isolated polypeptide with an isolated FGE enzyme (see Wu et al., *PNAS.* 106:3000-3005, 2009; Rush and Bertozzi, *J. Am Chem Soc.* 130:12240-1, 2008; and Carlson et al., *J Biol Chem.* 283:20117-25, 2008).

Hence, some embodiments include a p97 polypeptide or polypeptide agent (e.g., antibody) that comprises 1, 2, 3, 4, 5, 6, 7, 8, 9, 10 or more heterologous sulfatase motifs having a formylglycine residue, where the motif comprises the following structure:

$$X_1(FGly)X_2Z_2X_3 \quad \text{(SEQ ID NO: 20)}$$

where FGly is a formylglycine residue; $Z_2$ is a proline or alanine residue; $X_1$ is present or absent and, when present, is any amino acid, where $X_1$ is preferably present when the heterologous sulfatase motif is at an N-terminus of the aldehyde tagged polypeptide; and $X_2$ and $X_3$ are each independently any amino acid.

In particular embodiments, $X_1$, $X_2$, and $X_3$ are each independently an aliphatic amino acid, a sulfur-containing amino acid or a polar, uncharged amino acid. For instance, $X_1$ can be L, M, V, S or T; and $X_2$, and/or $X_3$ can be independently S, T, A, V, G or C.

In some embodiments, the heterologous sulfatase motif(s) can be (a) less than 16 amino acid residues in length, including about 4, 5, 6, 7, 8, 9, 10, 11, 12, 13, 14, or 15 residues in length, (b) positioned at the N-terminus of the polypeptide, (c) positioned at the C-terminus of the polypeptide, (d) positioned at an internal site of an amino acid sequence native to the polypeptide, (e) positioned in a terminal loop of the polypeptide, (f) positioned at a site of post-translational modification of the polypeptide (e.g., glycosylation site), or any combination thereof.

Some embodiments relate to conjugates of (i) a sulfatase motif (or aldehyde tag)-containing p97 polypeptide, and (ii) an agent (A) such as small molecule that is functionalized with an aldehyde reactive group, where (i) and (ii) are covalently linked via the FGly residue of the sulfatase motif and the aldehyde reactive group. Such conjugates can have one of the following general structures:

p97(FGly)-$R_1$-A where $R_1$ is at least one aldehyde reactive linkage; and FGly is a formylglycine residue within a heterologous sulfatase motif.

Some embodiments relate to conjugates of (i) a sulfatase motif (or aldehyde tag)-containing p97 polypeptide, and (ii) a polypeptide agent (pA) that is functionalized with an aldehyde reactive group, or vice versa, where (i) and (ii) are covalently linked via the FGly residue of the sulfatase motif and the aldehyde reactive group. Such conjugates can have one of the following general structures:

p97(FGly)-$R_1$-pA or p97-$R_1$-(FGly)pA where $R_1$ is at least one aldehyde reactive linkage; and FGly is a formylglycine residue within a heterologous sulfatase motif.

The agent or non-aldehyde tag-containing polypeptide (e.g., antibody, p97 polypeptide) can be functionalized with one or more aldehyde reactive groups such as aminooxy, hydrazide, and thiosemicarbazide, and then covalently linked to the aldehyde tag-containing polypeptide via the at least one FGly residue, to form an aldehyde reactive linkage. The attachment of an aminooxy functionalized agent (or non-aldehyde tag-containing polypeptide) creates an oxime linkage between the FGly residue and the functionalized agent (or non-aldehyde tag-containing polypeptide); attachment of a hydrazide-functionalized agent (or non-aldehyde tag-containing polypeptide) creates a hydrazine linkage between the FGly residue and the functionalized agent (or non-aldehyde tag-containing polypeptide); and attachment of a thiosemicarbazide-functionalized agent (or non-aldehyde tag-containing polypeptide) creates a hydrazine carbothiamide linkage between the FGly residue and the functionalized agent (or non-aldehyde tag-containing polypeptide). Hence, in these and related embodiments, $R_1$ can be a linkage that comprises a Schiff base, such as an oxime linkage, a hydrazine linkage, or a hydrazine carbothiamide linkage.

Certain embodiments include conjugates of (i) a sulfatase motif (or aldehyde tag)-containing p97 polypeptide and (ii) a sulfatase motif (or aldehyde tag)-containing polypeptide agent (A), where (i) and (ii) are covalently linked via their respective FGly residues, optionally via a bi-functionalized linker moiety or group. For instance, certain p97 conjugates may comprise the following structure:

p97(FGly)-$R_1$-L-$R_2$-(FGly)A where $R_1$ and $R_2$ are the same or different aldehyde reactive linkage; L is a linker moiety, p97(FGly) is a aldehyde-tag containing p97 polypeptide, and (FGly)A is an aldehyde tag-containing agent, such as an antibody or other polypeptide-based agent.

Merely by way of illustration, in some embodiments, the at least one heterologous sulfatase motif can be at the C-terminus of the p97 polypeptide and the N-terminus of the polypeptide-based agent. In other embodiments, the at least one heterologous sulfatase motif can be at the N-terminus of the p97 polypeptide and the C-terminus of the polypeptide-based agent. In still other embodiments, the at least one heterologous sulfatase motif can be at the N-terminus of the p97 polypeptide and the N-terminus of the polypeptide-based agent. In further embodiments, the at least one heterologous sulfatase motif can be at the C-terminus of the p97 polypeptide an the C-terminus of the polypeptide-based agent. As noted above, the at least one heterologous motif can be at an internal position in the p97 polypeptide and/or the polypeptide-based agent. Persons skilled in the art will recognize that other combinations are possible.

The aldehyde reactive linkages of $R_1$ and $R_2$ can be independently formed by any aldehyde reactive group that will form a covalent bond between (i) the formylglycine (FGly) residue of the aldehyde tag and (ii) a linker moiety that is functionalized with said aldehyde reactive group (e.g., a bi-functionalized linker with two aldehyde reactive groups, which can be the same or different). Examples of aldehyde reactive groups include aminooxy, hydrazide, and thiosemicarbazide groups, which will form Schiff-base containing linkages with a FGly residue, including oxime linkages, hydrazine linkages, and hydrazine carbothiamide linkages, respectively. Hence, $R_1$ and $R_2$ can be independently a linkage that comprises a Schiff base, such as an oxime linkage, a hydrazine linkage, or a hydrazine carbothiamide linkage.

In some embodiments, the aldehyde tag-containing p97 polypeptide and the aldehyde tag-containing agent are linked (e.g., covalently linked) via a multi-functionalized linker (e.g., bi-functionalized linker), the latter being functionalized with the same or different aldehyde reactive group(s). In these and related embodiments, the aldehyde reactive groups allow the linker to form a covalent bridge between the p97 polypeptide and the agent via their respective FGly residues. Linker moieties include any moiety or chemical that can be functionalized and preferably bi- or multi-functionalized with one or more aldehyde reactive groups. Particular examples include peptides, water-soluble polymers, detectable entities, other therapeutic compounds (e.g., cytotoxic compounds), biotin/streptavidin moieties, and glycans (see Hudak et al., *J Am Chem Soc.* 133:16127-35, 2011). Specific examples of glycans (or glycosides) include aminooxy glycans, such as higher-order glycans composed of glycosyl N-pentenoyl hydroxamates intermediates (supra). Exemplary linkers are described herein, and can be functionalized with aldehyde reactive groups according to routine techniques in the art (see, e.g., Carrico et al., *Nat Chem Biol.* 3:321-322, 2007; and U.S. Pat. Nos. 8,097,701 and 7,985,783).

p97 conjugates can also be prepared by a various "click chemistry" techniques, including reactions that are modular, wide in scope, give very high yields, generate mainly inoffensive byproducts that can be removed by non-chromatographic methods, and can be stereospecific but not necessarily enantioselective (see Kolb et al., *Angew Chem Int Ed Engl.* 40:2004-2021, 2001). Particular examples include conjugation techniques that employ the Huisgen 1,3-dipolar cycloaddition of azides and alkynes, also referred to as "azide-alkyne cycloaddition" reactions (see Hein et al., *Pharm Res.* 25:2216-2230, 2008). Non-limiting examples of azide-alkyne cycloaddition reactions include copper-catalyzed azide-alkyne cycloaddition (CuAAC) reactions and ruthenium-catalyzed azide-alkyne cycloaddition (RuAAC) reactions.

CuAAC works over a broad temperature range, is insensitive to aqueous conditions and a pH range over 4 to 12, and tolerates a broad range of functional groups (see Himo et al, *J Am Chem Soc.* 127:210-216, 2005). The active Cu(I) catalyst can be generated, for example, from Cu(I) salts or Cu(II) salts using sodium ascorbate as the reducing agent. This reaction forms 1,4-substituted products, making it region-specific (see Hein et al., supra).

RuAAC utilizes pentamethylcyclopentadienyl ruthenium chloride [Cp*RuCl] complexes that are able to catalyze the cycloaddition of azides to terminal alkynes, regioselectively leading to 1,5-disubstituted 1,2,3-triazoles (see Rasmussen et al., *Org. Lett.* 9:5337-5339, 2007). Further, and in contrast to CuAAC, RuAAC can also be used with internal alkynes to provide fully substituted 1,2,3-triazoles.

Certain embodiments thus include p97 polypeptides that comprise at least one unnatural amino acid with an azide side-chain or an alkyne side-chain, including internal and terminal unnatural amino acids (e.g., N-terminal, C-terminal). Certain of these p97 polypeptides can be formed by in vivo or in vitro (e.g., cell-free systems) incorporation of unnatural amino acids that contain azide side-chains or alkyne side-chains. Exemplary in vivo techniques include cell culture techniques, for instance, using modified *E. coli* (see Travis and Schultz, The *Journal of Biological Chemistry.* 285:11039-44, 2010; and Deiters and Schultz, *Bioorganic & Medicinal Chemistry Letters*. 15:1521-1524, 2005), and exemplary in vitro techniques include cell-free systems (see Bundy, *Bioconjug Chem.* 21:255-63, 2010).

In some embodiments, a p97 polypeptide that comprises at least one unnatural amino acid with an azide side-chain is conjugated by azide-alkyne cycloaddition to an agent (or linker) that comprises at least one alkyne group, such as a polypeptide agent that comprises at least one unnatural amino acid with an alkyne side-chain. In other embodiments, a p97 polypeptide that comprises at least one unnatural amino acid with an alkyne side-chain is conjugated by azide-alkyne cycloaddition to an agent (or linker) that comprises at least one azide group, such as a polypeptide agent that comprises at least one unnatural amino acid with an azide side-chain. Hence, certain embodiments include conjugates that comprise a p97 polypeptide covalently linked to an agent via a 1,2,3-triazole linkage.

Specific p97 conjugates can be formed by the following CuAAC-based or RuAAC-based reactions, to comprise the following respective structures (I) or (II).

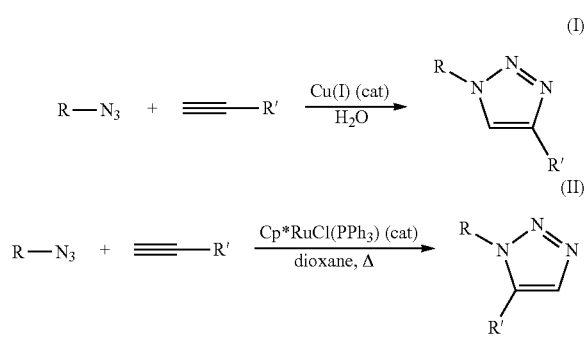

where R is a p97 polypeptide and R$^I$ is an agent of interest (or linker); or where R is an agent of interest (or linker) and R$^I$ is a p97 polypeptide.

In certain embodiments, the unnatural amino acid with the azide side-chain and/or the unnatural amino acid with alkyne side-chain are terminal amino acids (N-terminal, C-terminal). In certain embodiments, one or more of the unnatural amino acids are internal.

For instance, certain embodiments include a p97 polypeptide that comprises an N-terminal unnatural amino acid with an azide side-chain conjugated to an agent that comprises an alkyne group. Some embodiments, include a p97 polypeptide that comprises a C-terminal unnatural amino acid with an azide side-chain conjugated to an agent that comprises an alkyne group. Particular embodiments include a p97 polypeptide that comprises an N-terminal unnatural amino acid with an alkyne side-chain conjugated to an agent that comprises an azide side-group. Further embodiments include a p97 polypeptide that comprises an C-terminal unnatural amino acid with an alkyne side-chain conjugated to an agent that comprises an azide side-group. Some embodiments include a p97 polypeptide that comprises at least one internal unnatural amino acid with an azide side-chain conjugated to an agent that comprises an alkyne group. Additional embodiments include a p97 polypeptide that comprises at least one internal unnatural amino acid with an alkyne side-chain conjugated to an agent that comprises an azide side-group Particular embodiments include a p97 polypeptide that comprises an N-terminal unnatural amino acid with an azide side-chain conjugated to a polypeptide agent that comprises an N-terminal unnatural amino acid with an alkyne side-chain. Other embodiments include a p97 polypeptide that comprises a C-terminal unnatural amino acid with an azide side-chain conjugated to a polypeptide agent that comprises a C-terminal unnatural amino acid with an alkyne side-chain. Still other embodiments include a p97 polypeptide that comprises an N-terminal unnatural amino acid with an azide side-chain conjugated to a polypeptide agent that comprises a C-terminal unnatural amino acid with an alkyne side-chain. Further embodiments include a p97 polypeptide that comprises a C-terminal unnatural amino acid with an azide side-chain conjugated to a polypeptide agent that comprises an N-terminal unnatural amino acid with an alkyne side-chain.

Other embodiments include a p97 polypeptide that comprises an N-terminal unnatural amino acid with an alkyne side-chain conjugated to a polypeptide agent that comprises an N-terminal unnatural amino acid with an azide side-chain. Still further embodiments include a p97 polypeptide that comprises a C-terminal unnatural amino acid with an alkyne side-chain conjugated to a polypeptide agent that comprises a C-terminal unnatural amino acid with an azide side-chain. Additional embodiments include a p97 polypeptide that comprises an N-terminal unnatural amino acid with an alkyne side-chain conjugated to a polypeptide agent that comprises a C-terminal unnatural amino acid with an azide side-chain. Still further embodiments include a p97 polypeptide that comprises a C-terminal unnatural amino acid with an alkyne side-chain conjugated to a polypeptide agent that comprises an N-terminal unnatural amino acid with an azide side-chain.

Also included are methods of producing a p97 conjugate, comprising: (a) performing an azide-alkyne cycloaddition reaction between (i) a p97 polypeptide that comprises at least one unnatural amino acid with an azide side-chain and an agent that comprises at least one alkyne group (for instance, an unnatural amino acid with an alkyne side chain); or (ii) a p97 polypeptide that comprises at least one unnatural amino acid with an alkyne side-chain and an agent that comprises at least one azide group (for instance, an unnatural amino acid with an azide side-chain); and (b) isolating a p97 conjugate from the reaction, thereby producing a p97 conjugate.

In the case where the p97 conjugate is a fusion polypeptide, the fusion polypeptide may generally be prepared using standard techniques. Preferably, however, a fusion polypeptide is expressed as a recombinant polypeptide in an expression system, described herein and known in the art. Fusion polypeptides of the invention can contain one or multiple copies of a p97 polypeptide sequence and may contain one or multiple copies of a polypeptide-based agent of interest (e.g., antibody or antigen-binding fragment thereof), present in any desired arrangement.

For fusion proteins, DNA sequences encoding the p97 polypeptide, the polypeptide agent (e.g., antibody), and optionally peptide linker components may be assembled separately, and then ligated into an appropriate expression vector. The 3' end of the DNA sequence encoding one polypeptide component is ligated, with or without a peptide linker, to the 5' end of a DNA sequence encoding the other polypeptide component(s) so that the reading frames of the sequences are in phase. The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the most C-terminal polypeptide. This permits translation into a single fusion polypeptide that retains the biological activity of both component polypeptides.

Similar techniques, mainly the arrangement of regulatory elements such as promoters, stop codons, and transcription termination signals, can be applied to the recombinant production of non-fusion proteins, for instance, p97 polypeptides and polypeptide agents (e.g., antibody agents) for the production of non-fusion conjugates.

Polynucleotides and fusion polynucleotides of the invention can contain one or multiple copies of a nucleic acid encoding a p97 polypeptide sequence, and/or may contain one or multiple copies of a nucleic acid encoding a polypeptide agent.

In some embodiments, a nucleic acids encoding a subject p97 polypeptide, polypeptide agent, and/or p97-polypeptide fusion are introduced directly into a host cell, and the cell incubated under conditions sufficient to induce expression of the encoded polypeptide(s). The polypeptide sequences of this disclosure may be prepared using standard techniques well known to those of skill in the art in combination with the polypeptide and nucleic acid sequences provided herein.

Therefore, according to certain related embodiments, there is provided a recombinant host cell which comprises a polynucleotide or a fusion polynucleotide that encodes a polypeptide described herein. Expression of a p97 polypeptide, polypeptide agent, or p97-polypeptide agent fusion in the host cell may conveniently be achieved by culturing under appropriate conditions recombinant host cells containing the polynucleotide. Following production by expression, the polypeptide(s) may be isolated and/or purified using any suitable technique, and then used as desired.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary (CHO) cells, HeLa cells, baby hamster kidney cells, HEK-293 cells, NSO mouse melanoma cells and many others. A common, preferred bacterial host is E. coli. The expression of polypeptides in prokaryotic cells such as E. coli is well established in the art. For a review, see for example Pluckthun, A. Bio/Technology. 9:545-551 (1991). Expression in eukaryotic cells in culture is also available to those skilled in the art as an option for recombinant production of polypeptides (see Ref, Curr. Opinion Biotech. 4:573-576, 1993; and Trill et al., Curr. Opinion Biotech. 6:553-560, 1995.

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids, viral e.g. phage, or phagemid, as appropriate. For further details see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Current Protocols in Molecular Biology, Second Edition, Ausubel et al. eds., John Wiley & Sons, 1992, or subsequent updates thereto.

The term "host cell" is used to refer to a cell into which has been introduced, or which is capable of having introduced into it, a nucleic acid sequence encoding one or more of the polypeptides described herein, and which further expresses or is capable of expressing a selected gene of interest, such as a gene encoding any herein described polypeptide. The term includes the progeny of the parent cell, whether or not the progeny are identical in morphology or in genetic make-up to the original parent, so long as the selected gene is present. Host cells may be chosen for certain characteristics, for instance, the expression of a formylglycine generating enzyme (FGE) to convert a cysteine or serine residue within a sulfatase motif into a formylglycine (FGly) residue, or the expression of aminoacyl tRNA synthetase(s) that can incorporate unnatural amino acids into the polypeptide, including unnatural amino acids with an azide side-chain, alkyne side-chain, or other desired side-chain, to facilitate conjugation.

Accordingly there is also contemplated a method comprising introducing such nucleic acid(s) into a host cell. The introduction of nucleic acids may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage. The introduction may be followed by causing or allowing expression from the nucleic acid, e.g., by culturing host cells under conditions for expression of the gene. In one embodiment, the nucleic acid is integrated into the genome (e.g. chromosome) of the host cell. Integration may be promoted by inclusion of sequences which promote recombination with the genome, in accordance-with standard techniques.

The present invention also provides, in certain embodiments, a method which comprises using a nucleic acid construct described herein in an expression system in order to express a particular polypeptide, such as a p97 polypeptide, polypeptide agent, or p97-polypeptide agent fusion protein as described herein.

As noted above, certain p97 conjugates, such as fusion proteins, may employ one or more linker groups, including non-peptide linkers (e.g., non-proteinaceous linkers) and peptide linkers. Such linkers can be stable linkers or releasable linkers.

Exemplary non-peptide stable linkages include succinimide, propionic acid, carboxymethylate linkages, ethers, carbamates, amides, amines, carbamides, imides, aliphatic C—C bonds, thio ether linkages, thiocarbamates, thiocarbamides, and the like. Generally, a hydrolytically stable linkage is one that exhibits a rate of hydrolysis of less than about 1-2% to 5% per day under physiological conditions.

Exemplary non-peptide releasable linkages include carboxylate ester, phosphate ester, anhydride, acetal, ketal, acyloxyalkyl ether, imine, orthoester, thio ester, thiol ester, carbonate, and hydrazone linkages. Additional illustrative embodiments of hydrolytically unstable or weak linkages include, but are not limited to: —$O_2C$—$(CH_2)_b$—O—, where b is from 1 to 5, —O—$(CH_2)_b$—$CO_2$—$(CH_2)_c$—, where b is from 1 to 5 and c is from 2-5, —O—$(CH_2)_b$—$CO_2$—$(CH_2)_c$—O—, where b is from 1 to 5 and c is from 2-5, —$(CH_2)_b$—$OPO_3$—$(CH_2)_{b'}$—, where b is 1-5 and b' is 1-5, —C(O)—(NH—CHR—CO)$_a$—NH—CHR—, where a is 2 to 20 and R is a substituent found on an α-amino acid, —O—$(CH_2)_b$—$CO_2$—$CHCH_2$—$CH_2$—, where b is from 1-5, —O—$C_6H_4$—CH=N—$(CH_2)_b$—O—, where b is from 1-5, and —O—$(CH_2)_b$—$CH_2$—CH=N—$(CH_2)_b$—O—, where each b is independently from 1-5.

Other illustrative examples of releasable linkers can be benzyl elimination-based linkers, trialkyl lock-based linkers (or trialkyl lock lactonization based), bicine-based linkers, and acid labile linkers. Among the acid labile linkers can be disulfide bond, hydrazone-containing linkers and thiopropionate-containing linkers.

Also included are linkers that are releasable or cleavable during or upon internalization into a cell. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.). In one embodiment, an acid-labile linker may be used (*Cancer Research* 52:127-131, 1992; and U.S. Pat. No. 5,208,020).

In certain embodiments, "water soluble polymers" are used in a linker for coupling a p97 polypeptide sequence to an agent of interest. A "water-soluble polymer" refers to a polymer that is soluble in water and is usually substantially non-immunogenic, and usually has an atomic molecular weight greater than about 1,000 Daltons. Attachment of two polypeptides via a water-soluble polymer can be desirable as such modification(s) can increase the therapeutic index by increasing serum half-life, for instance, by increasing proteolytic stability and/or decreasing renal clearance. Additionally, attachment via of one or more polymers can reduce the immunogenicity of protein pharmaceuticals. Particular examples of water soluble polymers include polyethylene glycol, polypropylene glycol, polyoxyalkylenes, or copolymers of polyethylene glycol, polypropylene glycol, and the like.

In some embodiments, the water-soluble polymer has an effective hydrodynamic molecular weight of greater than about 10,000 Da, greater than about 20,000 to 500,000 Da, greater than about 40,000 Da to 300,000 Da, greater than about 50,000 Da to 70,000 Da, usually greater than about 60,000 Da. The "effective hydrodynamic molecular weight" refers to the effective water-solvated size of a polymer chain as determined by aqueous-based size exclusion chromatography (SEC). When the water-soluble polymer contains polymer chains having polyalkylene oxide repeat units, such as ethylene oxide repeat units, each chain can have an atomic molecular weight of between about 200 Da and about 80,000 Da, or between about 1,500 Da and about 42,000 Da, with 2,000 to about 20,000 Da being of particular interest. Linear, branched, and terminally charged water soluble polymers are also included.

Polymers useful as linkers between aldehyde tagged polypeptides can have a wide range of molecular weights, and polymer subunits. These subunits may include a biological polymer, a synthetic polymer, or a combination thereof. Examples of such water-soluble polymers include: dextran and dextran derivatives, including dextran sulfate, P-amino cross linked dextrin, and carboxymethyl dextrin, cellulose and cellulose derivatives, including methylcellulose and carboxymethyl cellulose, starch and dextrines, and derivatives and hydroylactes of starch, polyalklyene glycol and derivatives thereof, including polyethylene glycol (PEG), methoxypolyethylene glycol, polyethylene glycol homopolymers, polypropylene glycol homopolymers, copolymers of ethylene glycol with propylene glycol, wherein said homopolymers and copolymers are unsubstituted or substituted at one end with an alkyl group, heparin and fragments of heparin, polyvinyl alcohol and polyvinyl ethyl ethers, polyvinylpyrrolidone, aspartamide, and polyoxyethylated polyols, with the dextran and dextran derivatives, dextrine and dextrine derivatives. It will be appreciated that various derivatives of the specifically described water-soluble polymers are also included.

Water-soluble polymers are known in the art, particularly the polyalkylene oxide-based polymers such as polyethylene glycol "PEG" (see Poly(ethylene glycol) Chemistry: Biotechnical and Biomedical Applications, J. M. Harris, Ed., Plenum Press, New York, N.Y. (1992); and Poly(ethylene glycol) Chemistry and Biological Applications, J. M. Harris and S. Zalipsky, Eds., ACS (1997); and International Patent Applications: WO 90/13540, WO 92/00748, WO 92/16555, WO 94/04193, WO 94/14758, WO 94/17039, WO 94/18247, WO 94/28937, WO 95/11924, WO 96/00080, WO 96/23794, WO 98/07713, WO 98/41562, WO 98/48837, WO 99/30727, WO 99/32134, WO 99/33483, WO 99/53951, WO 01/26692, WO 95/13312, WO 96/21469, WO 97/03106, WO 99/45964, and U.S. Pat. Nos. 4,179,337; 5,075,046; 5,089,261; 5,100,992; 5,134,192; 5,166,309; 5,171,264; 5,213,891; 5,219,564; 5,275,838; 5,281,698; 5,298,643; 5,312,808; 5,321,095; 5,324,844; 5,349,001; 5,352,756; 5,405,877; 5,455,027; 5,446,090; 5,470,829; 5,478,805; 5,567,422; 5,605,976; 5,612,460; 5,614,549; 5,618,528; 5,672,662; 5,637,749; 5,643,575; 5,650,388; 5,681,567; 5,686,110; 5,730,990; 5,739,208; 5,756,593; 5,808,096; 5,824,778; 5,824,784; 5,840,900; 5,874,500; 5,880,131; 5,900,461; 5,902,588; 5,919,442; 5,919,455; 5,932,462; 5,965,119; 5,965,566; 5,985,263; 5,990,237; 6,011,042; 6,013,283; 6,077,939; 6,113,906; 6,127,355; 6,177,087; 6,180,095; 6,194,580; 6,214,966, incorporated by reference).

Exemplary polymers of interest include those containing a polyalkylene oxide, polyamide alkylene oxide, or derivatives thereof, including polyalkylene oxide and polyamide alkylene oxide comprising an ethylene oxide repeat unit of the formula —($CH_2$—$CH^2$—O)—. Further exemplary polymers of interest include a polyamide having a molecular weight greater than about 1,000 Daltons of the formula —[C(O)—X—C(O)—NH—Y—NH]$_n$— or —[NH—Y—NH—C(O)—X—C(O)]$_n$—, where X and Y are divalent radicals that may be the same or different and may be branched or linear, and n is a discrete integer from 2-100, usually from 2 to 50, and where either or both of X and Y comprises a biocompatible, substantially non-antigenic water-soluble repeat unit that may be linear or branched.

Further exemplary water-soluble repeat units comprise an ethylene oxide of the formula —($CH_2$—$CH_2$—O)— or —($CH_2$—$CH_2$—O)—. The number of such water-soluble repeat units can vary significantly, with the usual number of such units being from 2 to 500, 2 to 400, 2 to 300, 2 to 200, 2 to 100, and most usually 2 to 50. An exemplary embodiment is one in which one or both of X and Y is selected from: —(($CH_2$)$_{n1}$—($CH_2$—$CH_2$—O)$_{n2}$—($CH_2$)— or —(($CH_2$)$_{n1}$—(O—$CH_2$—$CH_2$)$_{n2}$—($CH_2$)$_{n1}$—), where n1 is 1 to 6, 1 to 5, 1 to 4 and most usually 1 to 3, and where n2 is 2 to 50, 2 to 25, 2 to 15, 2 to 10, 2 to 8, and most usually 2 to 5. A further exemplary embodiment is one in which X is —(CH$_2$—CH$_2$)—, and where Y is —(CH$_2$—CH$_2$—CH$_2$—O)$_3$—CH$_2$—CH$_2$—CH$_2$)— or —(CH$_2$—CH$_2$—CH$_2$—(O—CH$_2$—CH$_2$)$_3$—CH$_2$)—, among other variations.

In certain embodiments, a peptide linker sequence may be employed to separate or couple the components of a p97 conjugate. For instance, for polypeptide-polypeptide conjugates, peptide linkers can separate the components by a distance sufficient to ensure that each polypeptide folds into its secondary and tertiary structures. Such a peptide linker sequence may be incorporated into the conjugate (e.g., fusion protein) using standard techniques described herein and well-known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Amino acid sequences which may be usefully employed as linkers include those disclosed in Maratea et al., *Gene* 40:39-46, 1985; Murphy et al., *Proc. Natl. Acad. Sci. USA* 83:8258-8262, 1986; U.S. Pat. No. 4,935,233 and U.S. Pat. No. 4,751,180.

In certain illustrative embodiments, a peptide linker is between about 1 to 5 amino acids, between 5 to 10 amino acids, between 5 to 25 amino acids, between 5 to 50 amino acids, between 10 to 25 amino acids, between 10 to 50 amino acids, between 10 to 100 amino acids, or any intervening range of amino acids. In other illustrative embodiments, a peptide linker comprises about 1, 5, 10, 15, 20, 25, 30, 35, 40, 45, 50 or more amino acids in length. Particular linkers can have an overall amino acid length of about 1-200 amino acids, 1-150 amino acids, 1-100 amino acids, 1-90 amino acids, 1-80 amino acids, 1-70 amino acids, 1-60 amino acids, 1-50 amino acids, 1-40 amino acids, 1-30 amino acids, 1-20 amino acids, 1-10 amino acids, 1-5 amino acids, 1-4 amino acids, 1-3 amino acids, or about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100 or more amino acids.

A peptide linker may employ any one or more naturally-occurring amino acids, non-naturally occurring amino acid(s), amino acid analogs, and/or amino acid mimetics as described elsewhere herein and known in the art. Certain amino acid sequences which may be usefully employed as linkers include those disclosed in Maratea et al., *Gene* 40:39-46, 1985; Murphy et al., *PNAS USA*. 83:8258-8262, 1986; U.S. Pat. No. 4,935,233 and U.S. Pat. No. 4,751,180. Particular peptide linker sequences contain Gly, Ser, and/or Asn residues. Other near neutral amino acids, such as Thr and Ala may also be employed in the peptide linker sequence, if desired.

Certain exemplary linkers include Gly, Ser and/or Asn-containing linkers, as follows: [G]$_x$, [S]$_x$, [N]$_x$, [GS]$_x$, [GGS]$_x$, [GSS]$_x$, [GSGS]$_x$ (SEQ ID NO:21), [GGSG]$_x$ (SEQ ID NO:22), [GGGS]$_x$ (SEQ ID NO:23), [GGGGS]$_x$(SEQ ID NO:24), [GN]$_x$, [GGN]$_x$, [GNN]$_x$, [GNGN]$_x$(SEQ ID NO: 25), [GGNG]$_x$(SEQ ID NO:26), [GGGN]$_x$ (SEQ ID NO: 27), [GGGGN]$_x$ (SEQ ID NO: 28) linkers, where $_x$ is 1, 2, 3, 4, 5, 6, 7, 8, 9, 10, 11, 12, 13, 14, 15, 16, 17, 18, 19, or 20 or more.

Other combinations of these and related amino acids will be apparent to persons skilled in the art.

In specific embodiments, the linker sequence comprises a Gly3 linker sequence, which includes three glycine residues. In particular embodiments, flexible linkers can be rationally designed using a computer program capable of modeling both DNA-binding sites and the peptides themselves (Desjarlais & Berg, *PNAS*. 90:2256-2260, 1993; and *PNAS*. 91:11099-11103, 1994) or by phage display methods.

The peptide linkers may be physiologically stable or may include a releasable linker such as a physiologically degradable or enzymatically degradable linker (e.g., proteolytically cleavable linker). In certain embodiments, one or more releasable linkers can result in a shorter half-life and more rapid clearance of the conjugate. These and related embodiments can be used, for example, to enhance the solubility and blood circulation lifetime of p97 conjugates in the bloodstream, while also delivering an agent into the bloodstream (or across the BBB) that, subsequent to linker degradation, is substantially free of the p97 sequence. These aspects are especially useful in those cases where polypeptides or other agents, when permanently conjugated to a p97 sequence, demonstrate reduced activity. By using the linkers as provided herein, such antibodies can maintain their therapeutic activity when in conjugated form. In these and other ways, the properties of the p97 conjugates can be more effectively tailored to balance the bioactivity and circulating half-life of the antibodies over time.

Enzymatically degradable linkages suitable for use in particular embodiments of the present invention include, but are not limited to: an amino acid sequence cleaved by a serine protease such as thrombin, chymotrypsin, trypsin, elastase, kallikrein, or substilisin. Illustrative examples of thrombin-cleavable amino acid sequences include, but are not limited to: -Gly-Arg-Gly-Asp-(SEQ ID NO:29), -Gly-Gly-Arg-, -Gly-Arg-Gly-Asp-Asn-Pro-(SEQ ID NO: 30), -Gly-Arg-Gly-Asp-Ser-(SEQ ID NO:31), -Gly-Arg-Gly-Asp-Ser-Pro-Lys-(SEQ ID NO: 32), -Gly-Pro-Arg-, -Val-Pro-Arg-, and -Phe-Val-Arg-. Illustrative examples of elastase-cleavable amino acid sequences include, but are not limited to: -Ala-Ala-Ala-, -Ala-Ala-Pro-Val-(SEQ ID NO:33), -Ala-Ala-Pro-Leu-(SEQ ID NO: 34), -Ala-Ala-Pro-Phe-(SEQ ID NO:35), -Ala-Ala-Pro-Ala-(SEQ ID NO: 36), and -Ala-Tyr-Leu-Val-(SEQ ID NO:37).

Enzymatically degradable linkages suitable for use in particular embodiments of the present invention also include amino acid sequences that can be cleaved by a matrix metalloproteinase such as collagenase, stromelysin, and gelatinase. Illustrative examples of matrix metalloproteinase-cleavable amino acid sequences include, but are not limited to: -Gly-Pro-Y-Gly-Pro-Z-(SEQ ID NO: 38), -Gly-Pro-, Leu-Gly-Pro-Z-(SEQ ID NO: 39), -Gly-Pro-Ile-Gly-Pro-Z-(SEQ ID NO: 40), and -Ala-Pro-Gly-Leu-Z-(SEQ ID NO:41), where Y and Z are amino acids. Illustrative examples of collagenase-cleavable amino acid sequences include, but are not limited to: -Pro-Leu-Gly-Pro-D-Arg-Z-(SEQ ID NO: 42), -Pro-Leu-Gly-Leu-Leu-Gly-Z-(SEQ ID NO: 43), -Pro-Gln-Gly-Ile-Ala-Gly-Trp-(SEQ ID NO: 44), -Pro-Leu-Gly-Cys(Me)-His-(SEQ ID NO:45), -Pro-Leu-Gly-Leu-Tyr-Ala-(SEQ ID NO: 46), -Pro-Leu-Ala-Leu-Trp-Ala-Arg-(SEQ ID NO:47), and -Pro-Leu-Ala-Tyr-Trp-Ala-Arg-(SEQ ID NO: 48), where Z is an amino acid. An illustrative example of a stromelysin-cleavable amino acid sequence is -Pro-Tyr-Ala-Tyr-Tyr-Met-Arg-(SEQ ID NO: 49); and an example of a gelatinase-cleavable amino acid sequence is -Pro-Leu-Gly-Met-Tyr-Ser-Arg-(SEQ ID NO: 50).

Enzymatically degradable linkages suitable for use in particular embodiments of the present invention also include amino acid sequences that can be cleaved by an angiotensin converting enzyme, such as, for example, -Asp-Lys-Pro-, -Gly-Asp-Lys-Pro-(SEQ ID NO: 51), and -Gly-Ser-Asp-Lys-Pro-(SEQ ID NO: 52).

Enzymatically degradable linkages suitable for use in particular embodiments of the present invention also include amino acid sequences that can be degraded by cathepsin B, such as, for example, -Val-Cit-, -Ala-Leu-Ala-Leu- (SEQ ID NO:53), -Gly-Phe-Leu-Gly- (SEQ ID NO: 54) and -Phe-Lys-.

In certain embodiments, however, any one or more of the non-peptide or peptide linkers are optional. For instance, linker sequences may not required in a fusion protein where the first and second polypeptides have non-essential N-terminal and/or C-terminal amino acid regions that can be used to separate the functional domains and prevent steric interference.

The functional properties of the p97 polypeptides and p97 polypeptide conjugates described herein may be assessed using a variety of methods known to the skilled person, including, e.g., affinity/binding assays (for example, surface plasmon resonance, competitive inhibition assays); cytotoxicity assays, cell viability assays, cell proliferation or differentiation assays, cancer cell and/or tumor growth inhibition using in vitro or in vivo models. For instance, the conjugates described herein may be tested for effects on receptor internalization, in vitro and in vivo efficacy, etc., including the rate of transport across the blood brain barrier. Such assays may be performed using well-established protocols known to the skilled person (see e.g., Current Protocols in Molecular Biology (Greene Publ. Assoc. Inc. & John Wiley & Sons, Inc., NY, N.Y.); Current Protocols in Immunology (Edited by: John E. Coligan, Ada M. Kruisbeek, David H. Margulies, Ethan M. Shevach, Warren Strober 2001 John Wiley & Sons, NY, N.Y.); or commercially available kits.

Methods of Use and Pharmaceutical Compositions

Certain embodiments of the present invention relate to methods of using the compositions of p97 polypeptides and p97 conjugates described herein. Examples of such methods include methods of treatment and methods of diagnosis, including for instance, the use of p97 conjugates for medical imaging of certain organs/tissues, such as those of the nervous system. Specific embodiments include methods of diagnosing and/or treating disorders or conditions of the central nervous system (CNS), or disorders or conditions having a CNS component.

Accordingly, certain embodiments include methods of treating a subject in need thereof, comprising administering a composition that comprises a p97 conjugate described herein. Also included are methods of delivering an agent to the nervous system (e.g., central nervous system tissues) of a subject, comprising administering a composition that comprises a p97 conjugate described herein. In certain of these and related embodiments, the methods increase the rate of delivery of the agent to the central nervous system tissues, relative, for example, to delivery by a composition that comprises the agent alone.

In some instances, a subject has a disease, disorder, or condition of the CNS, where increased delivery of a therapeutic agent across the blood brain barrier to CNS tissues relative to peripheral tissues can improve treatment, for instance, by reducing side-effects associated with exposure of an agent to peripheral tissues. Exemplary diseases, disorders, and conditions of the CNS include various cancers, including primary and metastatic CNS cancers, lysosomal storage diseases, neurodegenerative diseases such as Alzheimer's disease, and auto-immune diseases such as multiple sclerosis.

Certain embodiments thus relate to methods for treating a cancer of the central nervous system (CNS), optionally the brain, where the subject in need thereof has such a cancer or is at risk for developing such a condition. In some embodiments, the cancer is a primary cancer of the CNS, such as a primary cancer of the brain. For instance, the methods can be for treating a glioma, meningioma, pituitary adenoma, vestibular schwannoma, primary CNS lymphoma, or primitive neuroectodermal tumor (medulloblastoma). In some embodiments, the glioma is an astrocytoma, oligodendroglioma, ependymoma, or a choroid plexus papilloma. In certain embodiments, the primary CNS or brain cancer is glioblastoma multiforme, such as a giant cell gliobastoma or a gliosarcoma.

In particular embodiments, the cancer is a metastatic cancer of the CNS, for instance, a cancer that has metastasized to the brain. Examples of such cancers include, without limitation, breast cancers, lung cancers, genitourinary tract cancers, gastrointestinal tract cancers (e.g., colorectal cancers, pancreatic carcinomas), osteosarcomas, melanomas, head and neck cancers, prostate cancers (e.g., prostatic adenocarcinomas), and lymphomas. Certain embodiments thus include methods for treating, inhibiting or preventing metastasis of a cancer by administering to a patient a therapeutically effective amount of a herein disclosed conjugate (e.g., in an amount that, following administration, inhibits, prevents or delays metastasis of a cancer in a statistically significant manner, i.e., relative to an appropriate control as will be known to those skilled in the art). In particular embodiments, the subject has a cancer that has not yet metastasized to the central nervous system, including one or more of the above-described cancers, among others known in the art.

In particular embodiments, the cancer (cell) expresses or overexpresses one or more of Her2/neu, B7H3, CD20, Her1/EGF receptor(s), VEGF receptor(s), PDGF receptor(s), CD30, CD52, CD33, CTLA-4, or tenascin.

Also included is the treatment of other cancers, including breast cancer, prostate cancer, gastrointestinal cancer, lung cancer, ovarian cancer, testicular cancer, head and neck cancer, stomach cancer, bladder cancer, pancreatic cancer, liver cancer, kidney cancer, squamous cell carcinoma, melanoma, non-melanoma cancer, thyroid cancer, endometrial cancer, epithelial tumor, bone cancer, or a hematopoietic cancer. Hence, in certain embodiments, the cancer cell being treated by a p97 conjugate overexpresses or is associated with a cancer antigen, such as human Her2/neu, Her1/EGF receptor (EGFR), Her3, A33 antigen, B7H3, CD5, CD19, CD20, CD22, CD23 (IgE Receptor), C242 antigen, 5T4, IL-6, IL-13, vascular endothelial growth factor VEGF (e.g., VEGF-A) VEGFR-1, VEGFR-2, CD30, CD33, CD37, CD40, CD44, CD51, CD52, CD56, CD74, CD80, CD152, CD200, CD221, CCR4, HLA-DR, CTLA-4, NPC-1C, tenascin, vimentin, insulin-like growth factor 1 receptor (IGF-1R), alpha-fetoprotein, insulin-like growth factor 1 (IGF-1), carbonic anhydrase 9 (CA-IX), carcinoembryonic antigen (CEA), integrin $\alpha_v\beta_3$, integrin $\alpha_5\beta_1$, folate receptor 1, transmembrane glycoprotein NMB, fibroblast activation protein alpha (FAP), glycoprotein 75, TAG-72, MUC1, MUC16 (or CA-125), phosphatidylserine, prostate-specific membrane antigen (PMSA), NR-LU-13 antigen, TRAIL-R1, tumor necrosis factor receptor superfamily member 10b (TNFRSF10B or TRAIL-R2), SLAM family member 7 (SLAMF7), EGP40 pancarcinoma antigen, B-cell activating factor (BAFF), platelet-derived growth factor receptor, glycoprotein EpCAM (17-1A), Programmed Death-1, protein disulfide isomerase (PDI), Phosphatase of Regenerating Liver 3 (PRL-3), prostatic acid phosphatase, Lewis-Y antigen, GD2 (a disialoganglioside expressed on tumors of neuroectodermal origin), glypican-3 (GPC3), and/or mesothelin.

The use of p97 conjugates for treating cancers including cancers of the CNS can be combined with other therapeutic modalities. For example, a composition comprising a p97 conjugate can be administered to a subject before, during, or after other therapeutic interventions, including symptomatic care, radiotherapy, surgery, transplantation, immunotherapy, hormone therapy, photodynamic therapy, antibiotic therapy, or any combination thereof. Symptomatic care includes administration of corticosteroids, to reduce cerebral edema, headaches, cognitive dysfunction, and emesis, and administration of anti-convulsants, to reduce seizures. Radiotherapy includes whole-brain irradiation, fractionated radiotherapy, and radiosurgery, such as stereotactic radiosurgery, which can be further combined with traditional surgery.

In specific combination therapies, the antibody portion of an p97-antibody conjugate comprises cetuximab, and the p97-cetuximab conjugate is used for treating a subject with locally or regionally advanced squamous cell carcinoma of the head and neck in combination with radiation therapy. In other aspects, the p97-cetuximab conjugate is used for treating a subject with recurrent locoregional disease or metastatic squamous cell carcinoma of the head and neck in combination with platinum-based therapy with 5-fluorouracil (5-FU). In some aspects, the p97-cetuximab conjugate is used in combination with irinotecan for treating a subject with EGFR-expressing colorectal cancer and that is refractory to irinotecan-based chemotherapy.

In some instances, the subject has or is at risk for having a lysosomal storage disease. Certain methods thus relate to the treatment of lysosomal storage diseases in a subject in need thereof, optionally those lysosomal storage diseases associated with the central nervous system. Exemplary lysosomal storage diseases include aspartylglucosaminuria, cholesterol ester storage disease, Wolman disease, cystinosis, Danon disease, Fabry disease, Farber lipogranulomatosis, Farber disease, fucosidosis, galactosialidosis types I/II, Gaucher disease types I/II/III, Gaucher disease, globoid cell leucodystrophy, Krabbe disease, glycogen storage disease II, Pompe disease, GM1-gangliosidosis types I/II/III, GM2-gangliosidosis type I, Tay Sachs disease, GM2-gangliosidosis type II, Sandhoff disease, GM2-gangliosidosis, α-mannosidosis types I/II, β-mannosidosis, metachromatic leucodystrophy, mucolipidosis type I, sialidosis types I/II mucolipidosis types II/III I-cell disease, mucolipidosis type IIIC pseudo-Hurler polydystrophy, mucopolysaccharidosis type I, mucopolysaccharidosis type II, Hunter syndrome, mucopolysaccharidosis type IIIA, Sanfilippo syndrome, mucopolysaccharidosis type IIIB, mucopolysaccharidosis type IIIC, mucopolysaccharidosis type IIID, mucopolysaccharidosis type IVA, Morquio syndrome, mucopolysaccharidosis type IVB Morquio syndrome, mucopolysaccharidosis type VI, mucopolysaccharidosis type VII, Sly syndrome, mucopolysaccharidosis type IX, multiple sulfatase deficiency, neuronal ceroid lipofuscinosis, CLN1 Batten disease, Niemann-Pick disease types NB, Niemann-Pick disease, Niemann-Pick disease type C1, Niemann-Pick disease type C2, pycnodysostosis, Schindler disease types I/II, Schindler disease, and sialic acid storage disease. In these and related embodiments, the p97 polypeptide can be conjugated to one or more polypeptides associated with a lysosomal storage disease, as described herein.

In certain instances, the subject has or is at risk for having an auto-immune disorder and/or a neurodegenerative disorder, optionally of the CNS. Hence, also included are methods of treating a degenerative or autoimmune disorder of the central nervous system (CNS) in a subject in need thereof. For instance, in specific embodiments, the degenerative or autoimmune disorder of the CNS is Alzheimer's disease, Huntington's disease, Parkinson's disease, or multiple sclerosis (MS). Hence, certain embodiments include administering a p97 conjugate to a subject having Alzheimer's disease, Huntington's disease, Parkinson's disease, or MS. In particular embodiments, the p97 polypeptide is conjugated to an antibody or other agent that specifically binds to amyloid-β (e.g., $A\beta_{(1-42)}$) for Alzheimer's Disease, Huntingtin for Huntington's Disease, α-synuclein for Parkinson's Disease, or α4 integrin, CD25, or IL-23 for MS. In some embodiments, the p97 polypeptide is conjugated to an interferon-β polypeptide, for the treatment of MS. In specific embodiments, the p97 polypeptide is conjugated to daclizumab for the treatment of MS.

Also included are methods of treating pain in a subject in need thereof. Examples include acute pain, chronic pain, and neuropathic pain, including combinations thereof. In some aspects, the pain has a centrally-acting component, such as central pain syndrome (CPS), where the pain is associated with damage to or dysfunction of the CNS, including the brain, brainstem, and/or spinal cord. In particular embodiments, the p97 polypeptide is conjugated to an antibody or other agent that specifically binds to NGF or TrkA. In specific embodiments, the p97 polypeptide is conjugated to tanezumab for the treatment of pain, optionally for the treatment of osteoarthritis of the knee or hip, chronic low back pain, bone cancer pain, or interstitial cystitis.

Also included are methods of treating inflammation or an inflammatory condition in a subject in need thereof. "Inflammation" refers generally to the biological response of tissues to harmful stimuli, such as pathogens, damaged cells (e.g., wounds), and irritants. The term "inflammatory response" refers to the specific mechanisms by which inflammation is achieved and regulated, including, merely by way of illustration, immune cell activation or migration, cytokine production, vasodilation, including kinin release, fibrinolysis, and coagulation, among others described herein and known in the art. Ideally, inflammation is a protective attempt by the body to both remove the injurious stimuli and initiate the healing process for the affected tissue or tissues. In the absence of inflammation, wounds and infections would never heal, creating a situation in which progressive destruction of the tissue would threaten survival. On the other hand, excessive or chronic inflammation may associate with a variety of diseases, such as hay fever, atherosclerosis, and rheumatoid arthritis, among others described herein and known in the art.

p97 conjugates of the invention may modulate acute inflammation, chronic inflammation, or both. Depending on the needs of the subject, certain embodiments relate to reducing acute inflammation or inflammatory responses, and certain embodiments relate to reducing chronic inflammation or chronic inflammatory responses.

Acute inflammation relates to the initial response of the body to presumably harmful stimuli and involves increased movement of plasma and leukocytes from the blood into the injured tissues. It is a short-term process, typically beginning within minutes or hours and ending upon the removal of the injurious stimulus. Acute inflammation may be characterized by any one or more of redness, increased heat, swelling, pain, and loss of function. Redness and heat are due mainly to increased blood flow at body core temperature to the inflamed site, swelling is caused by accumulation of fluid, pain is typically due to release of chemicals that stimulate nerve endings, and loss of function has multiple causes.

Acute inflammatory responses are initiated mainly by local immune cells, such as resident macrophages, dendritic cells, histiocytes, Kuppfer cells and mastocytes. At the onset of an infection, burn, or other injuries, these cells undergo activation and release inflammatory mediators responsible for the clinical signs of inflammation, such as vasoactive amines and eicosanoids. Vasodilation and its resulting increased blood flow cause the redness and increased heat. Increased permeability of the blood vessels results in an exudation or leakage of plasma proteins and fluid into the tissue, which creates swelling. Certain released mediators such as bradykinin increase sensitivity to pain, and alter the blood vessels to permit the migration or extravasation of leukocytes, such as neutrophils, which typically migrate along a chemotactic gradient created by the local immune cells.

Acute inflammatory responses also includes one or more acellular biochemical cascade systems, consisting of preformed plasma proteins modulate, which act in parallel to initiate and propagate the inflammatory response. These systems include the complement system, which is mainly activated by bacteria, and the coagulation and fibrinolysis systems, which are mainly activated by necrosis, such as the type of tissue damage that is caused by certain infections, burns, or other trauma. Hence, p97 conjugates may be used to modulate acute inflammation, or any of one or more of the individual acute inflammatory responses.

Chronic inflammation, a prolonged and delayed inflammatory response, is characterized by a progressive shift in the type of cells that are present at the site of inflammation, and often leads to simultaneous or near simultaneous destruction and healing of the tissue from the inflammatory process. At the cellular level, chronic inflammatory responses involve a variety of immune cells such as monocytes, macrophages, lymphocytes, plasma cells, and fibroblasts, though in contrast to acute inflammation, which is mediated mainly by granulocytes, chronic inflammation is mainly mediated by mononuclear cells such as monocytes and lymphocytes. Chronic inflammation also involves a variety of inflammatory mediators, such as IFN-γ and other cytokines, growth factors, reactive oxygen species, and hydrolytic enzymes. Chronic inflammation may last for many months or years, and may result in undesired tissue destruction and fibrosis.

Clinical signs of chronic inflammation are dependent upon duration of the illness, inflammatory lesions, cause and anatomical area affected. (see, e.g., Kumar et al., Robbins Basic Pathology-$8^{th}$ Ed., 2009 Elsevier, London; Miller, L M, Pathology Lecture Notes, Atlantic Veterinary College, Charlottetown, PEI, Canada). Chronic inflammation is associated with a variety of pathological conditions or diseases, including, for example, allergies, Alzheimer's disease, anemia, aortic valve stenosis, arthritis such as rheumatoid arthritis and osteoarthritis, cancer, congestive heart failure, fibromyalgia, fibrosis, heart attack, kidney failure, lupus, pancreatitis, stroke, surgical complications, inflammatory lung disease, inflammatory bowel disease, atherosclerosis, and psoriasis, among others described herein and known in the art. Hence, p97 conjugates may be used to treat or manage chronic inflammation, modulate any of one or more of the individual chronic inflammatory responses, or treat any one or more diseases or conditions associated with chronic inflammation.

In certain embodiments, p97 conjugates may modulate inflammatory responses at the cellular level, such as by modulating the activation, inflammatory molecule secretion (e.g., cytokine or kinin secretion), proliferation, activity, migration, or adhesion of various cells involved in inflammation. Examples of such cells include immune cells and vascular cells. Immune cells include, for example, granulocytes such as neutrophils, eosinophils and basophils, macrophages/monocytes, lymphocytes such as B-cells, killer T-cells (i.e., CD8+ T-cells), helper T-cells (i.e., CD4+ T-cells, including $T_h1$ and $T_h2$ cells), natural killer cells, γδ T-cells, dendritic cells, and mast cells. Examples of vascular cells include smooth muscle cells, endothelial cells, and fibroblasts. Also included are methods of modulating an inflammatory condition associated with one or more immune cells or vascular cells, including neutrophil-mediated, macrophage-mediated, and lymphocyte-mediated inflammatory conditions.

In certain embodiments, p97 conjugates may modulate the levels or activity of inflammatory molecules, including plasma-derived inflammatory molecules and cell-derived inflammatory molecules. Included are pro-inflammatory molecules and anti-inflammatory molecules. Examples of plasma-derived inflammatory molecules include, without limitation, proteins or molecules of any one or more of the complement system, kinin system, coagulation system, and the fibrinolysis system. Examples of members of the complement system include C1, which exists in blood serum as a molecular complex containing about 6 molecules of C1q, 2 molecules of C1r, and 2 molecules of C1s, C2 (a and b), C3(a and B), C4 (a and b), C5, and the membrane attack complex of C5a, C5b, C6, C7, C8, and C9. Examples of the kinin system include bradykinin, kallidin, kallidreins, carboxypeptidases, angiotensin-converting enzyme, and neutral endopeptidase.

Examples of cell-derived inflammatory molecules include, without limitation, enzymes contained within lysosome granules, vasoactive amines, eicosanoids, cytokines, acute-phase proteins, and soluble gases such as nitric oxide. Vasoactive amines contain at least one amino group, and target blood vessels to alter their permeability or cause vasodilation. Examples of vasoactive amines include histamine and serotonin. Eicosanoids refer to signaling molecules made by oxidation of twenty-carbon essential fatty acids, and include prostaglandins, prostacyclins, thromboxanes, and leukotrienes.

p97 conjugates may also modulate levels or activity of acute-phase proteins. Examples of acute-phase proteins include C-reactive protein, serum amyloid A, serum amyloid P, and vasopressin. In certain instances, expression of acute-phase proteins can cause a range of undesired systemic effects including amyloidosis, fever, increased blood pressure, decreased sweating, malaise, loss of appetite, and somnolence. Accordingly, p97 conjugates may modulate the levels or activity of acute-phase proteins, their systemic effects, or both.

In certain embodiments, p97 conjugates reduce local inflammation, systemic inflammation, or both. In certain embodiments, p97 conjugates may reduce or maintain (i.e., prevent further increases) local inflammation or local inflammatory responses. In certain embodiments, p97 conjugates may reduce or maintain (i.e., prevent further increases) systemic inflammation or systemic inflammatory responses.

In certain embodiments, the modulation of inflammation or inflammatory responses can be associated with one or more tissues or organs. Non-limiting examples of such tissues or organs include skin (e.g., dermis, epidermis, subcutaneous layer), hair follicles, nervous system (e.g., brain, spinal cord, peripheral nerves, meninges including the dura mater, arachnoid mater, and pia mater), auditory system or balance organs (e.g., inner ear, middle ear, outer ear), respiratory system (e.g., nose, trachea, lungs), gastroesophogeal tissues, the gastrointestinal system (e.g., mouth, esophagus, stomach, small intestines, large intestines, rectum), vascular system (e.g., heart, blood vessels and arteries), liver, gallbladder, lymphatic/immune system (e.g., lymph nodes, lymphoid follicles, spleen, thymus, bone marrow), uro-genital system (e.g., kidneys, ureter, bladder, urethra, cervix, Fallopian tubes, ovaries, uterus, vulva, prostate, bulbourethral glands, epidiymis, prostate, seminal vesicles, testicles), musculoskeletal system (e.g., skeletal muscles, smooth muscles, bone, cartilage, tendons, ligaments), adipose tissue, mammaries, and the endocrine system (e.g., hypothalamus, pituitary, thyroid, pancreas, adrenal glands). Accordingly, p97 conjugates may be used to modulate inflammation associated with any of these tissues or organs, such as to treat conditions or diseases that are associated with the inflammation of these tissues or organs.

In particular embodiments, the inflammatory condition has a nervous system or central nervous system component, including inflammation of the brain, spinal cord, and/or the meninges. In particular embodiments, the inflammatory condition of the CNS in meningitis (e.g., bacteria, viral), encephalitis (e.g., caused by infection or autoimmune inflammation such as Acute Disseminated Enchephalomyelitis), sarcoidosis, non-metastatic diseases associated with neoplasia. Particular examples of nervous system or CNS associated inflammatory conditions include, without limitation, meningitis (i.e., inflammation of the protective membranes covering the brain and spinal cord), myelitis, encaphaloymyelitis (e.g., myalgic encephalomyelitis, acute disseminated encephalomyelitis, encephalomyelitis disseminata or multiple sclerosis, autoimmune encephalomyelitis), arachnoiditis (i.e., inflammation of the arachnoid, one of the membranes that surround and protect the nerves of the central nervous system), granuloma, drug-induced inflammation or meningitis, neurodegenerative diseases such as Alzheimer's disease, stroke, HIV-dementia, encephalitis such viral encephalitis and bacterial encephalitis, parasitic infections, inflammatory demyelinating disorders, and auto-immune disorders such as CD8+ T Cell-mediated autoimmune diseases of the CNS. Additional examples include Parkinson's disease, myasthenia gravis, motor neuropathy, Guillain-Barre syndrome, autoimmune neuropathy, Lambert-Eaton myasthenic syndrome, paraneoplastic neurological disease, paraneoplastic cerebellar atrophy, non-paraneoplastic stiff man syndrome, progressive cerebellar atrophy, Rasmussen's encephalitis, amyotrophic lateral sclerosis, Sydeham chorea, Gilles de la Tourette syndrome, autoimmune polyendocrinopathy, dysimmune neuropathy, acquired neuromyotonia, arthrogryposis multiplex, optic neuritis, stiff-man syndrome, stroke, traumatic brain injury (TBI), spinal stenosis, acute spinal cord injury, and spinal cord compression.

As noted above, also included is inflammation associated with infections of the nervous system or CNS. Specific examples of bacterial infections associated with inflammation of the nervous system include, without limitation, streptococcal infection such as group B streptococci (e.g., subtypes III) and *Streptococcus pneumoniae* (e.g., serotypes 6, 9, 14, 18 and 23), *Escherichia coli* (e.g., carrying K1 antigen), *Listeria monocytogenes* (e.g., serotype IVb), neisserial infection such as *Neisseria meningitidis* (meningococcus), staphylococcal infection, heamophilus infection such as *Haemophilus influenzae* type B, *Klebsiella*, and *Mycobacterium tuberculosis*. Also included are infections by staphylococci and pseudomonas and other Gram-negative bacilli, mainly with respect to trauma to the skull, which gives bacteria in the nasal cavity the potential to enter the meningeal space, or in persons with cerebral shunt or related device (e.g., extraventricular drain, Ommaya reservoir). Specific examples of viral infections associated with inflammation of the nervous system include, without limitation, enteroviruses, herpes simplex virus type 1 and 2, human T-lymphotrophic virus, varicella zoster virus (chickenpox and shingles), mumps virus, human immunodeficiency virus (HIV), and lymphocytic choriomeningitis virus (LCMV). Meningitis may also result from infection by spirochetes such as *Treponema pallidum* (syphilis) and *Borrelia burgdorferi* (Lyme disease), parasites such as malaria (e.g., cerebral malaria), fungi such as *Cryptococcus neoformans*, and ameoba such as *Naegleria fowleri*.

Meningitis or other forms of nervous system inflammation may also associate with the spread of cancer to the meninges (malignant meningitis), certain drugs such as non-steroidal anti-inflammatory drugs, antibiotics and intravenous immunoglobulins, sarcoidosis (or neurosarcoidosis), connective tissue disorders such as systemic lupus erythematosus, and certain forms of vasculitis (inflammatory conditions of the blood vessel wall) such as Behçet's disease. Epidermoid cysts and dermoid cysts may cause meningitis by releasing irritant matter into the subarachnoid space. Accordingly, p97 conjugates may be used to treat or manage any one or more of these conditions.

As noted above, certain subjects are about to undergo, are undergoing, or have undergone therapy with an otherwise cardiotoxic agent, that is, an agent that displays cardiotoxicity in its unconjugated form (an agent that is not conjugated to p97). Such subjects can benefit from administration of a p97-agent conjugate, relative to administration of the agent alone, partly because p97 can exert a cardioprotective effect on otherwise cardiotoxic agents by a mechanism that is believed to differ from its BBB transport properties. Hence, such subjects can be treated with a p97-cardiotoxic agent conjugate for a variety of disease conditions, including diseases of the CNS described herein, and diseases relating to peripheral, non-CNS tissues.

Exemplary cardiotoxic agents are described elsewhere herein, and can be identified according to well-known in vivo diagnostic and in vitro screening techniques. See Bovelli et al., 2010, supra; Inoue et al., *AATEX* 14, Special Issue, 457-462, 2007; and Dorr et al., *Cancer Research*. 48:5222-5227, 1988.

For instance, subjects undergoing therapy with a suspected cardiotoxic agent can be monitored by imaging techniques to asses LV systolic and diastolic dysfunction, heart valve disease, pericarditis and pericardial effusion, and carotid artery lesions. LV fractional shortening and LVEF are the most common indexes of LV systolic function for cardiac function assessment, for instance, during chemotherapy. Also, Doppler-derived diastolic indexes represent an early sign of LV dysfunction in patients undergoing therapy, so that evaluation of mitral diastolic flow pattern, early peak flow velocity to atrial peak flow velocity (E/A) ratio, deceleration time of E wave and isovolumic relaxation time can be useful to detect diastolic changes of LV function before systolic dysfunction occurs. Pulsed tissue Doppler may be performed during a standard Doppler echocardiographic examination; it can be reliable in providing quantitative information on myocardial diastolic relaxation and systolic performance (E' wave, A' wave and S wave velocity). Tissue Doppler of LV lateral mitral annulus has a recognized prognostic role and, in combination with PW Doppler of mitral inflow, provides accurate information about the degree of LV filling pressure. Early changes in LV myocardial function have been identified by pulsed tissue Doppler of multiple LV sites, and can be relevant determinants of cardiotoxicity.

In particular embodiments, the cardiotoxic agent is a chemotherapeutic, and the subject has cancer. Specific examples of cancers include, without limitation, breast cancers, prostate cancers, gastrointestinal cancers, lung cancers, ovarian cancers, testicular cancers, head and neck cancers, stomach cancers, bladder cancers, pancreatic cancers, liver cancers, kidney cancers, squamous cell carcinomas, CNS or brain cancers (described herein), melanomas, non-melanoma cancers, thyroid cancers, endometrial cancers, epithelial tumors, bone cancers, and hematopoietic cancers.

In specific embodiments, the subject has a Her2/neu-expressing cancer, such as a breast cancer, ovarian cancer, stomach cancer, aggressive uterine cancer, or metastatic cancer, such as a metastatic CNS cancer, and the p97 polypeptide is conjugated to trastuzumab. Such patients can benefit not only from the therapeutic synergism resulting from the combination of p97 and trastuzumab, especially for CNS cancers, but also from the reduced cardiotoxicity of trastuzumab, resulting from the potential cardioprotective effects of p97.

Methods for identifying subjects with one or more of the diseases or conditions described herein are known in the art.

Also included are methods for imaging an organ or tissue component in a subject, comprising (a) administering to the subject a composition comprising a human p97 (melanotransferrin) polypeptide, or a variant thereof, where the p97 polypeptide is conjugated to a detectable entity, and (b) visualizing the detectable entity in the subject, organ, or tissue.

In particular embodiments, the organ or tissue compartment comprises the central nervous system (e.g., brain, brainstem, spinal cord). In specific embodiments, the organ or tissue compartment comprises the brain or a portion thereof, for instance, the parenchyma of the brain.

A variety of methods can be employed to visualize the detectable entity in the subject, organ, or tissue. Exemplary non-invasive methods include radiography, such as fluoroscopy and projectional radiographs, CT-scanning or CAT-scanning (computed tomography (CT) or computed axial tomography (CAT)), whether employing X-ray CT-scanning, positron emission tomography (PET), or single photon emission computed tomography (SPECT), and certain types of magnetic resonance imaging (MRI), especially those that utilize contrast agents, including combinations thereof.

Merely by way of example, PET can be performed with positron-emitting contrast agents or radioisotopes such as $^{18}$F, SPECT can be performed with gamma-emitting contrast agents or radioisotopes such as $^{201}$Tl, $^{99m}$TC, $^{123}$I, and $^{67}$Ga, and MRI can be performed with contrast agents or radioisotopes such as $^{3}$H, $^{13}$C, $^{19}$F, $^{17}$O, $^{23}$Na, $^{31}$P, and $^{129}$Xe, and Gd (gadolidinium; chelated organic Gd (III) complexes). Any one or more of these exemplary contrast agents or radioisotopes can be conjugated to or otherwise incorporated into a p97 polypeptide and administered to a subject for imaging purposes. For instance, p97 polypeptides can be directly labeled with one or more of these radioisotopes, or conjugated to molecules (e.g., small molecules) that comprise one or more of these radioisotopic contrast agents, or any others described herein.

For in vivo use, for instance, for the treatment of human disease, medical imaging, or testing, the conjugates described herein are generally incorporated into a pharmaceutical composition prior to administration. A pharmaceutical composition comprises one or more of the p97 polypeptides or conjugates described herein in combination with a physiologically acceptable carrier or excipient.

To prepare a pharmaceutical composition, an effective or desired amount of one or more of the p97 polypeptides or conjugates is mixed with any pharmaceutical carrier(s) or excipient known to those skilled in the art to be suitable for the particular mode of administration. A pharmaceutical carrier may be liquid, semi-liquid or solid. Solutions or suspensions used for parenteral, intradermal, subcutaneous or topical application may include, for example, a sterile diluent (such as water), saline solution (e.g., phosphate buffered saline; PBS), fixed oil, polyethylene glycol, glycerin, propylene glycol or other synthetic solvent; antimicrobial agents (such as benzyl alcohol and methyl parabens); antioxidants (such as ascorbic acid and sodium bisulfite) and chelating agents (such as ethylenediaminetetraacetic acid (EDTA)); buffers (such as acetates, citrates and phosphates). If administered intravenously, suitable carriers include physiological saline or phosphate buffered saline (PBS), and solutions containing thickening and solubilizing agents, such as glucose, polyethylene glycol, polypropylene glycol and mixtures thereof.

Administration of the polypeptides and conjugates described herein, in pure form or in an appropriate pharmaceutical composition, can be carried out via any of the accepted modes of administration of agents for serving similar utilities. The pharmaceutical compositions can be prepared by combining a polypeptide or conjugate or conjugate-containing composition with an appropriate physiologically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. In addition, other pharmaceutically active ingredients (including other anti-cancer agents as described elsewhere herein) and/or suitable excipients such as salts, buffers and stabilizers may, but need not, be present within the composition.

Administration may be achieved by a variety of different routes, including oral, parenteral, nasal, intravenous, intradermal, subcutaneous or topical. Preferred modes of administration depend upon the nature of the condition to be treated or prevented.

Carriers can include, for example, pharmaceutically acceptable carriers, excipients, or stabilizers that are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as polysorbate 20 (TWEEN™) polyethylene glycol (PEG), and poloxamers (PLURONICS™), and the like.

In certain aspects, the p97 polypeptide sequence and the agent are each, individually or as a pre-existing conjugate, bound to or encapsulated within a particle, e.g., a nanoparticle, bead, lipid formulation, lipid particle, or liposome, e.g., immunoliposome. For instance, in particular embodiments, the p97 polypeptide sequence is bound to the surface of a particle, and the agent of interest is bound to the surface of the particle and/or encapsulated within the particle. In some of these and related embodiments, the p97 polypeptide and the agent are covalently or operatively linked to each other only via the particle itself (e.g., nanoparticle, liposome), and are not covalently linked to each other in any other way; that is, they are bound individually to the same particle. In other embodiments, the p97 polypeptide and the agent are first covalently or non-covalently conjugated to each other, as described herein (e.g., via a linker molecule), and are then bound to or encapsulated within a particle (e.g., immunoliposome, nanoparticle). In specific embodiments, the particle is a liposome, and the composition comprises one or more p97 polypeptides, one or more agents of interest, and a mixture of lipids to form a liposome (e.g., phospholipids, mixed lipid chains with surfactant properties). In some aspects, the p97 polypeptide and the agent are individually mixed with the lipid/liposome mixture, such that the formation of liposome structures operatively links the p97 polypeptide and the agent without the need for covalent conjugation. In other aspects, the p97 polypeptide and the agent are first covalently or non-covalently conjugated to each other, as described herein, and then mixed with lipids to form a liposome. The p97 polypeptide, the agent, or the p97-agent conjugate may be entrapped in microcapsules prepared, for example, by coacervation techniques or by interfacial polymerization (for example, hydroxymethylcellulose or gelatin-microcapsules and poly-(methylmethacylate)microcapsules, respectively), in colloidal drug delivery systems (for example, liposomes, albumin microspheres, microemulsions, nano-particles and nanocapsules), or in macroemulsions. Such techniques are disclosed in Remington's Pharmaceutical Sciences, 16th edition, Oslo, A., Ed., (1980). The particle(s) or liposomes may further comprise other therapeutic or diagnostic agents, such as cytotoxic agents.

The precise dosage and duration of treatment is a function of the disease being treated and may be determined empirically using known testing protocols or by testing the compositions in model systems known in the art and extrapolating therefrom. Controlled clinical trials may also be performed. Dosages may also vary with the severity of the condition to be alleviated. A pharmaceutical composition is generally formulated and administered to exert a therapeutically useful effect while minimizing undesirable side effects. The composition may be administered one time, or may be divided into a number of smaller doses to be administered at intervals of time. For any particular subject, specific dosage regimens may be adjusted over time according to the individual need.

Typical routes of administering these and related pharmaceutical compositions thus include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Pharmaceutical compositions according to certain embodiments of the present invention are formulated so as to allow the active ingredients contained therein to be bioavailable upon administration of the composition to a patient. Compositions that will be administered to a subject or patient may take the form of one or more dosage units, where for example, a tablet may be a single dosage unit, and a container of a herein described conjugate in aerosol form may hold a plurality of dosage units. Actual methods of preparing such dosage forms are known, or will be apparent, to those skilled in this art; for example, see Remington: The Science and Practice of Pharmacy, 20th Edition (Philadelphia College of Pharmacy and Science, 2000). The composition to be administered will, in any event, contain a therapeutically effective amount of a p97 polypeptide, agent, or conjugate described herein, for treatment of a disease or condition of interest.

A pharmaceutical composition may be in the form of a solid or liquid. In one embodiment, the carrier(s) are particulate, so that the compositions are, for example, in tablet or powder form. The carrier(s) may be liquid, with the compositions being, for example, an oral oil, injectable liquid or an aerosol, which is useful in, for example, inhalatory administration. When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent. When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition intended for either parenteral or oral administration should contain an amount of a p97 polypeptide or conjugate as herein disclosed such that a suitable dosage will be obtained. Typically, this amount is at least 0.01% of the agent of interest in the composition. When intended for oral administration, this amount may be varied to be between 0.1 and about 70% of the weight of the composition. Certain oral pharmaceutical compositions contain between about 4% and about 75% of the agent of interest. In certain embodiments, pharmaceutical compositions and preparations according to the present invention are prepared so that a parenteral dosage unit contains between 0.01 to 10% by weight of the agent of interest prior to dilution.

The pharmaceutical composition may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device.

The pharmaceutical composition may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter, and polyethylene glycol.

The pharmaceutical composition may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule. The pharmaceutical composition in solid or liquid form may include an agent that binds to the conjugate or agent and thereby assists in the delivery of the compound. Suitable agents that may act in this capacity include monoclonal or polyclonal antibodies, one or more proteins or a liposome.

The pharmaceutical composition may consist essentially of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols may be delivered in single phase, bi-phasic, or tri-phasic systems in order to deliver the active ingredient(s). Delivery of the aerosol includes the necessary container, activators, valves, subcontainers, and the like, which together may form a kit. One of ordinary skill in the art, without undue experimentation may determine preferred aerosols.

The compositions comprising conjugates as described herein may be prepared with carriers that protect the conjugates against rapid elimination from the body, such as time release formulations or coatings. Such carriers include controlled release formulations, such as, but not limited to, implants and microencapsulated delivery systems, and biodegradable, biocompatible polymers, such as ethylene vinyl acetate, polyanhydrides, polyglycolic acid, polyorthoesters, polylactic acid and others known to those of ordinary skill in the art.

The pharmaceutical compositions may be prepared by methodology well known in the pharmaceutical art. For example, a pharmaceutical composition intended to be administered by injection can be prepared by combining a composition that comprises a conjugate as described herein and optionally, one or more of salts, buffers and/or stabilizers, with sterile, distilled water so as to form a solution. A surfactant may be added to facilitate the formation of a homogeneous solution or suspension. Surfactants are compounds that non-covalently interact with the conjugate so as to facilitate dissolution or homogeneous suspension of the conjugate in the aqueous delivery system.

The compositions may be administered in a therapeutically effective amount, which will vary depending upon a variety of factors including the activity of the specific compound (e.g., conjugate) employed; the metabolic stability and length of action of the compound; the age, body weight, general health, sex, and diet of the patient; the mode and time of administration; the rate of excretion; the drug combination; the severity of the particular disorder or condition; and the subject undergoing therapy. Generally, a therapeutically effective daily dose is (for a 70 kg mammal) from about 0.001 mg/kg (i.e., 0.07 mg) to about 100 mg/kg (i.e., ~7.0 g); preferably a therapeutically effective dose is (for a 70 kg mammal) from about 0.01 mg/kg (i.e., ~0.7 mg) to about 50 mg/kg (i.e., ~3.5 g); more preferably a therapeutically effective dose is (for a 70 kg mammal) from about 1 mg/kg (i.e., ~70 mg) to about 25 mg/kg (i.e., ~1.75 g).

Compositions comprising the conjugates described herein may also be administered simultaneously with, prior to, or after administration of one or more other therapeutic agents, as described herein. For instance, in one embodiment, the conjugate is administered with an anti-inflammatory agent. Anti-inflammatory agents or drugs include, but are not limited to, steroids and glucocorticoids (including betamethasone, budesonide, dexamethasone, hydrocortisone acetate, hydrocortisone, hydrocortisone, methylprednisolone, prednisolone, prednisone, triamcinolone), nonsteroidal anti-inflammatory drugs (NSAIDS) including aspirin, ibuprofen, naproxen, methotrexate, sulfasalazine, leflunomide, anti-TNF medications, cyclophosphamide and mycophenolate.

Such combination therapy may include administration of a single pharmaceutical dosage formulation which contains a compound of the invention and one or more additional active agents, as well as administration of compositions comprising conjugates of the invention and each active agent in its own separate pharmaceutical dosage formulation. For example, a conjugate as described herein and the other active agent can be administered to the patient together in a single oral dosage composition such as a tablet or capsule, or each agent administered in separate oral dosage formulations. Similarly, a conjugate as described herein and the other active agent can be administered to the patient together in a single parenteral dosage composition such as in a saline solution or other physiologically acceptable solution, or each agent administered in separate parenteral dosage formulations. Where separate dosage formulations are used, the compositions comprising conjugates and one or more additional active agents can be administered at essentially the same time, i.e., concurrently, or at separately staggered times, i.e., sequentially and in any order; combination therapy is understood to include all these regimens.

The following Examples are offered by way of illustration and not by way of limitation.

EXAMPLES

Example 1

Generation Fragments of Human Melanotransferrin (p97)

Scaled chemical and enzymatic digestions of human melanotransferrin (p97) were performed using cyanogen bromide (CNBr) and trypsin, to generate p97 fragments for testing in an in vitro model of blood-brain barrier (BBB) transport.

CNBr Digestion:
To a 500 µL protein sample of human p97 (10 mg/ml), 2.664 ml of 88% formic acid and 166.5 µL of 5 M CNBr in acetonitrile was added. The sample was vortexed, covered in aluminum foil, and incubated for 24 hours at room temperature in a chemical fume hood. To quench the reaction, 10 volumes of MS Grade Water was added. The digestion material was frozen at −80° C. and lyophilized overnight. The sample was stored at −20° C. until purification. Digestion material was re-solubilized in 5 mL 0.1% formic acid and purified using Sep-Pack C8 12cc cartridges from Waters. The purified digestion material was frozen at −80° C. and lyophilized overnight. The lyophilized product was then stored at −20° C. Table 1 shows an example of predicted p97 fragments from the CNBr digest.

TABLE 1

CNBr Predicted Digest

| Position Cleavage Site | Peptide Length (AA) | Peptide Mass (Da) | Predicted p97 fragment - Residues of Full-Length Human p97 (SEQ ID NO: 1) | SEQ ID NO: |
|---|---|---|---|---|
| 2 | 2 | 206.3 | 1-2 | N/A |
| 20 | 18 | 2091.3 | 3-20 | 19 |
| 137 | 117 | 12432.1 | 21-137 | 20 |
| 293 | 156 | 16894.7 | 138-293 | 21 |
| 333 | 40 | 4578.1 | 294-333 | 22 |
| 363 | 30 | 3447.1 | 334-363 | 23 |
| 388 | 25 | 2884.4 | 364-388 | 24 |
| 609 | 221 | 24044.7 | 389-609 | 25 |
| 641 | 32 | 3670.1 | 610-641 | 26 |
| 685 | 44 | 4892.5 | 642-685 | 27 |
| 692 | 7 | 695.7 | 686-692 | 28 |

SDS-PAGE analysis was performed on the digested and purified product. Native and digested protein samples were loaded onto a 4-12% Bis-Tris gel, and the gel was run using a constant voltage of 200V for 35 minutes with a starting current of 114 mA and an ending current of 65 mA. After electrophoresis, the gel was rinsed 3× for five minutes each with 200 mL of Milli-Q water. The gel was then stained with 20 mL of GelCode Blue Stain Reagent overnight, and subsequently de-stained with 200 mL of Milli-Q water for one hour. The SDS-PAGE analysis is shown in FIG. 1 (Lane 1, empty; Lane 2, SeeBlue Latter; Lanes 2-5, empty; Lane 6, 50 µg undigested p97; lanes 7-9, empty; Lane 10, 50 µg CNBr-digested p97; lanes 11-12, empty). Lane 6, the undigested protein sample, had many bands indicating that the p97 protein had impurities. Lane 10, the CNBr digest, and at least three bands visible as large digest fragments.

These three bands were excised, in-gel digested with trypsin, and extracted and analyzed by LC-MS/MS analysis. The results are shown in FIGS. 3-6. FIG. 3 shows the sequence coverage maps of the p97 fragments identified by MS/MS analysis of a CNBr digest of human p97; FIG. 3A shows the results for band 1, FIG. 3B shows the results for band 2, and FIG. 3B shows the results for band 3.

FIG. 4A shows the matching of the peptides detected in band 1 to the amino acid sequence of human p97; the sequence coverage of the matched peptides is indicated in bold. FIG. 4B lists the individual peptides along with certain physical characteristics. FIG. 5A shows the matching of the peptides detected in band 2 to the amino acid sequence of human p97; the sequence coverage of the matched peptides is indicated in bold. FIG. 5B lists the individual peptides along with certain physical characteristics. FIG. 6A shows the matching of the peptides detected in band 3 to the amino acid sequence of human p97; the sequence coverage of the matched peptides is indicated in bold. FIG. 6B lists the individual peptides along with certain physical characteristics.

Trypsin Digestion:

To a 500 µL protein sample of human p97 (10 mg/ml), 0.5 ml of 25 mM ammonium bicarbonate was added. Fifty microliters of 200 mM DTT (in 25 mM Ambic) was added and reduced for 30 minutes at 37° C. Two hundred microliters of 200 mM iodoacetamide (in 25 mM Ambic) was added and free cysteines were alkylated for 30 minutes at 37° C. Next, 250 µg of porcine trypsin (Promega) was added to the sample and digestion was performed overnight at 37° C. The digestion material was purified using Oasis HLB 6cc cartridges from Waters. The purified digestion material was frozen at 80 C and lyophilized overnight. The lyophilized product was stored at −20° C.

For MS analysis, the lyophilized p97 tryptic digests were rehydrated in 1 mL 0.1% formic acid and 3% acetonitrile. One microgram was loaded onto a C18 column and injected into an LTQ Orbitrap Velos mass spectrometer (Thermo). MS/MS analysis showed that the sample contained a number of protein contaminants, but also confirmed that the p97 trypsin digest was successful.

The results are shown in FIG. 2. FIGS. 2A-2D show a list of p97 fragments identified by MS/MS analysis of an in-solution trypsin digest of human p97, and FIG. 2E shows the sequence coverage map of that analysis.

Example 2

Testing P97 Fragments in an In Vitro Model of the Blood Brain Barrier

Experiments were performed to evaluate the passage of mixtures of p97 peptide fragments across the blood-brain barrier (BBB) using a relevant and predictive BBB in vitro model (see Cecchelli et al., *Adv. Drug Deliv. Rev.* 36:165-178, 1999). The model utilizes brain capillary endothelial cells co-cultured with glial cells, to closely mimic the in vivo BBB (see Lundquist et al., *Pharm. Res.* 16:976-981, 2002).

Figure 7:
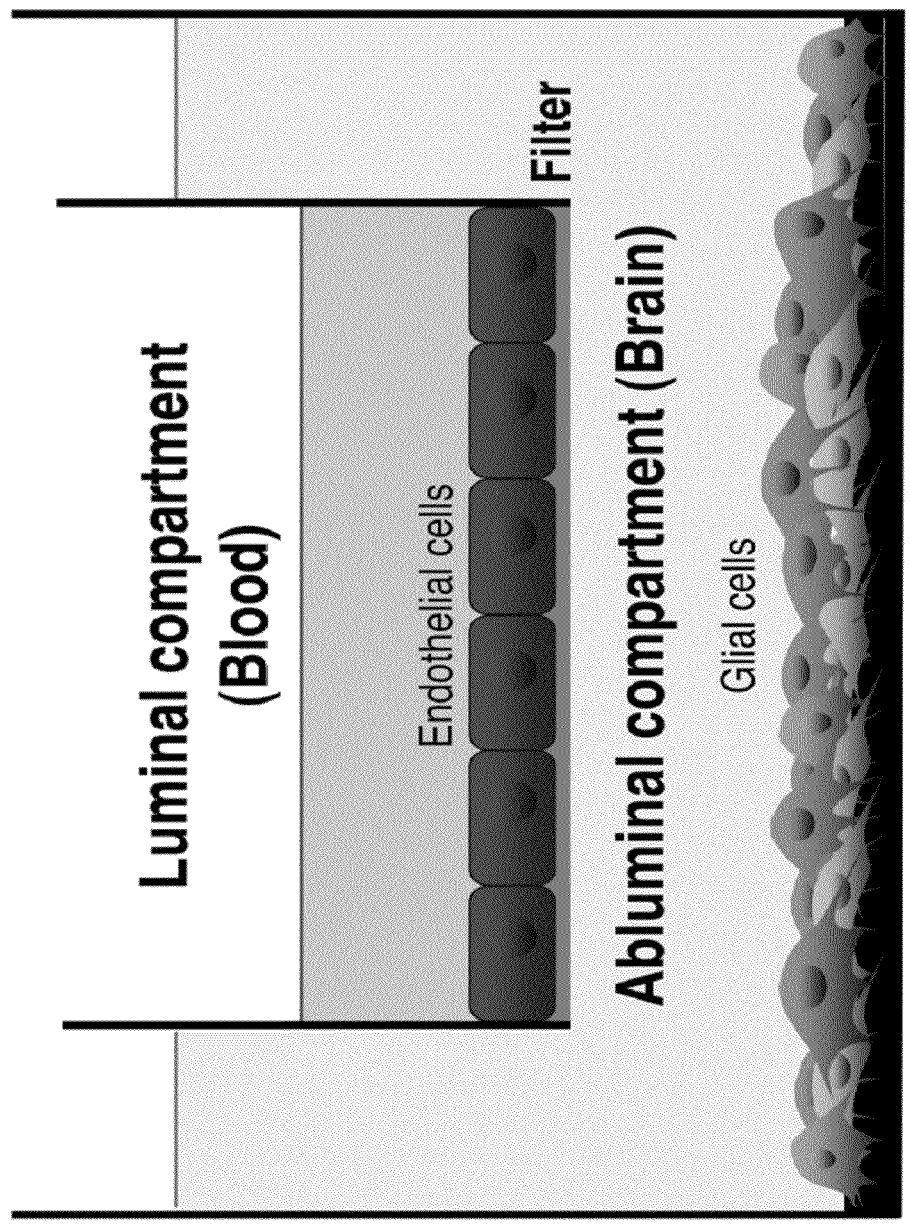
FIG. 7 illustrates the in vitro model of the blood brain barrier (BBB), with endothelial cells on a filter (either a 3 or 4 μm filter) in the luminal compartment to simulate the barrier from the blood to the central nervous system, and glial cells in the abluminal compartment to simulate the central nervous system.
Figure 8:
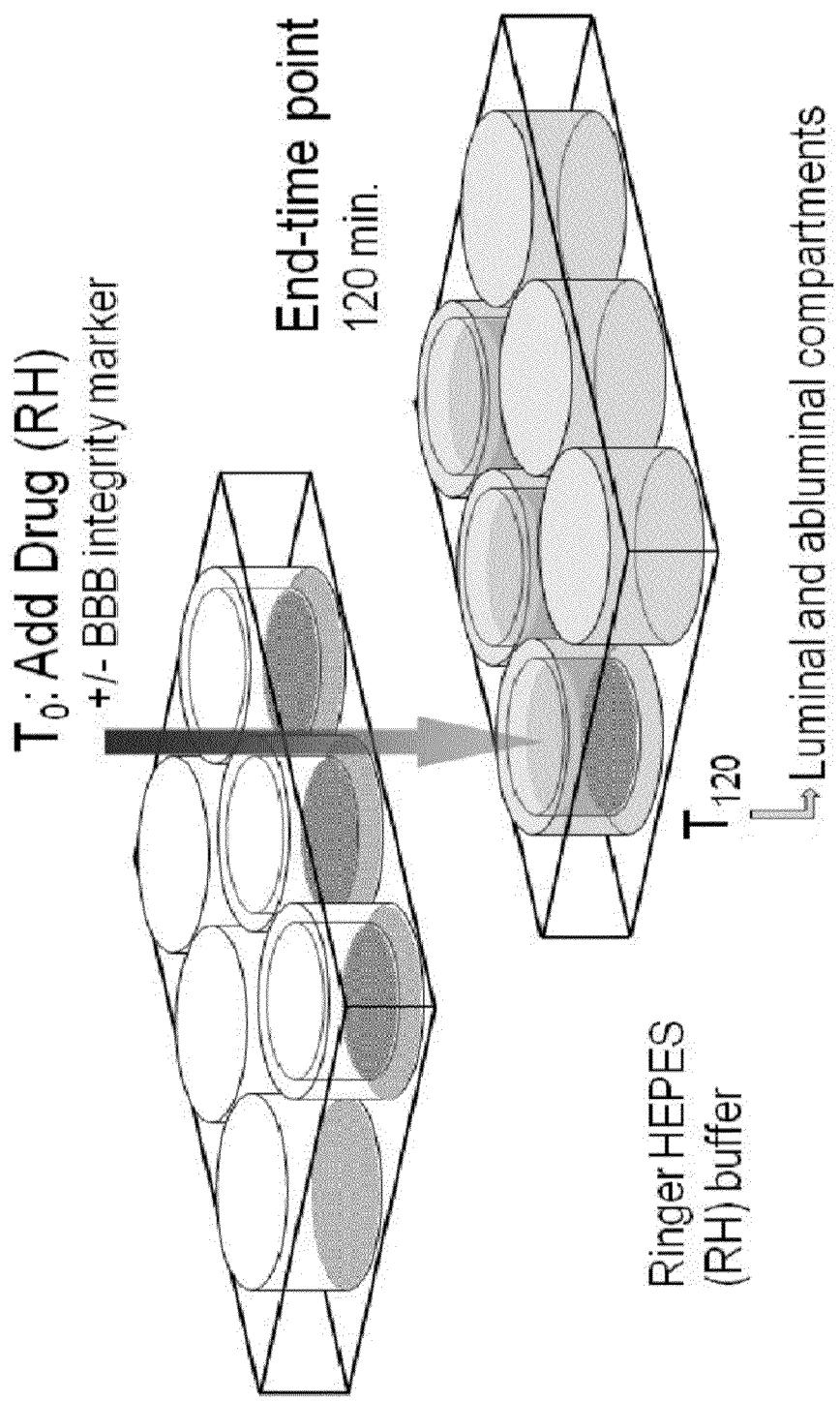
FIG. 8 shows a schematic of test protocols using the in vitro model of the BBB.

Cell-Based Model of the BBB:

To provide an in vitro system for studying brain capillary functions, a process of co-culture that closely mimics the in vivo BBB was established by culturing brain capillary endothelial cells on one side of a filter and supportive glial cells on the other side. Specifically, endothelial cells were cultured in the upper compartment on the filter and glial cells in the lower compartment on the plastic of a six-wells plate (see FIGS. 7 and 8). Under these conditions, endothelial cells retain the appropriate endothelial markers (e.g., factor VIII—related antigen, non-thrombogenic surface, production of prostacyclin, angiotensin-converting enzyme activity), and also retain the relevant characteristics of the BBB (e.g., presence of tight junctions, paucity of pinocytotic vesicles, monoamine oxidase activity, γ-glutamyltranspeptidase activity, P-glycoprotein activity, specific receptors for low density lipoproteins, and transferrin).

Glial Cell Culture.

Primary cultures of glial cells were isolated from newborn rat cerebral cortex (Booher & Sensenbrenner, *Neurobiology.* 2:97-105, 1972). After removing the meninges, the brain tissue was forced gently through a nylon sieve. DMEM (Dulbecco's modified Eagle medium) supplemented with 10% (v/v) fetal calf serum (FCS, same as Fetal Bovine Serum: FBS), 2 mM glutamine, and 50 µg·ml$^{-1}$ of gentamycin was used for the dissociation of cerebral tissue and development of glial cells. Three weeks after seeding, glial cultures were stabilized and composed of astrocytes (~60%), oligodendrocytes, and microglial cells (Descamps et al., *Glia.* 42:46-58, 2003).

Preparation of Filter Inserts.

Culture plate inserts (Transwell PE 3 µm pore size; 24-mm diameter, COSTAR, 3452/Transwell PC 3 µm pore size; 24-mm diameter, COSTAR, 3414) were coated on the upper side with rat-tail collagen.

Co-Culture of Brain Capillary Endothelial Cells with Glial Cells.

The glial cells were plated at a concentration of about $1.25 \times 10^5$ cells/ml in plastic six-well plates and incubated at 37° C. with 5% $CO_2$. The medium was changed twice a week. Three weeks after seeding, cultures of glial cells became stabilised. Then, sub-clones of endothelial cells frozen at passage 3 were cultured on a 60-mm-diameter gelatin-coated Petri dish. Confluent endothelial cells were trypsinized and plated on the upper side of the filters at a density of $4 \times 10^5$ cells/ml. The medium used for the co-culture was DMEM supplemented with 10% (v/v) calf serum (CS) and 10% (v/v) horse serum (HS), 2 mM glutamine, and 50 µg/ml of gentamycin, and 1 ng/ml of basic fibroblast growth factor was added every other day. Under these conditions, endothelial cells formed a confluent monolayer after about 12 days.

Lucifer Yellow was used as a paracellular marker during evaluation of the test peptides to confirm the integrity of the BBB model. This small hydrophilic molecule presents a low cerebral penetration and its endothelial permeability coefficient reveals the endothelial cell monolayer integrity, thereby serving as a useful control. On the day of the experiments, Ringer-HEPES (NaCl, 150 mM; KCl, 5.2 mM; $CaCl_2$, 2.2 mM; $MgCl_2$ $6H_2O$, 0.2 mM; $NaHCO_3$, 6 mM; HEPES, 5 mM; glucose, 2.8 mM) was added to the lower compartment (abluminal side) of a six-well plate (3 mL per well). Filters with or without endothelial cells were washed with the Ringer-HEPES solution for 10 minutes at 37° C. to minimize traces of serum, and were then transferred to each well of the six-well plate. A volume of 1 mL Ringer-HEPES solution containing the peptide fragments in combination with Lucifer Yellow (20 µM) was placed in the upper compartment (luminal side) of the well.

Experiments were performed in triplicate with filters containing a confluent monolayer of endothelial cells (for BBB integrity testing or evaluation of peptide fragment passage), or in triplicate with empty filters coated only with collagen (filter test). Incubations were performed on a rocking platform for 120 minutes at 37° C. At the end of the incubation period, aliquots of the luminal and abluminal liquids were collected for fluorescence counting to evaluate membrane integrity (Lucifer Yellow), and LC/MS analysis to evaluate passage of the p97 peptide fragments across the empty filter or the endothelial monolayer, as detailed below.

Fluorescence Analysis.

Lucifer Yellow (20 µM) was used as a paracellular marker for monitor the permeability of the BBB, and was analyzed by a fluorescence counter (Flouroskan Ascent, Thermolabs Systems). Fluorescence was determined in representative samples from each lower compartment of the triplicate and from the initial solution (containing test peptides and Lucifer Yellow). For the abluminal side (lower compartment), aliquots of 200 µL were added to 96-well plates and measured by fluorescence counting, and for the luminal side (upper compartment), aliquots of 204 from T0 and T120 minutes were added to 96-well plates and measured by fluorescence counting.

LC/MS Analysis of Trypsin Digests.

Three hundred microliters was removed from each well and pooled into a single tube for each timepoint/fraction/pore size. Five hundred microliters of 0.1% formic acid was added to each sample for acidification. The peptides were purified using Oasis HLB 10cc cartridges from Waters, and the purified peptides were frozen at −80° C. and lyophilized overnight. The samples were rehydrated in 30 µl (20% acetonitrile, 0.1% FA). Fifteen microliters of each sample was analyzed by LC-MS/MS on an LTQ Orbitrap Velos mass spectrometer (Thermo), and the data (Raw files) were analyzed with the Proteome Discoverer 1.3.0.339 software suite (Thermo Scientific). The peak lists were submitted to a Mascot 2.3 server against the Uniprot-Swissprot database. The peak areas were calculated for the top three peptides for each protein detected with high confidence.

Tryptic peptides were detected in the luminal and abluminal compartments for both the 0.3 and 0.4 µm pore sizes after 120 minutes. Based on the peak area of the top three p97 peptides, the ratio of peptides in the luminal side to the abluminal side was about 2:1. The results for specific p97 peptides are shown in Table 2 (3 micron pore size) and Table 3 (4 micron pore size) below.

TABLE 2

Tryptic Peptides at 3 Micron Pore Size

| Tryptic Peptide Sequence (SEQ ID NO:) | Ablum 120: Area | Lum 120: Area | Ablum 120 conf | IonScore Ablum 120 | Exp Value Ablum 120 | Lum 120 conf | IonScore Lum 120 | Exp Value Lum 120 |
|---|---|---|---|---|---|---|---|---|
| LFSHEGSSFQMFS SEAYGQK (SEQ ID NO: 55) | 1.28E+09 | 4.55E+09 | High | 115 | 2.50E-11 | High | 130 | 8.40E-13 |
| HTTVFDNTNGHNS EPWAAELR (SEQ ID NO: 56) | 1.28E+09 | 1.05E+10 | High | 106 | 2.80E-10 | High | 103 | 5.80E-10 |
| HTTVFDNTNGHNS EPWAAELR (SEQ ID NO: 56) | 7.04E+09 | 1.92E+10 | High | 101 | 9.50E-10 | High | 109 | 1.40E-10 |
| AVSDYFGGSCVPG AGETSYSESLCR (SEQ ID NO: 57) | 5.49E+08 | 5.51E+09 | High | 101 | 2.80E-10 | High | 125 | 1.20E-12 |
| NYPSSLCALCVGD EQGR (SEQ ID NO: 58) | 7.34E+07 | 6.15E+08 | High | 100 | 6.60E-10 | High | 111 | 6.40E-11 |

TABLE 2-continued

Tryptic Peptides at 3 Micron Pore Size

| Tryptic Peptide Sequence (SEQ ID NO:) | Ablum 120: Area | Lum 120: Area | Ablum 120 conf | IonScore Ablum 120 | Exp Value Ablum 120 | Lum 120 conf | IonScore Lum 120 | Exp Value Lum 120 |
|---|---|---|---|---|---|---|---|---|
| TLPSWGQALLSQD FELLCR (SEQ ID NO: 59) | 2.25E+06 | 1.94E+09 | High | 94 | 5.10E-09 | High | 133 | 6.80E-13 |
| AQDLFGDDHNKNGFK (SEQ ID NO: 15) | 9.09E+08 | 5.40E+08 | High | 87 | 2.40E-08 | High | 72 | 7.10E-07 |
| CLAEGAGDVAFVK (SEQ ID NO: 60) | 2.20E+09 | 4.38E+09 | High | 87 | 3.10E-08 | High | 92 | 7.90E-09 |
| MFDSSNYHGQDLLFK (SEQ ID NO: 61) | 9.62E+08 | 2.06E+09 | High | 86 | 2.50E-08 | High | 81 | 7.20E-08 |
| ADTDGGLIFR (SEQ ID NO: 10) | 1.59E+10 | 1.11E+10 | High | 82 | 8.50E-08 | High | 82 | 9.10E-08 |
| LFSHEGSSFQMFS SEAYGQK (SEQ ID NO: 55) | 1.94E+08 | 1.06E+09 | High | 81 | 5.50E-08 | High | 104 | 3.20E-10 |
| MFDSSNYHGQDLLFK (SEQ ID NO: 61) | 5.67E+09 | 1.73E+10 | High | 79 | 1.40E-07 | High | 79 | 1.50E-07 |
| MFDSSNYHGQDLLFK (SEQ ID NO: 61) | 3.22E+07 | 1.01E+08 | High | 79 | 1.10E-07 | High | 77 | 1.60E-07 |
| CGDMAVAFR (SEQ ID NO: 11) | 3.58E+09 | 7.79E+09 | High | 76 | 1.50E-07 | High | 79 | 7.30E-08 |
| GDSSGEGVCDKSPLER (SEQ ID NO: 6) | 1.93E+09 | 5.08E+08 | High | 74 | 3.10E-07 | High | 82 | 4.20E-08 |
| AQDLFGDDHNKNGFK (SEQ ID NO: 15) | 4.27E+08 | 7.66E+07 | High | 74 | 3.80E-07 | Medium | 28 | 1.50E-02 |
| CGDMAVAFR (SEQ ID NO: 11) | 4.54E+08 | 2.20E+08 | High | 71 | 3.40E-07 | High | 79 | 5.50E-08 |
| LFSHEGSSFQMFSS EAYGQKDLLFK (SEQ ID NO: 62) | 1.30E+07 | 8.27E+07 | High | 70 | 1.40E-06 | High | 33 | 6.00E-03 |
| RDSSHAFTLDELR (SEQ ID NO: 63) | 1.66E+09 | 5.02E+09 | High | 68 | 2.70E-06 | High | 80 | 1.60E-07 |
| AQDLFGDDHNK (SEQ ID NO: 64) | 3.69E+09 | 1.08E+09 | High | 63 | 4.50E-06 | High | 55 | 2.60E-05 |
| LSVMGCDVLK (SEQ ID NO: 65) | 2.43E+09 | 1.07E+10 | High | 62 | 9.70E-06 | High | 53 | 8.40E-05 |
| SEDYELLCPNGAR (SEQ ID NO: 14) | 2.52E+08 | 1.25E+08 | High | 62 | 3.90E-06 | High | 49 | 8.00E-05 |
| EAGIQPSLLCVR (SEQ ID NO: 66) | 8.66E+08 | 1.99E+09 | High | 60 | 1.20E-05 | High | 59 | 1.40E-05 |
| SSHVTIDTLKGVK (SEQ ID NO: 4) | 1.12E+08 | 4.73E+07 | High | 60 | 8.50E-06 | High | 57 | 1.30E-05 |
| WCATSDPEQHK (SEQ ID NO: 2) | 1.01E+09 | 1.37E+08 | High | 59 | 5.00E-06 | High | 57 | 7.90E-06 |
| HTTVFDNTNGHNS EPWAAELR (SEQ ID NO: 56) | 0.00E+00 | 2.95E+07 | High | 55 | 2.90E-05 | High | 51 | 6.20E-05 |
| LSVMGCDVLK (SEQ ID NO: 65) | 4.85E+08 | 3.08E+09 | High | 55 | 4.70E-05 | High | 53 | 8.10E-05 |
| DSSHAFTLDELR (SEQ ID NO: 13) | 5.87E+09 | 1.03E+10 | High | 54 | 5.20E-05 | High | 59 | 1.70E-05 |

TABLE 2-continued

Tryptic Peptides at 3 Micron Pore Size

| Tryptic Peptide Sequence (SEQ ID NO:) | Ablum 120: Area | Lum 120: Area | Ablum 120 conf | IonScore Ablum 120 | Exp Value Ablum 120 | Lum 120 conf | IonScore Lum 120 | Exp Value Lum 120 |
|---|---|---|---|---|---|---|---|---|
| LCRGDSSGEGVCDK (SEQ ID NO: 5) | 2.64E+05 | 2.17E+05 | High | 52 | 2.90E-05 | High | 47 | 9.70E-05 |
| SSHVTIDTLK (SEQ ID NO: 67) | 3.37E+09 | 1.74E+09 | High | 48 | 1.90E-04 | High | 43 | 6.80E-04 |
| LKPEIQCVSAK (SEQ ID NO: 12) | 4.39E+09 | 1.00E+09 | High | 46 | 3.00E-04 | High | 45 | 4.20E-04 |
| VPAHAVVVR (SEQ ID NO: 9) | 1.24E+08 | 3.48E+07 | High | 45 | 6.50E-05 | High | 40 | 2.00E-04 |
| ADVTEWR (SEQ ID NO: 8) | 1.05E+10 | 9.31E+08 | High | 44 | 4.80E-04 | High | 48 | 2.30E-04 |
| RSSHVTIDTLK (SEQ ID NO: 3) | 1.64E+08 | 9.53E+07 | High | 43 | 6.90E-04 | High | 45 | 4.10E-04 |
| SEDYELLCPNGAR (SEQ ID NO: 14) | 2.10E+09 | 2.51E+08 | High | 42 | 4.80E-04 | High | 60 | 7.40E-06 |
| WCVLSTPEIQK (SEQ ID NO: 68) | 1.09E+07 | 0.00E+00 | Medium | 37 | 4.20E-03 | | | |
| YYDYSGAFR (SEQ ID NO: 7) | 6.41E+09 | 1.00E+09 | Medium | 31 | 3.80E-03 | High | 51 | 3.70E-05 |
| GLLCDPNR (SEQ ID NO: 69) | 1.65E+09 | 1.97E+08 | Medium | 30 | 8.60E-03 | Medium | 29 | 1.20E-02 |
| DSSHAFTLDELRGK (SEQ ID NO: 70) | 1.99E+07 | 0.00E+00 | Low | 26 | 5.20E-02 | | | |
| GLLCDPNRLPPYLR (SEQ ID NO: 71) | 6.75E+09 | 2.32E+10 | Low | 25 | 3.20E-02 | Low | 19 | 1.40E-01 |
| EHGLKPVVGEVYDQ EVGTSYYAVAVVRR (SEQ ID NO: 72) | 1.70E+07 | 0.00E+00 | Low | 22 | 5.30E-02 | | | |
| GLLCDPNRLPPYLR (SEQ ID NO: 71) | 1.09E+07 | 2.00E+08 | Low | 18 | 2.00E-01 | Medium | 26 | 3.10E-02 |
| CVGNSQERYYGYR (SEQ ID NO: 73) | 4.94E+06 | 0.00E+00 | Low | 18 | 1.30E-01 | | | |
| CLVENAGDVAFVR (SEQ ID NO: 74) | 1.30E+08 | 5.49E+08 | Low | 16 | 4.10E-01 | High | 72 | 1.20E-06 |
| DSTSELVPIATQTY EAWLGHEYLHAMK (SEQ ID NO: 75) | 1.55E+07 | 3.56E+08 | Low | 15 | 4.10E-01 | Low | 11 | 1.00E+00 |
| DSTSELVPIATQTY EAWLGHEYLHAMK (SEQ ID NO: 75) | 0.00E+00 | 0.00E+00 | Low | 12 | 7.80E-01 | | | |
| TLPSWGQALLSQDF ELLCR (SEQ ID NO: 59) | 0.00E+00 | 0.00E+00 | | | | High | 111 | 1.00E-10 |
| LFSHEGSSFQMFSS EAYGQK (SEQ ID NO: 55) | 0.00E+00 | 0.00E+00 | | | | High | 79 | 1.20E-07 |
| IQAEQVDAVTLSGE DIYTAGK (SEQ ID NO: 76) | 0.00E+00 | 3.48E+06 | | | | High | 75 | 4.30E-07 |
| HSTVLENTDGK (SEQ ID NO: 77) | 0.00E+00 | 2.10E+07 | | | | High | 66 | 2.70E-06 |

TABLE 2-continued

Tryptic Peptides at 3 Micron Pore Size

| Tryptic Peptide Sequence (SEQ ID NO:) | Ablum 120: Area | Lum 120: Area | Ablum 120 conf | IonScore Ablum 120 | Exp Value Ablum 120 | Lum 120 conf | IonScore Lum 120 | Exp Value Lum 120 |
|---|---|---|---|---|---|---|---|---|
| TVGWNVPVGYLVESGR (SEQ ID NO: 78) | 0.00E+00 | 9.38E+07 | | | | High | 62 | 8.40E-06 |
| LLNEGQR (SEQ ID NO: 79) | 0.00E+00 | 1.71E+07 | | | | High | 43 | 4.30E-04 |
| LFSHEGSSFQMFSSE AYGQKDLLFK (SEQ ID NO: 80) | 0.00E+00 | 0.00E+00 | | | | High | 40 | 1.20E-03 |
| ADTDGGLIFRLLNEGQR (SEQ ID NO: 81) | 0.00E+00 | 3.69E+07 | | | | High | 40 | 1.50E-03 |
| HTTVFDNTNGHNS EPWAAELR (SEQ ID NO: 56) | 0.00E+00 | 0.00E+00 | | | | High | 38 | 1.20E-03 |

TABLE 3

Tryptic Peptides at 4 Micron Pore Size

| Tryptic Peptide Sequence | Ablum 120: Area | Lum 120: Area | Ablum 120 conf | IonScore Ablum 120 | Exp Value Ablum 120 | Lum 120 conf | IonScore Lum 120 | Exp ValueLum 120 |
|---|---|---|---|---|---|---|---|---|
| AVSDYFGGSCVPGA GETSYSESLCR (SEQ ID NO: 57) | 7.98E+08 | 5.03E+09 | High | 123 | 1.70E-12 | High | 110 | 3.80E-11 |
| HTTVFDNTNGHNSE PWAAELR (SEQ ID NO: 56) | 9.47E+09 | 1.79E+10 | High | 116 | 3.10E-11 | High | 102 | 6.70E-10 |
| LFSHEGSSFQMFSS EAYGQK (SEQ ID NO: 55) | 2.07E+09 | 4.14E+09 | High | 109 | 1.00E-10 | High | 127 | 1.50E-12 |
| TLPSWGQALLSQDF ELLCR (SEQ ID NO: 59) | 2.21E+06 | 1.94E+09 | High | 103 | 6.90E-10 | High | 125 | 3.80E-12 |
| HTTVFDNTNGHNSE PWAAELR (SEQ ID NO: 56) | 1.86E+09 | 1.01E+10 | High | 101 | 8.10E-10 | High | 97 | 2.20E-09 |
| LFSHEGSSFQMFSS EAYGQK (SEQ ID NO: 55) | 3.04E+08 | 1.24E+09 | High | 99 | 8.90E-10 | High | 97 | 1.60E-09 |
| ADTDGGLIFR (SEQ ID NO: 10) | 1.57E+10 | 8.04E+09 | High | 88 | 2.40E-08 | High | 85 | 4.70E-08 |
| NYPSSLCALCVGDE QGR (SEQ ID NO: 58) | 1.09E+08 | 5.52E+08 | High | 87 | 1.60E-08 | High | 84 | 2.70E-08 |
| AQDLFGDDHNKNGFK (SEQ ID NO: 15) | 5.25E+08 | 6.29E+07 | High | 85 | 3.20E-08 | High | 43 | 4.50E-04 |
| CLAEGAGDVAFVK (SEQ ID NO: 60) | 2.06E+09 | 5.13E+09 | High | 83 | 6.90E-08 | High | 103 | 7.10E-10 |
| MFDSSNYHGQDLLFK (SEQ ID NO: 61) | 9.03E+09 | 1.79E+10 | High | 78 | 1.60E-07 | High | 76 | 3.00E-07 |
| GDSSGEGVCDKSPLER (SEQ ID NO: 6) | 2.34E+09 | 4.75E+08 | High | 78 | 1.20E-07 | High | 82 | 5.00E-08 |

TABLE 3-continued

Tryptic Peptides at 4 Micron Pore Size

| Tryptic Peptide Sequence | Ablum 120: Area | Lum 120: Area | Ablum 120 conf | IonScore Ablum 120 | Exp Value Ablum 120 | Lum 120 conf | IonScore Lum 120 | Exp ValueLum 120 |
|---|---|---|---|---|---|---|---|---|
| CLVENAGDVAFVR (SEQ ID NO: 74) | 1.99E+08 | 5.41E+08 | High | 77 | 3.60E-07 | High | 72 | 1.20E-06 |
| CGDMAVAFR (SEQ ID NO: 11) | 3.92E+09 | 8.68E+09 | High | 76 | 1.40E-07 | High | 76 | 1.40E-07 |
| MFDSSNYHGQDLLFK (SEQ ID NO: 61) | 1.23E+09 | 2.13E+09 | High | 74 | 3.40E-07 | High | 90 | 9.30E-09 |
| LFSHEGSSFQMFSSEAYGQKDLLFK (SEQ ID NO: 80) | 0.00E+00 | 0.00E+00 | High | 73 | 6.80E-07 | Low | 15 | 4.70E-01 |
| CGDMAVAFR (SEQ ID NO: 11) | 5.90E+08 | 2.62E+08 | High | 70 | 3.60E-07 | High | 70 | 4.40E-07 |
| SSHVTIDTLKGVK (SEQ ID NO: 4) | 1.37E+08 | 5.71E+07 | High | 70 | 7.30E-07 | High | 60 | 7.20E-06 |
| AQDLFGDDHNKNGFK (SEQ ID NO: 15) | 2.84E+09 | 5.20E+08 | High | 70 | 1.10E-06 | High | 64 | 4.90E-06 |
| MFDSSNYHGQDLLFK (SEQ ID NO: 61) | 4.19E+07 | 1.06E+08 | High | 68 | 1.20E-06 | High | 86 | 2.10E-08 |
| AQDLFGDDHNK (SEQ ID NO: 64) | 4.05E+09 | 1.19E+09 | High | 67 | 1.80E-06 | High | 66 | 2.00E-06 |
| DSSHAFTLDELR (SEQ ID NO: 13) | 9.64E+09 | 9.87E+09 | High | 67 | 2.70E-06 | High | 51 | 9.50E-05 |
| SEDYELLCPNGAR (SEQ ID NO: 14) | 3.09E+08 | 9.88E+07 | High | 65 | 2.00E-06 | High | 35 | 2.10E-03 |
| WCATSDPEQHK (SEQ ID NO: 2) | 1.42E+09 | 1.70E+08 | High | 64 | 1.50E-06 | High | 59 | 5.30E-06 |
| RDSSHAFTLDELR (SEQ ID NO: 63) | 2.01E+09 | 5.70E+09 | High | 64 | 7.90E-06 | High | 75 | 5.90E-07 |
| LSVMGCDVLK (SEQ ID NO: 65) | 3.34E+09 | 1.06E+10 | High | 60 | 1.60E-05 | High | 55 | 5.00E-05 |
| LFSHEGSSFQMFSSEAYGQKDLLFK (SEQ ID NO: 80) | 2.40E+07 | 8.63E+07 | High | 57 | 2.40E-05 | High | 39 | 1.70E-03 |
| LSVMGCDVLK (SEQ ID NO: 63) | 6.72E+08 | 3.28E+09 | High | 53 | 7.00E-05 | High | 56 | 3.60E-05 |
| SEDYELLCPNGAR (SEQ ID NO: 14) | 2.40E+09 | 1.84E+08 | High | 52 | 5.60E-05 | High | 73 | 3.90E-07 |
| LCRGDSSGEGVCDK (SEQ ID NO: 5) | 5.97E+05 | 2.44E+05 | High | 51 | 3.70E-05 | High | 52 | 2.90E-05 |
| EAGIQPSLLCVR (SEQ ID NO: 66) | 1.15E+09 | 1.92E+09 | High | 50 | 1.10E-04 | High | 60 | 1.10E-05 |
| HTTVFDNTNGHNSEPWAAELR (SEQ ID NO: 56) | 1.48E+07 | 2.91E+07 | High | 49 | 9.70E-05 | High | 46 | 2.10E-04 |
| RSSHVTIDTLK (SEQ ID NO: 3) | 2.23E+08 | 1.08E+08 | High | 48 | 1.90E-04 | High | 48 | 1.90E-04 |
| CGNMSEAFR (SEQ ID NO: 82) | 2.53E+07 | 0.00E+00 | High | 48 | 4.70E-05 | | | |
| SSHVTIDTLK (SEQ ID NO: 67) | 3.87E+09 | 1.78E+09 | High | 46 | 5.20E-04 | High | 44 | 5.40E-04 |

TABLE 3-continued

Tryptic Peptides at 4 Micron Pore Size

| Tryptic Peptide Sequence | Ablum 120: Area | Lum 120: Area | Ablum 120 conf | IonScore Ablum 120 | Exp Value Ablum 120 | Lum 120 conf | IonScore Lum 120 | Exp ValueLum 120 |
|---|---|---|---|---|---|---|---|---|
| VPAHAVVVR (SEQ ID NO: 9) | 1.50E+08 | 4.52E+07 | High | 45 | 6.40E-05 | High | 39 | 2.70E-04 |
| ADVTEWR (SEQ ID NO: 8) | 1.10E+10 | 8.59E+08 | High | 44 | 4.80E-04 | High | 44 | 5.10E-04 |
| LKPEIQCVSAK (SEQ ID NO: 12) | 4.96E+09 | 1.03E+09 | High | 43 | 6.80E-04 | High | 57 | 2.50E-05 |
| DSTSELVPIATQTYEAWLGHEYLHAMK (SEQ ID NO: 75) | 1.42E+07 | 3.26E+08 | Medium | 41 | 1.00E-03 | Low | 18 | 1.80E-01 |
| WCVLSTPEIQK (SEQ ID NO: 68) | 1.67E+07 | 0.00E+00 | Medium | 40 | 1.90E-03 | | | |
| TVGWNVPVGYLVESGR (SEQ ID NO: 78) | 1.38E+07 | 1.01E+08 | Medium | 40 | 1.60E-03 | High | 57 | 2.70E-05 |
| YYDYSGAFR (SEQ ID NO: 7) | 6.88E+09 | 9.30E+08 | High | 39 | 7.90E-04 | High | 49 | 7.10E-05 |
| DSSHAFTLDELRGK (SEQ ID NO: 70) | 2.37E+07 | 0.00E+00 | Low | 33 | 8.70E-03 | | | |
| EHGLKPVVGEVYDQEVGTSYYAVAVVRR (SEQ ID NO: 72) | 2.62E+07 | 0.00E+00 | Medium | 31 | 5.80E-03 | | | |
| GLLCDPNR (SEQ ID NO: 69) | 1.84E+09 | 1.72E+08 | Low | 29 | 1.20E-02 | Medium | 30 | 9.00E-03 |
| GLLCDPNRLPPYLR (SEQ ID NO: 71) | 9.69E+09 | 2.33E+10 | Low | 26 | 2.40E-02 | Low | 24 | 4.20E-02 |
| ADTDGGLIFRLLNEGQR (SEQ ID NO: 81) | 5.53E+06 | 3.36E+07 | Low | 26 | 4.10E-02 | High | 40 | 1.60E-03 |
| CVGNSQERYYGYR (SEQ ID NO: 73) | 6.84E+06 | 0.00E+00 | Low | 19 | 7.60E-02 | | | |
| ADVTEWRQCHLAR (SEQ ID NO: 83) | 4.26E+06 | 0.00E+00 | Low | 15 | 5.00E-01 | | | |
| CLVENAGDVAFVR (SEQ ID NO: 74) | 5.55E+06 | 1.46E+07 | Low | 12 | 1.00E+00 | Low | 16 | 3.80E-01 |
| TLPSWGQALLSQDFELLCR (SEQ ID NO: 59) | 0.00E+00 | 0.00E+00 | | | | High | 107 | 2.90E-10 |
| LFSHEGSSFQMFSSEAYGQK (SEQ ID NO: 55) | 0.00E+00 | 1.27E+09 | | | | High | 72 | 3.30E-07 |
| HSTVLENTDGK (SEQ ID NO: 77) | 0.00E+00 | 2.59E+07 | | | | High | 62 | 6.70E-06 |
| IQAEQVDAVTLSGEDIYTAGK (SEQ ID NO: 76) | 0.00E+00 | 3.08E+06 | | | | High | 53 | 7.70E-05 |
| IQAEQVDAVTLSGEDIYTAGK (SEQ ID NO: 76) | 0.00E+00 | 4.79E+07 | | | | High | 49 | 1.60E-04 |
| LLNEGQR (SEQ ID NO: 79) | 0.00E+00 | 2.38E+07 | | | | High | 43 | 4.70E-04 |
| DLLFKDSTSELVPIATQTYEAWLGHEYLHAMK (SEQ ID NO: 84) | 0.00E+00 | 3.76E+07 | | | | High | 34 | 3.90E-03 |

TABLE 3-continued

Tryptic Peptides at 4 Micron Pore Size

| Tryptic Peptide Sequence | Ablum 120: Area | Lum 120: Area | Ablum 120 conf | IonScore Ablum 120 | Exp Value Ablum 120 | Lum 120 conf | IonScore Lum 120 | Exp ValueLum 120 |
|---|---|---|---|---|---|---|---|---|
| GLLCDPNRLPPYLR (SEQ ID NO: 71) | 0.00E+00 | 2.30E+08 | | | | Medium | 26 | 3.00E-02 |
| IQAEQVDAVTLSGEDIYTAGK (SEQ ID NO: 76) | 0.00E+00 | 0.00E+00 | | | | Low | 24 | 5.90E-02 |
| DSTSELVPIATQTYEAWLGHEYLHAMK (SEQ ID NO: 75) | 0.00E+00 | 0.00E+00 | | | | Low | 12 | 7.30E-01 |
| MFDSSNYHGQDLLFKDATVR (SEQ ID NO: 85) | 0.00E+00 | 0.00E+00 | | | | | | |
| AVPVGEKTTYR (SEQ ID NO: 86) | 0.00E+00 | 0.00E+00 | | | | | | |

LC/MS Analysis of CNBr Digests.

Three hundred microliters was removed from each well and pooled into a single tube for each timepoint/fraction/pore size. Five hundred microliters of 0.1% formic acid was added to each sample for acidification. The CNBr protein fragments were purified using Sep=Pak Vac 12cc C8 cartridges. Purified fragments were frozen at −80° C. and lyophilized overnight. The CNBr fragments were rehydrated with 25 mM ammonium bicarbonate, reduced with DTT, and alkylated with iodoacetamide. The alkylation was quenched with a section addition of DTT. Six micrograms of purified porcine trypsin was then added to each well and the samples were placed overnight in a 37° C. incubator. The following morning, the peptides were purified using Oasis HLB 10cc cartridges from Waters. Purified peptides were frozen at −80° C. and lyophilized overnight. The samples were rehydrated in 30 µl (20% acetonitrile, 0.1% FA). Fifteen microliters of each sample was analyzed by LC-MS/MS on an LTQ Orbitrap Velos mass spectrometer (Thermo), and the data (Raw files) were analyzed with the Proteome Discoverer 1.3.0.339 software suite (Thermo Scientific). The peak lists were submitted to a Mascot 2.3 server against the Uniprot-Swissprot database. The peak areas were calculated for the top three peptides for each protein detected with high confidence.

Tryptic peptides from CNBr p97 fragments were detected in the luminal and abluminal compartments for both the 0.3 and 0.4 µm pore sizes after 120 minutes. Based on the peak area of the top three p97 peptides, the ratio of peptides in the luminal side to the abluminal side was about 200:1. The results for specific p97 peptides are shown in Table 4 (3 micron pore size) and Table 5 (4 micron pore size) below. Tryptic peptides from three distinct p97 CNBr fragments were detected (see FIG. 9B).

TABLE 4

CNBr digests at 3 Micron Pore Size

| CNBr Peptide Sequence | Ablum 120: Area | Lum 120: Area | Ablumn 120 conf | IonScore Ablum 120 | Exp Value Ablum 120 | Lum 120 conf | IonScore Lum 120 | Exp Value Lum 120 |
|---|---|---|---|---|---|---|---|---|
| SEDYELLCPNGAR (SEQ ID NO: 14) | 3.92E+06 | 9.18E+08 | High | 65 | 1.50E-06 | High | 57 | 8.60E-06 |
| FDSSNYHGQDLLFK (SEQ ID NO: 87) | 1.46E+08 | 2.16E+10 | High | 57 | 8.20E-06 | High | 68 | 6.40E-07 |
| VRPDTNIFTVYGLLDK (SEQ ID NO: 88) | 1.71E+07 | 1.73E+10 | High | 56 | 3.70E-06 | High | 79 | 2.10E-08 |
| FSSEAYGQK (SEQ ID NO: 89) | 1.70E+06 | 2.39E+08 | High | 42 | 3.40E-04 | High | 42 | 3.20E-04 |
| DSSHAFTLDELR (SEQ ID NO: 13) | 1.79E+06 | 1.18E+07 | Medium | 32 | 4.10E-03 | High | 55 | 2.40E-05 |
| HTTVFDNTNGHNSEPWAAELR (SEQ ID NO: 56) | 0.00E+00 | 3.96E+08 | | | | High | 110 | 3.20E-11 |

TABLE 4-continued

CNBr digests at 3 Micron Pore Size

| CNBr Peptide Sequence | Ablum 120: Area | Lum 120: Area | Ablumn 120 conf | IonScore Ablum 120 | Exp Value Ablum 120 | Lum 120 conf | IonScore Lum 120 | Exp Value Lum 120 |
|---|---|---|---|---|---|---|---|---|
| AVSDYFGGSCVPGAGE TSYSESLCR (SEQ ID NO: 57) | 0.00E+00 | 1.02E+07 | | | | High | 107 | 1.80E-11 |
| NYPSSLCALCVGDEQGR (SEQ ID NO: 58) | 0.00E+00 | 2.34E+07 | | | | High | 87 | 5.00E-09 |
| ADTDGGLIFR (SEQ ID NO: 10) | 0.00E+00 | 3.25E+07 | | | | High | 85 | 2.80E-08 |
| SEDYELLCPNGAR (SEQ ID NO: 14) | 0.00E+00 | 5.04E+07 | | | | High | 77 | 7.90E-08 |
| CLVENAGDVAFVR (SEQ ID NO: 73) | 0.00E+00 | 2.69E+07 | | | | High | 75 | 2.00E-07 |
| TVGWNVPVGYLVESGR (SEQ ID NO: 74) | 0.00E+00 | 4.96E+07 | | | | High | 67 | 6.90E-07 |
| FDSSNYHGQDLLFK (SEQ ID NO: 86) | 0.00E+00 | 9.22E+07 | | | | High | 66 | 7.90E-07 |
| WCVLSTPEIQK (SEQ ID NO: 67) | 0.00E+00 | 1.04E+08 | | | | High | 66 | 1.80E-06 |
| EAGIQPSLLCVR (SEQ ID NO: 66) | 0.00E+00 | 6.26E+08 | | | | High | 64 | 1.50E-06 |
| AQDLFGDDHNK (SEQ ID NO: 64) | 0.00E+00 | 2.28E+08 | | | | High | 62 | 2.90E-06 |
| WCATSDPEQHK (SEQ ID NO: 2) | 0.00E+00 | 4.78E+06 | | | | High | 57 | 6.60E-06 |
| HTTVFDNTNGHNSEPW AAELR (SEQ ID NO: 56) | 0.00E+00 | 1.83E+07 | | | | High | 50 | 2.70E-05 |
| YYDYSGAFR (SEQ ID NO: 7) | 0.00E+00 | 9.70E+06 | | | | Medium | 30 | 3.70E-03 |
| LKPEIQCVSAK (SEQ ID NO: 12) | 0.00E+00 | 8.35E+06 | | | | Medium | 28 | 5.70E-03 |
| GTSADHCVQLIAAQEA DAITLDGGAIYEAGK (SEQ ID NO: 90) | 0.00E+00 | 2.39E+07 | | | | Low | 15 | 4.10E-02 |
| GTSADHCVQLIAAQEA DAITLDGGAIYEAGK (SEQ ID NO: 90) | 0.00E+00 | 0.00E+00 | | | | Low | 11 | 1.50E-01 |

TABLE 5

CNBr digests at 4 Micron Pore Size

| CNBr Peptide Sequence | Ablum 120: Area | Lum 120: Area | Ablum 120 conf | IonScore Ablum 120 | Exp Value Ablum 120 | Lum 120 conf | IonScore Lum 120 | Exp ValueLum 120 |
|---|---|---|---|---|---|---|---|---|
| VRPDTNIFTVYGLLDK (SEQ ID NO: 88) | 8.42E+07 | 1.86E+10 | High | 78 | 2.60E-08 | High | 78 | 2.60E-08 |
| SEDYELLCPNGAR (SEQ ID NO: 14) | 1.53E+07 | 1.04E+09 | High | 65 | 1.50E-06 | High | 59 | 6.20E-06 |
| DSSHAFTLDELR (SEQ ID NO: 13) | 1.69E+07 | 5.27E+07 | High | 47 | 1.20E-04 | High | 44 | 2.80E-04 |

TABLE 5-continued

CNBr digests at 4 Micron Pore Size

| CNBr Peptide Sequence | Ablum 120: Area | Lum 120: Area | Ablum 120 conf | IonScore Ablum 120 | Exp Value Ablum 120 | Lum 120 conf | IonScore Lum 120 | Exp ValueLum 120 |
|---|---|---|---|---|---|---|---|---|
| FSSEAYGQK (SEQ ID NO: 89) | 2.05E+06 | 1.59E+08 | High | 39 | 6.60E-04 | High | 45 | 1.60E-04 |
| LKPEIQCVSAK (SEQ ID NO: 12) | 5.38E+06 | 1.46E+07 | Medium | 32 | 2.10E-03 | High | 54 | 1.40E-05 |
| FDSSNYHGQDLLFK (SEQ ID NO: 87) | 1.32E+08 | 2.17E+10 | Low | 26 | 1.00E-02 | High | 67 | 7.60E-07 |
| HTTVFDNTNGHNSEPWAAELR (SEQ ID NO: 56) | 0.00E+00 | 4.20E+08 | | | | High | 115 | 1.10E-11 |
| NYPSSLCALCVGDEQGR (SEQ ID NO: 58) | 0.00E+00 | 5.79E+07 | | | | High | 96 | 7.10E-10 |
| CLVENAGDVAFVR (SEQ ID NO: 74) | 0.00E+00 | 6.68E+07 | | | | High | 79 | 7.00E-08 |
| ADTDGGLIFR (SEQ ID NO: 10) | 0.00E+00 | 1.02E+07 | | | | High | 73 | 4.50E-07 |
| AQDLFGDDHNK (SEQ ID NO: 64) | 0.00E+00 | 1.98E+08 | | | | High | 72 | 3.10E-07 |
| FDSSNYHGQDLLFK (SEQ ID NO: 87) | 0.00E+00 | 1.07E+08 | | | | High | 69 | 4.20E-07 |
| TVGWNVPVGYLVESGR (SEQ ID NO: 78) | 0.00E+00 | 6.98E+07 | | | | High | 67 | 7.80E-07 |
| EAGIQPSLLCVR (SEQ ID NO: 66) | 0.00E+00 | 6.83E+08 | | | | High | 66 | 1.00E-06 |
| SEDYELLCPNGAR (SEQ ID NO: 14) | 0.00E+00 | 5.03E+07 | | | | High | 65 | 1.30E-06 |
| WCATSDPEQHK (SEQ ID NO: 2) | 0.00E+00 | 2.28E+06 | | | | High | 62 | 1.90E-06 |
| IQAEQVDAVTLSGEDIYTAGK (SEQ ID NO: 76) | 0.00E+00 | 1.80E+05 | | | | High | 56 | 9.30E-06 |
| HTTVFDNTNGHNSEPWAAELR (SEQ ID NO: 56) | 0.00E+00 | 2.07E+07 | | | | High | 50 | 2.80E-05 |
| WCVLSTPEIQK (SEQ ID NO: 68) | 0.00E+00 | 2.22E+08 | | | | High | 49 | 7.60E-05 |
| GTSADHCVQLIAAQEADAITLDGGAIYEAGK (SEQ ID NO: 90) | 0.00E+00 | 3.05E+07 | | | | High | 40 | 1.50E-04 |
| TLPSWGQALLSQDFELLCR (SEQ ID NO: 56) | 0.00E+00 | 0.00E+00 | | | | | | |
| AVSDYFGGSCVPGAGETSYSESLCR (SEQ ID NO: 57) | 0.00E+00 | 0.00E+00 | | | | | | |
| IQAEQVDAVTLSGEDIYTAGK (SEQ ID NO: 76) | 0.00E+00 | 0.00E+00 | | | | | | |
| CLAEGAGDVAFVK (SEQ ID NO: 60) | 0.00E+00 | 0.00E+00 | | | | | | |

TABLE 5-continued

CNBr digests at 4 Micron Pore Size

| CNBr Peptide Sequence | Ablum 120: Area | Lum 120: Area | Ablum 120 conf | IonScore Ablum 120 | Exp Value Ablum 120 | Lum 120 conf | IonScore Lum 120 | Exp ValueLum 120 |
|---|---|---|---|---|---|---|---|---|
| HSTVLENTDGK (SEQ ID NO: 77) | 0.00E+00 | 0.00E+00 | | | | | | |
| GTSADHCVQLIAAQEA DAITLDGGAIYEAGK (SEQ ID NO: 90) | 0.00E+00 | 0.00E+00 | | | | | | |

Using the abluminal 120/luminal 120 peak area ratios as one possible criteria, the p97 peptides having the highest BBB transport activity are shown in Tables 6 (tryptic digests) and 7 below (CNBr digests). However, any of the p97 fragments in Tables 2-5 showing a value in the abluminal 120 area could be of potential interest for having BBB transport activity.

TABLE 6

Tryptic peptides that cross the BBB based on abluminal/luminal peak area ratios

| Peptide Sequence | CONF | Abl 120/Lum120 0.4 um insert | Abl 120/Lum120 3.0 um insert | AA position | Structure | SEQ ID NO: |
|---|---|---|---|---|---|---|
| WCATSDPEQHK | High | 8.92 | 7.41 | 25-35 | S—H | 2 |
| RSSHVTIDTLK | High | 2.06 | 1.23 | 115-125 | C—H | 3 |
| SSHVTIDTLKGVK | High | 2.42 | 2.38 | 116-128 | | 4 |
| LCRGDSSGEGVCDK | High | 2.45 | 1.21 | 188-201 | C—H—C | 5 |
| GDSSGEGVCDKSPLER | High | 4.93 | 3.80 | 191-206 | | 6 |
| YYDYSGAFR | High | 7.40 | NA | 207-215 | | 7 |
| ADVTEWR | High | 12.76 | 11.26 | 263-269 | C | 8 |
| VPAHAWVR | High | 3.32 | 3.56 | 276-284 | C—S—H | 9 |
| ADTDGGLIFR | High | 1.95 | 1.44 | 285-294 | | 10 |
| CGDMAVAFR | High | 2.26 | 2.06 | 379-387 | H | 11 |
| LKPEIQCVSAK | High | 4.81 | 4.37 | 391-401 | C—S—CE | 12 |
| DSSHAFTLDELR | High | 0.98 | NA | 460-471 | C—H—C | 13 |
| SEDYELLCPNGAR | High | 13.05 | 8.38 | 596-608 | C—S—C | 14 |
| AQDLFGDDHNKNGFK | High | 5.45 | 1.68 | 645-659 | H—C | 15 |

TABLE 7

CNBr p97 Fragments that Cross the BBB based on abluminal/luminal peak area ratios

| Peptide Sequence | SEQ ID NO: |
|---|---|
| FSSEAYGQKDLLFKDSTSELVPIATQTYEAWLGHEYLHAM | 16 |
| ERIQAEQVDAVTLSGEDIYTAGKTYGLVPAAGEHYAPEDS SNSYYVAVVRRDSSHAFTLDELRGKRSCHAGFGSPAGWD VPVGALIQRGFIRPKDCDVLTAVSEFFNASCVPVNNPKNY PSSLCALCVGDEQGRNKCVGNSQERYYGYRGAFRCLVENA GDVAFVRHTTVEDNTNGHNSEPWAAELRSEDYELLCPNGA RAEVSQFAACNLAQIPPHAVM | 17 |
| VRPDTNIFTVYGLLDKAQDLFGDDHNKNGFKM | 18 |

Example 3 p97 Fragment in an In Vivo Model of the Blood Brain Barrier

A p97 (Mtf) fragment (DSSHAFTLDELR; SEQ ID NO:13) was conjugated to a monoclonal antibody (mAb), administered peripherally to mice along with control proteins, and tested relative to the control proteins for distribution into brain tissues. For quantitative detection, all test proteins were labeled with Alexa Fluor 647 (AF647) according to routine techniques.

Figure 10:
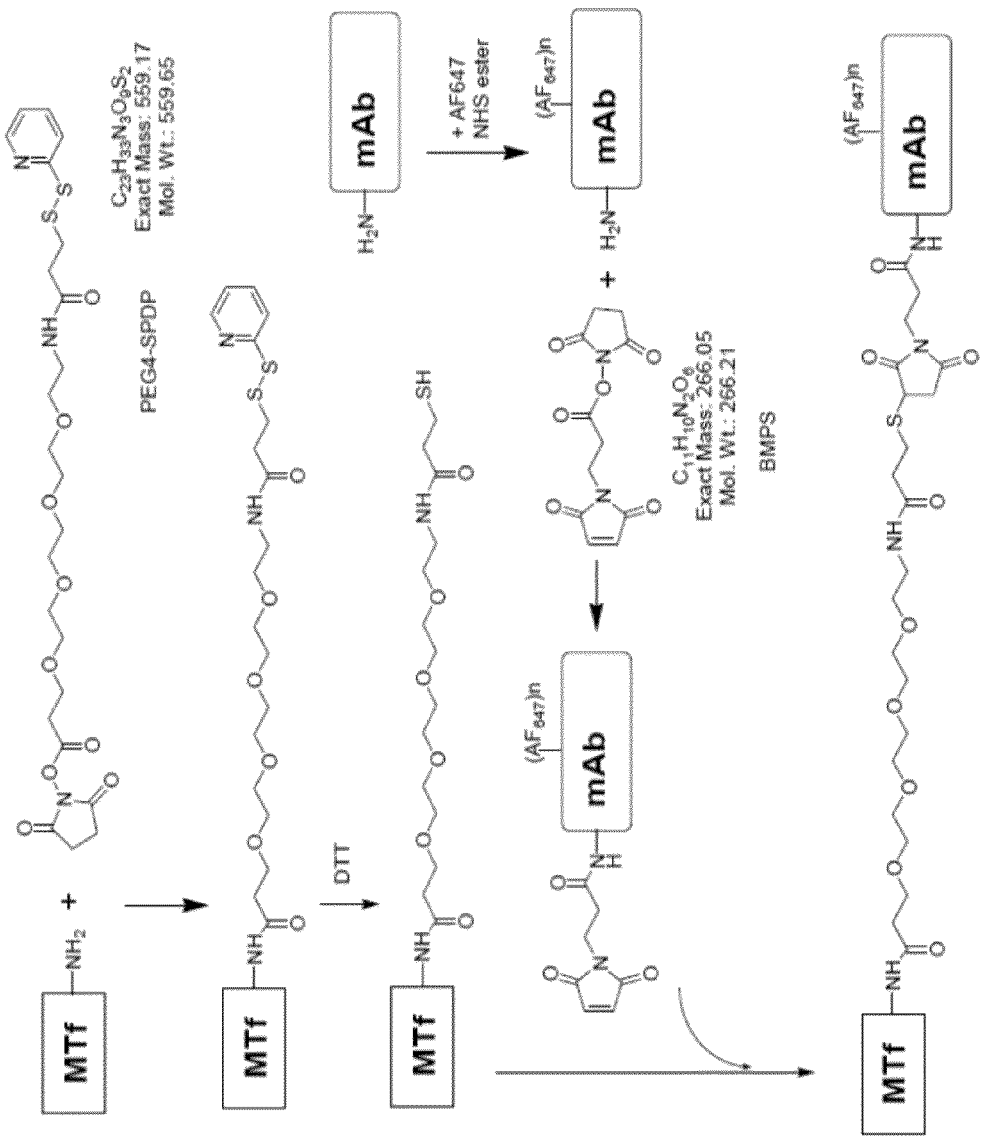
FIG. 10 shows the synthesis route for p97 (MTf)-antibody conjugates (see Example 3).

The following test proteins were prepared: AF647-labeled monoclonal antibody (mAb), AF647-labeled MTf-mAb conjugate (MTf-mAb; MTf is soluble human p97), AF647-labeled $MTf_{PEP}$-mAb conjugate ($MTf_{PEP}$-mAb; $MTF_{PEP}$ is the DSSHAFTLDELRYC (SEQ ID NO:92) fragment of human p97); and AF647-labeled MTf fragment without antibody ($MTf_{PEP}$). The synthesis route of the MTf-mAb and $MTf_{PEP}$-mAb conjugates is illustrated in FIG. 10.

The AF647-labeled test articles were administered to mice according to the study design in Table 8 below.

TABLE 8

Study Design for Testing Brain Biodistribution in Mice

| Test Proteins | Route[2] | Time Point (h) | Dose Level[1] (mg/kg) | Dose Level (nanomoles/kg) | Vascular Perfusion[3] | Number of Mice[4] |
|---|---|---|---|---|---|---|
| mAb | IV | 2 | 10 | 66.7 | yes | 3 |
| MTf-mAb | IV | 2 | 15 | 65.2 | yes | 3 |
| $MTf_{pep}$ | IV | 2 | 5 | 1690.9 | yes | 3 |
| $MTf_{pep}$-mAb | IV | 2 | 10.2 | 63.0 | yes | 3 |

[1]Injection Volume = 0.10 mL/mouse
[2]Injection Route = IV (tail vein)
[3]Vascular Perfusion = 5 min @ 4 ml/min with PBS pH 7.4 with 2.7% BSA, 100 U/mL heparin
[4]Mouse Strain = BALB/c female 6-8 weeks old (17.4 ± 1.1 grams (mean, S.D.)

At 2 hours post-administration of test proteins, Texas Red was administered, animals were sacrificed, and brain tissues were removed. Five to six random fields were cryosected from the mid-coronal sections and the cerebral cortex of brain tissues. Confocal microscopy was then performed to evaluate brain biodistribution of test proteins.

For confocal microscopy, confocal images of fluorescently labeled cells were acquired with an A Leica AOBS SP8 laser scanning confocal microscope (Leica, Heidelberg, Germany). The excitation wavelengths were at 405 (DAPI), 595 nm (Texas Red), and 653 nm (AF647), and an 80 MHz white light laser was used to collect the respective emission signals. All images and spectral data (except DAPI) were generated using highly sensitive HyD detectors. The backscattered emission signals from the sample were delivered through the tunable filter (AOBS).

For three-dimensional (3D) image/volume fraction analysis, a series of two-dimensional (2D) Images (1024×1024 pixels) for a 3D stack volume were acquired. The 3D stack images with optical section thickness (z-axis) of approximately 0.3 microns were captured from 20 micron brain tissue sections. For each tissue volume, z-section images were compiled and the 3-dimensional image restoration was performed with Imaris (BITPLANE Scientific Software).

The volume estimation was made on the 3D image data sets recorded from five or more different areas of the cerebral cortex. Gaussian noise removal filter was applied to define the boundary between foreground and background, and the lower threshold level in the histogram was set to exclude all possible background voxel values. The sum of all the voxels above this threshold level was determined to be the volume.

Figure 11:
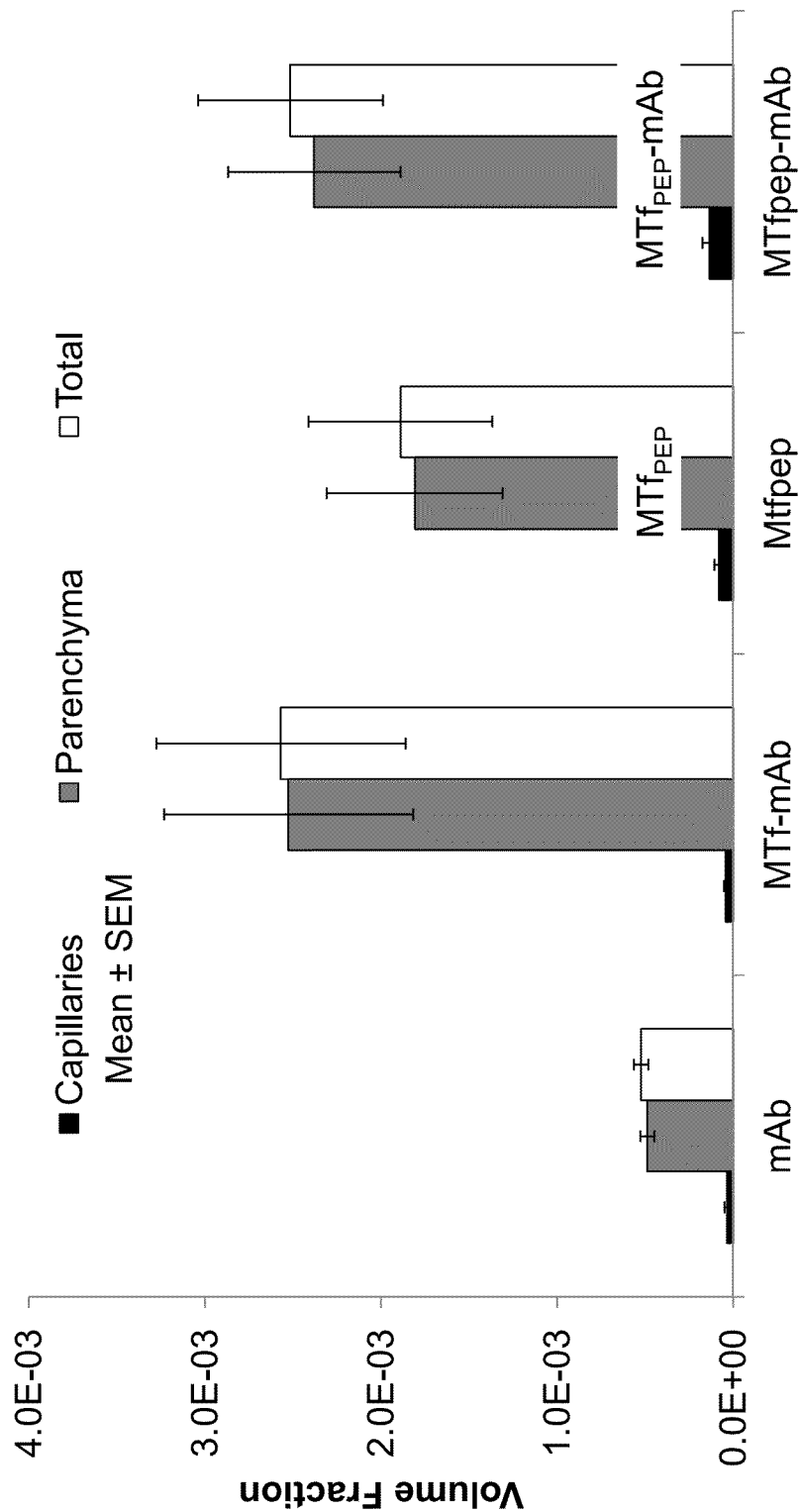
FIG. 11 shows the brain distribution of MTf-antibody conjugates and control proteins after administration to mice (see Example 3).

The $V_{BC}$ (volume fraction of test proteins in brain capillaries), $V_{BP}$ (volume fraction of test proteins in brain parenchyma), and $V_{TOT}$ (volume fraction of test proteins in brain capillaries and brain parenchyma) were calculated. As shown in FIG. 11, the unconjugated mAb did not effectively cross the BBB as illustrated by its low distribution in the brain parenchyma. In contrast, conjugation of the mAb to either MTf or $MTf_{PEP}$ increased distribution of the mAb to the brain parenchyma by about 5-fold. Also, the unconjugated $MTf_{PEP}$ effectively crossed the BBB and distributed to brain parenchyma. These results illustrate that conjugation to fragments of p97 can be used to significantly improve the delivery of polypeptides such as antibodies across the BBB and into CNS tissues such as the brain.

Example 4 p97 Peptide Conjugates

A $p97_{PEP}$ fragment (DSSHAFTLDELR; SEQ ID NO:13) was conjugated to the 44 kd test protein horseradish peroxidase (HRP). This conjugate was administered peripherally (by IV injection) to mice along with control proteins, and tested relative to the control proteins for distribution into brain tissues. For quantitative detection, all test proteins were labeled with Alexa Fluor 680 (AF680) according to routine techniques.

Figure 12:
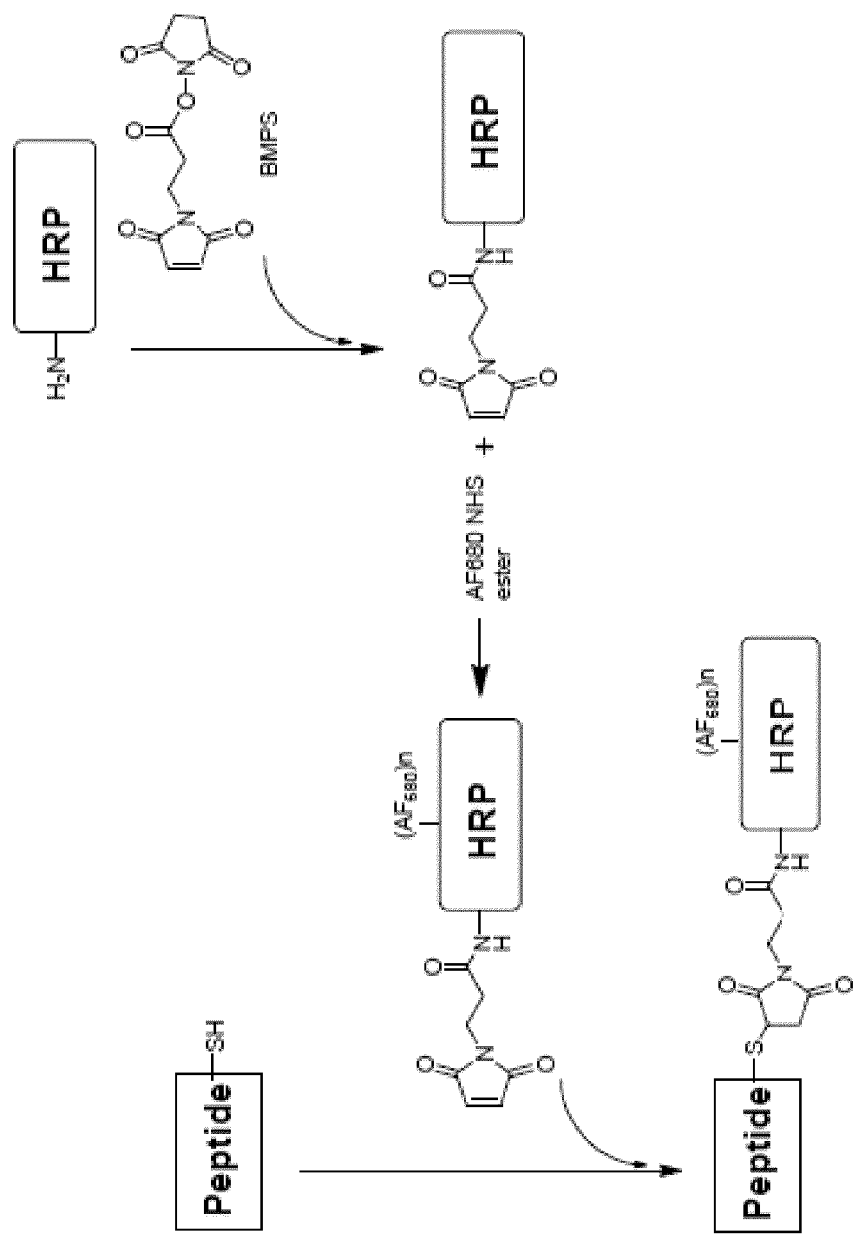
FIG. 12 shows the synthesis route for p97 (MTf)-HRP (12B) conjugates (see Example 4).

The following test proteins were prepared: AF680-labeled HRP (HRP); AF680-labeled $MTf_{PEP}$-HRP conjugate ($MTf_{PEP}$-HRP; $MTF_{PEP}$ is the DSSHAFTLDELRYC (SEQ ID NO:92) fragment of human p97). C-terminal cysteine and tyrosine residues were added to the MTf peptide for conjugation and iodination, respectively. The synthesis route of the HRP conjugates is illustrated in FIG. 12.

The AF680-labeled test articles were administered to mice according to the study design in Table 9 below.

TABLE

Study Design for Testing Brain Biodistribution in Mice

| Test Proteins | Route[2] | Time Point (h) | Dose Level[1] (mg/kg) | Dose Level (nanomoles/kg) | Vascular Perfusion[3] | Number of Mice[4] |
|---|---|---|---|---|---|---|
| PBS | IV | 2 | N/A | N/A | Yes | 1 |
| HRP | IV | 2 | 10.0 | 227 | yes | 3 |
| MTf$_{PEP}$-HRP | IV | 2 | 10.3 | 227 | yes | 3 |

[1]Injection Volume = 0.10 mL/mouse
[2]Injection Route = IV (tail vein)
[3]Vascular Perfusion = 10 min @ 1 ml/min with PBS pH 7.4 with 2.7% BSA, 100 U/mL heparin
[4]Mouse Strain = BALB/c female 6-8 weeks old (16-20 grams)

At 2 hours post-administration of test proteins, tomato Lectin-FITC was administered (80 µg for 10 minutes) to stain the brain vasculature followed by intracardiac perfusion of 10 ml heparinized saline, and brain tissues were removed and processed for microscopy analysis. Three random areas were cryosected from the mid-coronal sections brain tissues, fixed in cold acetone/methanol, and mounted for microscopy. Three-dimensional (3D) confocal microscopy was then performed to evaluate brain biodistribution of test proteins.

Figure 13:
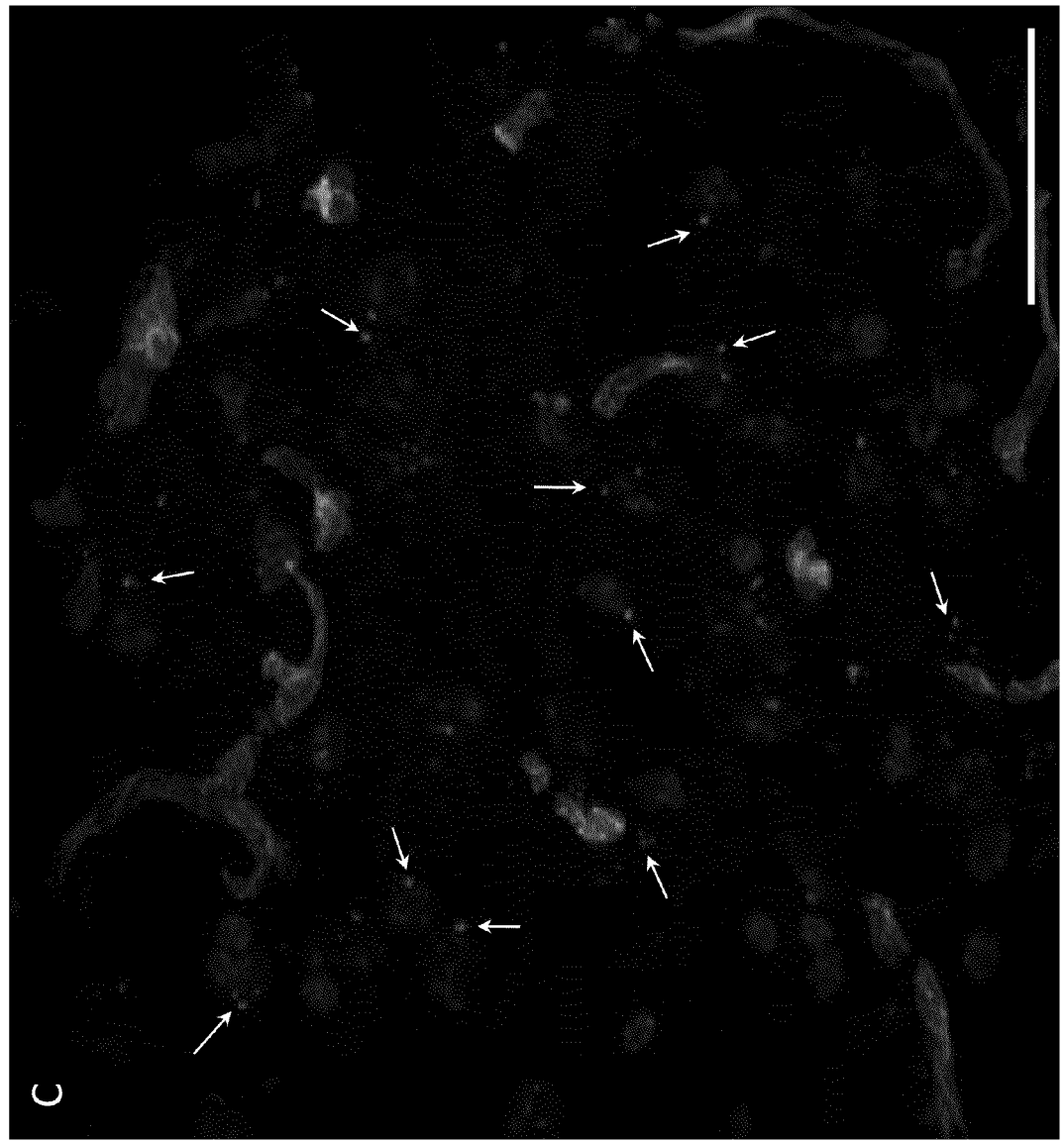
FIGS. 13A-13C show the results of three-dimensional (3D) confocal microscopy that was performed to evaluate brain biodistribution of test proteins.

The results are shown in FIGS. 13A-C. FIG. 13A shows the results for PBS, FIG. 13B shows the results for AF680-labeled HRP, and FIG. 13C shows the results for AF680-labeled MTf$_{PEP}$-HRP conjugate. FIGS. 13A and 13B show no detectable AF680-labeling in brain tissues. In contrast, FIG. 13C shows detectable AF680-labeling, as illustrated by the arrows. These results show that conjugation to the DSSHAFTLDELR peptide can significantly enhance the delivery of a protein of interest across the BBB and into tissues of the brain.

The various embodiments described herein can be combined to provide further embodiments. All of the U.S. patents, U.S. patent application publications, U.S. patent application, foreign patents, foreign patent application and non-patent publications referred to in this specification and/or listed in the Application Data Sheet are incorporated herein by reference, in their entirety. Aspects of the embodiments can be modified, if necessary to employ concepts of the various patents, application and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

We claim:

1. A composition, comprising a conjugate and a pharmaceutically acceptable carrier, where the conjugate comprises at least one isolated p97 polypeptide of up to 50 amino acids in length, where the polypeptide comprises an amino acid sequence at least 80% identical to DSSHAFTLDELR (SEQ ID NO:13), and where the p97 polypeptide is covalently or operatively linked to an agent, to form a p97-agent conjugate.

2. The composition of claim 1, where the p97 polypeptide comprises DSSHAFTLDELR (SEQ ID NO:13).

3. The composition of claim 1, where the p97 polypeptide comprises 2, 3, or 4 of DSSHAFTLDELR (SEQ ID NO:13).

4. The composition of claim 1, where the p97 polypeptide consists of SEQ ID NO:13, and optionally a C-terminal cysteine, a C-terminal tyrosine, or both.

5. The composition of claim 1, where the p97 polypeptide is up to 20 amino acids in length.

6. The composition of claim 1, where the conjugate is a fusion protein.

7. The composition of claim 1, where the agent is a molecule having a molecular weight of 50 to 2000 daltons, a polypeptide, a peptide mimetic, a peptoid, or an aptamer.

8. The composition of claim 7, where the molecule is a cytotoxic or chemotherapeutic or anti-angiogenic agent selected from one or more of alkylating agents, anti-metabolites, anthracyclines, anti-tumor antibiotics, platinums, type I topoisomerase inhibitors, type II topoisomerase inhibitors, vinca alkaloids, and taxanes.

9. The composition of claim 7, where the molecule is selected from one or more of chlorambucil, cyclophosphamide, cilengitide, lomustine (CCNU), melphalan, procarbazine, thiotepa, carmustine (BCNU), enzastaurin, busulfan, daunorubicin, doxorubicin, gefitinib, erlotinib idarubicin, temozolomide, epirubicin, mitoxantrone, bleomycin, cisplatin, carboplatin, oxaliplatin, camptothecins, irinotecan, topotecan, amsacrine, etoposide, etoposide phosphate, teniposide, temsirolimus, everolimus, vincristine, vinblastine, vinorelbine, vindesine, CT52923, paclitaxel, imatinib, dasatinib, sorafenib, pazopanib, sunitnib, vatalanib, geftinib, erlotinib, AEE-788, dichoroacetate, tamoxifen, fasudil, SB-681323, semaxanib, donepezil, galantamine, memantine, rivastigmine, tacrine, rasigiline, naltrexone, lubiprostone, safinamide, istradefylline, pimavanserin, pitolisant, isradipine, pridopidine (ACR16), tetrabenazine, bexarotene, glatirimer acetate, fingolimod, and mitoxantrone, including pharmaceutically acceptable salts and acids thereof.

10. The composition of claim 7, where the polypeptide is an antibody or antigen-binding fragment thereof.

11. The composition of claim 10, where the antibody or antigen-binding fragment thereof specifically binds to a cancer-associated antigen.

12. The composition of claim 11, where the cancer-associated antigen is one or more of human Her2/neu, Her1/EGF receptor (EGFR), Her3, A33 antigen, B7H3, CD5, CD19, CD20, CD22, CD23 (IgE Receptor), C242 antigen, 5T4, IL-6, IL-13, vascular endothelial growth factor VEGF (e.g., VEGF-A) VEGFR-1, VEGFR-2, CD30, CD33, CD37, CD40, CD44, CD51, CD52, CD56, CD74, CD80, CD152, CD200, CD221, CCR4, HLA-DR, CTLA-4, NPC-1C, tenascin, vimentin, insulin-like growth factor 1 receptor (IGF-1R), alpha-fetoprotein, insulin-like growth factor 1 (IGF-1), carbonic anhydrase 9 (CA-IX), carcinoembryonic antigen (CEA), integrin $\alpha v\beta 3$, integrin $\alpha 5\beta 1$, folate receptor 1, transmembrane glycoprotein NMB, fibroblast activation protein alpha (FAP), glycoprotein 75, TAG-72, MUC1, MUC16 (or CA-125), phosphatidylserine, prostate-specific membrane antigen (PMSA), NR-LU-13 antigen, TRAIL-R1, tumor necrosis factor receptor superfamily member 10b (TNFRSF10B or TRAIL-R2), SLAM family member 7 (SLAMF7), EGP40 pancarcinoma antigen, B-cell activating factor (BAFF), platelet-derived growth factor receptor, glycoprotein EpCAM (17-1A), Programmed Death-1, protein disulfide isomerase (PDI), Phosphatase of Regenerating Liver 3 (PRL-3), prostatic acid phosphatase, Lewis-Y antigen, GD2 (a disialoganglioside expressed on tumors of neuroectodermal origin), glypican-3 (GPC3), or mesothelin.

13. The composition of claim 10, where the antibody or antigen-binding fragment thereof specifically binds to a pain-associated antigen.

14. The composition of claim 13, where the pain associated-antigen is one or more of nerve growth factor (NGF) or tropomyosin-related kinase A (TrkA).

15. The composition of claim 10, where the antibody or antigen-binding fragment thereof specifically binds to a pro-inflammatory molecule, optionally a pro-inflammatory cytokine or chemokine.

16. The composition of claim 15, where the pro-inflammatory molecule is one or more of TNF-$\alpha$, TNF-$\beta$, FasL, CD27L, CD30L, CD40L, Ox40L, 4-1BBL, TRAIL, TWEAK, and Apo3L, IL-1$\alpha$, IL-1$\beta$, IL-2, interferon-$\gamma$ (IFN-$\gamma$), IFN-$\alpha$, IFN-$\beta$, IL-6, IL-8, IL-12, IL-15, IL-17, IL-18, IL-21, LIF, CCL5, GRO$\alpha$, MCP-1, MIP-1$\alpha$, MIP-1$\beta$, macrophage colony stimulating factor (MCSF), or granulocyte macrophage colony stimulating factor (GM-CSF).

17. The composition of claim 16, where the pro-inflammatory molecule is TNF-$\alpha$, and where the antibody or antigen-binding fragment is adalimumab, certolizumab pegol, etanercept, golimumab, infliximab, D2E7, CDP 571, or CDP 870, or an antigen-binding fragment or variant thereof.

18. The composition of claim 10, wherein the antibody or antigen-binding fragment thereof specifically binds to one or more of human Her2/neu, Her1/EGFR, TNF-$\alpha$, B7H3 antigen, CD20, VEGF, CD52, CD33, CTLA-4, tenascin, alpha-4 ($\alpha$4) integrin, IL-23, amyloid-$\beta$, Huntingtin, CD25, nerve growth factor (NGF), TrkA, or $\alpha$-synuclein.

19. The composition of claim 10, where the antibody is selected from one or more of trastuzumab, cetuximab, daclizumab, tanezumab, 3F8, 8H9, abagovomab, adecatumumab, afutuzumab, alemtuzumab, alacizumab (pegol), amatuximab, apolizumab, bavituximab, bectumomab, belimumab, bevacizumab, bivatuzumab (mertansine), brentuximab vedotin, cantuzumab (mertansine), cantuzumab (ravtansine), capromab (pendetide), catumaxomab, citatuzumab (bogatox), cixutumumab, clivatuzumab (tetraxetan), conatumumab, dacetuzumab, dalotuzumab, detumomab, drozitumab, ecromeximab, edrecolomab, elotuzumab, enavatuzumab, ensituximab, epratuzumab, ertumaxomab, etaracizumab, farletuzumab, FBTA05, figitumumab, flanvotumab, galiximab, gemtuzumab, ganitumab, gemtuzumab (ozogamicin), girentuximab, glembatumumab (vedotin), ibritumomab tiuxetan, icrucumab, igovomab, indatuximab ravtansine, intetumumab, inotuzumab ozogamicin, ipilimumab (MDX-101), iratumumab, labetuzumab, lexatumumab, lintuzumab, lorvotuzumab (mertansine), lucatumumab, lumiliximab, mapatumumab, matuzumab, milatuzumab, mitumomab, mogamulizumab, moxetumomab (pasudotox), nacolomab (tafenatox), naptumomab (estafenatox), narnatumab, necitumumab, nimotuzumab, nivolumab, Neuradiab® (with or without radioactive iodine), NR-LU-10, ofatumumab, olaratumab, onartuzumab, oportuzumab (monatox), oregovomab, panitumumab, patritumab, pemtumomab, pertuzumab, pritumumab, racotumomab, radretumab, ramucirumab, rilotumumab, rituximab, robatumumab, samalizumab, sibrotuzumab, siltuximab, tabalumab, taplitumomab (paptox), tenatumomab, teprotumumab, TGN1412, ticilimumab, tremelimumab, tigatuzumab, TNX-650, tositumomab, TRBS07, tucotuzumab (celmoleukin), ublituximab, urelumab, veltuzumab, volociximab, votumumab, and zalutumumab, including antigen-binding fragments thereof.

20. The composition of claim 7, where the polypeptide is an interferon-β polypeptide, or an active fragment or variant thereof.

21. The composition of claim 7, where the polypeptide associates with a lysosomal storage disease.

22. The composition of claim 21, where the polypeptide is selected from one or more of aspartylglucosaminidase, acid lipase, cysteine transporter, Lamp-2, α-galactosidase A, acid ceramidase, α-L-fucosidase, β-hexosaminidase A, GM2-ganglioside activator (GM2A), α-D-mannosidase, β-D-mannosidase, arylsulfatase A, saposin B, neuraminidase, α-N-acetylglucosaminidase phosphotransferase, phosphotransferase γ-subunit, L-iduronidase, iduronate-2-sulfatase, heparan-N-sulfatase, α-N-acetylglucosaminidase, acetylCoA:N-acetyltransferase, N-acetylglucosamine 6-sulfatase, galactose 6-sulfatase, β-galactosidase, N-acetylgalactosamine 4-sulfatase, hyaluronoglucosaminidase, sulfatases, palmitoyl protein thioesterase, tripeptidyl peptidase I, acid sphingomyelinase, cathepsin A, cathepsin K, α-galactosidase B, NPC1, NPC2, sialin, and sialic acid transporter, including active fragments and variants thereof.

23. The composition of claim 7, where the agent is a cardiotoxic agent in its unconjugated form.

24. The composition of claim 23, where the cardiotoxic agent is an anthracycline/anthraquinolone, cyclophosphamide, antimetabolite, antimicrotubule agent, tyrosine kinase inhibitor, bevacizumab, or trastuzumab.

25. The composition of claim 23, where the cardiotoxic agent is cyclopentenyl cytosine, 5-fluorouracil, capecitabine, paclitaxel, docataxel, adriamycin, doxorubucin, epirubicin, emetine, isotamide, mitomycin C, erlotinib, gefitinib, imatinib, sorafenib, sunitinib, cisplatin, thalidomide, busulfan, vinblastine, bleomycin, vincristine, arsenic trioxide, methotrexate, rosiglitazone, or mitoxantrone.

* * * * *

SEQUENCE LISTING

```
<160> NUMBER OF SEQ ID NOS: 143

<210> SEQ ID NO 1
<211> LENGTH: 738
<212> TYPE: PRT
<213> ORGANISM: Homo sapiens

<400> SEQUENCE: 1

Met Arg Gly Pro Ser Gly Ala Leu Trp Leu Leu Leu Ala Leu Arg Thr
1               5                   10                  15

Val Leu Gly Gly Met Glu Val Arg Trp Cys Ala Thr Ser Asp Pro Glu
            20                  25                  30

Gln His Lys Cys Gly Asn Met Ser Glu Ala Phe Arg Glu Ala Gly Ile
        35                  40                  45

Gln Pro Ser Leu Leu Cys Val Arg Gly Thr Ser Ala Asp His Cys Val
    50                  55                  60

Gln Leu Ile Ala Ala Gln Glu Ala Asp Ala Ile Thr Leu Asp Gly Gly
65                  70                  75                  80

Ala Ile Tyr Glu Ala Gly Lys Glu His Gly Leu Lys Pro Val Val Gly
                85                  90                  95

Glu Val Tyr Asp Gln Glu Val Gly Thr Ser Tyr Tyr Ala Val Ala Val
            100                 105                 110

Val Arg Arg Ser Ser His Val Thr Ile Asp Thr Leu Lys Gly Val Lys
        115                 120                 125

Ser Cys His Thr Gly Ile Asn Arg Thr Val Gly Trp Asn Val Pro Val
    130                 135                 140
```

-continued

```
Gly Tyr Leu Val Glu Ser Gly Arg Leu Ser Val Met Gly Cys Asp Val
145                 150                 155                 160
Leu Lys Ala Val Ser Asp Tyr Phe Gly Ser Cys Val Pro Gly Ala
            165                 170                 175
Gly Glu Thr Ser Tyr Ser Glu Ser Leu Cys Arg Leu Cys Arg Gly Asp
            180                 185                 190
Ser Ser Gly Glu Gly Val Cys Asp Lys Ser Pro Leu Glu Arg Tyr Tyr
        195                 200                 205
Asp Tyr Ser Gly Ala Phe Arg Cys Leu Ala Glu Gly Ala Gly Asp Val
    210                 215                 220
Ala Phe Val Lys His Ser Thr Val Leu Glu Asn Thr Asp Gly Lys Thr
225                 230                 235                 240
Leu Pro Ser Trp Gly Gln Ala Leu Leu Ser Gln Asp Phe Glu Leu Leu
                245                 250                 255
Cys Arg Asp Gly Ser Arg Ala Asp Val Thr Glu Trp Arg Gln Cys His
            260                 265                 270
Leu Ala Arg Val Pro Ala His Ala Val Val Arg Ala Asp Thr Asp
        275                 280                 285
Gly Gly Leu Ile Phe Arg Leu Leu Asn Glu Gly Gln Arg Leu Phe Ser
    290                 295                 300
His Glu Gly Ser Ser Phe Gln Met Phe Ser Ser Glu Ala Tyr Gly Gln
305                 310                 315                 320
Lys Asp Leu Leu Phe Lys Asp Ser Thr Ser Glu Leu Val Pro Ile Ala
                325                 330                 335
Thr Gln Thr Tyr Glu Ala Trp Leu Gly His Glu Tyr Leu His Ala Met
            340                 345                 350
Lys Gly Leu Leu Cys Asp Pro Asn Arg Leu Pro Pro Tyr Leu Arg Trp
        355                 360                 365
Cys Val Leu Ser Thr Pro Glu Ile Gln Lys Cys Gly Asp Met Ala Val
    370                 375                 380
Ala Phe Arg Arg Gln Arg Leu Lys Pro Glu Ile Gln Cys Val Ser Ala
385                 390                 395                 400
Lys Ser Pro Gln His Cys Met Glu Arg Ile Gln Ala Glu Gln Val Asp
                405                 410                 415
Ala Val Thr Leu Ser Gly Glu Asp Ile Tyr Thr Ala Gly Lys Thr Tyr
            420                 425                 430
Gly Leu Val Pro Ala Ala Gly Glu His Tyr Ala Pro Glu Asp Ser Ser
        435                 440                 445
Asn Ser Tyr Tyr Val Val Ala Val Val Arg Arg Asp Ser Ser His Ala
    450                 455                 460
Phe Thr Leu Asp Glu Leu Arg Gly Lys Arg Ser Cys His Ala Gly Phe
465                 470                 475                 480
Gly Ser Pro Ala Gly Trp Asp Val Pro Val Gly Ala Leu Ile Gln Arg
                485                 490                 495
Gly Phe Ile Arg Pro Lys Asp Cys Asp Val Leu Thr Ala Val Ser Glu
            500                 505                 510
Phe Phe Asn Ala Ser Cys Val Pro Val Asn Asn Pro Lys Asn Tyr Pro
        515                 520                 525
Ser Ser Leu Cys Ala Leu Cys Val Gly Asp Glu Gln Gly Arg Asn Lys
    530                 535                 540
Cys Val Gly Asn Ser Gln Glu Arg Tyr Tyr Gly Tyr Arg Gly Ala Phe
545                 550                 555                 560
Arg Cys Leu Val Glu Asn Ala Gly Asp Val Ala Phe Val Arg His Thr
```

```
                            565                 570                 575
Thr Val Phe Asp Asn Thr Asn Gly His Asn Ser Glu Pro Trp Ala Ala
                580                 585                 590

Glu Leu Arg Ser Glu Asp Tyr Glu Leu Leu Cys Pro Asn Gly Ala Arg
            595                 600                 605

Ala Glu Val Ser Gln Phe Ala Ala Cys Asn Leu Ala Gln Ile Pro Pro
        610                 615                 620

His Ala Val Met Val Arg Pro Asp Thr Asn Ile Phe Thr Val Tyr Gly
625                 630                 635                 640

Leu Leu Asp Lys Ala Gln Asp Leu Phe Gly Asp His Asn Lys Asn
                645                 650                 655

Gly Phe Lys Met Phe Asp Ser Ser Asn Tyr His Gly Gln Asp Leu Leu
                660                 665                 670

Phe Lys Asp Ala Thr Val Arg Ala Val Pro Val Gly Glu Lys Thr Thr
            675                 680                 685

Tyr Arg Gly Trp Leu Gly Leu Asp Tyr Val Ala Ala Leu Glu Gly Met
        690                 695                 700

Ser Ser Gln Gln Cys Ser Gly Ala Ala Ala Pro Ala Pro Gly Ala Pro
705                 710                 715                 720

Leu Leu Pro Leu Leu Leu Pro Ala Leu Ala Ala Arg Leu Leu Pro Pro
                725                 730                 735

Ala Leu

<210> SEQ ID NO 2
<211> LENGTH: 11
<212> TYPE: PRT
<213> ORGANISM: Homo sapiens

<400> SEQUENCE: 2

Trp Cys Ala Thr Ser Asp Pro Glu Gln His Lys
1               5                   10

<210> SEQ ID NO 3
<211> LENGTH: 11
<212> TYPE: PRT
<213> ORGANISM: Homo sapiens

<400> SEQUENCE: 3

Arg Ser Ser His Val Thr Ile Asp Thr Leu Lys
1               5                   10

<210> SEQ ID NO 4
<211> LENGTH: 13
<212> TYPE: PRT
<213> ORGANISM: Homo sapiens

<400> SEQUENCE: 4

Ser Ser His Val Thr Ile Asp Thr Leu Lys Gly Val Lys
1               5                   10

<210> SEQ ID NO 5
<211> LENGTH: 14
<212> TYPE: PRT
<213> ORGANISM: Homo sapiens

<400> SEQUENCE: 5

Leu Cys Arg Gly Asp Ser Ser Gly Glu Gly Val Cys Asp Lys
1               5                   10
```

```
<210> SEQ ID NO 6
<211> LENGTH: 16
<212> TYPE: PRT
<213> ORGANISM: Homo sapiens

<400> SEQUENCE: 6

Gly Asp Ser Ser Gly Glu Gly Val Cys Asp Lys Ser Pro Leu Glu Arg
1               5                   10                  15

<210> SEQ ID NO 7
<211> LENGTH: 9
<212> TYPE: PRT
<213> ORGANISM: Homo sapiens

<400> SEQUENCE: 7

Tyr Tyr Asp Tyr Ser Gly Ala Phe Arg
1               5

<210> SEQ ID NO 8
<211> LENGTH: 7
<212> TYPE: PRT
<213> ORGANISM: Homo sapiens

<400> SEQUENCE: 8

Ala Asp Val Thr Glu Trp Arg
1               5

<210> SEQ ID NO 9
<211> LENGTH: 9
<212> TYPE: PRT
<213> ORGANISM: Homo sapiens

<400> SEQUENCE: 9

Val Pro Ala His Ala Val Val Val Arg
1               5

<210> SEQ ID NO 10
<211> LENGTH: 10
<212> TYPE: PRT
<213> ORGANISM: Homo sapiens

<400> SEQUENCE: 10

Ala Asp Thr Asp Gly Gly Leu Ile Phe Arg
1               5                   10

<210> SEQ ID NO 11
<211> LENGTH: 9
<212> TYPE: PRT
<213> ORGANISM: Homo sapiens

<400> SEQUENCE: 11

Cys Gly Asp Met Ala Val Ala Phe Arg
1               5

<210> SEQ ID NO 12
<211> LENGTH: 11
<212> TYPE: PRT
<213> ORGANISM: Homo sapiens

<400> SEQUENCE: 12

Leu Lys Pro Glu Ile Gln Cys Val Ser Ala Lys
1               5                   10

<210> SEQ ID NO 13
<211> LENGTH: 12
```

```
<212> TYPE: PRT
<213> ORGANISM: Homo sapiens

<400> SEQUENCE: 13

Asp Ser Ser His Ala Phe Thr Leu Asp Glu Leu Arg
1               5                   10

<210> SEQ ID NO 14
<211> LENGTH: 13
<212> TYPE: PRT
<213> ORGANISM: Homo sapiens

<400> SEQUENCE: 14

Ser Glu Asp Tyr Glu Leu Leu Cys Pro Asn Gly Ala Arg
1               5                   10

<210> SEQ ID NO 15
<211> LENGTH: 15
<212> TYPE: PRT
<213> ORGANISM: Homo sapiens

<400> SEQUENCE: 15

Ala Gln Asp Leu Phe Gly Asp Asp His Asn Lys Asn Gly Phe Lys
1               5                   10                  15

<210> SEQ ID NO 16
<211> LENGTH: 40
<212> TYPE: PRT
<213> ORGANISM: Homo sapiens

<400> SEQUENCE: 16

Phe Ser Ser Glu Ala Tyr Gly Gln Lys Asp Leu Leu Phe Lys Asp Ser
1               5                   10                  15

Thr Ser Glu Leu Val Pro Ile Ala Thr Gln Thr Tyr Glu Ala Trp Leu
            20                  25                  30

Gly His Glu Tyr Leu His Ala Met
        35                  40

<210> SEQ ID NO 17
<211> LENGTH: 221
<212> TYPE: PRT
<213> ORGANISM: Homo sapiens

<400> SEQUENCE: 17

Glu Arg Ile Gln Ala Glu Gln Val Asp Ala Val Thr Leu Ser Gly Glu
1               5                   10                  15

Asp Ile Tyr Thr Ala Gly Lys Thr Tyr Gly Leu Val Pro Ala Ala Gly
            20                  25                  30

Glu His Tyr Ala Pro Glu Asp Ser Asn Ser Tyr Tyr Val Val Ala
        35                  40                  45

Val Val Arg Arg Asp Ser Ser His Ala Phe Thr Leu Asp Glu Leu Arg
50                  55                  60

Gly Lys Arg Ser Cys His Ala Gly Phe Gly Ser Pro Ala Gly Trp Asp
65                  70                  75                  80

Val Pro Val Gly Ala Leu Ile Gln Arg Gly Phe Ile Arg Pro Lys Asp
                85                  90                  95

Cys Asp Val Leu Thr Ala Val Ser Glu Phe Phe Asn Ala Ser Cys Val
            100                 105                 110

Pro Val Asn Asn Pro Lys Asn Tyr Pro Ser Ser Leu Cys Ala Leu Cys
        115                 120                 125
```

```
Val Gly Asp Glu Gln Gly Arg Asn Lys Cys Val Gly Asn Ser Gln Glu
    130                 135                 140

Arg Tyr Tyr Gly Tyr Arg Gly Ala Phe Arg Cys Leu Val Glu Asn Ala
145                 150                 155                 160

Gly Asp Val Ala Phe Val Arg His Thr Thr Val Phe Asp Asn Thr Asn
                165                 170                 175

Gly His Asn Ser Glu Pro Trp Ala Ala Glu Leu Arg Ser Glu Asp Tyr
                180                 185                 190

Glu Leu Leu Cys Pro Asn Gly Ala Arg Ala Glu Val Ser Gln Phe Ala
                195                 200                 205

Ala Cys Asn Leu Ala Gln Ile Pro Pro His Ala Val Met
    210                 215                 220

<210> SEQ ID NO 18
<211> LENGTH: 32
<212> TYPE: PRT
<213> ORGANISM: Homo sapiens

<400> SEQUENCE: 18

Val Arg Pro Asp Thr Asn Ile Phe Thr Val Tyr Gly Leu Leu Asp Lys
1               5                   10                  15

Ala Gln Asp Leu Phe Gly Asp Asp His Asn Lys Asn Gly Phe Lys Met
                20                  25                  30

<210> SEQ ID NO 19
<211> LENGTH: 5
<212> TYPE: PRT
<213> ORGANISM: Artificial Sequence
<220> FEATURE:
<223> OTHER INFORMATION: Heterologous sulfatase motif
<220> FEATURE:
<221> NAME/KEY: MISC_FEATURE
<222> LOCATION: (1)..(1)
<223> OTHER INFORMATION: Xaa = any amino acid or may be absent
<220> FEATURE:
<221> NAME/KEY: MISC_FEATURE
<222> LOCATION: (2)..(2)
<223> OTHER INFORMATION: Xaa = Cys or Ser
<220> FEATURE:
<221> NAME/KEY: MISC_FEATURE
<222> LOCATION: (3)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = Pro or Ala
<220> FEATURE:
<221> NAME/KEY: MISC_FEATURE
<222> LOCATION: (5)..(5)
<223> OTHER INFORMATION: Xaa = Any amino acid

<400> SEQUENCE: 19

Xaa Xaa Xaa Xaa Xaa
1               5

<210> SEQ ID NO 20
<211> LENGTH: 5
<212> TYPE: PRT
<213> ORGANISM: Artificial Sequence
<220> FEATURE:
<223> OTHER INFORMATION: Heterologous sulfatase motif
<220> FEATURE:
<221> NAME/KEY: MISC_FEATURE
<222> LOCATION: (1)..(1)
<223> OTHER INFORMATION: X = Any Amino Acid or may be absent
<220> FEATURE:
<221> NAME/KEY: MOD_RES
<222> LOCATION: (2)..(2)
```

```
<223> OTHER INFORMATION: C-alpha-formylglycine (FGly)
<220> FEATURE:
<221> NAME/KEY: MISC_FEATURE
<222> LOCATION: (3)..(3)
<223> OTHER INFORMATION: Xaa = Any Amino Acid
<220> FEATURE:
<221> NAME/KEY: MISC_FEATURE
<222> LOCATION: (4)..(4)
<223> OTHER INFORMATION: Xaa = Ala or Pro
<220> FEATURE:
<221> NAME/KEY: MISC_FEATURE
<222> LOCATION: (5)..(5)
<223> OTHER INFORMATION: Xaa = Any amino acid

<400> SEQUENCE: 20

Xaa Gly Xaa Xaa Xaa
1               5

<210> SEQ ID NO 21
<211> LENGTH: 4
<212> TYPE: PRT
<213> ORGANISM: Artificial Sequence
<220> FEATURE:
<223> OTHER INFORMATION: Peptide linker

<400> SEQUENCE: 21

Gly Ser Gly Ser
1

<210> SEQ ID NO 22
<211> LENGTH: 4
<212> TYPE: PRT
<213> ORGANISM: Artificial Sequence
<220> FEATURE:
<223> OTHER INFORMATION: Peptide linker

<400> SEQUENCE: 22

Gly Gly Ser Gly
1

<210> SEQ ID NO 23
<211> LENGTH: 4
<212> TYPE: PRT
<213> ORGANISM: Artificial Sequence
<220> FEATURE:
<223> OTHER INFORMATION: Peptide linker

<400> SEQUENCE: 23

Gly Gly Gly Ser
1

<210> SEQ ID NO 24
<211> LENGTH: 5
<212> TYPE: PRT
<213> ORGANISM: Artificial Sequence
<220> FEATURE:
<223> OTHER INFORMATION: Peptide Linker

<400> SEQUENCE: 24

Gly Gly Gly Gly Ser
1               5

<210> SEQ ID NO 25
<211> LENGTH: 4
<212> TYPE: PRT
<213> ORGANISM: Artificial Sequence
<220> FEATURE:
<223> OTHER INFORMATION: Peptide linker
```

```
<400> SEQUENCE: 25

Gly Asn Gly Asn
1

<210> SEQ ID NO 26
<211> LENGTH: 4
<212> TYPE: PRT
<213> ORGANISM: Artificial Sequence
<220> FEATURE:
<223> OTHER INFORMATION: Peptide linker

<400> SEQUENCE: 26

Gly Gly Asn Gly
1

<210> SEQ ID NO 27
<211> LENGTH: 4
<212> TYPE: PRT
<213> ORGANISM: Artificial Sequence
<220> FEATURE:
<223> OTHER INFORMATION: Peptide linker

<400> SEQUENCE: 27

Gly Gly Gly Asn
1

<210> SEQ ID NO 28
<211> LENGTH: 5
<212> TYPE: PRT
<213> ORGANISM: Artificial Sequence
<220> FEATURE:
<223> OTHER INFORMATION: Peptide linker

<400> SEQUENCE: 28

Gly Gly Gly Gly Asn
1               5

<210> SEQ ID NO 29
<211> LENGTH: 4
<212> TYPE: PRT
<213> ORGANISM: Artificial Sequence
<220> FEATURE:
<223> OTHER INFORMATION: Thrombin cleavable linker

<400> SEQUENCE: 29

Gly Arg Gly Asp
1

<210> SEQ ID NO 30
<211> LENGTH: 6
<212> TYPE: PRT
<213> ORGANISM: Artificial Sequence
<220> FEATURE:
<223> OTHER INFORMATION: Thrombin cleavable linker

<400> SEQUENCE: 30

Gly Arg Gly Asp Asn Pro
1               5

<210> SEQ ID NO 31
<211> LENGTH: 5
<212> TYPE: PRT
<213> ORGANISM: Artificial Sequence
<220> FEATURE:
<223> OTHER INFORMATION: Thrombin cleavable linker

<400> SEQUENCE: 31
```

```
Gly Arg Gly Asp Ser
1               5

<210> SEQ ID NO 32
<211> LENGTH: 7
<212> TYPE: PRT
<213> ORGANISM: Artificial Sequence
<220> FEATURE:
<223> OTHER INFORMATION: Thrombin cleavable linker

<400> SEQUENCE: 32

Gly Arg Gly Asp Ser Pro Lys
1               5

<210> SEQ ID NO 33
<211> LENGTH: 4
<212> TYPE: PRT
<213> ORGANISM: Artificial Sequence
<220> FEATURE:
<223> OTHER INFORMATION: Elastase cleavable linker

<400> SEQUENCE: 33

Ala Ala Pro Val
1

<210> SEQ ID NO 34
<211> LENGTH: 4
<212> TYPE: PRT
<213> ORGANISM: Artificial Sequence
<220> FEATURE:
<223> OTHER INFORMATION: Elastase cleavable linker

<400> SEQUENCE: 34

Ala Ala Pro Leu
1

<210> SEQ ID NO 35
<211> LENGTH: 4
<212> TYPE: PRT
<213> ORGANISM: Artificial Sequence
<220> FEATURE:
<223> OTHER INFORMATION: Elastase cleavable linker

<400> SEQUENCE: 35

Ala Ala Pro Phe
1

<210> SEQ ID NO 36
<211> LENGTH: 4
<212> TYPE: PRT
<213> ORGANISM: Artificial Sequence
<220> FEATURE:
<223> OTHER INFORMATION: Elastase cleavable linker

<400> SEQUENCE: 36

Ala Ala Pro Ala
1

<210> SEQ ID NO 37
<211> LENGTH: 4
<212> TYPE: PRT
<213> ORGANISM: Artificial Sequence
<220> FEATURE:
<223> OTHER INFORMATION: Elastase cleavable linker

<400> SEQUENCE: 37
```

```
Ala Tyr Leu Val
1

<210> SEQ ID NO 38
<211> LENGTH: 6
<212> TYPE: PRT
<213> ORGANISM: Artificial Sequence
<220> FEATURE:
<223> OTHER INFORMATION: Matrix metalloproteinase cleavable linker
<220> FEATURE:
<221> NAME/KEY: VARIANT
<222> LOCATION: (3)..(3)
<223> OTHER INFORMATION: Xaa = Any amino acid
<220> FEATURE:
<221> NAME/KEY: VARIANT
<222> LOCATION: (6)..(6)
<223> OTHER INFORMATION: Xaa = Any amino acid

<400> SEQUENCE: 38

Gly Pro Xaa Gly Pro Xaa
1               5

<210> SEQ ID NO 39
<211> LENGTH: 4
<212> TYPE: PRT
<213> ORGANISM: Artificial Sequence
<220> FEATURE:
<223> OTHER INFORMATION: Matrix metalloproteinase cleavable linker
<220> FEATURE:
<221> NAME/KEY: VARIANT
<222> LOCATION: (4)..(4)
<223> OTHER INFORMATION: Xaa = Any amino acid

<400> SEQUENCE: 39

Leu Gly Pro Xaa
1

<210> SEQ ID NO 40
<211> LENGTH: 6
<212> TYPE: PRT
<213> ORGANISM: Artificial Sequence
<220> FEATURE:
<223> OTHER INFORMATION: Matrix metalloproteinase cleavable linker
<220> FEATURE:
<221> NAME/KEY: VARIANT
<222> LOCATION: (6)..(6)
<223> OTHER INFORMATION: Xaa = Any amino acid

<400> SEQUENCE: 40

Gly Pro Ile Gly Pro Xaa
1               5

<210> SEQ ID NO 41
<211> LENGTH: 5
<212> TYPE: PRT
<213> ORGANISM: Artificial Sequence
<220> FEATURE:
<223> OTHER INFORMATION: Matrix metalloproteinase cleavable linker
<220> FEATURE:
<221> NAME/KEY: VARIANT
<222> LOCATION: (5)..(5)
<223> OTHER INFORMATION: Xaa = Any amino acid

<400> SEQUENCE: 41

Ala Pro Gly Leu Xaa
1               5

<210> SEQ ID NO 42
<211> LENGTH: 7
<212> TYPE: PRT
```

<213> ORGANISM: Artificial Sequence
<220> FEATURE:
<223> OTHER INFORMATION: Collagenase cleavable linker
<220> FEATURE:
<221> NAME/KEY: VARIANT
<222> LOCATION: (7)..(7)
<223> OTHER INFORMATION: Xaa = Any amino acid

<400> SEQUENCE: 42

Pro Leu Gly Pro Asp Arg Xaa
1               5

<210> SEQ ID NO 43
<211> LENGTH: 7
<212> TYPE: PRT
<213> ORGANISM: Artificial Sequence
<220> FEATURE:
<223> OTHER INFORMATION: Collagenase cleavable linker
<220> FEATURE:
<221> NAME/KEY: VARIANT
<222> LOCATION: (7)..(7)
<223> OTHER INFORMATION: Xaa = Any amino acid

<400> SEQUENCE: 43

Pro Leu Gly Leu Leu Gly Xaa
1               5

<210> SEQ ID NO 44
<211> LENGTH: 7
<212> TYPE: PRT
<213> ORGANISM: Artificial Sequence
<220> FEATURE:
<223> OTHER INFORMATION: Collagenase cleavable linker

<400> SEQUENCE: 44

Pro Gln Gly Ile Ala Gly Trp
1               5

<210> SEQ ID NO 45
<211> LENGTH: 5
<212> TYPE: PRT
<213> ORGANISM: Artificial Sequence
<220> FEATURE:
<223> OTHER INFORMATION: Collagenase cleavable linker

<400> SEQUENCE: 45

Pro Leu Gly Cys His
1               5

<210> SEQ ID NO 46
<211> LENGTH: 6
<212> TYPE: PRT
<213> ORGANISM: Artificial Sequence
<220> FEATURE:
<223> OTHER INFORMATION: Collagenase cleavable linker

<400> SEQUENCE: 46

Pro Leu Gly Leu Tyr Ala
1               5

<210> SEQ ID NO 47
<211> LENGTH: 7
<212> TYPE: PRT
<213> ORGANISM: Artificial Sequence
<220> FEATURE:
<223> OTHER INFORMATION: Collagenase cleavable linker

<400> SEQUENCE: 47

```
Pro Leu Ala Leu Trp Ala Arg
1               5

<210> SEQ ID NO 48
<211> LENGTH: 7
<212> TYPE: PRT
<213> ORGANISM: Artificial Sequence
<220> FEATURE:
<223> OTHER INFORMATION: Collagenase cleavable linker

<400> SEQUENCE: 48

Pro Leu Ala Tyr Trp Ala Arg
1               5

<210> SEQ ID NO 49
<211> LENGTH: 7
<212> TYPE: PRT
<213> ORGANISM: Artificial Sequence
<220> FEATURE:
<223> OTHER INFORMATION: Stromelysin cleavable linker

<400> SEQUENCE: 49

Pro Tyr Ala Tyr Tyr Met Arg
1               5

<210> SEQ ID NO 50
<211> LENGTH: 7
<212> TYPE: PRT
<213> ORGANISM: Artificial Sequence
<220> FEATURE:
<223> OTHER INFORMATION: Gelatinase cleavable linker

<400> SEQUENCE: 50

Pro Leu Gly Met Tyr Ser Arg
1               5

<210> SEQ ID NO 51
<211> LENGTH: 4
<212> TYPE: PRT
<213> ORGANISM: Artificial Sequence
<220> FEATURE:
<223> OTHER INFORMATION: Angiotensin converting enzyme cleavable linker

<400> SEQUENCE: 51

Gly Asp Lys Pro
1

<210> SEQ ID NO 52
<211> LENGTH: 5
<212> TYPE: PRT
<213> ORGANISM: Artificial Sequence
<220> FEATURE:
<223> OTHER INFORMATION: Angiotensin converting enzyme cleavable linker

<400> SEQUENCE: 52

Gly Ser Asp Lys Pro
1               5

<210> SEQ ID NO 53
<211> LENGTH: 4
<212> TYPE: PRT
<213> ORGANISM: Artificial Sequence
<220> FEATURE:
<223> OTHER INFORMATION: Cathepsin B cleavable linker

<400> SEQUENCE: 53

Ala Leu Ala Leu
```

```
<210> SEQ ID NO 54
<211> LENGTH: 4
<212> TYPE: PRT
<213> ORGANISM: Artificial Sequence
<220> FEATURE:
<223> OTHER INFORMATION: Cathepsin B cleavable linker

<400> SEQUENCE: 54

Gly Phe Leu Gly
1

<210> SEQ ID NO 55
<211> LENGTH: 20
<212> TYPE: PRT
<213> ORGANISM: Homo sapiens

<400> SEQUENCE: 55

Leu Phe Ser His Glu Gly Ser Ser Phe Gln Met Phe Ser Ser Glu Ala
1               5                   10                  15

Tyr Gly Gln Lys
            20

<210> SEQ ID NO 56
<211> LENGTH: 21
<212> TYPE: PRT
<213> ORGANISM: Homo sapiens

<400> SEQUENCE: 56

His Thr Thr Val Phe Asp Asn Thr Asn Gly His Asn Ser Glu Pro Trp
1               5                   10                  15

Ala Ala Glu Leu Arg
            20

<210> SEQ ID NO 57
<211> LENGTH: 25
<212> TYPE: PRT
<213> ORGANISM: Homo sapiens

<400> SEQUENCE: 57

Ala Val Ser Asp Tyr Phe Gly Gly Ser Cys Val Pro Gly Ala Gly Glu
1               5                   10                  15

Thr Ser Tyr Ser Glu Ser Leu Cys Arg
            20                  25

<210> SEQ ID NO 58
<211> LENGTH: 17
<212> TYPE: PRT
<213> ORGANISM: Homo sapiens

<400> SEQUENCE: 58

Asn Tyr Pro Ser Ser Leu Cys Ala Leu Cys Val Gly Asp Glu Gln Gly
1               5                   10                  15

Arg

<210> SEQ ID NO 59
<211> LENGTH: 19
<212> TYPE: PRT
<213> ORGANISM: Homo sapiens

<400> SEQUENCE: 59

Thr Leu Pro Ser Trp Gly Gln Ala Leu Leu Ser Gln Asp Phe Glu Leu
```

```
1               5                   10                  15

Leu Cys Arg

<210> SEQ ID NO 60
<211> LENGTH: 13
<212> TYPE: PRT
<213> ORGANISM: Homo sapiens

<400> SEQUENCE: 60

Cys Leu Ala Glu Gly Ala Gly Asp Val Ala Phe Val Lys
1               5                   10

<210> SEQ ID NO 61
<211> LENGTH: 15
<212> TYPE: PRT
<213> ORGANISM: Homo sapiens

<400> SEQUENCE: 61

Met Phe Asp Ser Ser Asn Tyr His Gly Gln Asp Leu Leu Phe Lys
1               5                   10                  15

<210> SEQ ID NO 62
<211> LENGTH: 25
<212> TYPE: PRT
<213> ORGANISM: Homo sapiens

<400> SEQUENCE: 62

Leu Phe Ser His Glu Gly Ser Ser Phe Gln Met Phe Ser Ser Glu Ala
1               5                   10                  15

Tyr Gly Gln Lys Asp Leu Leu Phe Lys
            20                  25

<210> SEQ ID NO 63
<211> LENGTH: 13
<212> TYPE: PRT
<213> ORGANISM: Homo sapiens

<400> SEQUENCE: 63

Arg Asp Ser Ser His Ala Phe Thr Leu Asp Glu Leu Arg
1               5                   10

<210> SEQ ID NO 64
<211> LENGTH: 11
<212> TYPE: PRT
<213> ORGANISM: Homo sapiens

<400> SEQUENCE: 64

Ala Gln Asp Leu Phe Gly Asp Asp His Asn Lys
1               5                   10

<210> SEQ ID NO 65
<211> LENGTH: 10
<212> TYPE: PRT
<213> ORGANISM: Homo sapiens

<400> SEQUENCE: 65

Leu Ser Val Met Gly Cys Asp Val Leu Lys
1               5                   10

<210> SEQ ID NO 66
<211> LENGTH: 12
<212> TYPE: PRT
<213> ORGANISM: Homo sapiens
```

```
<400> SEQUENCE: 66

Glu Ala Gly Ile Gln Pro Ser Leu Leu Cys Val Arg
1               5                   10

<210> SEQ ID NO 67
<211> LENGTH: 10
<212> TYPE: PRT
<213> ORGANISM: Homo sapiens

<400> SEQUENCE: 67

Ser Ser His Val Thr Ile Asp Thr Leu Lys
1               5                   10

<210> SEQ ID NO 68
<211> LENGTH: 11
<212> TYPE: PRT
<213> ORGANISM: Homo sapiens

<400> SEQUENCE: 68

Trp Cys Val Leu Ser Thr Pro Glu Ile Gln Lys
1               5                   10

<210> SEQ ID NO 69
<211> LENGTH: 8
<212> TYPE: PRT
<213> ORGANISM: Homo sapiens

<400> SEQUENCE: 69

Gly Leu Leu Cys Asp Pro Asn Arg
1               5

<210> SEQ ID NO 70
<211> LENGTH: 14
<212> TYPE: PRT
<213> ORGANISM: Homo sapiens

<400> SEQUENCE: 70

Asp Ser Ser His Ala Phe Thr Leu Asp Glu Leu Arg Gly Lys
1               5                   10

<210> SEQ ID NO 71
<211> LENGTH: 14
<212> TYPE: PRT
<213> ORGANISM: Homo sapiens

<400> SEQUENCE: 71

Gly Leu Leu Cys Asp Pro Asn Arg Leu Pro Pro Tyr Leu Arg
1               5                   10

<210> SEQ ID NO 72
<211> LENGTH: 28
<212> TYPE: PRT
<213> ORGANISM: Homo sapiens

<400> SEQUENCE: 72

Glu His Gly Leu Lys Pro Val Val Gly Glu Val Tyr Asp Gln Glu Val
1               5                   10                  15

Gly Thr Ser Tyr Tyr Ala Val Ala Val Val Arg Arg
            20                  25

<210> SEQ ID NO 73
<211> LENGTH: 13
<212> TYPE: PRT
<213> ORGANISM: Homo sapiens
```

```
<400> SEQUENCE: 73

Cys Val Gly Asn Ser Gln Glu Arg Tyr Tyr Gly Tyr Arg
1               5                   10

<210> SEQ ID NO 74
<211> LENGTH: 13
<212> TYPE: PRT
<213> ORGANISM: Homo sapiens

<400> SEQUENCE: 74

Cys Leu Val Glu Asn Ala Gly Asp Val Ala Phe Val Arg
1               5                   10

<210> SEQ ID NO 75
<211> LENGTH: 27
<212> TYPE: PRT
<213> ORGANISM: Homo sapiens

<400> SEQUENCE: 75

Asp Ser Thr Ser Glu Leu Val Pro Ile Ala Thr Gln Thr Tyr Glu Ala
1               5                   10                  15

Trp Leu Gly His Glu Tyr Leu His Ala Met Lys
            20                  25

<210> SEQ ID NO 76
<211> LENGTH: 21
<212> TYPE: PRT
<213> ORGANISM: Homo sapiens

<400> SEQUENCE: 76

Ile Gln Ala Glu Gln Val Asp Ala Val Thr Leu Ser Gly Glu Asp Ile
1               5                   10                  15

Tyr Thr Ala Gly Lys
            20

<210> SEQ ID NO 77
<211> LENGTH: 11
<212> TYPE: PRT
<213> ORGANISM: Homo sapiens

<400> SEQUENCE: 77

His Ser Thr Val Leu Glu Asn Thr Asp Gly Lys
1               5                   10

<210> SEQ ID NO 78
<211> LENGTH: 16
<212> TYPE: PRT
<213> ORGANISM: Homo sapiens

<400> SEQUENCE: 78

Thr Val Gly Trp Asn Val Pro Val Gly Tyr Leu Val Glu Ser Gly Arg
1               5                   10                  15

<210> SEQ ID NO 79
<211> LENGTH: 7
<212> TYPE: PRT
<213> ORGANISM: Homo sapiens

<400> SEQUENCE: 79

Leu Leu Asn Glu Gly Gln Arg
1               5
```

<210> SEQ ID NO 80
<211> LENGTH: 25
<212> TYPE: PRT
<213> ORGANISM: Homo sapiens

<400> SEQUENCE: 80

Leu Phe Ser His Glu Gly Ser Ser Phe Gln Met Phe Ser Glu Ala
1               5                   10                  15

Tyr Gly Gln Lys Asp Leu Leu Phe Lys
            20                  25

<210> SEQ ID NO 81
<211> LENGTH: 17
<212> TYPE: PRT
<213> ORGANISM: Homo sapiens

<400> SEQUENCE: 81

Ala Asp Thr Asp Gly Gly Leu Ile Phe Arg Leu Leu Asn Glu Gly Gln
1               5                   10                  15

Arg

<210> SEQ ID NO 82
<211> LENGTH: 9
<212> TYPE: PRT
<213> ORGANISM: Homo sapiens

<400> SEQUENCE: 82

Cys Gly Asn Met Ser Glu Ala Phe Arg
1               5

<210> SEQ ID NO 83
<211> LENGTH: 13
<212> TYPE: PRT
<213> ORGANISM: Homo sapiens

<400> SEQUENCE: 83

Ala Asp Val Thr Glu Trp Arg Gln Cys His Leu Ala Arg
1               5                   10

<210> SEQ ID NO 84
<211> LENGTH: 32
<212> TYPE: PRT
<213> ORGANISM: Homo sapiens

<400> SEQUENCE: 84

Asp Leu Leu Phe Lys Asp Ser Thr Ser Glu Leu Val Pro Ile Ala Thr
1               5                   10                  15

Gln Thr Tyr Glu Ala Trp Leu Gly His Glu Tyr Leu His Ala Met Lys
            20                  25                  30

<210> SEQ ID NO 85
<211> LENGTH: 20
<212> TYPE: PRT
<213> ORGANISM: Homo sapiens

<400> SEQUENCE: 85

Met Phe Asp Ser Ser Asn Tyr His Gly Gln Asp Leu Leu Phe Lys Asp
1               5                   10                  15

Ala Thr Val Arg
            20

<210> SEQ ID NO 86
<211> LENGTH: 11

```
<212> TYPE: PRT
<213> ORGANISM: Homo sapiens

<400> SEQUENCE: 86

Ala Val Pro Val Gly Glu Lys Thr Thr Tyr Arg
1               5                   10

<210> SEQ ID NO 87
<211> LENGTH: 14
<212> TYPE: PRT
<213> ORGANISM: Homo sapiens

<400> SEQUENCE: 87

Phe Asp Ser Ser Asn Tyr His Gly Gln Asp Leu Leu Phe Lys
1               5                   10

<210> SEQ ID NO 88
<211> LENGTH: 16
<212> TYPE: PRT
<213> ORGANISM: Homo sapiens

<400> SEQUENCE: 88

Val Arg Pro Asp Thr Asn Ile Phe Thr Val Tyr Gly Leu Leu Asp Lys
1               5                   10                  15

<210> SEQ ID NO 89
<211> LENGTH: 9
<212> TYPE: PRT
<213> ORGANISM: Homo sapiens

<400> SEQUENCE: 89

Phe Ser Ser Glu Ala Tyr Gly Gln Lys
1               5

<210> SEQ ID NO 90
<211> LENGTH: 31
<212> TYPE: PRT
<213> ORGANISM: Homo sapiens

<400> SEQUENCE: 90

Gly Thr Ser Ala Asp His Cys Val Gln Leu Ile Ala Ala Gln Glu Ala
1               5                   10                  15

Asp Ala Ile Thr Leu Asp Gly Gly Ala Ile Tyr Glu Ala Gly Lys
                20                  25                  30

<210> SEQ ID NO 91
<211> LENGTH: 690
<212> TYPE: PRT
<213> ORGANISM: Homo sapiens

<400> SEQUENCE: 91

Gly Met Glu Val Arg Trp Cys Ala Thr Ser Asp Pro Glu Gln His Lys
1               5                   10                  15

Cys Gly Asn Met Ser Glu Ala Phe Arg Glu Ala Gly Ile Gln Pro Ser
                20                  25                  30

Leu Leu Cys Val Arg Gly Thr Ser Ala Asp His Cys Val Gln Leu Ile
            35                  40                  45

Ala Ala Gln Glu Ala Asp Ala Ile Thr Leu Asp Gly Gly Ala Ile Tyr
        50                  55                  60

Glu Ala Gly Lys Glu His Gly Leu Lys Pro Val Val Gly Glu Val Tyr
65                  70                  75                  80

Asp Gln Glu Val Gly Thr Ser Tyr Tyr Ala Val Ala Val Val Arg Arg
```

-continued

```
                85                  90                  95
Ser Ser His Val Thr Ile Asp Thr Leu Lys Gly Val Lys Ser Cys His
            100                 105                 110
Thr Gly Ile Asn Arg Thr Val Gly Trp Asn Val Pro Val Gly Tyr Leu
            115                 120                 125
Val Glu Ser Gly Arg Leu Ser Val Met Gly Cys Asp Val Leu Lys Ala
            130                 135                 140
Val Ser Asp Tyr Phe Gly Gly Ser Cys Val Pro Gly Ala Gly Glu Thr
145                 150                 155                 160
Ser Tyr Ser Glu Ser Leu Cys Arg Leu Cys Arg Gly Asp Ser Ser Gly
                165                 170                 175
Glu Gly Val Cys Asp Lys Ser Pro Leu Glu Arg Tyr Tyr Asp Tyr Ser
                180                 185                 190
Gly Ala Phe Arg Cys Leu Ala Glu Gly Ala Gly Asp Val Ala Phe Val
                195                 200                 205
Lys His Ser Thr Val Leu Glu Asn Thr Asp Gly Lys Thr Leu Pro Ser
            210                 215                 220
Trp Gly Gln Ala Leu Leu Ser Gln Asp Phe Glu Leu Leu Cys Arg Asp
225                 230                 235                 240
Gly Ser Arg Ala Asp Val Thr Glu Trp Arg Gln Cys His Leu Ala Arg
                245                 250                 255
Val Pro Ala His Ala Val Val Arg Ala Asp Thr Asp Gly Gly Leu
                260                 265                 270
Ile Phe Arg Leu Leu Asn Glu Gly Gln Arg Leu Phe Ser His Glu Gly
            275                 280                 285
Ser Ser Phe Gln Met Phe Ser Ser Glu Ala Tyr Gly Gln Lys Asp Leu
            290                 295                 300
Leu Phe Lys Asp Ser Thr Ser Glu Leu Val Pro Ile Ala Thr Gln Thr
305                 310                 315                 320
Tyr Glu Ala Trp Leu Gly His Glu Tyr Leu His Ala Met Lys Gly Leu
                325                 330                 335
Leu Cys Asp Pro Asn Arg Leu Pro Pro Tyr Leu Arg Trp Cys Val Leu
                340                 345                 350
Ser Thr Pro Glu Ile Gln Lys Cys Gly Asp Met Ala Val Ala Phe Arg
            355                 360                 365
Arg Gln Arg Leu Lys Pro Glu Ile Gln Cys Val Ser Ala Lys Ser Pro
            370                 375                 380
Gln His Cys Met Glu Arg Ile Gln Ala Glu Gln Val Asp Ala Val Thr
385                 390                 395                 400
Leu Ser Gly Glu Asp Ile Tyr Thr Ala Gly Lys Thr Tyr Gly Leu Val
                405                 410                 415
Pro Ala Ala Gly Glu His Tyr Ala Pro Glu Asp Ser Ser Asn Ser Tyr
                420                 425                 430
Tyr Val Val Ala Val Val Arg Arg Asp Ser Ser His Ala Phe Thr Leu
            435                 440                 445
Asp Glu Leu Arg Gly Lys Arg Ser Cys His Ala Gly Phe Gly Ser Pro
            450                 455                 460
Ala Gly Trp Asp Val Pro Val Gly Ala Leu Ile Gln Arg Gly Phe Ile
465                 470                 475                 480
Arg Pro Lys Asp Cys Asp Val Leu Thr Ala Val Ser Glu Phe Phe Asn
                485                 490                 495
Ala Ser Cys Val Pro Val Asn Asn Pro Lys Asn Tyr Pro Ser Ser Leu
                500                 505                 510
```

```
Cys Ala Leu Cys Val Gly Asp Glu Gln Gly Arg Asn Lys Cys Val Gly
            515                 520                 525

Asn Ser Gln Glu Arg Tyr Tyr Gly Tyr Arg Gly Ala Phe Arg Cys Leu
        530                 535                 540

Val Glu Asn Ala Gly Asp Val Ala Phe Val Arg His Thr Thr Val Phe
545                 550                 555                 560

Asp Asn Thr Asn Gly His Asn Ser Glu Pro Trp Ala Ala Glu Leu Arg
                565                 570                 575

Ser Glu Asp Tyr Glu Leu Leu Cys Pro Asn Gly Ala Arg Ala Glu Val
            580                 585                 590

Ser Gln Phe Ala Ala Cys Asn Leu Ala Gln Ile Pro Pro His Ala Val
        595                 600                 605

Met Val Arg Pro Asp Thr Asn Ile Phe Thr Val Tyr Gly Leu Leu Asp
610                 615                 620

Lys Ala Gln Asp Leu Phe Gly Asp Asp His Asn Lys Asn Gly Phe Lys
625                 630                 635                 640

Met Phe Asp Ser Ser Asn Tyr His Gly Gln Asp Leu Leu Phe Lys Asp
                645                 650                 655

Ala Thr Val Arg Ala Val Pro Val Gly Glu Lys Thr Thr Tyr Arg Gly
            660                 665                 670

Trp Leu Gly Leu Asp Tyr Val Ala Ala Leu Glu Gly Met Ser Ser Gln
        675                 680                 685

Gln Cys
    690

<210> SEQ ID NO 92
<211> LENGTH: 14
<212> TYPE: PRT
<213> ORGANISM: Homo sapiens

<400> SEQUENCE: 92

Asp Ser Ser His Ala Phe Thr Leu Asp Glu Leu Arg Tyr Cys
1               5                   10

<210> SEQ ID NO 93
<211> LENGTH: 12
<212> TYPE: PRT
<213> ORGANISM: Jaculus jaculus

<400> SEQUENCE: 93

Asp Ser Ser Asp Ala Phe Thr Leu Asp Glu Leu Arg
1               5                   10

<210> SEQ ID NO 94
<211> LENGTH: 12
<212> TYPE: PRT
<213> ORGANISM: Otolemur garnettii

<400> SEQUENCE: 94

Asp Ser Ser His Ser Phe Thr Leu Asp Glu Leu Arg
1               5                   10

<210> SEQ ID NO 95
<211> LENGTH: 12
<212> TYPE: PRT
<213> ORGANISM: Pongo abelii

<400> SEQUENCE: 95

Asp Ser Ser Asp Ala Phe Thr Leu Asp Glu Leu Arg
```

<210> SEQ ID NO 96
<211> LENGTH: 12
<212> TYPE: PRT
<213> ORGANISM: Ictidomys tridecemlineatus

<400> SEQUENCE: 96

Asp Ser Ser Tyr Ala Phe Thr Leu Asp Glu Leu Arg
1               5                   10

<210> SEQ ID NO 97
<211> LENGTH: 12
<212> TYPE: PRT
<213> ORGANISM: Ceratotherium simum simum

<400> SEQUENCE: 97

Asn Ser Ser His Ala Phe Thr Leu Asp Glu Leu Arg
1               5                   10

<210> SEQ ID NO 98
<211> LENGTH: 12
<212> TYPE: PRT
<213> ORGANISM: Vicugna pacos

<400> SEQUENCE: 98

Asn Ser Ser Tyr Ala Phe Thr Leu Asp Glu Leu Arg
1               5                   10

<210> SEQ ID NO 99
<211> LENGTH: 12
<212> TYPE: PRT
<213> ORGANISM: Ochotona princeps

<400> SEQUENCE: 99

Asp Ser Ser Tyr Ala Phe Pro Leu Asp Glu Leu Arg
1               5                   10

<210> SEQ ID NO 100
<211> LENGTH: 12
<212> TYPE: PRT
<213> ORGANISM: Pteropus alecto

<400> SEQUENCE: 100

Asn Ser Ser Tyr Ala Phe Thr Leu Asp Glu Leu Arg
1               5                   10

<210> SEQ ID NO 101
<211> LENGTH: 12
<212> TYPE: PRT
<213> ORGANISM: Tursiops truncatus

<400> SEQUENCE: 101

Asn Ser Ser Tyr Ala Phe Thr Leu Asp Glu Leu Arg
1               5                   10

<210> SEQ ID NO 102
<211> LENGTH: 12
<212> TYPE: PRT
<213> ORGANISM: Tupaia chinensis

<400> SEQUENCE: 102

Asp Ser Thr His Ala Phe Thr Val Asp Glu Leu Arg
1               5                   10

-continued

<210> SEQ ID NO 103
<211> LENGTH: 12
<212> TYPE: PRT
<213> ORGANISM: Pantholops hodgsonii

<400> SEQUENCE: 103

Asn Ser Ser Tyr Ala Phe Thr Leu Asp Glu Leu Arg
1               5                   10

<210> SEQ ID NO 104
<211> LENGTH: 12
<212> TYPE: PRT
<213> ORGANISM: Felis catus

<400> SEQUENCE: 104

Asn Ser Ser Tyr Ala Phe Thr Leu Asp Glu Leu Arg
1               5                   10

<210> SEQ ID NO 105
<211> LENGTH: 12
<212> TYPE: PRT
<213> ORGANISM: Bos taurus

<400> SEQUENCE: 105

Asn Ser Ser Tyr Ala Phe Thr Leu Asp Glu Leu Arg
1               5                   10

<210> SEQ ID NO 106
<211> LENGTH: 12
<212> TYPE: PRT
<213> ORGANISM: Mustela putorius furo

<400> SEQUENCE: 106

Asn Ser Ser Tyr Ala Phe Thr Leu Asp Glu Leu Arg
1               5                   10

<210> SEQ ID NO 107
<211> LENGTH: 12
<212> TYPE: PRT
<213> ORGANISM: Ailuropoda Melanoleuca

<400> SEQUENCE: 107

Asn Ser Ser Tyr Ala Phe Thr Leu Asp Glu Leu Arg
1               5                   10

<210> SEQ ID NO 108
<211> LENGTH: 12
<212> TYPE: PRT
<213> ORGANISM: Capra hircus

<400> SEQUENCE: 108

Asn Ser Ser Tyr Ala Phe Thr Leu Asp Glu Leu Arg
1               5                   10

<210> SEQ ID NO 109
<211> LENGTH: 12
<212> TYPE: PRT
<213> ORGANISM: Mus musculus

<400> SEQUENCE: 109

Asp Ser Ser Tyr Ser Phe Thr Leu Asp Glu Leu Arg
1               5                   10

<210> SEQ ID NO 110

```
<211> LENGTH: 12
<212> TYPE: PRT
<213> ORGANISM: Orcinus orca

<400> SEQUENCE: 110

Asn Ser Ser Asn Ala Phe Thr Leu Asp Glu Leu Arg
1               5                   10

<210> SEQ ID NO 111
<211> LENGTH: 12
<212> TYPE: PRT
<213> ORGANISM: Chinchilla lanigera

<400> SEQUENCE: 111

Asp Ser Ser Ser Ala Phe Thr Leu Asn Glu Leu Arg
1               5                   10

<210> SEQ ID NO 112
<211> LENGTH: 12
<212> TYPE: PRT
<213> ORGANISM: Dasypus novemcinctus

<400> SEQUENCE: 112

Asp Ser Ser Tyr Ala Phe Thr Leu Asp Glu Leu Trp
1               5                   10

<210> SEQ ID NO 113
<211> LENGTH: 12
<212> TYPE: PRT
<213> ORGANISM: Rattus norvegicus

<400> SEQUENCE: 113

Asp Ser Ser Tyr Ser Phe Thr Leu Asp Glu Leu Arg
1               5                   10

<210> SEQ ID NO 114
<211> LENGTH: 12
<212> TYPE: PRT
<213> ORGANISM: Odobenus rosmarus divergens

<400> SEQUENCE: 114

Asn Ser Ser Ser Ala Phe Thr Leu Asp Glu Leu Arg
1               5                   10

<210> SEQ ID NO 115
<211> LENGTH: 12
<212> TYPE: PRT
<213> ORGANISM: Microtus ochrogaster

<400> SEQUENCE: 115

Asp Ser Ser Tyr Ser Phe Thr Leu Asp Glu Leu Arg
1               5                   10

<210> SEQ ID NO 116
<211> LENGTH: 12
<212> TYPE: PRT
<213> ORGANISM: Ovis aries

<400> SEQUENCE: 116

Asn Ser Ser Tyr Ala Phe Thr Leu Asp Glu Leu Arg
1               5                   10

<210> SEQ ID NO 117
<211> LENGTH: 12
<212> TYPE: PRT
```

```
<213> ORGANISM: Leptonychotes weddellii

<400> SEQUENCE: 117

Asn Ser Ser Tyr Ala Phe Thr Leu Asp Glu Leu Arg
1               5                   10

<210> SEQ ID NO 118
<211> LENGTH: 12
<212> TYPE: PRT
<213> ORGANISM: Camelus ferus

<400> SEQUENCE: 118

Asn Ser Ser Tyr Ala Phe Thr Leu Asp Glu Leu Arg
1               5                   10

<210> SEQ ID NO 119
<211> LENGTH: 12
<212> TYPE: PRT
<213> ORGANISM: Sus scrofa

<400> SEQUENCE: 119

Asn Ser Ser Tyr Ala Phe Thr Leu Asp Glu Leu Arg
1               5                   10

<210> SEQ ID NO 120
<211> LENGTH: 12
<212> TYPE: PRT
<213> ORGANISM: Bos mutus

<400> SEQUENCE: 120

Asn Ser Ser Tyr Ala Phe Thr Leu Asp Glu Leu Arg
1               5                   10

<210> SEQ ID NO 121
<211> LENGTH: 12
<212> TYPE: PRT
<213> ORGANISM: Cyphellophora europaea

<400> SEQUENCE: 121

Ala Thr Ser His Ala Ile Thr Leu Asp Glu Leu Arg
1               5                   10

<210> SEQ ID NO 122
<211> LENGTH: 12
<212> TYPE: PRT
<213> ORGANISM: Loxodonta africana

<400> SEQUENCE: 122

Asn Ser Ser Tyr Ala Phe Thr Met Asp Glu Leu Arg
1               5                   10

<210> SEQ ID NO 123
<211> LENGTH: 12
<212> TYPE: PRT
<213> ORGANISM: Cricetulus griseus

<400> SEQUENCE: 123

Asp Arg Ser Tyr Ser Phe Thr Leu Asp Glu Leu Arg
1               5                   10

<210> SEQ ID NO 124
<211> LENGTH: 12
<212> TYPE: PRT
<213> ORGANISM: Oryctolagus cuniculus
```

```
<400> SEQUENCE: 124

Asp Ser Ala Tyr Ala Phe Thr Val Asp Glu Leu Arg
1               5                   10

<210> SEQ ID NO 125
<211> LENGTH: 12
<212> TYPE: PRT
<213> ORGANISM: Octodon degus

<400> SEQUENCE: 125

Asp Ser Ser Ser Ala Phe Asn Leu Asn Glu Leu Arg
1               5                   10

<210> SEQ ID NO 126
<211> LENGTH: 12
<212> TYPE: PRT
<213> ORGANISM: Canis lupus familiaris

<400> SEQUENCE: 126

Asn Ser Ser Asp Ala Phe Ser Leu Asp Glu Leu Arg
1               5                   10

<210> SEQ ID NO 127
<211> LENGTH: 12
<212> TYPE: PRT
<213> ORGANISM: Cavia porcellus

<400> SEQUENCE: 127

Asp Ser Ser Ser Ala Phe Ser Leu Asn Glu Leu Arg
1               5                   10

<210> SEQ ID NO 128
<211> LENGTH: 12
<212> TYPE: PRT
<213> ORGANISM: Sorex araneus

<400> SEQUENCE: 128

Asn Ser Ser Asp Ala Phe Ser Leu Asp Glu Leu Arg
1               5                   10

<210> SEQ ID NO 129
<211> LENGTH: 12
<212> TYPE: PRT
<213> ORGANISM: Trichechus manatus latirostris

<400> SEQUENCE: 129

Asn Ser Ser Tyr Ala Phe Thr Met Asp Glu Leu Arg
1               5                   10

<210> SEQ ID NO 130
<211> LENGTH: 12
<212> TYPE: PRT
<213> ORGANISM: Mesocricetus auratus

<400> SEQUENCE: 130

Asp Arg Ser Tyr Ser Phe Thr Leu Asp Glu Leu Arg
1               5                   10

<210> SEQ ID NO 131
<211> LENGTH: 12
<212> TYPE: PRT
<213> ORGANISM: Monodelphis domestica

<400> SEQUENCE: 131
```

Asn Ser Ser Tyr Ser Phe Thr Leu Asp Glu Leu Arg
1               5                   10

<210> SEQ ID NO 132
<211> LENGTH: 12
<212> TYPE: PRT
<213> ORGANISM: Equus caballus

<400> SEQUENCE: 132

Asn Ser Ser Tyr Ala Phe Thr Val Asp Glu Leu Arg
1               5                   10

<210> SEQ ID NO 133
<211> LENGTH: 12
<212> TYPE: PRT
<213> ORGANISM: Echinops telfairi

<400> SEQUENCE: 133

Asn Ser Ser Tyr Ala Phe Thr Val Asp Glu Leu Arg
1               5                   10

<210> SEQ ID NO 134
<211> LENGTH: 12
<212> TYPE: PRT
<213> ORGANISM: Condylura cristata

<400> SEQUENCE: 134

Asn Ser Ser Tyr Ala Phe Ser Leu Asp Glu Leu Arg
1               5                   10

<210> SEQ ID NO 135
<211> LENGTH: 11
<212> TYPE: PRT
<213> ORGANISM: Homo sapien

<400> SEQUENCE: 135

Ser Ala Ser Asp Leu Thr Trp Asp Asn Leu Lys
1               5                   10

<210> SEQ ID NO 136
<211> LENGTH: 11
<212> TYPE: PRT
<213> ORGANISM: Homo sapien

<400> SEQUENCE: 136

Ser Asp Thr Ser Leu Thr Trp Asn Ser Val Lys
1               5                   10

<210> SEQ ID NO 137
<211> LENGTH: 28
<212> TYPE: PRT
<213> ORGANISM: Homo sapiens

<400> SEQUENCE: 137

Leu Leu Asn Glu Gly Gln Arg Leu Phe Ser His Glu Gly Ser Ser Phe
1               5                   10                  15

Phe Gln Met Phe Ser Ser Glu Ala Tyr Gly Gln Lys
            20                  25

<210> SEQ ID NO 138
<211> LENGTH: 8
<212> TYPE: PRT
<213> ORGANISM: Homo sapiens

<400> SEQUENCE: 138

```
Ser Pro Gln His Cys Met Glu Arg
1               5

<210> SEQ ID NO 139
<211> LENGTH: 26
<212> TYPE: PRT
<213> ORGANISM: Homo sapiens

<400> SEQUENCE: 139

Thr Val Gly Trp Asn Val Pro Val Gly Tyr Leu Val Glu Ser Gly Arg
1               5                   10                  15

Leu Ser Val Met Gly Cys Asp Val Leu Lys
            20                  25

<210> SEQ ID NO 140
<211> LENGTH: 35
<212> TYPE: PRT
<213> ORGANISM: Homo sapiens

<400> SEQUENCE: 140

Asp Ser Thr Ser Glu Leu Val Pro Ile Ala Thr Gln Thr Tyr Glu Ala
1               5                   10                  15

Trp Leu Gly His Glu Tyr Leu His Ala Met Lys Gly Leu Leu Cys Asp
            20                  25                  30

Pro Asn Arg
        35

<210> SEQ ID NO 141
<211> LENGTH: 22
<212> TYPE: PRT
<213> ORGANISM: Homo sapiens

<400> SEQUENCE: 141

Ser Cys His Ala Gly Phe Gly Ser Pro Ala Gly Trp Asp Val Pro Val
1               5                   10                  15

Gly Ala Leu Ile Gln Arg
            20

<210> SEQ ID NO 142
<211> LENGTH: 28
<212> TYPE: PRT
<213> ORGANISM: Homo sapiens

<400> SEQUENCE: 142

Lys Tyr Gly Leu Val Pro Ala Ala Gly Glu His Tyr Ala Pro Glu Asp
1               5                   10                  15

Ser Ser Asn Ser Tyr Tyr Val Val Ala Val Val Arg
            20                  25

<210> SEQ ID NO 143
<211> LENGTH: 24
<212> TYPE: PRT
<213> ORGANISM: Homo sapiens

<400> SEQUENCE: 143

Cys Leu Ala Glu Gly Ala Gly Asp Val Ala Phe Val Lys His Ser Thr
1               5                   10                  15

Val Leu Glu Asn Thr Asp Gly Lys
            20
```